US012767687B2

(12) United States Patent
Al-Abed

(10) Patent No.: US 12,767,687 B2
(45) Date of Patent: Oct. 20, 2026

(54) PEPTIDOMIMETIC AGENTS, SYNTHESIS AND USES THEREOF

(71) Applicant: THE FEINSTEIN INSTITUTES FOR MEDICAL RESEARCH, Manhasset, NY (US)

(72) Inventor: Yousef Al-Abed, Great Neck, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 465 days.

(21) Appl. No.: 16/869,692

(22) Filed: May 8, 2020

(65) Prior Publication Data

US 2020/0354404 A1 Nov. 12, 2020

Related U.S. Application Data

(60) Provisional application No. 62/845,611, filed on May 9, 2019.

(51) Int. Cl.

*C07K 7/06* (2006.01)
*A61K 38/00* (2006.01)
*C07K 1/00* (2006.01)
*C07K 5/02* (2006.01)
*C07K 5/10* (2006.01)

(52) U.S. Cl.

CPC ................ *C07K 7/06* (2013.01); *C07K 1/006* (2013.01); *C07K 5/02* (2013.01); *C07K 5/10* (2013.01); *A61K 38/00* (2013.01)

(58) Field of Classification Search

CPC .................................. C07K 7/06; A61K 38/00
See application file for complete search history.

(56) References Cited

U.S. PATENT DOCUMENTS

| | | | | |
|---|---|---|---|---|
| 5,602,231 | A | 2/1997 | Cotton et al. | |
| 6,784,293 | B1 * | 8/2004 | Wu | C07D 239/22 548/312.7 |
| 8,563,565 | B2 | 10/2013 | Norimine et al. | |
| 9,186,371 | B2 | 11/2015 | Taniguchi et al. | |
| 10,919,882 | B2 | 2/2021 | Al-Abed et al. | |
| 11,414,405 | B2 | 8/2022 | Al-Abed et al. | |
| 11,440,881 | B2 | 9/2022 | Al-Abed et al. | |
| 11,471,507 | B2 | 10/2022 | Al-Abed et al. | |
| 11,471,508 | B2 | 10/2022 | Al-Abed et al. | |
| 11,524,048 | B2 | 12/2022 | Al-Abed | |
| 2006/0281686 | A1 | 12/2006 | Lopez Areiza et al. | |
| 2011/0086836 | A1 | 4/2011 | Soeberdt et al. | |
| 2018/0344808 | A1 | 12/2018 | Tracey et al. | |
| 2019/0055283 | A1 | 2/2019 | Ekici et al. | |
| 2020/0354418 | A1 | 11/2020 | Al-Abed | |
| 2022/0306577 | A1 | 9/2022 | Al-Abed et al. | |
| 2022/0372022 | A1 | 11/2022 | Al-Abed et al. | |

FOREIGN PATENT DOCUMENTS

| | | | | |
|---|---|---|---|---|
| WO | WO-0140515 | A1 * | 6/2001 | ............ C07H 19/04 |
| WO | WO 2004/050689 | A2 | 6/2004 | |
| WO | WO 2004/050689 | A3 | 6/2004 | |
| WO | WO 2016/094899 | A2 | 6/2016 | |
| WO | WO 2020/227594 | A1 | 11/2020 | |

OTHER PUBLICATIONS

Andre et al., Tetrahedron Letters, vol. 37, No. 2, pp. 183-186, 1996 (Year: 1996).*
Triphosgene Product Data Sheet, Aldrich Chemical Company, 2 pages, 1996 (Year: 1996).*
Scientific Update 2014 regarding Deprotection when using Phthalimide, 2 pages, obtained online Aug. 28, 2021 from https://archive.is/20141203032450/http://scientificupdate.co.uk/process-chemistry-information/item/deprotection-removal-of-amine-protecting-groups-phthalimide-and-dimethylaminosulphonyl.htm (Year: 2014).*
Verma et al., Hindawi Publishing Corporation, Journal of Chemistry, vol. 2013, Article ID 329412, 12 pages (Year: 2013).*
Boeglin and Lubell, J. Comb. Chem., 7, 864-878 (2005) (Year: 2005).*
The Chemistry of Benzotriazole Derivatives, Monbaliu, Ed., Topic in Heterocyclic Chemistry, Springer, 2016, cover page to p. 2, p. 69 and pp. 95-142 provided (Year: 2016).*
Mcarthur et al., Syn. Commns., 13:5, 393-401 (1983) (Year: 1983).*
Sigma-Aldrich Amino Acids Reference Chart, 2014, downloaded from the internet Aug. 4, 2014 (Year: 2014).*
Suppo et al., Org. Synth. 2015, 92, 296-308 (Year: 2015).*
Ollivier et al., Bioconjugate Chem., 2009, 20, 1397-1403 (Year: 2009).*
Abbas et al., Tetrahedron Letters, 50, 2009, 4158-4160 (Year: 2009).*
Che and Marshall, Biopolymers, 2006, 81, 392-406 (Year: 2006).*
Chingle et al., Acc. Chem. Res. 2017, 50, 1541-1556 (Year: 2017).*
Zorc et al., Croat. Chem. Acta 85 (4) (2012) 595-602 (Year: 2012).*
International Search Report issued on Sep. 2, 2020, from corresponding International Application No. PCT/US20/31998.
Written Opinion of the International Searching Authority issued on Sep. 2, 2020, from corresponding International Application No. PCT/US20/31998.
PubChem CID-136595533 "(2,5-Dioxopyrrol-1-yl) N-(2,5-dihydroxypyrrol-1-yl)-N-(1,3-dioxoisoindol-2-yl)carbamate" Created on Jan. 4, 2019.
PubChem CID-132255576 "(2S)-2-(Imidazole-1-carbonylamino)pentanedioic acid" Created on Jan. 29, 2018.
International Search Report issued on Jul. 31, 2020, from corresponding International Application No. PCT/US20/32025.
Written Opinion of the International Searching Authority issued on Jul. 31, 2020, from corresponding International Application No. PCT/US20/32025.
Yang et al. "MD-2 is required for disulfide HMGB1-dependent TLR4 signaling" The Journal of Experimental Medicine; Published on Jan. 5, 2015; vol. 212; p. 5-14.
Sun et al. "Folic acid derived-P5779 mimetics regulate DAMP-mediated inflammation through disruption of HMGB1:TLR4:MD-2 axes" PLOS ONE; Published on Feb. 15, 2018; vol. 13; p. 1-14.

(Continued)

*Primary Examiner* — Joseph Fischer
(74) *Attorney, Agent, or Firm* — DAVIDSON KAPPEL LLC

(57) ABSTRACT

Compounds for use in synthesis of peptidomimetic agents; synthesis of peptidomimetic agents; peptidomimetic diagnostic and therapeutic agents; and uses of the compounds and peptidomimetic agents in drug discovery, diagnosis, prevention and treatment of diseases are described.

15 Claims, 13 Drawing Sheets

(56) References Cited

OTHER PUBLICATIONS

International Search Report issued on Sep. 10, 2020, from corresponding International Application No. PCT/US20/31992.
Written Opinion of the International Searching Authority issued on Sep. 10, 2020, from corresponding International Application No. PCT/US20/31992.
PubChem CID-519335 "Methanethioic S-acid" Created on Mar. 27, 2005.
Heffeter et al. "Anticancer Thiosemicarbazones: Chemical Properties, Interaction with Iron Metabolism, and Resistance Development" Antioxidants & Redox Signaling; vol. 30, No. 8, 2019.
International Search Report issued on Sep. 16, 2020, from corresponding International Application No. PCT/US20/31988.
Written Opinion of the International Searching Authority issued on Sep. 16, 2020, from corresponding International Application No. PCT/US20/31988.
PubChem CID-67548889 "Methyl (2S)-1-(imidazole-1-carbonyl)pyrrolidine-2-carboxylate" Created on Nov. 30, 2012.
PubChem CID-1089188 "(2s)-1-(1-Imidazolylcarbonyl)pyrrolidine-2-carboxylic acid benzyl ester" Created on Oct. 26, 2006.
Abo-Dya, N.E., Biswas, S., Basak, A., Avan, I., Alamry, K.A., and Katritzky, A.R., Benzotriazole-Mediated Synthesis of Aza-peptides: En Route to an Aza-Leuenkephalin Analogue. The Journal of Organic Chemistry 78, 3541-3552 (2013).
Avan, I., Hall, C.D., and Katritzky, A.R., Peptidomimetics via modifications of amino acids and peptide bonds. Chemical Society Reviews 43, 3575-3594 (2014).
Joachim Gante, "Azapeptides", Synthesis, Georg Thieme Verlag, Stuttgart, DE, No. 6, pp. 405-413, Jun. 1, 1989.
Caroline Proulx, et al., "Azapeptides and their therapeutic potential", Future Medical Chemistry, vol. 3, No. 9, pp. 1139-1164, Jul. 1, 2011.
Noam S. Freeman, et al., "Microwave-Assited Solid-Phase Azapeptide Synthesis: Aza Scan of a PKB/Akt Inhibitor Using Aza-arginine and Aza-proline Precursors", The Journal of Organic Chemistry, vol. 76, No. 9, pp. 3078-3085, May 6, 2011.
David Sabatino, et al., "Exploring Side-Chain Diversity by Submonomer Solid-Phase Aza-Peptide Synthesis", Organic Letters, vol. 11, No. 16, pp. 3650-3653, retrieved on Jul. 16, 2009.
Reda Mhidia, et al. "Selective cleavage of an azaGly peptide bond of copper(II). Long-range effect of histidine residue", Journal of Peptide Science, Jan. 1, 2010.
Reda Mhidia, et al., Synthesis of Peptide-Protein Conjugates Using N-Succinimidyl Carbamate Chemistry, Bioconjugate Chemistry, vol. 21, No. 2, pp. 219-228, Feb. 17, 2010.
Carine B. Bourguet et al., "Solution-phase submonomer diversification of the aza-dipeptide building blocks and their application in aza-peptide and aza-DKP synthesis", Journal of Peptide Science, vol. 16, No. 6, Jun. 1, 2010, pp. 284-296.
Cécile Abbas et al., "Original and efficient synthesis of 2:1-[α/aza]-oligomer precursors", Tetrahedron Letters, vol. 50, No. 28, pp. 4158-4160, Jul. 15, 2009.

* cited by examiner

Individual plasma concentrations of K883 after intravenous administration at 1mg/kg in male Sprague-dawley rats k883 reduced APAP-induced pro-inflammatory cytokines and serum live enzymes k883 reduced APAP-induced survival in mice

*:P<0.05 vs. control group

Endomorphin-2

K763

Stability of EM2 and K763 in mice serum

Pharmacokinetics (PK) of K763 at 60min in mice (IP) with Acetonitrile extraction

PEPTIDOMIMETIC AGENTS, SYNTHESIS AND USES THEREOF

This application claims the benefit of U.S. Provisional Application No. 62/845,611, filed on May 9, 2019, hereby incorporated by reference.

FIELD OF THE INVENTION

The present invention is directed to compounds or synthons for use in synthesis of peptidomimetic agents; peptidomimetic agents; synthesis of peptidomimetic agents; and uses of these synthons and peptidomimetic agents in drug discovery, diagnosis, prevention and treatment of diseases.

BACKGROUND OF THE INVENTION

The in vitro and in vivo stability, in vitro and in vivo half-lives and efficacy of peptides are limited, e.g., by the rate of hydrolysis and enzymatic degradation of the peptides. As the result of the rapid hydrolysis and enzymatic degradation, a number of peptides have a half-life that is too short to be used in drug discovery, diagnosis, prevention and treatment of diseases. For example, the in vivo half-life of bradykinin is less than 1 minute, and the the in vivo half-life of tetramer peptide FSSE is less than 5 minutes.

In addition, as the result of the rapid hydrolysis and enzymatic degradation, a number of peptides are not stable enough to be used in drug discovery, diagnosis, prevention and treatment of diseases. For example, the amount of endomorphin-2 (e.g., AUC (O.D.254)) in mouse serum at 2 hours after endomorphin-2 was placed in mouse serum is about 95% less than the amount of endomorphin-2 originally placed in the mouse serum. Similarly, the amount of bradykinin (e.g., AUC (O.D.220)) in mouse serum at 3 hours after bradykinin was placed in mouse serum is about 97% less than the original amount bradykinin placed in the mouse serum.

Moreover, as the result of the rapid hydrolysis and enzymatic degradation, a number of peptides are not orally bioavailable or have an oral bioavailability that is insufficient for formulation into an oral dosage form.

There is a need for analogues of peptides that are more stable to hydrolysis and enzymatic degradation and/or are more active than the original peptides.

There is also a need for building blocks or synthons for the synthesis of analogues of peptides and methods of synthesizing analogues of peptides that are more stable to hydrolysis and enzymatic degradation and/or more active than the original peptides.

SUMMARY OF THE INVENTION

The present invention provides building blocks or synthons for synthesis of analogues of peptides ("peptidomimetic agents"). Peptidomimetic agents assembled from these building blocks or synthons are more resistant to hydrolysis and enzymatic degradation than the original peptides. As compared to the original peptides, the peptidomimetic agents contain one or more nitrogen(s) instead of one or more α-carbon(s) of the original peptides, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide). The replacement of one or more α-carbon(s)

with one or more nitrogen(s) results, e.g., in an improved stability of the peptidomimetic agent to hydrolysis and enzymatic degradation, as compared to the original peptide. The use of the building blocks disclosed herein may allow, e.g., for synthesis of peptidomimetic agents that have longer in vitro and in vivo half-lifes than the original peptides, and correspondingly have utility in treating humans for a wide variety of diseases and conditions; and/or for synthesis of peptidomimetic agents at a reduced cost and/or increased yields, as compared to conventional syntheses which do not use these building blocks. The synthesis of peptidomimetic agents using the building blocks disclosed herein, the peptidomimetic agents and uses of the peptidomimetic agents in drug discovery, diagnosis, prevention and treatment of diseases are within the scope of the present invention.

It is an object of the invention to provide compounds or synthons for use in synthesis of peptidomimetic agents.

It is an additional object of the invention to provide peptidomimetic agents for use in drug discovery, diagnosis, prevention and treatment of diseases.

It is yet an additional object of the invention to provide peptidomimetic diagnostic and therapeutic agents.

It is a further object of the invention to diagnose, prevent and treat diseases with peptidomimetic agents.

In connection with the above objects and others, the invention is directed in part to the compounds of Formula (IA):

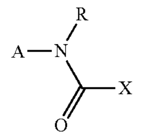

(IA)

wherein A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl, or R and $R_1$ are connected and together form a side chain radical of proline;

X is imidazolyl or benzotriazolyl; and

R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, and glutamine. Imidazolyl and benzotriazolyl may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., $—CF_3$, $—CHF_2$, $—CH_2F$, $—CBr_3$, $—CHBr_2$, $—CH_2Br$, $—CCl_3$, $—CHCl_2$, $—CH_2Cl$), $—NH_2$, or $NH_3$. In certain embodiments, the imidazolyl and benzotriazolyl are substituted with $—CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, threonine, tyrosine, isoleucine (including, R-isoleucine, S-isoleucine and RS-isoleucine), arginine, asparagine, and glutamine. Compounds of Formula (IA) could be used in drug discovery, diagnosis, prevention and treatment of diseases, or as building blocks for synthesis of peptidomimetic agents, e.g., for use in drug discovery, diagnosis, prevention and treatment of diseases.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is imidazolyl or benzotriazolyl; and

R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, and glutamine. Imidazolyl and benzotriazolyl may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or $NH_3$. In certain embodiments, the imidazolyl and benzotriazolyl are substituted with —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, threonine, tyrosine, isoleucine (including, R-isoleucine, S-isoleucine and RS-isoleucine), arginine, asparagine, and glutamine.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is imidazolyl substituted with —$CF_3$, —$CHF_2$, —$CH_2F$, —$CBr_3$, —$CHBr_2$, —$CH_2Br$, —$CCl_3$, —$CHCl_2$, —$CH_2Cl$; and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, threonine, tyrosine, isoleucine (including, R-isoleucine, S-isoleucine and RS-isoleucine), arginine, asparagine, and glutamine.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is benzotriazolyl substituted with —$CF_3$, —$CHF_2$, —$CH_2F$, —$CBr_3$, —$CHBr_2$, —$CH_2Br$, —$CCl_3$, —$CHCl_2$, or —$CH_2Cl$; and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (IA) is a compound in which X is imidazolyl or benzotriazolyl, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, a compound of Formula (IA) is a compound in which X is imidazolyl substituted with —$CF_3$, —$CHF_2$, —$CH_2F$, —$CBr_3$, —$CHBr_2$, —$CH_2Br$, —$CCl_3$, —$CHC_2$, or —$CH_2Cl$, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, a compound of Formula (IA) is a compound in which X is benzotriazolyl substituted with —$CF_3$, —$CHF_2$, —$CH_2F$, —$CBr_3$, —$CHBr_2$, —$CH_2Br$, —$CCl_3$, —$CHCl_2$, or —$CH_2Cl$, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurometyl, etc.) or a protecting group (e.g., Phth, Boc, Fmoc, Ddz, etc.).

In certain embodiments, compound of Formula (IA) is a compound, in which $R_1$ and R are $CH_2CH_2CH_2$, and $R_2$ is tert-butoxycarbonyl, 9-fluorenylmethoxycarbonyl, 2-(3,5-dimethoxyphenyl)propan-2-yloxycarbonyl, and X is is imidazolyl or benzotriazolyl.

In certain embodiments, compound of Formula (IA) is a compound, in which $R_1$ and R are $CH_2CH_2CH_2$, and $R_2$ is tert-butoxycarbonyl, 9-fluorenylmethoxycarbonyl, 2-(3,5-dimethoxyphenyl)propan-2-yloxycarbonyl, and X is is imidazolyl or benzotriazolyl.

The invention is also directed in part to compounds of Formula (IA):

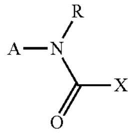

(IA)

wherein

X is imidazolyl or benzotriazolyl, and wherein (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl; and R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, cysteine, serine, threonine, and glutamine.

The invention is also directed in part to compounds of Formula (IA):

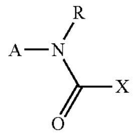

(IA)

wherein

X is imidazolyl or benzotriazolyl, and wherein (i) A and R are connected and form a side chain of proline, or (ii) A is a protecting group selected from the group consisting of phthalimidyl, tert-butoxycarbonyl, 9-fluorenylmethoxycarbonyl, 2-(3,5-dimethoxyphenyl)propan-2-yloxycarbonyl; and R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, cysteine, serine, threonine, and glutamine.

The invention is also directed in part to compounds of Formula (IB):

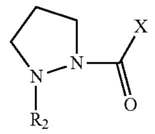

(IB)

wherein $R_2$ is a protecting group (e.g., tert-butoxycarbonyl, 9-fluorenylmethoxycarbonyl, 2-(3,5-dimethoxyphenyl)propan-2-yloxycarbonyl), and X is is imidazolyl or benzotriazolyl. Compounds of Formula (IB) could be used in drug discovery, diagnosis, prevention and treatment of diseases, or as building blocks for synthesis of peptidomimetic agents, e.g., for use in drug discovery, diagnosis, prevention and treatment of diseases.

In certain embodiments, the invention is directed to Phth-protected carbamoyl aza-imidazole derivatives and Phth-protected carbamoyl aza-benzotriazole derivatives of unnatural amino acids, including, e.g., aza-imidazole derivatives and Phth-protected carbamoyl aza-benzotriazole derivatives of β-amino acids (e.g., L-β-homotyrosine, β-alanine, L-β-homoasparagine, L-β-homoalanine, L-β-homophenylalanine, L-β-homoproline, L-β-holysine, L-β-homorarginine, L-β-proline, etc.), aliphatic amino acids (e.g., 6-aminohexanoic acid, 2-amino-3-methoxybutanoic acid, 1-aminocyclopentane-1-carboxylic acid, 2-(aminooxy)acetic acid, 6-aminohaxanoic acid, 2-[2-(amino)-ethoxy]-ethoxy}acetic acid), β-cyclohexyl-L-alanine, 6-aminohexanoic acid, L-α,β-diaminopropionic acid, L-propargylglycinel, L-α,β-diaminopropionic acid, α-aminoisobutyric acid, 3-(2-pyridyl)-L-alanine, β-(3-pyridyl)-L-alanine, β-cyclopropyl-L-alanine, β-t-butyl-L-alanine, (2,4-dinitrophenyl))-L-α,β-diaminopropionic acid, (allyloxycarbonyl)-L-α,β-diaminopropionic acid, D-α,β-diaminopropionic acid, L-α,β-diaminopropionic acid, (N-γ-1-(4,4-dimethyl-2,6-dioxocyclohex-1-ylidene)ethyl)-L-α,γ-diaminobutyric acid, (N-γ-4-methyltrityl)-L-α,γ-diaminobutyric acid, L-α,γ-diaminobutyric acid, 4-fluoro-L-phenylglycine, 5,5,5-trifluoro-DL-leucine, epsilon-aminohexanoic-OH, L-α-t-butylglycine, L-2-amino-3-(dimethylamino)propionic acid, L-2-aminocaproic acid, L-allylglycine, lysine azide, (Nδ-4-methyltrityl)-L-ornithine, Arg(Me)(Pbf)-OH, dimethyl-L-arginine (symmetrical and unsymmetrical), L-2-amino-3-guanidinopropionic acid, L-citrulline, F-acetyl-L-lysine, Lys(ivDde)-OH, Lys(Me)2-OH·HCl, Lys(Me3)-OHchloride, α-methyl-DL-glutamic acid, γ-carboxy-L-glutamic acid γ,γ-di-t-butyl ester, (N-γ-ethyl)-L-glutamine, 2,6-diaminopimelic acid, Glu(OAll)-OH, L-cysteic acid, α-methyl-DL-methionine, DL-buthionine, L-cysteic acid, L-selenomethionine, S-[2-(4-pyridyl) ethyl]-L-cysteine, S-[2-(4-pyridyl)ethyl]-L-cysteine, S-diphenylmethyl-L-cysteine, S-trityl-L-homocysteine, S-trityl-L-penicillamine, (Se-p-methoxybenzyl)-L-selenocysteine, β-hydroxyphenylalanine, 2-cyano-L-phenylalanine, L-thyroxine, O-methyl-L-tyrosine, β-methyl-DL-phenylalanine, 2-cyano-L-phenylalanine, L-thyroxine, O-methyl-L-tyrosine, β-methyl-DL-phenylalanine, 2-cyano-L-phenylalanine, 3,4-dichloro-L-phenylalanine, 3,4-difluoro-L-phenylalanine, 3,4-dihydroxy-L-phenylalanine, 3,4-dihydroxy-phenylalanine, 3-amino-L-tyrosine, 3-chloro-L-tyrosine, 3-fluoro-DL-tyrosine, 3-nitro-L-tyrosine, 4-amino-L-phenylalanine, 4-aminomethyl-L-phenylalanine, 4-(phosphonomethyl)-phenylalanine, 4-benzoyl-D-phenylalanine, 4-bis(2-chloroethyl)amino-L-phenylalanine, 4-cyano-L-phenylalanine, 4-fluoro-L-phenylalanine, 4-iodo-L-phenylalanine, DL-m-tyrosine, 2,6-dimethyl-tyrosine, L-homophenylalanine, O-methyl-L-tyrosine, Phe(4-guanidino)-OH, O-benzyl-L-phosphotyrosine, (2S,3R)-3-phenylpyrrolidine-2-carboxylic acid, (2S,4S)-4-phenyl-pyrrolidine-2-carboxylic acid, (2S,3aS,7aS)-Octahydro-1H-indole-2-carboxylic acid, (2S,3R)-3-phenylpyrrolidine-2-carboxylic acid, (2S,4R)-(−)-4-t-butoxypyrrolidine-2-carboxylic acid, trans-4-Fluoro-L-proline, (3S,4S)-4-amino-3-hydroxy-6-methylheptanoic acid, 4-amino-3-hydroxybutanoic acid, L-α-methylserine, (2S,3S)-2-amino-3-methoxybutanoic acid, Thr(β-D-GlcNAc(Ac)3)-OH, O-benzyl-L-phosphoserine, O-benzyl-D-phosphothreonine, O-benzyl-L-phosphothreonine, 4-methyl-DL-tryptophan, 6-fluoro-DL-tryptophan, 6-methyl-DL-tryptophan, DL-7-azatryptophan, (R)-7-Azatryptophan, 5-benzyloxy-DL-tryptophan, 5-bromo-DL-tryptophan, 5-chloro-DL-tryptophan, 5-fluoro-DL-tryptophan, 5-hydroxy-L-tryptophan, 5-methoxy-L-tryptophan, 6-chloro-L-tryptophan, 6-methyl-DL-tryptophan, 7-methyl-DL-tryptophan, DL-7-azatryptophan, 5-azido-pentanoic acid, 2-Amino-N-(3-azidopropyl)-3-mercaptopropionamide, 2-Amino-N-(3-azidopropyl)-3-mercaptopropionamide, Azidohomoalanine, L-propargylglycine·DCHA, azidolysine, p-azidophenylalanine, Azidohomoalanine, D-propargylglycine, L-propargylglycine, azidolysine, Tris[(1-benzyl-1H-1,2,3-triazol-4-yl) methyl] amine, 2-(7'-octenyl) alanine, 2-(4'-pentenyl) alanine, 2-(4'-pentenyl)glycine, 2-(7'-octenyl) alanine, [5-((2-Aminoethyl)amino)naphthalene-1-sulfonic acid], L-glutamic acid-7-[2-(1-sulfonyl-5-naphthyl)-aminoethylamide], N-ε-(5-carboxyfluorescein)-L-lysine, N-ε-(5/6-carboxyfluorescein)-L-lysine, N-ε-(4,4-dimethylazobenzene-4'carbonyl)-L-lysine, Nε-2,4-dinitrophenyl-L-lysine, N-ε-[(7-methoxycoumarin-4-yl)-acetyl-L-lysine, glycosylated amino acids (e.g., Ser(β-D-GlcNAc(Ac)3)-OH, Thr(β-D-GlcNAc(Ac)3)-OH), 3-azabicyclo[3.1.0]hexane-2-carboxylic acid, 4-amino-(1-carboxymethyl) piperidine, 4-phenylpiperidine-4-carboxylic acid, Nα-methyl-N-im-trityl-L-histidine, Nα-methyl-O-benzyl-L-serine dicyclohexylammonium salt, Nalpha-methyl-Nomega-(4-methoxy-2,3,6-trimethylbenzenesulfonyl)-L-arginine, Nalpha-methyl-L-leucine, Nalpha-methyl-L-norvaline, Nalpha-methyl-L-phenylalanine, Nalpha-methyl-N-im-trityl-L-histidine, Nalpha-methyl-O-t-butyl-L-serine, Nalpha-methylglycine, 21-amino-4,7,10,13,16,19-hexaoxaheneicosanoic acid, {2-[2-(amino)-ethoxy]-ethoxy}acetic acid, 6-Amino-4-oxa-hexanoic acid, 5-Amino-3-Oxapentamoic Acid, NH-(PEG) 10-CH2CH2COOH, NH-(PEG)12-CH2CH2COOH, 9-Amino-4; 7-Dioxanonanoic acid, 9-Amino-4; 7-Dioxanonanoic acid, 12-amino-4,7,10-trioxadodecanoic acid, 15-amino-4,7,10,13-tetraoxapentadecacanoic acid, 18-amino-4,7,10,13,16-pentaoxaoctadecanoic acid, 21-amino-4,7,10,13,16,19-hexaoxaheneicosanoic acid, NH-(PEG)8-CH2CH2COOH, 11-amino-3,6,9-trioxaundecanoic acid, N-(Fmoc-8-amino-3,6-dioxa-octyl)succinamic acid, —N-ε-acetyl-L-lysine, L-citrulline, Arg(Me)(Pbf)-OH, Nω,ω-dimethyl-L-arginine (assymetrical and symmetrical), Lys(Me)2-OH chloride, N-ε,ε-t-methyl-L-lysine, Lys(Me3)-OH chloride, O-benzyl-L-phosphoserine, O-benzyl-D-phosphothreonine, O-benzyl-L-phosphothreonine, O-benzyl-L-phosphotyrosine.

The invention is also directed to compounds of Formula (II):

(II)

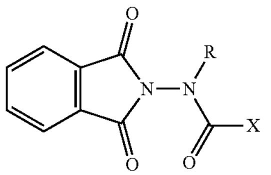

wherein X is imidazolyl or benzotriazolyl; and

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., N-Phth, N-Boc, N-Fmoc, N-Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. Compounds of Formula (II) could be used in drug discovery, diagnosis, prevention and treatment of diseases, or as building blocks for synthesis of peptidomimetic agents, e.g., for use in drug discovery, diagnosis, prevention and treatment of diseases.

The invention is further directed to compounds of Formula (III):

(III)

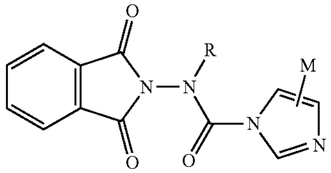

wherein R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, and glutamine; and M is an optional substituent selected from the group consisting of a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or $NH_3$. In certain embodiments, M is —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurometyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, threonine, tyrosine, isoleucine (including, R-isoleucine, S-isoleucine and RS-isoleucine), arginine, asparagine, and glutamine. Compounds of Formula (III) could be used in drug discovery, diagnosis, prevention and treatment of diseases, or as building blocks for synthesis of peptidomimetic agents, e.g., for use in drug discovery, diagnosis, prevention and treatment of diseases.

The invention is also directed in part to the synthesis of compounds of Formula (IA), (IB), (II) and (III), the synthesis comprising reacting a Phth-protected alkylhydrazine derivative with 1,1'-carbonyldiimidazole (CDI) or 1'-carbonyl-bis(3-ethylimidazolium) triflate (CBEIT).

The invention is further directed to compounds of Formula (IV):

(IV)

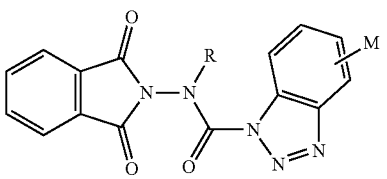

wherein R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, and glutamine; and M is an optional substituent selected from the group consisting of a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or $NH_3$. In certain embodiments, M is —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurometyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. Compounds of Formula (IV) could be used in drug discovery, diagnosis, prevention and treatment of diseases, or as building blocks for synthesis of peptidomimetic agents, e.g., for use in drug discovery, diagnosis, prevention and treatment of diseases.

The invention is also directed in part to the synthesis of the compounds of Formula (IV), the synthesis comprising reacting an acid chloride with benzotriazole:

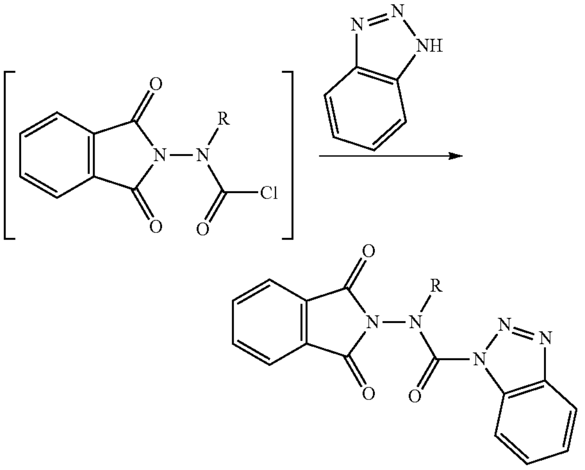

The invention is further directed to the use of compounds of Formulas (I)-(IV) in the preparation of compounds of Formula (V):

(V)

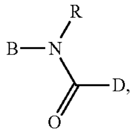

wherein

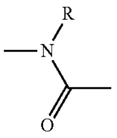

is (i) at the N-terminus and/or the C-terminus and/or (ii) adjacent to the N-terminus and/or the C-terminus of the compound of Formula (V), wherein B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, threonine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, compounds of Formula (V) are peptidomimetic analogues of compounds of Formula (VI):

(VI)

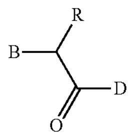

or a pharmaceutically acceptable salt thereof; wherein

B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and compounds of Formula (V) are more resistant to hydrolysis and/or enzymatic degradation than compounds of Formula (VI). In some of these embodiments, compounds of Formula (V) are more potent than compounds of Formula (VI), e.g., due to a better fit into a biological receptor.

The invention is further directed to the use of compounds of Formulas (I)-(IV) in the preparation of compounds of Formula (V):

(V)

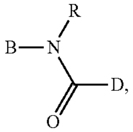

wherein

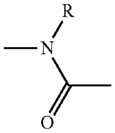

is at or adjacent to a cleavage and/or a hydrolysis site of the compound of Formula (V), wherein B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurومethyl, etc.) or a protecting group (e.g., Phth, Boc, Fmoc, Ddz, etc.). In certain embodiments, compounds of Formula (V) are peptidomimetic analogues of compounds of Formula (VI):

(VI)

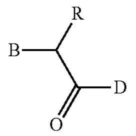

or a pharmaceutically acceptable salt thereof; wherein

- B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;
- D is selected from the group consisting of —$OR_4$, —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;
- $R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);
- R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and compounds (V) are more resistant to hydrolysis and/or enzymatic degradation than compounds of Formula (VI). In some of these embodiments, compounds of Formula (V) are more potent than compounds of Formula (VI), e.g., due to a better fit into a biological receptor.

In certain embodiments, B of compounds of Formula (V) and (VI) is each independently selected from the group consisting of hydrogen, —$NH_2$, —$NNH_2$, —$CONH_2$, —$COOR_3$, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

- D of compounds of Formula (V) and (VI) is each independently selected from the group consisting of —$OR_4$, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;
- $R_3$ and $R_4$ of compounds of Formula (V) and (VI) is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and
- R of compounds of Formula (V) and (VI) is each independently selected from the group consisting of side chain radicals of aspartic acid, phenylalanine, alanine, histidine, glutamic acid, tryptophan, valine, leucine, lysine, serine, threoinine, methionine, tyrosine, isoleucine (including, R-isoleucine, S-isoleucine and RS-isoleucine), arginine, glycine, asparagine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

The invention is further directed to the use of compounds of Formulas (I)-(IV) in the preparation of compounds of Formula (V):

(V)

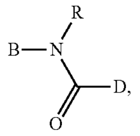

wherein

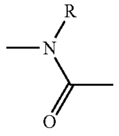

is adjacent to the N-terminus and/or the C-terminus of the compound of Formula (V), wherein

- B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;
- D is selected from the group consisting of —$OR_4$, —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;
- $R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, compounds of Formula (V) are peptidomimetic analogues of compounds of Formula (VI):

(VI)

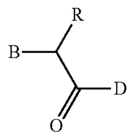

or a pharmaceutically acceptable salt thereof; wherein

B is selected from the group consisting of hydrogen, —$NH_2$, —$NNH_2$, —$CONH_2$, —$COOR_3$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)2$, —$CONH_2$, —COH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COGH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and compounds (V) are more resistant to hydrolysis and/or enzymatic degradation than compounds of Formula (VI). In some of these embodiments, compounds of Formula (V) are more potent than compounds of Formula (VI), e.g., due to a better fit into a biological receptor.

Compounds of Formula (V) could be used, e.g., in drug discovery, diagnosis, prevention and treatment of diseases.

The invention is further directed to the use of compounds of Formulas (I)-(IV) in the preparation of compounds of Formula (VII):

(VII)

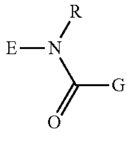

or a pharmaceutically acceptable salt thereof, wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;

G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;

R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine, wherein

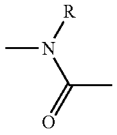

is at or adjacent to a cleavage and/or a hydrolysis site and/or at the N-terminus and/or the C-terminus of the compound of Formula (VII). The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, R is methyl serine, methyl threonine or methyl cysteine. Compounds of Formula (VII) are more resistant to hydrolysis and/or enzymatic degradation than compounds that contain

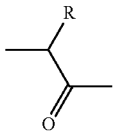

instead of

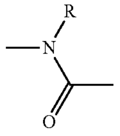

but are otherwise identical to the compounds of Formula (VII).

The invention is further directed to the use of compounds of Formulas (I)-(IV) in the preparation of compounds of Formula (VII):

(VII)

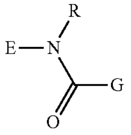

or a pharmaceutically acceptable salt thereof, wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;

G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;

R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine, wherein

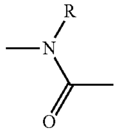

is adjacent the N-terminus and/or the C-terminus of the compound of Formula (VII). The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, R is methyl serine, methyl threonine or methyl cysteine. Compounds of Formula (VII) are more resistant to hydrolysis and/or enzymatic degradation than compounds that contain

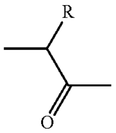

instead of

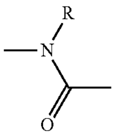

but are otherwise identical to the compounds of Formula (VII).

The invention is further directed to the use of compounds of Formulas (I)-(IV) in the preparation of compounds of Formula (VII):

(VII)

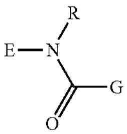

or a pharmaceutically acceptable salt thereof, wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;

G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;

R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine arginine, glycine, asparagine, serine, and glutamine, wherein

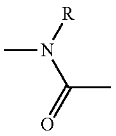

is adjacent the N-terminus of the compound of Formula (VII). The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, R is methyl serine, methyl threonine or methyl cysteine. Compounds of Formula (VII) are more resistant to hydrolysis and/or enzymatic degradation than compounds that contain

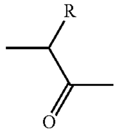

instead of

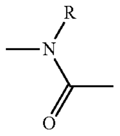

but are otherwise identical to the compounds of Formula (VII).

The invention is further directed to the use of compounds of Formulas (I)-(IV) in the preparation of compounds of Formula (VII):

(VII)

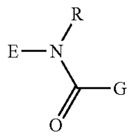

or a pharmaceutically acceptable salt thereof,

- wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;
- G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;
- R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine, wherein

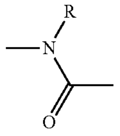

is adjacent the C-terminus of the compound of Formula (VII). The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, R is methyl serine, methyl threonine or methyl cysteine. Compounds of Formula (VII) are more resistant to hydrolysis and/or enzymatic degradation than compounds that contain

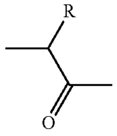

instead of

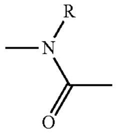

but are otherwise identical to the compounds of Formula (VII).

The invention is further directed to the use of compounds of Formulas (I)-(IV) in the preparation of compounds of Formula (VII):

(VII)

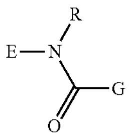

or a pharmaceutically acceptable salt thereof, wherein

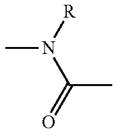

is at or adjacent to a cleavage and/or a hydrolysis site and/or at the N-terminus and/or the C-terminus of the compound of Formula (VII),

- wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;
- G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;
- R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, R is methyl serine, methyl threonine or methyl cysteine. In certain embodiments, compounds of Formula (VII) are peptidomimetic analogues of compounds of Formula (VIII)

(VIII)

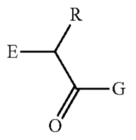

or a pharmaceutically acceptable salt thereof, wherein E is hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60 mer aza peptide, or a 2 to 60-mer azatide;

G is —OH, —$NH_2$, —$NNH_2$, —$NHCOCH_3$, —$NHCH_3$, —$N(CH_3)2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, or a 2 to 60-mer azatide;

R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine;

wherein the side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.);

wherein compounds of Formula (VII) are more resistant to hydrolysis and/or enzymatic degradation than compounds of Formula (VIII). In some of these embodiments, compounds of Formula (VII) are more potent than compounds of Formula (VIII), e.g., due to a better fit into a biological receptor. In some embodiments, R of each compound is selected from a group consisting of methyl serine, methyl threonine and methyl cysteine.

The invention is also directed to compounds of Formula (V) and compounds of Formula (VII). Compounds of Formula (V) and (VII) could be used, e.g., in drug discovery, diagnosis, prevention and treatment of diseases.

The replacement of

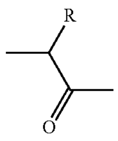

at the N-terminus and/or the C-terminus and/or at or adjacent to a cleavage and/or a hydrolysis site of compounds of Formula (VI) and Formula (VIII) with

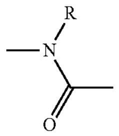

results in a loss of asymmetry associated with

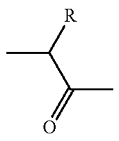

in compounds of Formula (VI) and Formula (VIII). Because of the change in configuration, compounds of Formula (V) and Formula (VII) may be therapeutically effective, whereas compounds of Formula (VI) and Formula (VIII) are not, and/or compounds of Formula (V) and Formula (VII) may have a greater bioavailability (e.g., oral and/or transdermal and/or intranasal) than compounds of Formula (VI) and compounds of Formula (VIII), and/or compounds of Formula (V) and Formula (VII) may have an in vivo half-life greater than (e.g., more than twice, three times, five times or ten times) the in vivo half-life of the compounds of Formula (VI) and (VIII), while maintaining therapeutic efficacy, and/or compounds of Formula (V) and Formula (VII) may have a longer duration of therapeutic activity than compounds of Formula (VI) and Formula (VIII), and/or compounds of Formula (V) and Formula (VII) may have a greater affinity to a biological receptor than compounds of Formula (VI) and Formula (VIII), and/or compounds of Formula (V) and Formula (VII) may act as agonists at a biological receptor, whereas compounds of Formula (VI) and Formula (VIII) act as antagonists of the biological receptor, and/or compounds of Formula (V) and Formula (VII) may act as antagonists at the biological receptor, whereas compounds of Formula (VI) and Formula (VIII) act as agonists at the biological receptor.

Therefore, in certain embodiments, the invention is directed to a compound of Formula (V), which is a peptidomimetic analogue of a compound of Formula (VI) and is more resistant to enzymatic degradation (e.g., peptidase degradation) than the compound of Formula (VI). In some of these embodiments, the compound of Formula (V) is at least 1.5, 2, 3, 4 or 5 more resistant to enzymatic degradation than the compound of Formula (VI). In certain embodiments, the compounds of Formula (V) is about 10, 12, 14, 16, 18, or 20 times more resistant to enzymatic degradation than the compound of Formula (VI).

In certain embodiments, the invention is directed to a compound of Formula (V), which is a peptidomimetic analogue of a compound of Formula (VI) and has a longer in vitro and/or in vivo half-life than the compound of Formula (VI). In some of these embodiments the in vitro and/or in vivo half-life of the compound of Formula (IX) is at least 1.5, 2, 3, 4 or 5 times longer than the corresponding half-life of the compound of Formula (VI). In certain embodiments, the compound of Formula (V) has an in vivo half-life greater than (e.g., twice, three times, five times or ten times) of the in vivo half-life of the compound of Formula (VI) and maintains therapeutic efficacy of the compound of Formula (VI).

In certain embodiments, the in vivo half-life of the compound of Formula (V) may, e.g., be from about 1 minute to about 30 days, and the in vivo half-life of the compound of Formula (VI) may, e.g., be from 5 seconds to about 10 days. In certain embodiments, the in vivo half-life of the compound of Formula (V) is from about 1 minute to about 72 hours, and the in vivo half-life of the compound of Formula (VI) is from about 10 seconds to 24 hours.

In certain embodiments, the invention is directed to a compound of Formula (V), which is a peptidomimetic analogue of a compound of Formula (VI) and has a greater biovailability than the compound of Formula (VI). The bio-availability (e.g., oral) of compound of Formula (V) may, e.g., be at least 10, 20, 30, 40, 50, 60, or 70% better than the bio-availabilty of the compound of Formula (VI).

In certain embodiments, the invention is directed to a compound of Formula (V), which is a peptidomimetic analogue of a compound of Formula (VI) and has greater blood brain barrier (BBB) permeability than a compound of Formula (VI). The BBB permeability of compound of Formula (V) may, e.g., be at least 10, 20, 30, 40, 50, 60, or 70% better than the BBB permeability of the compound of Formula (VI).

In certain embodiments, the invention is directed to a compound of Formula (V), which is a peptidomimetic analogue of a compound of Formula (VI) and has a greater therapeutic efficacy than the compound of Formula (VI).

In certain embodiments, the invention is directed to a compound of Formula (V), which is a peptidomimetic analogue of a compound of Formula (VI) and has a longer duration of therapeutic activity than the compound of Formula (VI). In some of these embodiments, the duration of action of the compound of Formula (V) is at least double, triple, or quadriple the duration of action of the compound of Formula (V). In certain embodiments, the duration of action of the compound of Formula (V) is from about 5 minutes to about 24 hours, from about 10 minutes to about 22 hours, from about 15 minutes to about 20 hours, from about 30 minutes to about 20 hours, from about 45 minutes to about 20 hours, from about 1 hour to about 20 hours, from about 2 hours to about 18 hours, from about 2 hours to about 16 hours, from about 2 hours to about 14 hours, from about 2 hours to about 12 hours, from about 2 hours to about 10 hours, from about 3 hours to about 12 hours, from about 4 hours to about 12 hours, from about 4 hours to about 10 hours, or from about 4 hours to about 8 hours.

In certain embodiments, the invention is directed to a compound of Formula (V), which is a peptidomimetic analogue of a compound of Formula (VI) and has a greater affinity for a biological receptor than the compound of Formula (VI). For example, the binding affinity (KD) of the compound of Formula (V) to the biological receptor may, e.g., be from $1\times10^{-12}$ M to $1\times10^{-4}$ M, and is at least 1.5, 2, 3, 4 or 5 times stronger than the affinity of the compound of formula (VI) to the biological receptor. The biological receptor, may e.g., be an ANP receptor, an AVP receptor, a B2 receptor, a BNP receptor, a CCK receptor, a CALC receptor, a CALC receptor and RAMPs, a CRH receptor, a CD 36 receptor, a CD110 receptor, a CXCR4 receptor, an EPO receptor, a FGF receptor, a ET-B receptor, a GCG receptor, a GH receptor, a GNRH receptor, a GnRH R receptor, a GPL-1 receptor, a GPL-2 receptor, a GHS receptor, a GPR54, a Guanylate cyclase-C, a IL2 receptor, a IGF-1 receptor, a PGE2 receptor, a NGF receptor, a NMDA receptor, a NOD protein receptor, a NPY receptor, a MC receptor, a M1 receptor, a NTS1 receptor, a NK receptor, a PTH receptor, a Delta opioid receptor, a Kappa opioid receptor, a Mu opioid receptor, an ORL1 receptor, an OGF receptor, an OT receptor, a PAR receptor, a SCT receptor, a SST receptor, a SST receptor and Dopamine D2 receptor, a TRH receptor, a VPAC receptor, or RAMPs receptor.

In certain embodiments, the invention is directed to a compound of Formula (V), which is a peptidomimetic analogue of a compound of Formula (VI) and binds a biological receptor slower but stronger than the compound of Formula (VI). The compound of Formula (V), preferably, has a better KD affinity than the parent peptide.

In certain embodiments, the invention is directed to a compound of Formula (V), which is a peptidomimetic analogue of a compound of Formula (VI), wherein the compound of Formula (V) is an agonist at a biological receptor and the compound of Formula (VI) is an antagonist at the biological receptor. The biological receptor, may e.g., be an ANP receptor, an AVP receptor, a B2 receptor, a BNP receptor, a CCK receptor, a CALC receptor, a CALC receptor and RAMPs, a CRH receptor, a CD 36 receptor, a CD110 receptor, a CXCR4 receptor, an EPO receptor, a FGF receptor, a ET-B receptor, a GCG receptor, a GH receptor, a GNRH receptor, a GnRH R receptor, a GPL-1 receptor, a GPL-2 receptor, a GHS receptor, a GPR54, a Guanylate cyclase-C, a TL2 receptor, a IGF-1 receptor, a PGE2 receptor, a NGF receptor, a NMDA receptor, a NOD protein receptor, a NPY receptor, a MC receptor, a M1 receptor, a NTS1 receptor, a NK receptor, a PTH receptor, a Delta opioid receptor, a Kappa opioid receptor, a Mu opioid receptor, an ORL1 receptor, an OGF receptor, an OT receptor, a PAR receptor, a SCT receptor, a SST receptor, a SST receptor and Dopamine D2 receptor, a TRH receptor, a VPAC receptor, or RAMPs receptor.

In certain embodiments, the invention is directed to a compound of Formula (V), which is a peptidomimetic analogue of a compound of Formula (VI), wherein the compound of Formula (V) is an antagonist at a biological receptor and the compound of Formula (VI) is an agonist at the biological receptor. The biological receptor may, e.g., be an ANP receptor, an AT receptor, a B-cell activating factor, a B2 receptor, a BB2 receptor, N-Cadherin, calcium channel, a CCRP5 receptor, a CALC receptor and RAMPs, a CD4 receptor, a C5a receptor, a CD29 receptor, a CXCR4 receptor, a GCG receptor, a Erb-3 receptor, a GnRH R, a GP IIb IIIa receptor, an integrin alpha-5/beta-3, an integrin alpha-4/beta-1, an NMDA receptor, a Nicotinic ACH receptor, an OT receptor, a PTH receptor, a SST receptor, a TAC1 receptor, a TAC2 receptor, a TBXA2 receptor, a VEGF receptor, a VE-Cadherin receptor, or a zonulin receptor.

In certain embodiments, the invention is directed to a compound of Formula (V), which is a peptidomimetic analogue of a compound of Formula (VI), wherein the compound of Formula (VI) is not therapeutically effective, and the compound of Formula (V) is therapeutically effective.

The invention is also directed in part to a method of preparing a compound of Formula (V), the method comprising activating a compound of Formula (IA), Formula (IB), Formula (II), Formula (III) or Formula (IV) to form an activated compound of Formula (IA), Formula (IB), Formula (II), Formula (III), or Formula (IV), and coupling the activated compound of Formula (IA), Formula (IB), Formula (II), Formula (III), or Formula (IV) with N-terminal of an amino acid, N-terminal of an aza-mino acid, provided that, if a side chain of the amino acid or aza-amino acid contains a group selected from amino, amide, guanidino N, carboxyl, sulfhydryl, carboxyl, hydroxyl, indole, imidazole phenol, the group is protected with a protecting group selected from tert-butoxycarbonyl, 9-fluorenylmethoxycarbonyl, or 2-(3,5-dimethoxyphenyl)propan-2-yloxycarbonyl, phthalimide, carboxybenzyl, 2,2,4,6,7-pentamethyl-dihydrobenzofuran-5-sulfonyl, trityl or triphenylmethyl, t-butyl ester, t-butyl ether, s-t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester acetamidomethyl, and the like to form a protected compound of Formula (V), and deprotecting the protected compound of Formula (V), e.g., with hydrazine, piperadine, TFA, acetic acid, thioanisole, EDT, anisole, etc., to form the compound of Formula (V).

In certain embodiments, the compound of Formula (IA), Formula (IB), Formula (II), or Formula (III) is phthalimide-protected carbamoyl imidazole and is activated by MeI.

In certain embodiments, the compound of Formula (IA), Formula (IB), Formula (II) or Formula (III) is phthalimide-protected carbamoyl benzotriazole and is activated by DIPEA in acetonitrile.

The invention is also directed in part to a method of preparing a compound of Formula (V), the method comprising coupling a compound of Formula (IA), (IB), (II), (III), or (IV) with an aza-amino acid to form a protected di-azatide, and deprotecting the protected di-azatide, e.g., with hydrazine, TFA, acetic acid, thioanisole, EDT, anisole, a mixture of any of the foregoing, or another de-protecting compound, to form a compound of Formula (VI).

The invention is further directed in part to a solution phase synthesis of the compounds of Formula (V), the solution phase synthesis comprising converting a compound of Formula (IA), I(B), (II), (III), or (IV) to an amide of the compound of Formula (IA), I(B), (II), (III), or (IV), deprotectecting the amide of the compound of Formula (IA), I(B), (II), (III), or (IV), and coupling the deprotected amide of Formula (IA), I(B), (II), (III), or (IV) with an additional compound of Formula (IA), I(B), (II), (III), or (IV), or a protected amino acid, or a protected aza-amino acid to form a protected azapeptide, and deprotecting the protected azapeptide to provide a compound of Formula (V).

The invention is further directed in part to a solid phase synthesis of the compounds of Formula (V), the solid phase synthesis comprising coupling a protected compound of Formula (IA), I(B), (II), (III), or (IV) to a support, deptrotecting the protected compound of Formula (IA), I(B), (II), (III), or (IV), and coupling the deprotected compound of Formula (IA), I(B), (II), (III), or (IV) to an additional protected compound of Formula (IA), I(B), (II), (III), or (IV), an additional protected amino acid, or an additional protected aza-amino acid to form a protected peptide, and deprotecting and cleaving the protected peptide to provide a compound of Formula (V).

The invention is also directed in part to a process of preparing a compound of Formula (V) comprising cleaving a peptide at its N-terminus and/or C-terminus, and coupling the cleaved peptide with a compound of Formula (IA), I(B), (II), (III), or (IV) to form a compound of Formula (V). In certain embodiments, the compound of Formula (IA), I(B), (II), (III), or (IV) is activated prior to the coupling with the cleaved peptide.

The invention is also directed in part to a process of preparing a compound of Formula (V) comprising cleaving a peptide at its cleavage site to form two smaller peptides, replacing the last amino acid of at least one of the smaller peptides with an aza-amino acid to form an azapeptide, and conjugating the azapeptide with the remaining smaller peptide to provide a compound of Formula (V).

The invention is also directed in part to a process of preparing a compound of Formula (V) comprising hydrolizing a peptide at its cleavage site, and reacting the cleaved peptide with a compound of Formula (IA), I(B), (II), (III), or (IV) to provide a compound of Formula (V).

The processes for preparing compounds of Formula (VII) are identical to the processes of preparing compounds of Formula (V).

The invention is also directed in part to a method of synthesis of an azapeptide comprising coupling a compound of Formula (IA), I(B), (II), (III), or (IV) to an amino acid or an aza-amino acid, wherein the azapeptide is a compound of Formula (V):

(V)

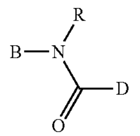

or a pharmaceutically acceptable salt thereof, wherein

B is selected from the group consisting of hydrogen, —$NH_2$, —$NNH_2$, —$CONH_2$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-mer azatide;

D is selected from the group consisting of —OH, —NH2, —NNH2, —CONH2, —COOH, —COH, —COC1-C4 alkyl, —COC1-C4 haloalkyl, an amino acid, an aza amino acid, a 2 to 60-mer peptide, a 2 to 60-mer aza peptide, a 2 to 60-mer azatide; and R is selected from the group consisting of unsubstituted and substituted side chain radicals of aspartic acid, phenylalanine, alanine, histidine, glutamic acid, tryptophan, valine, leucine, lysine, methionine, tyrosine, isoleucine, arginine, glycine, asparagine, serine, and glutamine. The coupling can be either during a solid phase peptide synthesis or a liquid phase peptide synthesis. The method may comprise activating the compound Formula (IA), I(B), (II), (III), or (IV) prior to the coupling. The activating may be with, e.g., with Me or DIPEA. In certain embodiments, the compound of Formula (V) is produced in a yield of at least about 50% (e.g., about 55%, about 60%, about 65%, about 70%, about 75%, about 80%, about 85%, about 90%, about 95%, or about 97%) and the compound of Formula (IA) is:

(IA)

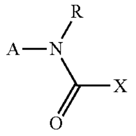

wherein

X is imidazolyl or benzotriazolyl, and wherein (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl; and R is selected from the group consisting of side chain radicals of aspartic acid, phenylalanine, alanine, histidine, glutamic acid, tryptophan, valine, leucine, lysine, methionine, tyrosine, isoleucine, arginine, glycine, asparagine, serine, cysteine, serine, threonine, and glutamine.

The invention is further directed in part to a method of azapeptide synthesis comprising reacting (i) an imidazole derivative comprising an aza-amino acid, wherein the aza-amino acid is covalently bound (conjugated) to a protecting group at its N-terminus and to imidazole at its C-terminus and is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-asparagine, aza-glutamine, aza-histidine, aza-lysine, and aza-arginine with (ii) an aza-amino acid, an amino acid, or a peptide to form the azapeptide, wherein the imidazole derivative is a compound of Formula (IA), (IIB) or (III), and the azapeptide is a compound of formula (V) or (VII).

The invention is also directed in part to a method of an azapeptide synthesis comprising reacting (i) an imidazole derivative comprising an aza-amino acid, wherein the aza-amino acid is covalently bound (conjugated) to a protecting group at its N-terminus and to imidazole at its C-terminus and is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a peptide to form the azapeptide, wherein the imidazole derivative is a compound of Formula (IA), (IB), (II) or (III), and the azapeptide is a compound of formula (V) or (VII).

In addition, the invention is directed in part to a method of an azapeptide synthesis comprising reacting (i) a benzotriazole derivative comprising an aza-amino acid covalently bound (conjugated) to a first protecting group at its N-terminus and to benzotriazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-aspartic acid, aza-glutamine, aza-histidine, aza-lysine, and aza-arginine with (ii) a an aza-amino acid, an an amino acid, or a peptide to form the azapeptide, wherein the benzotriazole derivative is a compound of Formula (IV), and the azapeptide is a compound of formula (V) or (VII), provided that if a side chain of the aza-amino acid comprises a group selected from amino, amide, guanidino N, carboxyl, sulfhydryl, carboxyl, hydroxyl, indole, imidazole phenol, the group is protected by a second protecting group. The first and the second protecting group may independently be, e.g., a protecting group selected from tert-butoxycarbonyl, 9-fluorenylmethoxycarbonyl, or 2-(3,5-dimethoxyphenyl) propan-2-yloxycarbonyl, phthalimide, carboxybenzyl, 2,2,4,6,7-pentamethyl-dihydrobenzofuran-5-sulfonyl, trityl or triphenylmethyl, t-butyl ester, t-butyl ether, s-t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, acetamidomethyl, and the like. In certain embodiments, the first and second protecting group is each independently selected from the group consisting of be tert-butoxycarbonyl, 9-fluorenylmethoxycarbonyl, or 2-(3,5-dimethoxyphenyl)propan-2-yloxycarbonyl, phthalimide, or carboxybenzyl.

The invention is also directed to a method of azapeptide synthesis comprising reacting (i) a benzotriazole derivative comprising an aza-amino acid, wherein the aza-amino acid is covalently bound (conjugated) to a first protecting group at its N-terminus and to benzotriazole at its C-terminus and is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-aspartic acid, aza-glutamine, aza-histidine, aza-lysine, and aza-arginine with (ii) a peptide to form the azapeptide, wherein the benzotriazole derivative is a compound of Formula (IV), and the azapeptide is a compound of formula (V) or (VII), provided that if a side chain of the aza-amino acid comprises a group selected from amino, amide, guanidino N, carboxyl, sulfhydryl, carboxyl, hydroxyl, indole, imidazole phenol, the group is protected by a second protecting group. The first and the second protecting group may independently be, e.g., a protecting group selected from tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), carboxybenzyl (Cbz), 2,2,4,6,7-pentamethyl-dihydrobenzofuran-5-sulfonyl (Pbf), trityl or triphenylmethyl (Trt), t-butyl ester (OtBu), t-butyl ether (tBu), s-t-butyl ether, allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), acetamidomethyl (Acm), and the like. In certain embodiments, the first and second protecting group is each independently selected from the group consisting of be tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), or carboxybenzyl (Cbz).

The compounds of Formula (IA), (IB), (II), (III), or (IV) and process of the invention allow, e.g., for preparation of a compound of Formula (V) in yields of at least about 50% (e.g., from about 55% to about 99%, from about 60% to about 95%, or from about 65% to about 95%). Thus, the yield may, e.g., be about 55%, about 60%, about 65%, about 75%, about 80%, about 85%, about 90%, about 95%, about 97%, or about 99%. In certain embodiments, the yield is greater than 85%.

The invention is further directed in part to prolonging an in vitro and/or in vivo half-life of a peptide, comprising synthesizing a peptidomimetic analogue of the peptide with the compounds of Formula (I), (II), (III) or (IV), the peptidomimetic analogue containing an aza amino acid instead of amino acid at the N-terminus of the peptide, but is otherwise identical to the peptide. In certain embodiments, the peptidomimetic analogue is a compound of Formula (V), (VII), (IX), or (X), and is synthesized by liqid phase or solid phase chemistry.

The invention is further directed in part to prolonging an in vitro and/or in vivo half-life of a peptide, comprising synthesizing a peptidomimetic analogue of the peptide with the compounds of Formula (I), (II), (III) or (IV), the peptidomimetic analogue containing an aza amino acid instead of amino acid at a position adjacent to the N-terminus of the peptide, but is otherwise identical to the peptide. In certain embodiments, the peptidomimetic analogue is a compound of Formula (V), (VII), (IX), or (X), and is synthesized by liqid phase or solid phase chemistry.

The invention is further directed in part to the use of compounds of Formula (V), (VII), (IX), or (X) in prevention, diagnosis and treatment of medical conditions, including, e.g., cardiovascular disorders, CNS disorders, neurodegenerative disorders, immune system disorders, metabolic disorders, fertility, dental conditions, pain, inflammation, dermatological conditions, blood disorders, infection, eye disorders, gynecologic disorders, urologic disorders, bone and connective tissue disorders, respiratory disorders, gastrointestinal disorders, disorders of endocrine system, and cancer.

The methods of diagnosing, prevention and treatment of medical conditions in accordance with the present invention comprise administering a therapeutically effective amount of a compound of Formula (V) or Formula (VII) to a subject in need thereof at specific times in a pharmaceutically acceptable formulation.

In certain embodiments, the method of treating a disorder comprising co-administering a compound of Formula (V) or (VII) along with a compound of Formula (VI) or (VIII). In certain embodiments, the compound of Formula (V) or Formula (VII) acts as a competitive inhibitor of the compound of Formula (VI) or Formula (VIII). In certain embodiments, the administration of the compound of Formula (V) or (VII) results in higher plasma concentrations of the compound of Formula (VI) or (VIII).

In certain embodiments, the invention is directed to a method of prolonging effects of a 2 to 50 amino acid peptide comprising administering, before, after or concurrently with the peptide, an aza-analogue of the amino acid peptide, the analogue differing from peptide in that at least one of the amino acids of the peptide is replaced with a corresponding aza-amino acid.

The invention is further directed to a pharmaceutically acceptable formulation comprising a therapeutically effective amount of a compound of Formula (V) or Formula (VII) and one or more pharmaceutically acceptable excipient(s). The pharmaceutically acceptable excipients are described in the the Handbook of Pharmaceutical Excipients, Pharmaceutical Press and American Pharmacists Association, sixth ed., (2009), incorporated by reference herein, for all purposes.

The invention is further directed to a diagnostic formulation comprising a compound of Formula (V) or Formula (VII).

Definitions

The term "about" in the present specification means a value within 15% (±15%) of the value recited immediately after the term "about," including the value equal to the upper limit (i.e., +15%) and the value equal to the lower limit (i.e., —15%) of this range. For example, the phrase "about 100" encompasses any numeric value that is between 85 and 115, including 85 and 115.

The terms "administration" or "administering" compound should be understood to mean providing a compound of the present invention to a subject in a form that can be introduced into that subject's body in an amount effective for prophylaxis, treatment, or diagnosis, as applicable. Such forms may include e.g., oral dosage forms, injectable dosage forms, transdermal dosage forms, inhalation dosage forms, and rectal dosage forms.

An "azapeptide" means a peptide in which one or more α-carbon(s) are replaced by nitrogen trivalent atom(s).

An "azatide" means a peptide in which all α-carbons are replaced by nitrogen trivalent atoms.

An "aza-amino acid" is defined as an amino acid where the chiral α-carbon atom is replaced by a nitrogen atom.

An "α-nitrogen" means a nitrogen atom bonded to a carbonyl group in an azapeptide or or an azatide. The carbon atom next to the α-nitrogen is called the β-carbon.

A "peptidomimetic" means a compound which differs from a peptide that it "mimics" in that one or more α-carbon atoms of the peptide have been replaced by a nitrogen atom with or without additional structural modification(s) to the side chain(s) of the amino acid residues of the peptide. The one or more α-carbon atoms of the peptide that are replaced by be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide). Despite having a backbone different from the peptide, the peptidomimetic agent preserves, extends and/or improves functional activity of the peptide. The peptidomimentic agent is more resistant to degradation than the peptide and/or has an improved therapeutic activity than the peptide and/or has an improved selectivity for a biological receptor than the peptide and/or improved affinity to a biological receptor and/or reversed activity at a biological receptor (agonistic activity instead of antagonist activity or antagonistic activity instead of agonistic activity).

The term "protected" as it is used herein means that one or more group(s) (e.g., —OH) in an amino acid, an aza-amino acid, a peptide, an azapeptide, or a compound is protected with a protecting group (e.g., Phth, Ddz, etc.). Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups include, for example, nitrogen protecting groups and hydroxy-protecting groups. Examples of protective group include, e.g., benzyl, diphenylmethyl, trityl, Cbz, Boc, Fmoc, methoxycarbonyl, ethoxycarbonyl, Phth, Ddz, as well as other protective groups known to those skilled in the art.

A "side chain radical" of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine have the following structures:

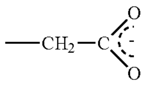

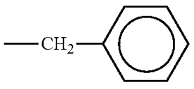

$—CH_3$

Aspartic Acid Phenylalanine Alanine

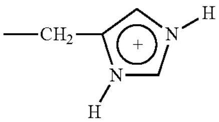

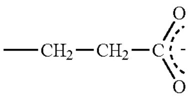

Histidine Glutamic Acid

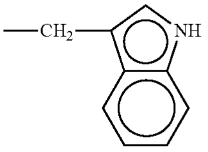

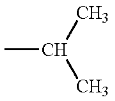

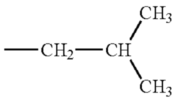

Tryptophan Valine Leucine $—CH_2—CH_2—CH_2—CH_2—NH_3^+$ $—CH_2—CH_2—S—CH_3$

Lysine Methionine

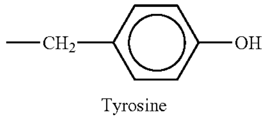

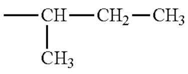

Tyrosine Isoleucine

-continued

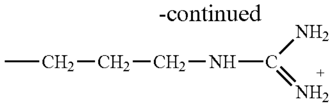

—H

Arginine

Glycine

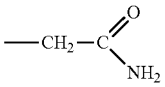

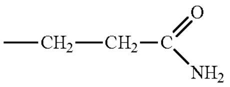

Asparagine

Glutamine

A"side chain radical of proline" is a secondary amine, in that the alpha-amino group is attached directly to the main chain, making the a carbon a direct substituent of the side chain:

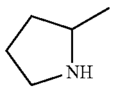

Amino acids which can be used in the present invention are L and D-amino acids.

The term "pharmaceutically acceptable excipient", as used herein, means, e.g., a non-toxic, inert solid, semi-solid or liquid filler, diluent, encapsulating material or formulation auxiliary of any type, etc. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Unless otherwise indicated, the terms "prevent," "preventing" and "prevention" contemplate an action that occurs before a patient begins to suffer from the symptoms of specified disease or disorder, which inhibits or reduces the severity of the disease or disorder or of one or more of its symptoms. The terms encompass prophylaxis.

The compounds of the invention can be used in the form of pharmaceutically acceptable salts derived from inorganic or organic acids. For clarity, the term "pharmaceutically acceptable salt[s]" as used herein generally refers to salts prepared from pharmaceutically acceptable acids or bases including inorganic acids and bases and organic acids and bases. Suitable pharmaceutically acceptable base addition salts include, e.g., metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific acids include, e.g., hydrochloric, hydrobromic, phosphoric, sulfuric, and methanesulfonic acids. Examples of specific salts include, e.g., hydrochloride and mesylate salts. Others are well-known in the art. See, e.g., Remington's Pharmaceutical Sciences, 18th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom. In preferred embodiments, methods of diagnosis of the present invention comprise administration of such an isotopically labelled compound.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Unless otherwise indicated, a "diagnostically effective amount" of a compound is an amount sufficient to diagnose a disease or condition. In general, administration of a compound for diagnostic purposes does not continue for as long as a therapeutic use of a compound, and could be administered only once if such is sufficient to produce the diagnosis.

Unless otherwise indicated, a "therapeutically effective amount" of a compound is an amount sufficient to treat a disease or condition, or one or more symptoms associated with the disease or condition. The appropriate amount depends upon, among other things, the stage of the disease or condition; the age of the patient; the weight of the patient; the bioavailability of the compound with respect to a target tissue; the concentration of compound required in vivo to result in a beneficial effect relative to control; or the concentration of compound required to result in a pharmacodynamic effect upon a target amyloid protein at the target tissue.

The term "subject" is intended to include living organisms in which disease may occur. Examples of subjects generally include mammals, e.g., humans, monkeys, cows, sheep, goats, dogs, cats, mice, rats, and transgenic species thereof.

The term "Phth-protected carbamoyl aza-imidazole derivative of an unnatural amino acid" as used herein means an unnatural aza-amino acid covalently bound (conjugated) to phthalimidyl at its N-terminus and to imidazole at its C-terminus. The unnatural amino acid may be substituted and unsubstituted.

The term "Phth-protected carbamoyl aza-benzotriazole derivative of an unnatural amino acid" as used herein means means an unnatural aza-amino acid covalently bound (conjugated) to phthalimidyl at its N-terminus and to benzotriazole at its C-terminus. The unnatural amino acid may be substituted and unsubstituted.

The term "solid-phase synthesis" means a method in which molecules or atoms (e.g., amino acids, aza-amino acids, etc.) are covalently bound on a solid support material and synthesised step-by-step in a single reaction vessel utilising selective protecting group chemistry. In this method, building blocks are typically protected at all reactive functional groups. The order of functional group reactions can be controlled by the order of deprotection. For example, in an aza-peptide synthesis, an amino-protected amino acid or an amino-protected aza-amino acid is bound to a solid phase material (e.g., low cross-linked polystyrene beads), forming a covalent bond between the carbonyl group and the resin, e.g., an amido or an ester bond. Then the amino group is deprotected and reacted with the carbonyl group of the next amino-protected amino acid or amino-protected aza-amino acid. This cycle is repeated to form the desired peptide or aza-peptide chain. After all reactions are complete, the synthesised peptide or aza-peptide is cleaved from the bead.

The terms "solution phase synthesis" and "liquid phase synthesis" means a method in which molecules or atoms (e.g., amino acids, aza-amino acids, etc.) are synthesized in a solution without being covalently bound on a solid support material.

The term "synthon" means a building block.

The term "room temperature" means 20° C.

The term "ambient temperature" means 18-28° C.

The terms "parent peptide" and "corresponding peptide" mean a native peptide (i.e., natural or convention peptide) that differs from an azapeptide in that one or more of the amino residue(s) of the native peptide is (are) replaced by a semicarbazide or a substituted semicarbazide (i.e., one or more α-carbon(s) of the native peptide are replaced by nitrogen trivalent atom(s)) in the azapeptide. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

The term "phthalimidyl" means:

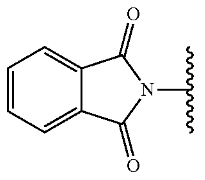 [SMILES: *N1C(=O)c2ccccc2C1=O]

The term "phthaloyl" means:

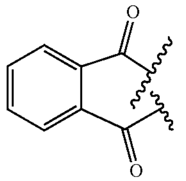 [SMILES: *C(=O)c1ccccc1C(*)=O]

The abbreviation "N-Phth" means "N-phthalimidyl."

The abbreviation "Boc" means "tert-butoxycarbonyl."

The abbreviation "Fmoc" means "9-fluorenylmethoxycarbonyl."

The abbreviation "Ddz" means "2-(3,5-dimethoxyphenyl) propan-2-yloxycarbonyl."

The abbreviation "HOBt" means "1-OH-Benzotriazole."

The abbreviation "SPPS" means "Solid Phase Peptide Synthesis."

The abbreviation "TCCA" means "trichloroisocyanuric acid."

The abbreviation "TBACl" means "tetrabutyl ammonium chloride."

The abbreviation "Phth" means "phthaloyl."

The abbreviation "Cbz" means "carboxybenzyl."

The abbreviation "Pbf" means "2,2,4,6,7-pentamethyldihydrobenzofuran-5-sulfonyl."

The abbreviation "Trt" means "trityl or triphenylmethyl."

The abbreviation "OtBu" means "O-t-butyl."

The abbreviation "tBu" means "t-butyl."

The abbreviation "StBu" means "s-t-butyl."

The abbreviation "Aloc" means "allyloxycarbonyl."

The abbreviation "Mtr" means "methoxytrimethylbenzene sulfonyl."

The abbreviation "Mbh" means "4,4-dimethyloxybenzhydryl."

The abbreviation "Pmc" means "2,2,5,7,8-pentamethylchroman-6-sulfonyl chloride."

The abbreviation "Tmob" means 2,4,6-trimethoxybenzyl.

The abbreviation "OA" means "allyl ester."

The abbreviation "Acm" means "acetamidomethyl."

The abbreviation "DEAD" means "Diethyl Azodicarboxylate."

In peptide chemistry, "deprotection" refers to a process of removing the protecting groups (e.g., phthaloyl, Boc, Cbz, Fmoc, etc) by a chemical agent. For example, Boc protecting group could be removed under acidic conditions (e.g., 4M HCl, or neat trifluoroacetic acid TFA); Fmoc protecting group could be removed under basic conditions when pH is higher than 12 (20% pipyridine/DMF or DCM); and Phthaloyl group can be cleaved, e.g., under basic conditions or by the use of hydrazine.

DETAILED DESCRIPTION

Figure 1:
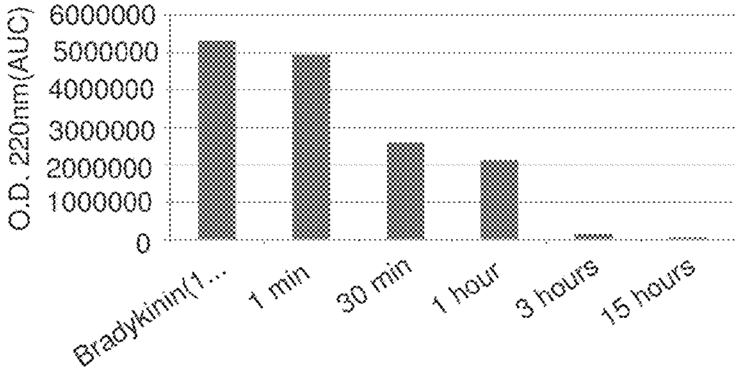
FIG. 1 is a graph depicting the stability of bradykinin amide in serum as monitored by area under curve at different timepoints using HPLC at wavelength 220 nm.

A replacement of one or more α-carbon(s) with nitrogen in a peptide converts the peptide to an "azapeptide"; and replacement of all α-carbon(s) with nitrogen(s) in a peptide converts the peptide to an "azatide."

Azapeptides and azatides are peptidomimetics frequently more resistant to enzymatic hydrolysis than the corresponding peptides. The increase in resistance to enzymatic degradation may lead to increased metabolic stability of the compounds and and improved receptor binding. Therefore, azapeptides and azatides are useful tools for drug design, applications in medicinal chemistry, and in diagnosis, prevention and treatment of diseases.

Azapeptides and azatides may, therefore, be used instead of peptides, as peptidomimetic agents ("peptidomimetics"). For example, azapeptides and azatides may act used as receptor agonists and antagonists or as protease inhibitors.

Compounds of Formula (IA), I(B), (II), (III), and (IV) of the present invention serve as "building blocks" or synthons for the synthesis of azapeptides and azatides, including compounds of Formula (V) and (VII), both in solution and solid phase synthesis.

The synthesided azapeptides and azatides, including compounds of Formula (V) and (VII), may, then, be used, e.g., as peptidomimentic agents, e.g., peptidomimetic diagnostic and therapeutic agents, instead of peptides in drug discovery and in diagnosis, prevention and treatment of diseases.

Compounds of Formula (IA), (IB), (II) and (III)

Compounds of Formula (IA), (IB), (II), and (III) could be used in drug discovery, diagnosis, prevention and treatment of diseases, or as building blocks for synthesis of peptidomimetic agents, e.g., for use in drug discovery, diagnosis, prevention and treatment of diseases.

In certain embodiments, a compound of Formula (IA), (IB), (II) and (III) is an imidazole derivative of an aza-amino acid, the imidazole derivative comprising an aza-amino acid covalently bound (conjugated) to a protecting group at its N-terminus and to imidazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine. In some of these embodiments, the protecting group comprises phthalimide. In additional embodiments, the protecting group comprises fluorenylmethyloxycarbonyl. In further embodiments, the protecting group comprises 2-(3, 5-dimethoxyphenyl)propan-2-yloxycarbonyl or tert-butoxycarbonyl.

In certain embodiments, the imidazole derivative is stable at 37° C. in an aqueous medium (e.g., an aqueous solution) with a pH of about 7 for at least 30 minutes, 60 minutes, 90 minutes, 1 hour, 2 hours, 3 hours, 4 hours or 5 hours. In certain embodiments, the imidazole derivative is stable at 37° C. in mouse serum for at least 30 minutes, 60 minutes, 90 minutes, 1 hour, 2 hours, 3 hours, 4 hours or 5 hours.

Compounds of Formula (IA), (IB), (II), and (III) include, e.g., Phth-protected carbamoyl imidazoles and are Phth-protected carbamoyl benzotriazoles.

Phth-Protected Carbamoyl Imidazoles

In certain embodiments, compounds of Formula (IA), (TB), (II) and (III) are Phth-protected carbamoyl imidazoles. In some of these embodiments, the compounds of Formula (IA), (B), (II) and (III) are selected from the group consisting of:

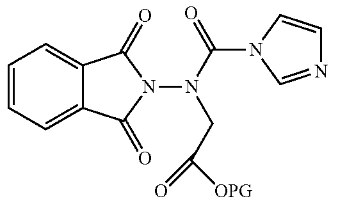

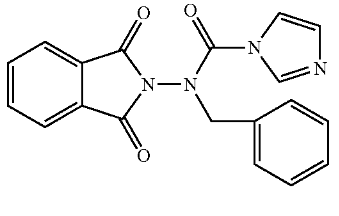

-continued

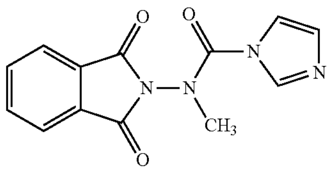

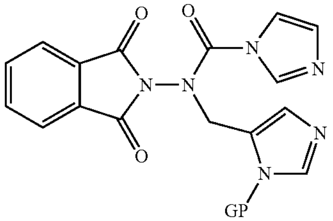

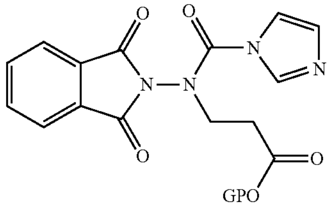

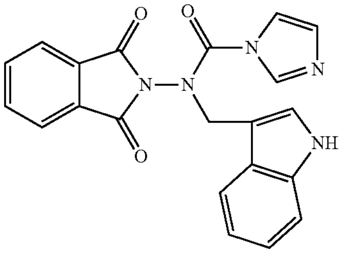

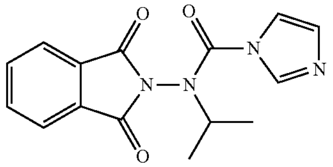

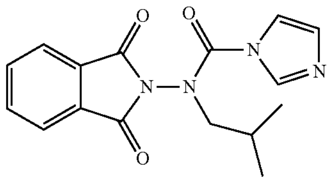

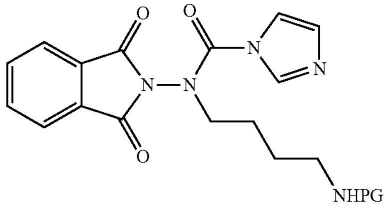

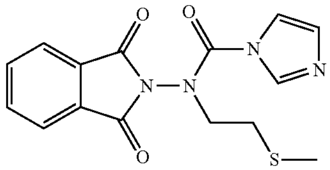

-continued

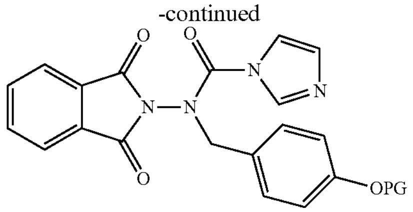

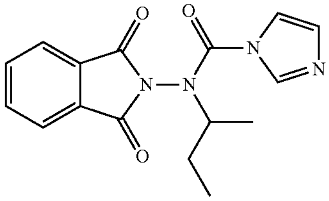

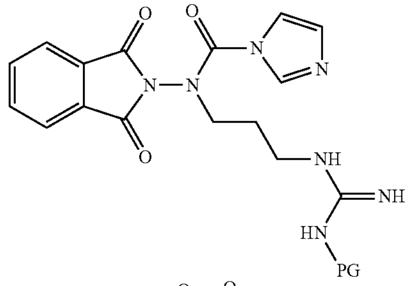

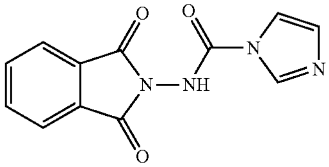

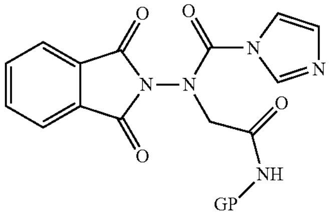

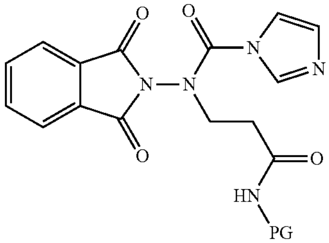

and pharmaceutically acceptable salts thereof, wherein “PG” is H or a protecting group (e.g., N-phthalimidyl, tert-butoxycarbonyl, 9-fluorenylmethoxycarbonyl, 2-(3,5-dimethoxyphenyl)propan-2-yloxycarbonyl).

In certain embodiments, compounds of Formula (IA), (IB), (II) and (III) are selected from the group consisting of Phth-aza-aspartic acid-carbamoyl imidazole, Phth-aza-phenylalanine-carbamoyl imidazole, Phth-aza-alanine-carbamoyl imidazole, Phth-aza-histidine-carbamoyl imidazole, Phth-aza-glutamic acid-carbamoyl imidazole, Phth-aza-tryptophan-carbamoyl imidazole, Phth-aza-valine-carbamoyl imidazole, Phth-aza-leucine-carbamoyl imidazole, Phth-aza-lysine-carbamoyl imidazole, Phth-aza-cysteine-carbamoyl imidazole, Phth-aza-tyrosine-carbamoyl imidazole, Phth-aza-iso-leucine-carbamoyl imidazole, Phth-aza-arginine-carbamoyl imidazole, Phth-aza-glycine-carbamoyl imidazole, Phth-aza-asparagine-carbamoyl imidazole, Phth-aza-glutamine-carbamoyl imidazole, and salts thereof.

In certain embodiments, a compounds of Formula (IA), I(B), (II), (III), or (IV) is a Phth-protected carbamoyl imidazole derivative of aza-proline.

Compounds of Formula (IV)

Compounds of Formula (IV) could be used in drug discovery, diagnosis, prevention and treatment of diseases, or as building blocks for synthesis of peptidomimetic agents, e.g., for use in drug discovery, diagnosis, prevention and treatment of diseases.

In certain embodiments, a compound of Formula (IV) is a benzotriazole derivative of an aza-amino acid comprising the aza-amino acid covalently bound (conjugated) to a protecting group at its N-terminus and to benzotriazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine. In certain embodiments, the protecting group comprises phthalimide. In additional embodiments, the protecting group comprises frorenylmethoxycarbonyl (FMOC). In further embodiments, the protecting group comprises 2-(3,5-dimethoxyphenyl)propan-2-yloxycarbonyl.

In certain embodiments, the compound of Formula (IV) is stable at 37° C. in an aqueous medium (e.g., an aqueous solution) with a pH of about 7 for at least 30 minutes, 60 minutes, 90 minutes, 1 hour, 2 hours, 3 hours, 4 hours or 5 hours.

Phth-Protected Carbamoyl Benzotriazoles

In certain embodiments, the compound of Formula (IV) is a Phth-protected carbamoyl benzotriazole.

In certain embodiments, the compound of Formula (IV) is selected from the group consisting of:

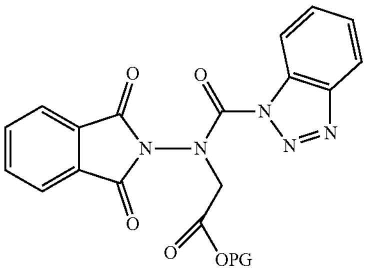

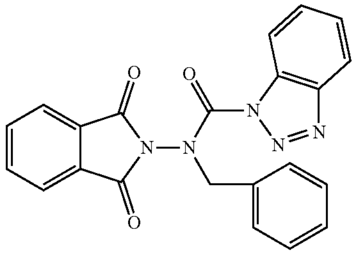

-continued

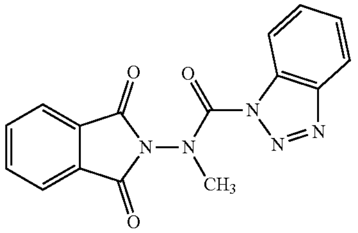

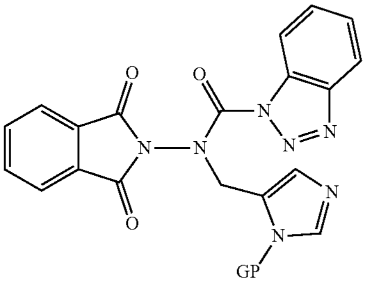

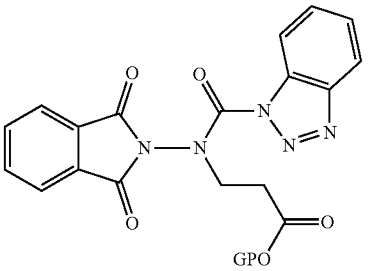

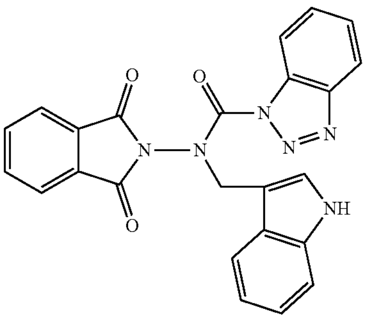

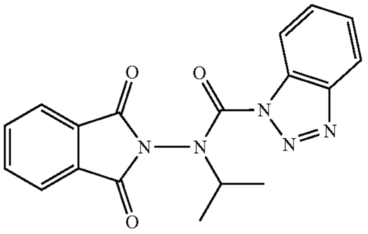

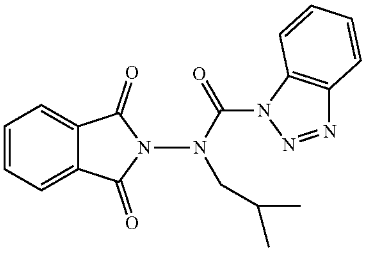

-continued

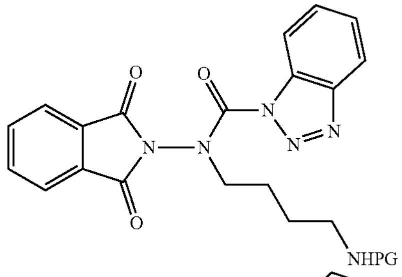

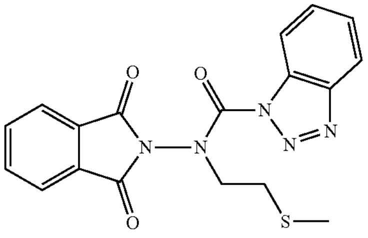

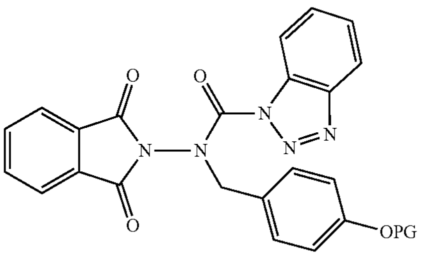

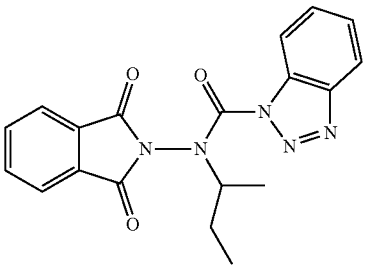

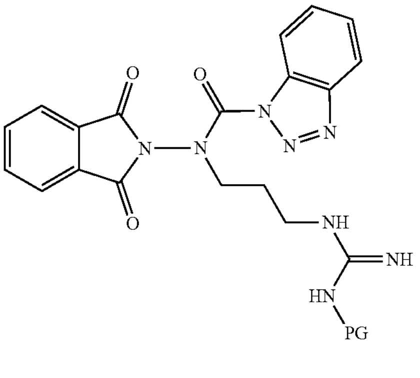

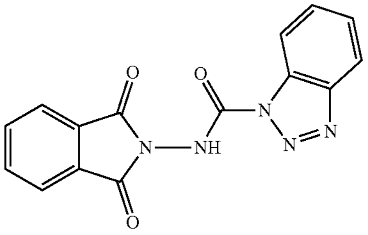

-continued

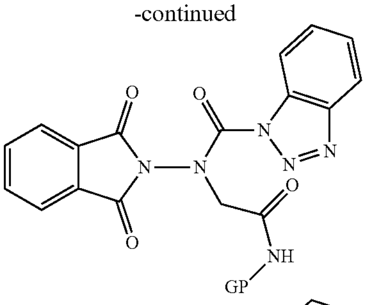

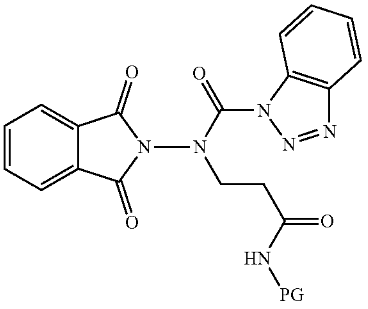

and pharmaceutically acceptable salts thereof, wherein "PG" is H or a protecting group (e.g., N-phthalimidyl, tert-butoxycarbonyl, 9-fluorenylmethoxycarbonyl, 2-(3,5-dimethoxyphenyl)propan-2-yloxycarbonyl).

In certain embodiments, the compound of Formula (IV) is selected from the group consisting of Phth-aza-aspartic acid-carbamoyl benzotriazole, Phth-aza-phenylalanine-carbamoyl benzotriazole, Phth-aza-alanine-carbamoyl benzotriazole, Phth-aza-histidine-carbamoyl benzotriazole, Phth-aza-glutamic acid-carbamoyl benzotriazole, Phth-aza-tryptophan-carbamoyl benzotriazole, Phth-aza-valine-carbamoyl benzotriazole, Phth-aza-leucine-carbamoyl benzotriazole, Phth-aza-lysine-carbamoyl benzotriazole, Phth-aza-cysteine-carbamoyl benzotriazole, Phth-aza-tyrosine-carbamoyl benzotriazole, Phth-aza-leucine-carbamoyl benzotriazole, Phth-aza-arginine-carbamoyl benzotriazole, Phth-aza-glycine-carbamoyl benzotriazole, Phth-aza-asparagine-carbamoyl benzotriazole, and salts thereof.

In certain embodiments, a compound of Formula (IA), (IB), (II), (III) or (IV) is a Phth-protected carbamoyl benzotriazole derivative of aza-proline.

Compounds of Formula (IA), (IB), (II), (III) and (IV) serve as "building block" for compounds of Formula (V) and (VII).

Compounds of Formula (V) and (VII)

Compounds of Formula (V) and (VII) are peptidomimetic analogues of compounds of Formula (VI) and and (VIII), respectively. In the preferred embodiments, compounds of Formula (V) and (VII) are more resistant to hydrolysis and/or enzymatic degradation than compounds of Formula (VI) and (VIII).

Compounds of Formula (V) and (VII) may be used to inhibit peptidases, both in vitro and in vivo. The peptidase may, e.g., be an endopeptidase, an exopeptidase, an aspartic protease, a glutamic protease, an asparagine peptide lyase, or a retroviral protease.

In some of these preferred embodiments, compounds of Formula (V) and (VII) are more potent than compounds of Formula (VI) and (VIII), e.g., due to a better fit into a biological receptor. Compounds of Formula (V) and (VII) could be used, e.g., in drug discovery, diagnosis, prevention and treatment of diseases.

Compounds of Formulas (V) and Formula (VII) may each comprise from 2 to 200 carbonyl group(s). For example, compounds of Formula (V) and (VII) may each comprise 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 36, 37, 38, 39, 40, 41, 43, 44, 56, or 166 carbonyl groups. In certain embodiments, compounds of Formula (V) and (VII) comprise from 2 to 60 carbonyl groups, from 2 to 50 carbonyl groups, from 2 to 40 carbonyl groups, from 2 to 30 carbonyl groups, from 2 to 25 carbonyl groups, from 2 to 20 carbonyl groups, from 2 to 15 carbonyl groups, from 2 to 12 carbonyl groups, from 2 to 10 carbonyl groups, from 2 to 9 carbonyl groups, from 3 to 40 carbonyl groups, from 3 to 30 carbonyl groups, from 3 to 25 carbonyl groups, from 3 to 20 carbonyl groups, from 3 to 15 carbonyl groups, from 3 to 12 carbonyl groups, from 3 to 10 carbonyl groups, or from 3 to 9 carbonyl groups.

In certain embodiments, compounds of Formula (V) and (VII) comprise from 2 to 200 carbonyl groups and at least one α-nitrogen covalently bound to at least one of said carbonyl groups, and have a greater bioavailability (e.g., oral, transdermal, and/or intranasal) than a peptide structurally different from the compounds of Formula (V) and (VII) only in that that the peptide comprises α-carbon instead of said α-nitrogen. In certain embodiments, the α-nitrogen is at the N-termini or C-termini of the compounds of Formula (V) and (VII). In certain embodiments, the α-nitrogen is one carbonyl group away from the N-termini or C-termini of the compounds of Formula (V) and (VII). In certain embodiments, the α-nitrogen is adjacent to the N-termini and the C-termini of the compounds of Formula (V) and (VII). In certain embodiments, the α-nitrogen is not at the N-termini and not at the C-termini of the compounds of Formula (V) and (VII) and is more than one carbonyl group away for the N-termini and the C-termini. In certain embodiments, the α-nitrogen is at a cleavage or hydrolysis site(s) of the compounds of Formula (V) and (VII).

In certain embodiments, compounds of Formula (V) and (VII) comprise from 2 to 200 carbonyl groups and at least one α-nitrogen covalently bound to at least one of said carbonyl groups, wherein said at least one carbonyl group is at the N-termini or C-termini residue of the compounds of Formula (V) and (VII).

In certain embodiments, compounds of Formula (V) and (VII) are aza-analogues of therapeutic peptides.

In certain embodiments, compounds of Formula (V) and (VII) are aza-analogues of diagnostic peptides.

Compounds of Formula (V) and Formula (VII) may be used in drug discovery, diagnosis, prevention and treatment of diseases.

In certain embodiments, compounds of Formula (V) and (VII) comprise a backbone comprising from 2 to 200 carbonyl groups and α-nitrogen covalently bound to at least one of said carbonyl groups, and are therapeutically effective for the treatment of a disorder in a subject, while a peptide structurally different from the compounds of Formula (V) and (VII) only in that that the peptide comprises α-carbon instead of said α-nitrogen is not therapeutically effective for the treatment of the disorder.

In certain embodiments, compounds of Formula (V) and (VII) comprise from 2 to 200 carbonyl groups and α-nitrogen covalently bound to at least one of said carbonyl groups, and have a therapeutic efficacy greater than a peptide structurally different from the compounds of Formula (V) and (VII) only in that the peptide comprises an α-carbon instead of said α-nitrogen.

In certain embodiments, compounds of Formula (V) and (VII) comprise from 2 to 200 carbonyl groups and α-nitrogen covalently bound to at least one of said carbonyl groups, and have a longer duration of therapeutic activity than a peptide structurally different from the compounds of Formula (V) and (VII) only in that that the peptide comprises α-carbon instead of said α-nitrogen.

In certain embodiments, compounds of Formula (V) and (VII) comprise from 2 to 75 carbonyl groups and at least one α-nitrogen covalently bound to at least one of said carbonyl groups, and have an in vivo half-life greater than a peptide structurally different from the compounds of Formula (V) and (VII) only in that said at least one α-nitrogen is replaced with α-carbon.

In certain embodiments, compounds of Formula (V) and (VII) comprise a backbone comprising from 2 to 75 carbonyl groups, wherein at least two carbonyl groups are covalently bound to a trivalent nitrogen, and compounds of Formula (V) and (VII) have an in vivo half-life greater than a peptide structurally different from the compounds of Formula (V) and (VII) only in that one or more alpha nitrogen(s) of the compounds of Formula (V) and (VII) is replaced with alpha carbon(s).

In certain embodiments, compounds of Formula (V) and (VII) comprise at least one aza-amino acid, and have an in vivo half-life greater than a peptide structurally different from the compounds of Formula (V) and (VII) only in that the aza-amino acid(s) is replaced with a corresponding amino acid.

In certain embodiments, compounds of Formula (V) and (VII) comprise from 2 to 200 carbonyl groups and α-nitrogen covalently bound to at least one of said carbonyl groups, and are more resistant to protease degradation than a peptide structurally different from the compounds of Formula (V) and (VII) only in that that the peptide comprises α-carbon instead of said α-nitrogen.

In certain embodiments, compounds of Formula (V) and (VII) comprise from 2 to 200 carbonyl groups and α-nitrogen covalently bound to at least one of said carbonyl groups, and have a greater affinity to a biological receptor than a peptide structurally different from the compounds of Formula (V) and (VII) only in that that the peptide comprises α-carbon instead of said α-nitrogen.

In certain embodiments, compounds of Formula (V) and (VII) comprises from 2 to 60 carbonyl groups.

In certain embodiments, compounds of Formula (V) and (VII) are linear.

In certain embodiments, compounds of Formula (V) and (VII) are cyclic.

In certain embodiments, compounds of Formula (V) and (VII) are pegylated.

In certain embodiments, compounds of Formula (V) and (VII) are conjugated to an immunoglobulin.

In certain embodiments, compounds of Formula (V) and (VII) comprise α-nitrogen at the N-terminus of its backbone.

In certain embodiments, compounds of Formula (V) and (VII) comprise α-nitrogen at the C-terminus of its backbone In certain embodiments, compounds of Formula (V) and (VII) comprise two carbonyl groups and two α-nitrogens.

In certain embodiments, compounds of Formula (V) and Formula (VII) comprise three carbonyl groups and one α-nitrogen.

In certain embodiments, a compound of Formula (V) or a compound of Formula (VII) comprises three carbonyl groups and two α-nitrogens.

In certain embodiments, compounds of Formula (V) and (VII) comprise three carbonyl groups and three α-nitrogens.

In certain embodiments, compounds of Formula (V) comprise four carbonyl groups and one α-nitrogen.

In certain embodiments, compounds of Formula (V) comprise four carbonyl groups and two α-nitrogens.

In certain embodiments, compounds of Formula (V) and (VII) comprise four carbonyl groups and three α-nitrogens.

In certain embodiments, compounds of Formula (V) and (VII) comprise four carbonyl groups and four α-nitrogens.

In certain embodiments, compounds of Formula (V) and (VII) are aza-analogues of a 2 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) and (VII) are aza-analogues of a 2 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine, wherein the analogue includes at least one corresponding aza-amino acid of the amino acid.

In certain embodiments, compounds of Formula (V) and (VII) are aza-analogues of a 2 to 200 amino acid peptide, the 2 to 200 amino acid peptide comprising amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, the analogue differing from the amino acid peptide in that that the aza-analogues comprise an aza-amino acid instead of at least one of the amino acids, wherein the aza-analogues comprise aza-glycine instead of glycine, and/or the aza-analogues comprise aza-alanine instead of alanine, and/or the aza-analogues comprise aza-valine instead of valine, and/or the aza-analogues comprise aza-leucine instead of leucine, or/and the aza-analogues comprise aza-isoleucine instead of iso-leucine, and/or the aza-analogues comprise aza-proline instead of proline, and/or the aza-analogues comprise aza-phenylalanine instead of phenylalanine, or/and the aza-analogues comprise comprises aza-tyrosine instead of tyrosine, and/or the aza-analogues comprise aza-tryptophan instead of tryptophan, or/and the aza-analogues comprise aza-aspartic acid instead of aspartic acid, and/or the aza-analogues comprise aza-glutamic acid instead of glutamic acid, and/or the aza-analogues comprise aza-aspargine instead of aspargine, and/or the aza-analogues comprise aza-glutamine instead of glutamine, and/or the aza-analogues comprise aza-histidine instead of histadine, and/or the aza-analogues comprise aza-lysine instead of lysine, and/or the aza-analogues comprise aza-arginine instead of arginine.

In certain embodiments, compounds of Formula (V) and (VII) are aza-analogues of a peptide comprising from 2 to 50 amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, and at least 2, 3, 4, 5, 6, 7, 8, 9 or 10 of the amino acids are replaced with corresponding aza-amino acids. In some of these embodiments, the replaced amino acid is the first amino acid of the peptide. In some of these embodiments, the replaced amino acid is the second amino acid of the peptide. In some of these embodiments, the replaced amino acid is the last amino acid of the peptide. In some of these embodiments, the first and the last amino acids of the peptide are both replaced with corresponding aza-amino acids. In some of these embodiments, the amino acids of the peptide adjacent to the N-termini and the C-termini of the peptide are both replaced with corresponding aza-amino acids.

In certain embodiments, the last amino acid of the peptide is selected from the group consisting of aspartic acid, phenylalanine, and arginine.

In certain embodiment, the first amino acid of the peptide is selected from the group consisting of tyrosine, phenylalanine, and arginine.

In certain embodiments, the first and the last amino acid of the peptide are the same.

In certain embodiments, the first and the last amino acids of the peptide are different.

In certain embodiments, compounds of Formula (V) and (VII) are not azatides.

In certain embodiments, compounds of Formula (V) and (VII) comprise an amino acid selected from the group consisting of cysteine, methionine, serine and threonine.

In certain embodiments, compounds of Formula (V) and (VII) comprises at least one, at least two or at least three aza-glycine(s).

In certain embodiments, compounds of Formula (V) and (VII) comprise at least one, at least two or at least three aza-alanine(s).

In certain embodiments, compounds of Formula (V) and (VII) comprise at least one, at least two or at least three aza-valine(s).

In certain embodiments, compounds of Formula (V) and (VII) comprise at least one, at least two or at least three aza-leucine(s).

In certain embodiments, compounds of Formula (V) and (VII) comprise at least one, at least two or at least three aza-isoleucine(s).

In certain embodiments, compounds of Formula (V) and (VII) comprise at least one, at least two or at least three aza-proline(s).

In certain embodiments, compounds of Formula (V) and (VII) comprise at least one, at least two or at least three aza-phenylalanine(s).

In certain embodiments, compounds of Formula (V) and (VII) comprise at least one, at least two or at least three aza-tyrosine(s).

In certain embodiments, compounds of Formula (V) and (VII) comprise at least one, at least two or at least three aza-tryptophan(s).

In certain embodiments, compounds of Formula (V) and (VII) comprise at least one, at least two or at least three aza-aspartic acid(s).

In certain embodiments, compounds of Formula (V) and (VII) comprise at least one, at least two or at least three aza-glutamic acid(s).

In certain embodiments, compounds of Formula (V) and (VII) comprise at least one, at least two or at least three aza-aspargine(s).

In certain embodiments, compounds of Formula (V) and (VII) comprise at least one, at least two or at least three aza-glutamine(s).

In certain embodiments, compounds of Formula (V) and (VII) comprise at least one, at least two or at least three aza-histidine(s).

In certain embodiments, compounds of Formula (V) and (VII) comprise at least one, at least two or at least three aza-lysine(s).

In certain embodiments, compounds of Formula (V) and (VII) comprise at least one, at least two or at least three aza-arginine(s).

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini.

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, and have a greater bioavailability (e.g., oral, transdermal, and/or intranasal) than the therapeutic peptide (in its unaltered state).

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, maintain the therapeutic efficacy of the therapeutic peptide and have an in vivo half-life greater than the in vivo half-life of the therapeutic peptide. In some of these embodiments, the in vivo half-life of the compounds of Formula (V) and (VII) is greater than twice of the in vivo half-life of the therapeutic peptide. In some of these embodiments, the in vivo half-life of the compounds of Formula (V) and (VII) is three times greater than the in vivo half-life of the therapeutic peptide. In additional embodiments, the in vivo half-life of the compounds of Formula (V) and (VII) is four times greater than the in vivo half-life of the therapeutic peptide. In yet additional embodiments, the in vivo half-life of the compounds of Formula (V) and (VII) is five times greater than the in vivo half-life of the therapeutic peptide. In further embodiments, the in vivo half-life of the compounds of Formula (V) and (VII) is six times greater than the in vivo half-life of the therapeutic peptide. In additional embodiments, the in vivo half-life of the compounds of Formula (V) and (VII) is ten times greater than the in vivo half-life of the therapeutic peptide. The in vivo half-life of the compounds of Formula (V) and (VII) may, e.g., be from about 1 minute to about 72 hours.

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a longer duration of therapeutic activity than the therapeutic peptide.

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and are more resistant to protease degradation than the therapeutic peptide.

In certain embodiments, compounds of Formula (V) and (VII) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a greater affinity to a biological receptor than the therapeutic peptide.

In certain embodiments, compounds of Formula (V) and (VII) are compounds of formula:

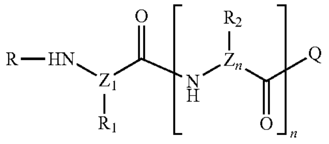

wherein $Z_1$ and $Z_n$ is each independently C or N;

R is hydrogen, $-NH_2$, $-NNH_2$, $-CONH_2$, $-COOR_3$, $-COOH$, $-COH$, $-COC_1$-$C_4$ alkyl, $-COC_1$-$C_4$ haloalkyl, $-OH$, an amino acid, an aza amino acid, a 2 to 60-mer peptide, a 2 to 60-mer aza peptide, a 2 to 60-mer azatide;

$R_1$ and $R_2$ is each independently selected from the group consisting of H, methyl, isopropyl, isobutyl, benzyl, and side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, and glutamine;

Q is $NH_2$ or OH;

at least one of $Z_1$ and $Z_n$ is N; and n is an integer from 1 to 200.

For example, n could be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, etc. In certain embodiments, n is 2, 3, 4, 5, 6, 7, 8, 9, 10, 11, 12, 13, 14, 15, 16, 17, 18, 19, or 20. The side chain radicals may be unsubstituted or substituted with one or more of the following: a halogen (Cl, F, or Br), a $C_1$-$C_6$ alkyl (e.g., methyl), hydroxyl, $-COOH$, $-COH$, methoxyl, ethoxyl, propoxyl, a $C_1$-$C_6$ haloalkyl (e.g., a chloromethyl, a fluromethyl, etc.).

Di-Mer Azapeptides

In certain embodiments, a compound of Formula (V) or (VII) is a compound of formula:

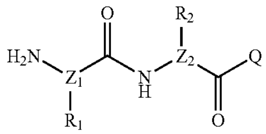

wherein $Z_1$ and $Z_2$ is each independently C or N;

$R_1$ and $R_2$ is each independently selected from the group consisting of H, methyl, isopropyl, isobutyl, benzyl, and side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine;

Z is $NH_2$ or OH; and at least one of $Z_1$ and $Z_2$ is N. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, $R_1$ and $R_2$ is each independently selected from the group consisting of H, $H_2$ and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (V) or (VII) is a di-azatide of a compound of Formula (IX)

(IX)

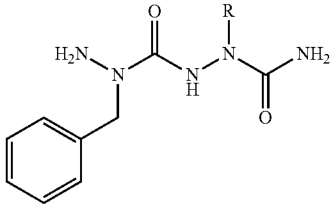

or a pharmaceutically acceptable salt thereof, wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine.

The di-azatides may, e.g., be prepared by a solution phase or a solid phase synthesis:

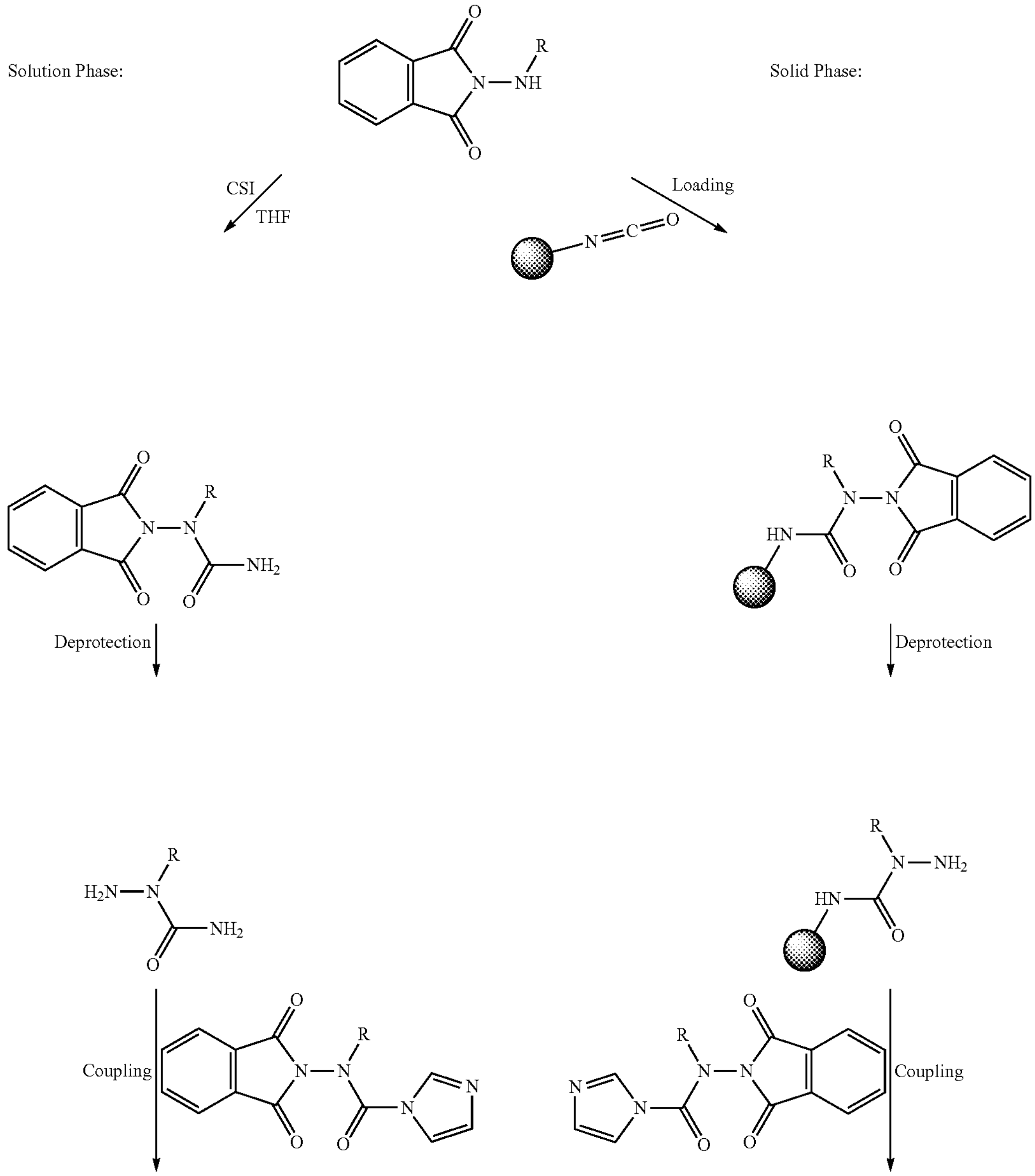

-continued

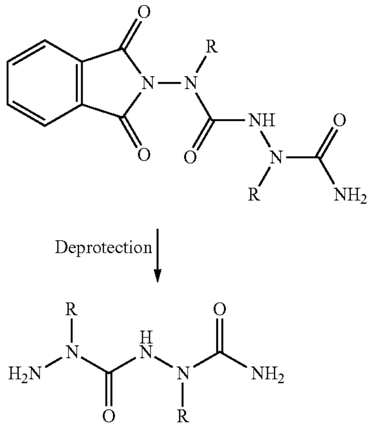

Diazatides

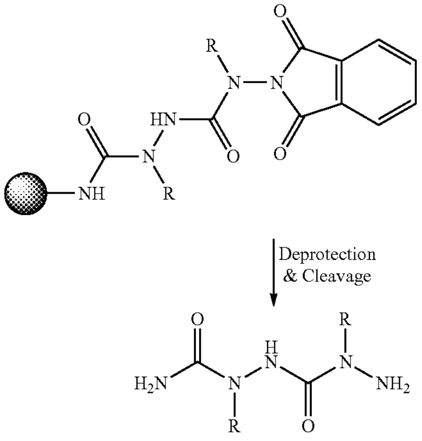

Diazatides

The di-azatides may be prepared both with C-to-N terminal construction and N-to-C terminal construction.

C-to-N-Terminal Construction

In the method of C-to-N-terminal construction, the di-azatide amide can be made by coupling of hydrazine amide (1) with acid chloride (2) in DCM/toluene at about 25° C. or 50° C. to yield the N-Fmoc protected Di-azatide amide (3) which may be de-protected, e.g., with piperidine to yield the final Di-azatide amide (4):

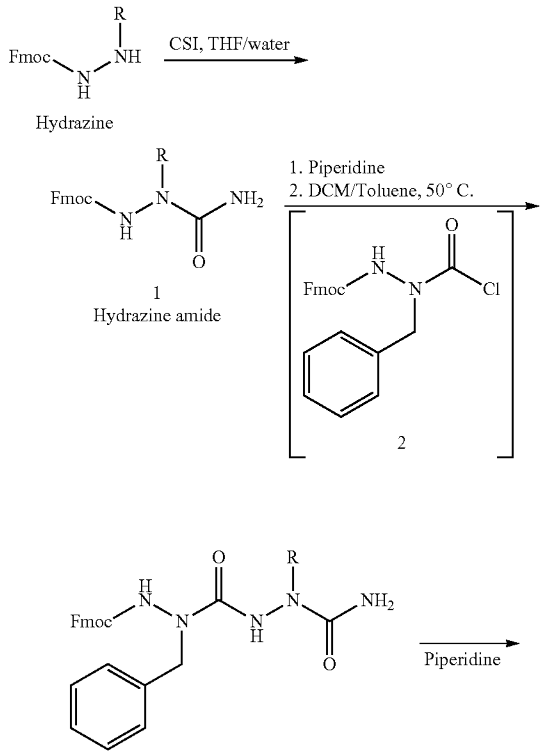

Hydrazine
1
Hydrazine amide
2
3
Fmoc-Di-aztide amide

-continued

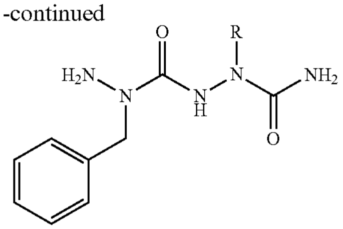
4
Di-azatide amide

The following General Procedure may be used for coupling of hydrazine amide with acid chloride (C-to-N-terminal construction): The solution of acid chloride (0.367 mmol) and hydrazine amide (0.367 mmol) in anhydrous DCM (3 mL) and anhydrous toluene (3 mL) is stirred at about 50° C. under nitrogen for, e.g., about 15 hours. The mixture is concentrated to dryness and then the crude product is purified by flash silica gel column chromatography eluting with hexane/EtOAc mixtures to afford the products as a white solids or clear oils in, e.g., 50-70% yield.

N-to-C-Terminal Construction

In the method of N-to-C-terminal construction to the Di-azatide (4) by formation of protected carbazide (5) from acid chloride (2) and then coupled with an appropriate aldehyde to form an acyl hydrazone which may be reduced by, e.g, the catalytic hydrogenation and hydride addition to yield Di-azatide (6). Chlorosulfonyl isocyanate (CSI) may be used to convert amine into the corresponding amide which may then de-protected, e.g., with piperidine to yield the final Di-azatide amide (4):

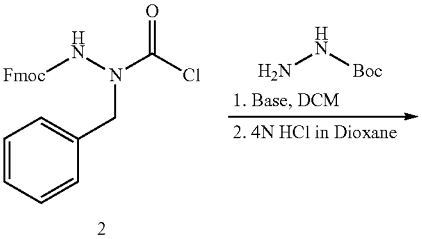

2
Acid Chloride

-continued

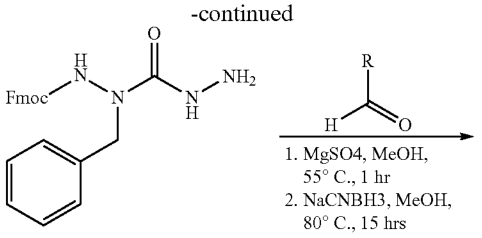

5
Carbazide

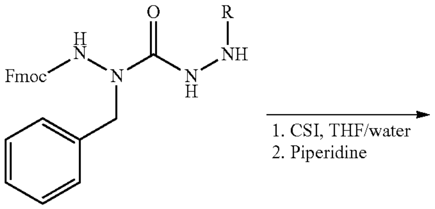

6
Di-azatide

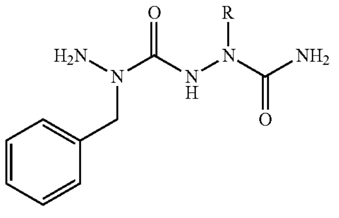

4
Di-azatide amide wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine.

The following General Procedure may be used for coupling of protected carbazide with aldehydes (N-to-C-terminal construction): To a solution of protected carbazide (0.46 mmol) and aldehyde (0.69 mmol) in anhydrous methanol (20 mL) triethyl amine (60 uL until pH=7) is added and followed by anhydrous $MgSO_4$ (200 mg). The mixture is stirred at about 55° C. under nitrogen for, e.g., about 1 hour. Then, $NaCNBH_3$ (2.3 mmol) is added, followed by acetic acid (2.3 mmol). The mixture is stirred at 80° C. under nitrogen for, e.g., about 15 hours then concentrated to dryness and partitioned between water (100 mL) and EtOAc (100 mL). The aqueous layer is extracted with EtOAc (2×50 mL) and the combined organic phase are washed with brine (50 mL), dried over $Na_2SO_4$, filtered and concentrated to afford the crude product which is purified by flash silica gel column chromatography eluting with hexane/EtOAc mixtures to afford the products as white solids or clear oils, e.g., in 40 to 60% yield.

The following General Procedure may also be used for coupling of hydrazine with acid chloride: To a solution of acid chloride (0.367 mmol) and hydrazine (3.67 mmol) in anhydrous DCM (6 mL) was added N,N,N', N'-Tetramethyl-1,8-naphthalenediamine (0.734 mmol). The solution was stirred at about 25° C. under nitrogen for, e.g., about 15 hours, concentrated to dryness and partitioned between 0.5N HCl (20 mL) and EtOAc (20 mL). The aqueous layer is extracted with EtOAc (2×25 mL) and the combined organic phase are washed with brine (25 mL), dried over $Na_2SO_4$, filtered and concentrated to afford the crude product which was purified by flash silica gel column chromatography eluting with hexane/EtOAc mixtures to afford the products as a white solids or clear oils, e.g., in 70-80% yield.

The following General Procedure may be used for removing Fmoc group with piperidine: The solution of N-Fmoc protected azatide (1.0 mmol) in piperidine (5 mL) is stirred at about 35° C. under nitrogen for about 15 mins. The mixture is concentrated to dryness and then the crude product is purified by flash silica gel column chromatography eluting with hexane/EtOAc mixtures to afford the products as a white solids, e.g., in 90-95% yield.

Compounds of Formula (IX) can be used as diagnostic peptidomimetic agents, therapeutic peptidomimetic agents, and in drug discovery, e.g., to synthese longer peptidomimetic agents (e.g., tri-azatides, tetra-azatides, etc.).

Tri-Mer Azapeptides and Azatides

In certain embodiments, a compound of Formula (V) or (VII) is a compound of:

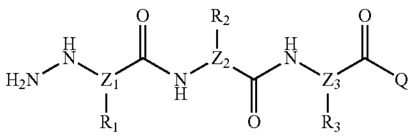

wherein $Z_1$, $Z_2$ and $Z_3$ is each independently C or N;

$R_1$, $R_2$, and $R_3$ is each independently selected from the group consisting of H, methyl, isopropyl, isobutyl, benzyl, and side chain radicals of aspartic acid, phenylalanine, alanine, histidine, glutamic acid, tryptophan, valine, leucine, lysine, methionine, threonine tyrosine, isoleucine (including, R-isoleucine, S-isoleucine and RS-isoleucine), arginine, glycine, asparagine, serine, and glutamine;

Q is $NH_2$ or OH; and at least one of $Z_1$, $Z_2$ and $Z_3$ is N. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). In certain embodiments, $R_1$, $R_2$, and $R_3$ is each independently selected from the group consisting of H, $H_2$ and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (V) or (VII) is a tri-azatide of Formula (X):

(X)

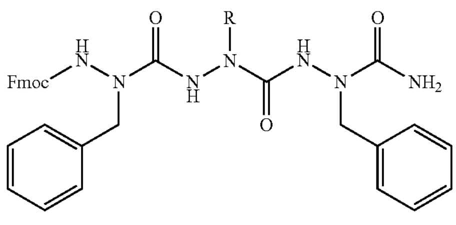

or a pharmaceutically acceptable salt thereof, wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, proline, and glutamine.

The tri-azatides may be prepared, e.g., by coupling of di-azatide amide (7) with acid chloride (2) in DCM/toluene at about 50° C. to yield the N-Fmoc protected Tri-azatide amide (8):

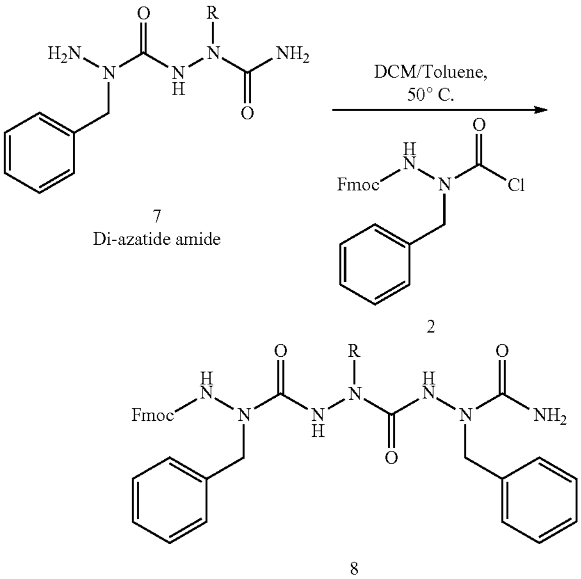

7
Di-azatide amide

2

8
Fmoc-Tri-aztide amide wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine.

The following General Procedure may be used to remove Fmoc group with piperidine: The solution of N-Fmoc protected azatide (1.0 mmol) in piperidine (5 mL) is stirred at about 35° C. under nitrogen for about 15 mins. The mixture is concentrated to dryness and then the crude product is purified by flash silica gel column chromatography eluting with hexane/EtOAc mixtures to afford the products as white solids, e.g., in 90-95% yield.

Compounds of Formula (X) can be used as diagnostic peptidomimetic agents, therapeutic peptidomimetic agents, and in drug discovery, e.g., to synthesize longer peptidomimetic agents (e.g., tetra-azatides, etc.).

Four-Mer Azapeptides

In certain embodiments, a compound of Formula (V) or (VII) is a compound of formula:

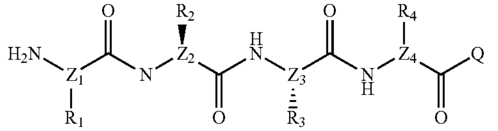

wherein $Z_1$, $Z_2$, $Z_3$, and $Z_4$ is each independently C or N;

$R_1$, $R_2$, $R_3$, and $R_4$ is each independently selected from the group consisting of H, methyl, isopropyl, isobutyl, benzyl, and side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine;

Q is $NH_2$ or OH; and at least one of $Z_1$, $Z_2$, $Z_3$, and $Z_4$ is N. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). In certain embodiments, $R_1$, $R_2$, $R_3$, and $R_4$ is each independently selected from the group consisting of H, $H_2$ and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (V) or (VII) is a compound of formula:

K763

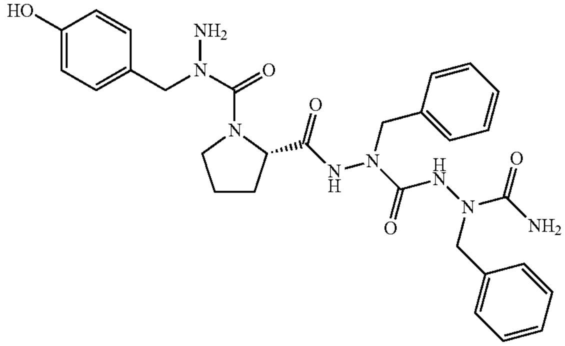

$C_{29}H_{34}N_8O_5$
Exact Mass: 574.27 or a pharmaceutically acceptable salt thereof.

In certain embodiments, a compound of Formula (V) or (VII) is a compound of formula:

K883

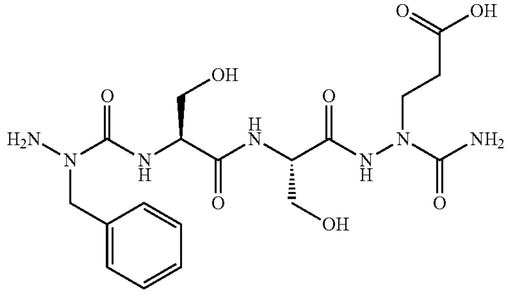

$C_{18}H_{27}N_7O_8$
Exact Mass: 469.19 or a pharmaceutically acceptable salt thereof.

Nine-Mer Azapeptides

In certain embodiments, a compound of Formula (V) or (VII) is a compound of formula:

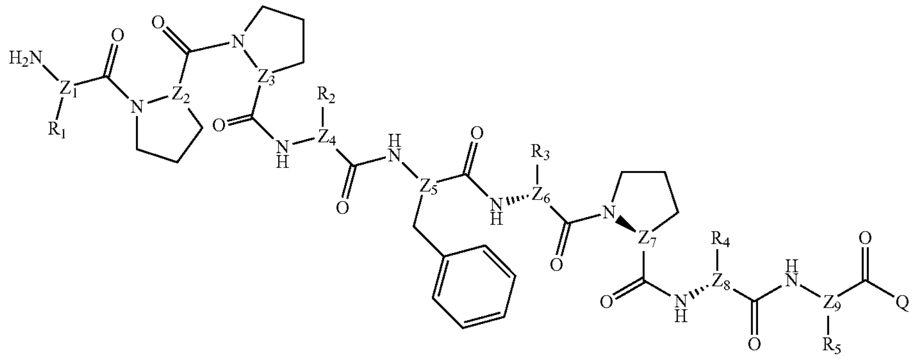

wherein $Z_1$, $Z_2$, $Z_3$, $Z_4$, an Zs is each independently or N;

Q is $NH_2$ or OH;

$R_1$, $R_2$, $R_3$, and $R_4$ is each independently selected from the group consisting of H and side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, asparagine, and glutamine; and at least one of $Z_1$, $Z_2$, $Z_3$, $Z_4$, and Zs is N.

In certain embodiments, a compound of Formula (V) or (VII) is a compound of formula:

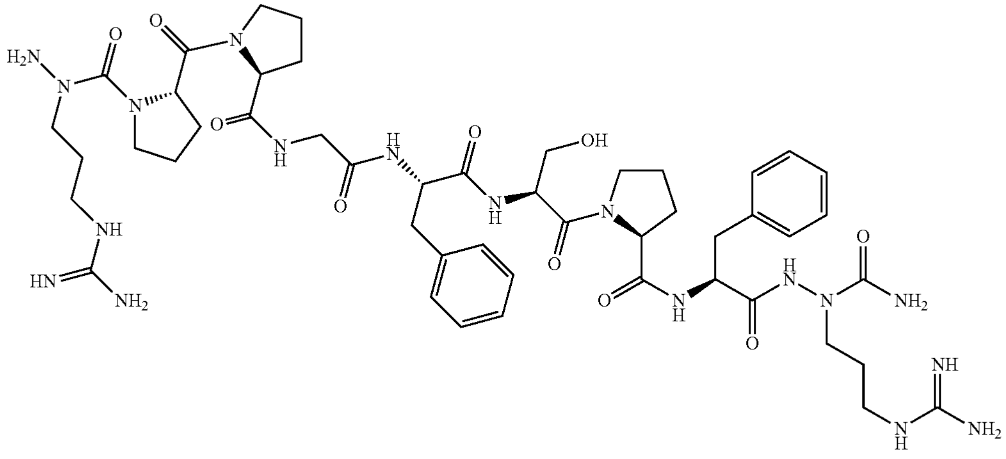

Aza-Bradykinin tyrosine, isoleucine (including, R-isoleucine, S-isoleucine and RS-isoleucine), arginine, glycine, asparagine, serine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, $R_1$, $R_2$, $R_3$, and $R_4$ is each independently selected from the group consisting of H, methyl, isopropyl, isobutyl, benzyl, and side chain radicals of aspartic acid, histidine, glutamic acid, tryptophan, lysine, methionine, or a pharmaceutically acceptable salt thereof.

Utility of Compounds of Formula (V) and (VII)

In certain embodiments, compounds of Formula (V) and (VII) are used in drug discovery, e.g., to provide a library of compounds suitable for the diagnosis, prevention or treatment of a pathological condition(s).

In certain embodiments, compounds of Formula (V) and (VII) are used as diagnostic agents.

In certain embodiments, compounds of Formula (V) and (VII) are used as therapeutic agents.

In certain embodiments, compounds of Formula (V) and (VII) are used as inhibitors of proteases (e.g., an endopeptidase, an exopeptidase, an aspartic protease, a glutamic protease, an asparagine peptide lyase, a retroviral protease, etc.).

In certain embodiments, compounds of Formula (V) and (VII) are therapeutically effective for the treatment of acne, acromegaly, alopecia, anemia, asthma, cancer, age-related macular degeneration, bone cysts, dental caries, cognitive enhancement, cystic fibrosis, chemoprevention, Cushing's syndrome, anorexia nervosa, depression, obsessive-compulsive disorder, diabetic retinopathy, diabetic macular edema, diabetic nephropathy, dyspepsia, brain edema, epilepsy, renal failure, gingivitis, lupus erythematosus, chronic lyphocytic leukemia, obesity, estrogen deficiency, emesis, endometriosis, endometrial thinning, gastrointestinal disorders, gigantism, bone injuries, tooth restoration, heart failure, myocardial infarction, cerebrovascular ischemia, ischemia, unstable angina pectoris, hypertension, isolated systolic hypertension, cardiovascular disease, coronary disorder, atherosclerosis, peripheral artery disease, arrhythmia, pain, vasodilatory hypotension, intradialytic hypotension, stroke, sepsis, thromboembolism, restenosis, hypercalcemia, inflammation, type 1 diabetes, type 2 diabetes, wound healing, eryrthropietic protoporphyria, photodamage, actinic keratosis, myasthenia gravis, multiple sclerosis, transplant rejection, lipid metabolism disorder, malnutrition, HIV, hepatitis, herpes, glaucoma, osteoporosis, erectile dysfunction, rheumatoid arthritis, Alzheimer's disease, dermal scarring, kelid scarring, atopic dermatitis, impetigo, uveitis, uterine contractions, acute coronary syndrome, thrombosis, neutropenia, thrombocytopenia (e.g., heparin-induced thrombocytopenia), female sexual dysfunction, female infertility, postpartum uterine atony, postpartum hemorrhage bleeding, Paget's disease, gastric disorders, Gram negative bacterial infection, mycosesm, bacteremia, candidemia, diarrhea, candida ablicants infection, vulvovaginal candidiasis, pancreatic dysfunction, benign prostatic hyperplasia, uterine fibroids, growth disorder, metabolic syndrome, metabolic disorder, HIV-associated lipodystrophy, cachexia, Factor VIII deficiency, multiple sclerosis, Graft versus host disease, epilepsy, Parkinson's disease, schizophrenia, functional bowel disease, inflammatory bowel disease, irritable bowel syndrome, ulcerative colitis, Crohn's disease, Celiac disease, short bowel syndrome, ileus, systemic inflammatory response syndrome, brain edema, head injury, precocious puberty, polycystic ovary syndrome, uterine fibroids, nocturia, diabetis insipidus, enuresis, polyuria, primary nocturnal enuresis, Von Willebrand's disease, Hemophilia, hemopoietic disorder, female contraception, male contraception, scleroderma, diabetic foot ulcer, septic shock, cognition disorder, dementia, HIV-associated dementia, mild cognitive impairment, systemic lupus erythematosus, somatotropin deficiency, muscle wasting, skin disorders, reperfusion injury, inhibition of premature LH surges, Leukopenia, drug induced fungal infection, onychomycosis, immune disorder, viral infection, immune deficiency, Huntington's chorea, motor neuron disease, neurodegenerative disorder, psoriasis, tuberculosis, respiratory tract disorders, postoperative infections, lung disorders, radiation sickness, transplant rejection, hereditary angioedema, rhinitis, allergy, asthma, osteoarthritis, liver cirrhosis, respiratory distress syndrome, stomatitis, pneumonia, nutritional disorders, short stature, respiratory distress syndrome, lung malformation, postoperative ileus, vasoactive intestinal peptide, stem cell mobilisation, stem cell transplantation, myelofibrosis, catheter infection, rosacea, otitis, conjunctivitis, neuropathy, control of bleeding, delivery induction, labor initiation, labor stimulation, pemphigus vulgaris, muscle weakness, immune thrombocytopenic purpura, myelodysplastic syndrome, spinal fusion, chronic wounds, bleeding esophageal varices, spinocerebellar degeneration, renal disease, hepatorenal syndrome, insomnia, influenza virus, aspergillus infection, lung infection, primary immunodeficiencies, angiogenesis disorder, recurrent autoimmune cytopenia, decubitus ulcer, varicose ulcer, epidermolysis bullosa, eye surgery, deafness, or labyrinthitis (inflammation of inner ear).

In certain embodiments, compounds of Formula (V) and (VII) are therapeutically effective for treatment of coronary thrombosis.

In certain embodiments, compounds of Formula (V) and (VII) are therapeutically effective for treatment of *Clostridium defficile*-associated diarrhea.

In certain embodiments, compounds of Formula (V) and (VII) are therapeutically effective for treatment of neonatal respiratory distress syndrome.

In certain embodiments, compounds of Formula (V) and (VII) are therapeutically effective for treatment of a ventricular arrhythmia.

In certain embodiments, compounds of Formula (V) and (VII) are therapeutically effective for treatment of atrial fibrillation.

In certain embodiments, compounds of Formula (V) and (VII) are therapeutically effective for treatment of respiratory disorder.

In certain embodiments, compounds of Formula (V) and (VII) are therapeutically effective for treatment of adult neonatal distress syndrome.

In certain embodiments, compounds of Formula (V) and (VII) are therapeutically effective for treatment of allergic rhinitis.

In certain embodiments, compounds of Formula (V) and (VII) are therapeutically effective for treatment of allergic conjunctivitis.

In certain embodiments, compounds of Formula (V) and (VII) are therapeutically effective for treatment of postmenoposal osteoporosis.

In certain embodiments, compounds of Formula (V) and (VII) are therapeutically effective for treatment of chemotherapy induced diarrhea.

In certain embodiments, compounds of Formula (V) and (VII) are therapeutically effective for treatment of a bone fracture.

In certain embodiments, compounds of Formula (V) and (VII) are therapeutically effective for treatment of *Staphylococcus aureus* infection.

In certain embodiments, compounds of Formula (V) and (VII) are therapeutically effective for the treatment of breast cancer, colorectal cancer, carcinoid cancers, carcinoma, renal cell carcinoma, endometrial carcinoma, glioma, glioblastoma, hepatocellular carcinoma, lymphoma, non-small lung cancer, ovarian cancer, gastrointestinal cancer, pancreatic cancer, prostate cancer, sarcoma, solid tumors, metastatic melanoma, multiple myeloma, malignant melanoma, neuroblastoma, skin cancer, non-hodgkin lymphoma, small-cell lung cancer, non-small-lung cancer, mesothelioma, pancreatic cancer, hematological neoplasm, neuroendocrine tumors, pituitary cancer, uterine cancer, or osteosarcoma.

In certain embodiments, compounds of Formula (V) and (VII) are therapeutically effective for the treatment of neuropathic pain, neuralgia, postoperative pain, cancer pain, inflammatory pain, or pain without inflammation.

In certain embodiments, compounds of Formula (V) and (VII) are therapeutically effective for the treatment of diabetic neuropathy.

In certain embodiments, compounds of Formula (V) and (VII) are therapeutically effective for the treatment of hypoplastic anemia.

In certain embodiments, a compound of Formula (V) or a compound of Formula (VII) compounds of Formula (V) and (VII) are for the treatment of hepatitis A, hepatitis B, or hepatitis C.

In certain embodiments, compounds of Formula (V) and (VII) are selected from the group consisting of antagonists of ANP receptor, AT receptor, B-cell activating factor, B2 receptor, BB2 receptor, N-Cadherin, calcium channel, CCRP5 receptor, CALC receptor and RAMPs, CD4 receptor, C5a receptor, CD29 receptor, CXCR4 receptor, GCG receptor, Erb-3 receptor, GnRH R, GP IIb IIIa receptor, integrin alpha-5/beta-3, integrin alpha-4/beta-1, NMDA receptor, Nicotinic ACH receptor, OT receptor, PTH receptor, SST receptor, TAC1 receptor, TAC2 receptor, TBXA2 receptor, VEGF receptor, VE-Cadherin receptor, and zonulin receptor.

In certain embodiments, compounds of Formula (V) and (VII) are selected from the group consisting of agonists of an ANP receptor, AVP receptor, B2 receptor, BNP receptor, CCK receptor, CALC receptor, CALC receptor and RAMPs, CRH receptor, CD 36 receptor, CD110 receptor, CXCR4 receptor, EPO receptor, FGF receptor, ET-B receptor, GCG receptor, GH receptor, GNRH receptor, GnRH R receptor, GPL-1 receptor, GPL-2 receptor, GHS receptor, GPR54, Guanylate cyclase-C, IL2 receptor, IGF-1 receptor, PGE2 receptor, NGF receptor, NMDA receptor, NOD protein receptor, NPY receptor, MC receptor, M1 receptor, NTS1 receptor, NK receptor, PTH receptor, Delta opioid receptor, Kappa opioid receptor, Mu opioid receptor, ORL1 receptor, OGF receptor, OT receptor, PAR receptor, SCT receptor, SST receptor, SST receptor and Dopamine D2 receptor, TRH receptor, VPAC receptor, and RAMPs receptor.

In certain embodiments, compounds of Formula (V) and (VII) are immunomodulators.

In certain embodiments, compounds of Formula (V) and (VII) modulate NOD protein.

In certain embodiments, compounds of Formula (V) and (VII) modulate STAT protein.

In certain embodiments, compounds of Formula (V) and (VII) modulate actin.

In certain embodiments, compounds of Formula (V) and (VII) modulate PTH receptor.

In certain embodiments, compounds of Formula (V) and (VII) modulate GHS receptor.

In certain embodiments, compounds of Formula (V) and (VII) modulate tubulin.

In certain embodiments, compounds of Formula (V) and (VII) inhibit a protease.

In certain embodiments, compounds of Formula (V) and (VII) are JNK inhibitors.

In certain embodiments, compounds of Formula (V) and (VII) inhibit HIV Tat protein.

In certain embodiments, compounds of Formula (V) and (VII) are thrombin inhibitors.

In certain embodiments, compounds of Formula (V) and (VII) are inhibitors of HDAC.

In certain embodiments, compounds of Formula (V) and (VII) are inhibitors of protein kinase C delta.

In certain embodiments, compounds of Formula (V) and (VII) are inhibitors of enkephalinase.

In certain embodiments, compounds of Formula (V) and (VII) stimulate ERK.

In certain embodiments, compounds of Formula (V) and (VII) activate protein kinase C epsilon.

In certain embodiments, compounds of Formula (V) and (VII) are inhibitors of renin.

In certain embodiments, compounds of Formula (V) and (VII) are ligands for DNA.

In certain embodiments, compounds of Formula (V) and (VII) are ligands for GP41.

In certain embodiments, compounds of Formula (V) and (VII) are ligands for angiopoietin 2.

In certain embodiments, compounds of Formula (V) and (VII) are ligands for CD4.

In certain embodiments, compounds of Formula (V) and (VII) are ligands in cholesterol transport.

In certain embodiments, compounds of Formula (V) and (VII) are ligands of TGF beta 1.

In certain embodiments, compounds of Formula (V) and (VII) are ligands of HIV p24.

In certain embodiments, compounds of Formula (V) and (VII) are ligands of iron.

In certain embodiments, compounds of Formula (V) and (VII) are insulinotropic.

In certain embodiments, compounds of Formula (V) and (VII) are ligands of Aβ42.

In certain embodiments, compounds of Formula (V) and (VII) are ligands of glycosphingolipids.

In certain embodiments, compounds of Formula (V) and (VII) are inhibitors of Serine-Threonine kinase.

In certain embodiments, compounds of Formula (V) and (VII) are chloride channel inhibitors.

In certain embodiments, compounds of Formula (V) and (VII) are inhibitors of compliment C3 enzyme.

In certain embodiments, compounds of Formula (V) and (VII) are inhibitors of beta-secretase.

In certain embodiments, compounds of Formula (V) and (VII) are inhibitors of matrix metalloproteinase-9.

In certain embodiments, compounds of Formula (V) and (VII) are modulators of a gap junction.

In certain embodiments, compounds of Formula (V) and (VII) are used as adjuvants to a local anesthetic.

In certain embodiments, a compound of Formula (V) is desmopressin.

In certain embodiments, compounds of Formula (V) and (VII) are conjugated to a small molecule.

In certain embodiments, compounds of Formula (V) and (VII) are dopamine agonists.

In certain embodiments, compounds of Formula (V) and (VII) are dopamine antagonists.

In certain embodiments, compounds of Formula (V) and (VII) are conjugated to a phospholipid.

In certain embodiments, compounds of Formula (V) and (VII) are surfactants.

In certain embodiments, compounds of Formula (V) and (VII) are GnRH receptor targeting ligands.

In certain embodiments, compounds of Formula (V) and (VII) exclude [azaVal3]-angiotensin II; azaAsn5-oxytocin; azaGly9-oxytocin; [azaAsn5]-eledoisin; azaGly10-analogues of leutinizing hormone-releasing hormone (LH-RH) (azaGy10-LH-RH, [D-Ser(But)6, azaGly10]-LH-RH); azaGly analoges of encephalin; aza analogues of the native peptide ligand, Arg-Gly-Asp (RGD) (i.e., azaAla-RGD; azaGly-RGD, and azaGly aminopyridine analog of RGD); azaPhe4 analog of the growth hormone releasing peptides (GIRP-6) [His-D-Trp-Ala-Trp-D-Phe-Lys-$NH_2$]; azaD-Phe and azaArg analogues of melanocortin receptor (MCR) [Ac-His-D-Phe-Arg-Trp-$NH_2$]; analogue of MCR in which Trp was replaced with aza-Nal-1, aza-Nal-2 and aza-Bip; azaGly33 analog of calcitonin gene-related peptide (CGRP); azaTyr analog of the insulin receptor tyrosine kinase (IRTK); Boc-azaPhe-trans-Chx-Arg-CONH(s-PhEt); Marocyclic azapeptide inhibitor, BILN 2061, and Atazanavir (CGP 7354 or BMS-232332) (Reyataz®), and azapeptides inhibitors of serine and cysteine proteases described in [27]-[35], all herein incorporated by reference.

The concept of employing an electrophilic aza-residue at the P1 position was effective against cysteine proteases such as potent inhibitors of papain, cathepsin B, calpains. Caspase-1 and the 3C protease from human rhinovirus strain 1, without having inhibitory activity on the serine peptidases, trypsin and porcine pancreatic elastase. (Reference 28).

In certain embodiments, compounds of Formula (V) and (VII) exclude the following compounds:

Azapeptide inhibitors of serine and cysteine proteases

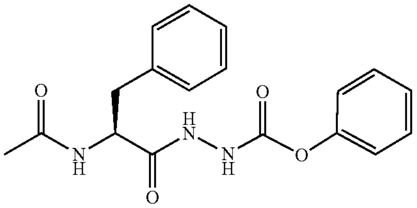

aza-Gly inhibitor of papein cysteine protease activity

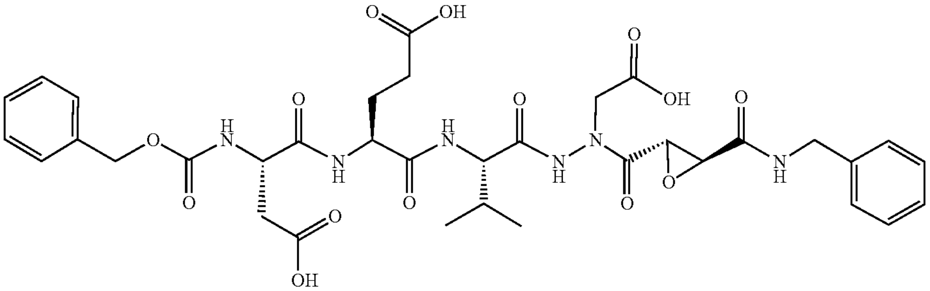

aza-Asp epoxide inhibitor of caspase cysteine portease activity

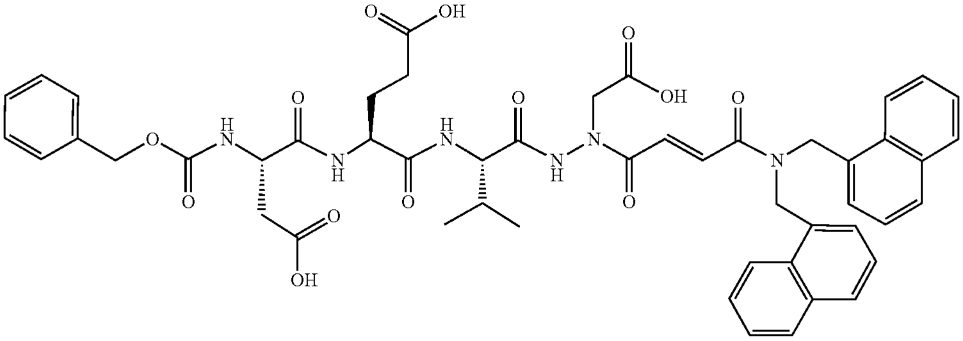

aza-Asp Michael acceptor inhibitor of caspase cysteine protease activity

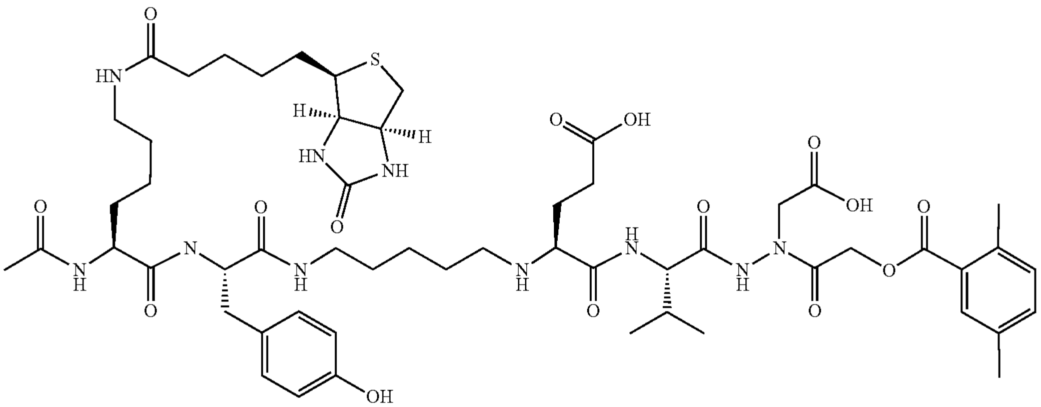

aza-Asp acyloxymethyl ketone inhibitor of caspase cysteine protease activity

-continued

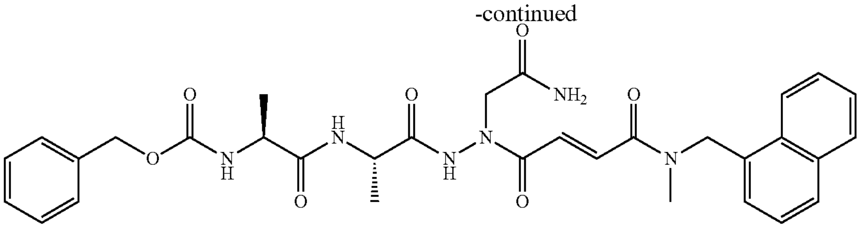

aza-Asp Michael acceptor inhibitor for the asparaginyl endopeptidases activity

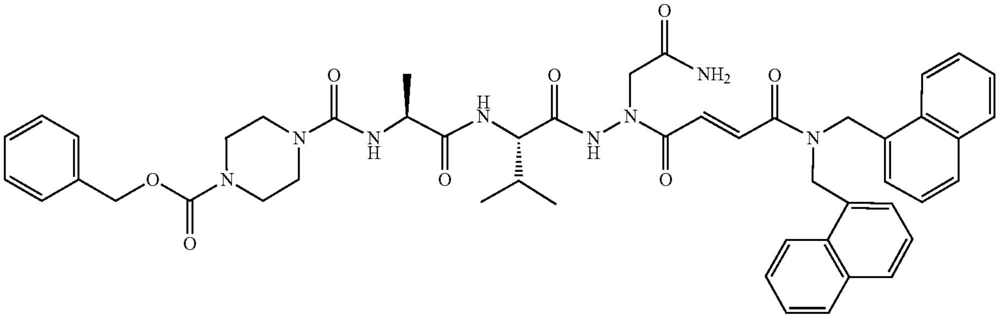

aza-Asn Michael acceptor inhibitor of caspase cysteine protease activity

In certain embodiments, compounds of Formula (V) and (VI) are selected from the group consisting of aza-analogues of A-6, A-623 (AMG-623), A-71378, A-75998, Abarelix (PPI-149), ABT-510, AC-100, AC-162352 (PYY 3-36), AC-253, AC-2592, AC-625, ACV-1, ADH-1, AEZS-108 (AN-152) (ZEN-008), AF-37702, Afamelanotide (EP-1647) (CUV-1647) (Melanotan I), AG2/102, AG-284, AI-502, AKL-0707 (LAB GHRH), Albiglutide (GSK-716155), Albuvirtide, ALG-889, Alloferon, Allotrap 2702 (B-2702), ALTY-0601, ALX-40-4C, Ambamustine (PTT-119), Anaritide, Antagonist G (PTL-68001), AOD-9604, APL-180, ATN-161, Atosiban (ORF-22164), Atriopeptin, Aviptadil (PSD-510), Avorelin (EP-23904), AZD-2315, Azetirelin (YM-14673), AZX-100, B27PD, BA-058, Barusiban (FE-200400), BAY-73-7977, BDM-E, BGC-728, BIM-23190, BIM-44002, BIO-1211, Bivalirudin (BG-8865), BMS-686117, Bremelanotide (PT-141), BRX-0585, Buserelin, Calcitonin (Human), Calcitonin (Salmon), Carbetocin, Carfilzomib (PR-171), Cargutocin (Y-5350), Carperitide (SUN-4936), Casokefamide, CB-182804, CB-183315, CBP-501, CBT-101, CCK (25-33), CD-NP, Cemadotin (LU-103793), Cetrorelix (NS-75), CG-77X56, CGRP (LAB-CGRP), Chlorotoxin (TM-601), Cilengitide (EMD-121974) (EMD-85189), CJC-1008 (DAC: Dynorphin A), CJC-1131 (DAC: GLP-1), CJC-1134 (PC-DAC) (Exendin-4), CJC-1295 (DAC:GRF), Cnsnqic-Cyclic (802-2), Compstatin (POT-4), Conantokin G, Contulakin G (CGX-1007), Corticorelin (NEU-3002), CP-95253, C-peptide (SPM-933), CR-665, CR-845, CTCE-0214, CTCE-9908, CTS-21166 (ASP-1702) (ATG-Z1) (OM-00-3) (OM-99-2), CVX-045, CVX-060, CVX-096 (PF-4856883), CZEN-002, D-4F (APP-018), Danegaptide (ZP-1609) (WAY-261134) (GAP-134), Davalintide (AC-2307), Davunetide (AL-108) (AL-208), Degarelix (FE 200486), Delmitide (RDP-58), Deltibant (CP-0127), Deslorelin, Desmopressin, Detirelix (RS-68439), DG-3173 (PTR-3173), Didemnin B (NSC-325319), Dirucotide (MBP-8298) Disitertide (NAFB-001) (P-144), DMP-728 (DU-728), dnaJP1 (AT-001), Dopastatin (BIM-23A760), DPK-060, DRF-7295, DSC-127, Dynorphin A, E-2078, EA-230, Ebiratide (Hoe-427), Edotreotide (SMT-487), Edratide (TV-4710), Efegatran (LY-294468), Elcatonin, Eledoisin (ELD-950), Elisidepsin (PM-02734), EMD-73495, Enfuvirtide (T-20), EP-100, EP-51216 (EP-51389), Eptifibatide ($C_{68}$-22), ET-642 (RLT-peptide), ETRX 101, Examorelin (EP-23905) (MF-6003), Exenatide (AC-2993) (LY-2148568), Exsulin (INGAP Peptide), F-991, FAR-404, FE 202158, Felypressin, FGLL, Frakefamide (LEF-576) (SPD-759) (BCH-3963), FX-06, Ganirelix (Org-37462) (RS-26306), Glaspimod (SKF-107647), Glatiramer (COP-1), Glucagon, Glucosamyl muramyl tripeptide, Glutoxim (NOV-002), Glypromate, GMDP, Golotimod (SCV-07), Goralatide (BIM-32001), Goserelin (ICI-118630), GPG-$NH_2$, GTP-200, GTP-300, H-142, Hemoparatide (PTH(1-37)), Hexapeptide copper II (PC-1358), Histrelin, hLF(1-11), HP-228, I-040302 (KUR-112), Icatibant (JE-049) (HOE-140), lcrocaptide (ITF-1697), IMX-942, lpamorelin (NNC-26-0161), IPP-201101, Iseganan (IB-367), ISF402, Iturelix (ORF-23541), JTP-2942, KAI-1455, KAI-1678, KM-9803, KP-101 (GHRP-1), L-346670, L-364343, Labradimil (RMP-7), Lagatide (BN-52080), Lanreotide (ITM-014), Larazotide (AT-1001) (SPD-550), Leconotide (AM-336), Leuprolide (SOT-375), Linaclotide (MD-1100) (MM-41775), Liraglutide (NN-2211), Lixisenatide (AVE-0010) (ZP-10), LSI-518P, Lucinactant, Lusupultide (BY-2001), LY-2189265, LY-2510924, LY-548806, LYN-001, Lypressin, MER-104, Met-enkephalin (INNO-105), Metkephamide (LY-127623), Mifamurtide (CGP-19835) (MLV-19835), Montirelin (CG-3703), MPL-TLB100, MS peptide, MT-li (PT-14), Murabutide (VA-101) (CY-220), Muramyl tripeptide, Nafarelin (RS-94991), NBI-6024, Nemifitide (INN-00835), Neogen, Nepadutant (MEN-11420), Nesiritide, Nifalatide (BW942C), NNZ-2566, NP-213, NFC-567, NPY (24-36) (PTL-041120), NT-13, Obinepitide (TM-30338), Octreotide (SMS-201-995), Oglufanide (IM-862), OGP 10-14L, Omiganan (CPI-226), OP-145, ORG-2766 Org-42982 (AG-4263), Ornithine vasopressin, Oxytocin, Ozarelix (D-63153) (SPI-153), p-1025, P-113 (PAC-113), Pasireotide (SOM-230), peg-TPOmp (RWJ-800088), Pentigetide(TA-521), Pep-F (5K), Peptide renin inhibitor, Peptide T (AIDS000530), Peptide YY 3-36, Pexiganan (MSI- 78), PF-4603629, PI-0824, PI-2301, PL-3994, PLD-116, PMX-53, POL-6326, Posatirelin, PPI-1019, Pralmorelin, Pramlintide, Protirelin, PTH (7-34), PTHrP-(1-36), PTL-0901, PXL-01, R-1516, R-15-K, R-7089, RA peptide, Ramorelix (Hoe-013), RC-3095, Re-188-P-2045 (P2045), rGRF, Romiplostim (AMG-531), Romurtide (DJ-7041), ROSE-010 (GTP-010) (LY-307161), Rotigaptide (ZP-123) (GAP-486), Rusalatide (TP-508), SAN-134, Saralasin (P-113), Secretin (human) (PGN-52) (R-52), Secretin (human) (RG-1068), Semaglutide (NN-9535), SGS-111 Sifuvirtide, SKF-101926, SKF-105494, SKF-110679 (U-75799E), Soblidotin (YHI-501) (TZT-1027), Somatostatin, Somatostatin (D-Trp, D-Cys analog), SP-304 (Guanilib), SPC-3, SPI-1620, SST analog, SUN-11031, SUN-E7001 (CS-872), SYN-1002, Tabilautide (RP-56142), TAK-448, TAK-683, Taltirelin (TA-0910), Tasidotin (ILX-651) (BSF-223651), Taspoglutide (BIM-51077), TCMP-80, Teduglutide(ALX-0600), Teriparatide (LY-333334), Terlakiren (CP-80794), Terlipressin, Tesamorelin (TH-9507), Teverelix (EP-24332), TH-0318, TH-9506, Thymalfasin, Thymodepressin, Thymonoctan (FCE-25388), Thymopentin (TP-5), Thymosin beta-4, Tifuvirtide (R-724) (T-1249), Tigapotide (PCK-3145), Tiplimotide (NBI-5788), TKS-1225 (Oxyntomodulin), TLN-232 (CAP-232)(TT-232), TM-30339, TP-9201, TRI-1144, Tridecactide (AP-214), Triletide (Z-420) (ZAMI-420), Triptorelin (WY-42462), TT-223 (E1-INT), TT-235, TX14(A), Tyroserleutide (CMS-024), Tyroservatide (CMS-024-02), Ularitide (CDD-95-126) (ESP-305), Unacylated ghrelin (AZP-01) (TH-0332), Urocortin 11, Vapreotide (RC-160), Vasopressin, VIR-576, Xen-2174, XG-102, XOMA-629, Ziconotide (SNX-111), ZP-120, and ZP-1846.

In certain embodiments, compounds of Formula (V) and (VII) are selected from the group consisting of aza-analogues of AC-2592, AC-625, Anaritide, APL-180, Atriopeptin, BGC-728, Carperitide (SUN-4936), CD-NP, CG-77X56, D-4F (APP-018), Danegaptide (ZP-1609) (WAY-261134) (GAP-134), DMP-728 (DU-728), Efegatran (LY-294468), EMD-73495, Eptifibatide (C68-22), ET-642 (RLT-peptide), FE 202158, FX-06, Icatibant (JE-049) (HOE-140), lcrocaptide (ITF-1697), KAI-1455, KM-9803, L-346670, L-364343, LSI-518P, Nesiritide, Peptide renin inhibitor, PL-3994, Rotigaptide (ZP-123) (GAP-486), Saralasin (P-113), SKF-105494, Terlakiren (CP-80794), Tridecactide (AP-214), Ularitide (CDD-95-126) (ESP-305), Urocortin 11, Ziconotide (SNX-111), and ZP-120; and have utility in the treatment of cardiovascular diseases.

In certain embodiments, compounds of Formula (V) and (VII) are selected from the group consisting of aza-analogues of Azetirelin (YM-14673), Conantokin G, Corticorelin (NEU-3002), CTS-21166 (ASP-1702) (ATG-Z1) (OM-00-3) (OM-99-2), Davunetide (AL-108) (AL-208), Deltibant (CP-0127), Ebiratide (Hoe-427), FGLL, Glypromate, JTP-2942, Montirelin (CG-3703), Nemifitide (INN-00835), NNZ-2566, NT-13, ORG-2766, Peptide T (AIDS000530), Posatirelin, PPI-1019, Protirelin, Secretin (human) (RG-1068), SGS-111, Taltirelin (TA-0910), XG-102, and Ziconotide (SNX-111), and have utility in the treatment of CNS disorders.

In certain embodiments, compounds of Formula (V) and (VII) are selected from the group consisting of aza-analogues of A-6, Abarelix (PPI-149), ABT-510, ADH-1, AEZS-108 (AN-152) (ZEN-008), Ambamustine (PTT-119), Antagonist G (PTL-68001), ATN-161, Avorelin (EP-23904), Buserelin, Carfilzomib (PR-171), CBP-501, Cemadotin (LU-103793), Chlorotoxin (TM-601), Cilengitide (EMD-121974) (EMD-85189), CTCE-9908, CVX-045, CVX-060, Degarelix (FE 200486), Didemnin B (NSC-325319), DRF-7295, Edotreotide (SMT-487), Elisidepsin (PM-02734), EP-100, Glutoxim (NOV-002), Goralatide (BIM-32001), Goserelin (ICI-118630),Histrelin, Labradimil (RMP-7), Leuprolide (SOT-375), LY-2510924, Met-enkephalin (INNO-105), Mifamurtide (CGP-19835) (MLV-19835), Muramyl tripeptide, Ozarelix (D-63153) (SPI-153), POL-6326, Ramorelix (Hoe-013), RC-3095, Re-188-P-2045 (P2045), Romurtide (DJ-7041), Soblidotin (YHI-501) (TZT-1027), SPI-1620, Tabilautide (RP-56142), TAK-448, TAK-683, Tasidotin (ILX-651) (BSF-223651), Teverelix (EP-24332), Tigapotide (PCK-3145), TLN-232 (CAP-232)(TT-232), Triptorelin (WY-42462), Tyroserleutide (CMS-024), Tyroservatide (CMS-024-02), ZP-1848, in ZT0131; and have utility in the treatment of oncological conditions.

In certain embodiments, compounds of Formula (V) and (VII) are selected from the group consisting of aza-analogues of A-623 (AMG-623), AG-284, AI-502, Allotrap 2702 (B-2702), AZD-2315, Cnsnqic-Cyclic (802-2), Delmitide (RDP-58), Dirucotide (MBP-8298) Disitertide (NAFB-001) (P-144), dnaJP1 (AT-001), Edratide (TV-4710), F-991, FAR-404, Glaspimod (SKF-107647), Glatiramer (COP-1), GMDP, IPP-201101, Icatibant (JE 049)(HOE-140), MS peptide, Org-42982 (AG-4263), Pentigetide(TA-521), PI-0824, PI-2301, PLD-116, PMX-53, PTL-0901, RA peptide, TCMP-80, Thymodepressin, Thymopentin (TP-5), Tiplimotide (NBI-5788), and ZP-1848; and have utility in the treatment of allergy and immunology disorders.

In certain embodiments, compounds of Formula (V) and (VII) are selected from the group consisting of aza-analogues of A-71378, AC-162352 (PYY 3-36), AC-253, AG2/102, AKL-0707 (LAB GHRH), Albiglutide (GSK-716155), AOD-9604, BAY-73-7977, BIM-44002, BMS-686117, BRX-0585, CJC-1131 (DAC:GLP-1), CJC-1134 (PC-DAC) (Exendin-4), CJC-1295 (DAC:GRF), CP-95253, CVX-096 (PF-4856883), Davalintide (AC-2307), Exenatide (AC-2993) (LY-2148568), Exsulin (INGAP Peptide), Glucagon, ISF402, Liraglutide (NN-2211), Lixisenatide (AVE-0010) (ZP-10), LY-2189265, LY-548806, nafarelin (RS 94991), NBI-6024, Obinepitide (TM-30338), Peptide YY 3-36, PF-4603629, Pramlintide, R-7089, Semaglutide (NN-9535), SST analog, SUN-E7001 (CS-872), Taspoglutide (BIM-51077), Tesamorelin (TH-9507), TH-0318, TKS-1225 (Oxyntomodulin), TM-30339, TT-223 (El-INT), Unacylated ghrelin (AZP-01) (TH-0332), and ZT0131, and have utility in the treatment of metabolic disordrs.

In certain embodiments, compounds of Formula (V) and (VII) are selected from the group consisting of aza-analogues of A-75998, Buserelin, Cetrorelix (NS-75), Detirelix (RS-68439), Ganirelix (Org-37462) (RS-26306), Iturelix, Nafarelin (RS-94991), and triproletin (WY-42462); and have utility in the treatment of fertility.

In certain embodiments, compounds of Formula (V) and (VII) are selected from the group consisting of aza-analogues of AC-100 and p-1025, and have utility in the treatment of dental disorders.

In certain embodiments, compounds of Formula (V) and (VII) are selected from the group consisting of aza-analogues of ACV-1, Conantokin G, CJC-1008 (DAC: Dynorphin A), Contulakin G (CGX-1007), CR-665, CR-845, Dynorphin A, E-2078, Felypressin, Frakefamide (LEF-576) (SPD-759) (BCH-3963), HP-228, Icatibant (JE-049) (HOE-140), KAI-1678, Leconotide (AM-336), Metkephamide (LY-127623), MPL-TLB100, NT-13, SYN-1002, TX14(A), Xen-2174, and Ziconotide (SNX-111); and have utility in the treatment of pain.

In certain embodiments, compounds of Formula (V) and (VII) are selected from the group consisting of aza-analogues of Afamelanotide (EP-1647) (CUV-1647) (Melanotan I), AZX-100, DPK-060, DSC-127, Hemoparatide (PTH (1-37)), Hexapeptide copper II (PC-1358), Pexiganan (MSI-78), PTH (7-34), PXL-01, SKF-110679 (U-75799E), and Thymosin beta-4; and have utility in the treatment of dermatologic conditions.

In certain embodiments, compounds of Formula (V) and (VII) are selected from the group consisting of aza-analogues of AF-37702, Bivalirudin (BG-8865), carfilomib, (PR-171), CTCE-0214, ETRX 101, H-142, OGP 10-14L, Ornithine vasopressin, peg-TPOmp (RWJ-800088), R-1516, Romiplostim (AMG-531), and TP-9201; and have utility in the treatment of hematology disorders.

In certain embodiments, compounds of Formula (V) and (VII) are selected from the group consisting of aza-analogues of Albuvirtide, ALG-889, Alloferon, ALX-40-4C, CB-182804, CB-183315, CZEN-002, Enfuvirtide (T-20), Glucosamyl muramyl tripeptide, Golotimod (SCV-07), GPG-NH2, hLF(1-11), IMX-942, Iseganan (IB-367), Murabutide (VA-101) (CY-220), Neogen, NP-213, Oglufanide (IM-862), Omiganan (CPI-226), OP-145, p-1025, P-113 (PAC-113), Pep-F (5K), R-15-K, Sifuvirtide, SPC-3, Thymalfasin, Thymonoctan (FCE-25388), Tifuvirtide (R-724) (T-1249), TRI-1144, VIR-576, and XOMA-629; and have utility as an antimicrobial or antiviral agent.

In certain embodiments, compounds of Formula (V) and (VII) are selected from the group consisting of aza-analogues of ALTY-0601, B27PD, BDM-E, BIM-23190, CBT-101, Compstatin (POT-4), Eledoisin (ELD-950), and LYN-001, and have utility in the treatment of ophthalmologic disorders.

In certain embodiments, compounds of Formula (V) and (VII) are selected from the group consisting of aza-analogues of Atosiban (ORF-22164), Barusiban (FE-200400), Carbetocin, Cargutocin (Y-5350), Deslorelin, Oxytocin, and TT-235, and have utility in the treatment of OB-GYN disorders.

In certain embodiments, compounds of Formula (V) and (VII) are selected from the group consisting of aza-analogues of Aviptadil (PSD-510), Bremelanotide (PT-141), C-peptide (SPM-933), Desmopressin, EA-230, Lypressin, MER-104, MT-Il (PT-14), SKF-101926, and Vasopressin, and have utility in the treatment of urologic conditions.

In certain embodiments, compounds of Formula (V) and (VII) are selected from the group consisting of aza-analogues of AC-100, BA-058, Calcitonin (Human), Calcitonin (Salmon), Elcatonin, I-040302 (KUR-112), PTHrP-(1-36), Rusalatide (TP-508), SAN-134, Teriparatide (LY-333334), and ZT031; and have utility in the treatment of bones and connective tissue disorders.

In certain embodiments, compounds of Formula (V) and (VII) are selected from the group consisting of aza-analogues of BIO-1211, CGRP (LAB-CGRP), Glucosamyl muramyl tripeptide, GMDP, Icrocaptide (ITF-1697), Lucinactant, Lusupultide (BY-2001), NPC-567, NPY (24-36) (PTL-041120), and Secretin (human) (PGN-52) (R-52); and have utility in the treatment of respiratory conditions.

In certain embodiments, compounds of Formula (V) and (VII) are selected from the group consisting of aza-analogues of Casokefamide, CCK (25-33), Lagatide (BN-52080), Larazotide (AT-1001) (SPD-550), Linaclotide (MD-1100) (MM-41775), Nepadutant (MEN-11420), Nifalatide (BW942C), ROSE-010 (GTP-010) (LY-307161), Somatostatin, Somatostatin (D-Trp, D-Cys analog), SP-304 (Guanilib), Teduglutide(ALX-0600), Terlipressin, Triletide (Z-420) (ZAMI-420), Vapreotide (RC-160), ZP-1846, and ZP-1846; and have utility in the treatment of gastroenterologic disorders.

In certain embodiments, compounds of Formula (V) and (VII) are selected from the group consisting of aza-analogues of CJC-1295 (DAC:GRF), DG-3173 (PTR-3173), Dopastatin (BIM-23A760), EP-51216 (EP-51389), Examorelin (EP-23905) (MF-6003), GTP-200 (GTP-300), lpamorelin (NNC-26-0161), Iturelix (ORF-23541), KP-101 (GHRP-1), Lanreotide (ITM-014), Octreotide (SMS-201-995), Pasireotide (SOM-230), Pralmorelin, rGRF, SUN-11031, TH-9506, ZT0131, and vapreotide (RC-160); and have utility in the treatment of endocrinology disorders.

Compounds of Formula (VI) and (VIII)

Compounds of Formula (VI) and (VIII) are compounds that have utility in drug discovery, diagnosis, treatment and prevention of a disease.

Compounds of Formula (VI) and (VIII) differ from the compounds of Formula (V), (VII), (IX), and (X) in that compounds of Formula (V), (VII), (IX), and (X) comprise

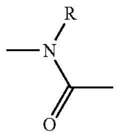

instead of

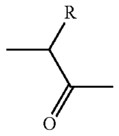

at or adjacent to a cleavage and/or a hydrolysis site and/or at the N-terminus and/or the C-terminus of the compound of Formula (VI) or (VIII). R may be selected, e.g., from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, the cleavage site is between the $2^{nd}$ and $3^{rd}$, $4^{th}$ and $5^{th}$, $6^{th}$ and $7^{th}$, $7^{th}$ and $8^{th}$, $8^{th}$ and $9^{th}$ and $10^{th}$ and $11^{th}$, $10^{th}$ and $11^{th}$, $15^{th}$ and $16^{th}$, $20^{th}$ and $21^{st}$, $24^{th}$ and $25^{th}$, $30^{th}$ and $31^{st}$, $33^{rd}$ and $34^{th}$, $36^{th}$ and $37^{th}$, $39^{th}$ and $40^{th}$, $50^{th}$ and $51^{st}$, $24^{th}$ and $55^{th}$, $58^{th}$ and $59^{th}$, $63^{rd}$ and $64^{th}$, $66^{th}$ and $67^{th}$, $69^{th}$ and $70^{th}$, $72^{nd}$ and $73^{rd}$, $75^{th}$ and $76^{th}$, $79^{th}$ and $80^{th}$, $82^{nd}$ and $83^{rd}$, $85^{th}$ and $86^{th}$, $88^{th}$ and $89^{th}$, $91^{st}$ and $99^{th}$, $105^{th}$ and $106^{th}$, $114^{th}$ and $115^{th}$ amino acid of the peptide (the numbering starting from the C-terminus of the peptide). In certain embodiments, the cleavage site is Ala-Glu.

Proteins and peptides undergo proteolysis. This process is catalysed by cellular enzymes called proteases. Proteases can be classified into seven broad groups: (i) serine proteases, (ii) cysteine proteases, (iii) threonine proteases, (iv) aspartic proteases, (v)glutamic proteases, (vi) metalloproteases, and (vii) asparagine peptide lyases. In certain embodiments, the mechanism used to cleave a peptide bond comprises making an amino acid residue that has the cysteine and threonine (proteases) or a water molecule (aspartic acid, metallo- and acid proteases) nucleophilic so that it can attack the peptide carboxyl group. In certain embodiments, a nucleophile is made by a catalytic triad, where a histidine residue is used to activate serine, cysteine, or threonine as a nucleophile.

Endopeptidase or endoproteinase are proteolytic peptidases that break peptide bonds of nonterminal amino acids (i.e. within the molecule), as compared to exopeptidases, which break peptide bonds from end-pieces of terminal amino acids. For this reason, endopeptidases cannot break down peptides into monomers, while exopeptidases can break down proteins into monomers. A particular case of endopeptidase is the oligopeptidase, whose substrates are oligopeptides instead of proteins. Endopeptidases are usually very specific for certain amino acids. Endopeptidases include, e.g., trypsin (cuts after Arg or Lys, unless followed by Pro), chymotrypsin (cuts after Phe, Trp, or Tyr, unless followed by Pro; and cuts more slowly after His, Met or Leu), elastase (cuts after Ala, Gly, Ser, or Val, unless followed by Pro), thermolysin (cuts before Ile, Met, Phe, Trp, Tyr, or Val, unless preceded by Pro; and sometimes cuts after Ala, Asp, His or Thr), pepsin (cuts before Leu, Phe, Trp or Tyr, unless preceded by Pro; and also others, quite nonspecific), glutamyl endopeptidase (cuts after Glu), and neprilysin An exopeptidase is any peptidase that catalyzes the cleavage of the terminal (or the penultimate) peptide bond. The process releases a single amino acid or dipeptide from the peptide chain. Depending on whether the amino acid is released from the amino or the carboxy terminal, an exopeptidase is further classified as an aminopeptidase or a carboxypeptidase, respectively. Thus, an aminopeptidase, an enzyme in the brush border of the small intestine, will cleave a single amino acid from the amino terminal, whereas carboxypeptidase, which is a digestive enzyme present in pancreatic juice, will cleave a single amino acid from the carboxylic end of the peptide.

Cleavage can also take place via i) intra-molecular digestion, ii) low pH or iii) high temperatures can also cause proteolysis non-enzymatically.

The cleavage and/or a hydrolysis site of the compound of Formula (VI) or compound of Formula (VIII) can be determined by one of ordinary skill in the art without undue experimentation.

In certain embodiments, compounds of Formula (VI) and Formula (VIII) may, e.g., be selected from the group consisting of A-6, blisibimod (A-623), A-71378 (L-Phenylalaninamide, N-(1-oxo-3-(4-(sulfooxy)phenyl)propyl)-L-norleucylglycyl-L-tryptophyl-L-norleucyl-N-methyl-L-alpha-aspartyl), A-75998, Abarelix (PPI-149), ABT-510, AC-100, AC-162352 (PYY 3-36), AC-253, AC-2592, AC-625, ACV-1, ADH-1, AEZS-108 (AN-152) (ZEN-008), AF-37702, Afamelanotide (EP-1647) (CUV-1647) (Melanotan I), AG2/102, AG-284, AI-502, AKL-0707 (LAB GHRH), Albiglutide (GSK-716155), Albuvirtide, ALG-889, Alloferon, Allotrap 2702 (B-2702), ALTY-0601, ALX-40-4C, Ambamustine (PTT-119), Anaritide, Antagonist G (PTL-68001), AOD-9604, APL-180, ATN-161, Atosiban (ORF-22164), Atriopeptin, Aviptadil (PSD-510), Avorelin (EP-23904), AZD-2315, Azetirelin (YM-14673), AZX-100, B27PD, BA-058, Barusiban (FE-200400), BAY-73-7977, BDM-E, BGC-728, BIM-23190, BIM-44002, BIO-1211, Bivalirudin (BG-8865), BMS-686117, Bremelanotide (PT-141), BRX-0585, Buserelin, Calcitonin (Human), Calcitonin (Salmon), Carbetocin, Carfilzomib (PR-171), Cargutocin (Y-5350), Carperitide (SUN-4936), Casokefamide, CB-182804, CB-183315, CBP-501, CBT-101, CCK (25-33), CD-NP, Cemadotin (LU-103793), Cetrorelix (NS-75), CG-77X56, CGRP (LAB-CGRP), Chlorotoxin (TM-601), Cilengitide (EMD-121974) (EMD-85189), CJC-1008 (DAC: Dynorphin A), CJC-1131 (DAC:GLP-1), CJC-1134 (PC-DAC) (Exendin-4), CJC-1295 (DAC:GRF), Cnsnqic-Cyclic (802-2), Compstatin (POT-4), Conantokin G, Contulakin G (CGX-1007), Corticorelin (NEU-3002), CP-95253, C-peptide (SPM-933), CR-665, CR-845, CTCE-0214, CTCE-9908, CTS-21166 (ASP-1702) (ATG-Z1) (OM-00-3) (OM-99-2), CVX-045, CVX-060, CVX-096 (PF-4856883), CZEN-002, D-4F (APP-018), Danegaptide (ZP-1609) (WAY-261134) (GAP-134), Davalintide (AC-2307), Davunetide (AL-108) (AL-208), Degarelix (FE 200486), Delmitide (RDP-58), Deltibant (CP-0127), Deslorelin, Desmopressin, Detirelix (RS-68439), DG-3173 (PTR-3173), Didemnin B (NSC-325319), Dirucotide (MBP-8298) Disitertide (NAFB-001) (P-144), DMP-728 (DU-728), dnaJP1 (AT-001), Dopastatin (BIM-23A760), DPK-060, DRF-7295, DSC-127, Dynorphin A, E-2078, EA-230, Ebiratide (Hoe-427), Edotreotide (SMT-487), Edratide (TV-4710), Efegatran (LY-294468), Elcatonin, Eledoisin (ELD-950), Elisidepsin (PM-02734), EMD-73495, Enfuvirtide (T-20), EP-100, EP-51216 (EP-51389), Eptifibatide (C68-22), ET-642 (RLT-peptide), ETRX 101, Examorelin (EP-23905) (MF-6003), Exenatide (AC-2993) (LY-2148568), Exsulin (INGAP Peptide), F-991, FAR-404, FE 202158, Felypressin, FGLL, Frakefamide (LEF-576) (SPD-759) (BCH-3963), FX-06, Ganirelix (Org-37462) (RS-26306), Glaspimod (SKF-107647), Glatiramer (COP-1), Glucagon, Glucosamyl muramyl tripeptide, Glutoxim (NOV-002), Glypromate, GMDP, Golotimod (SCV-07), Goralatide (BIM-32001), Goserelin (ICI-118630), GPG-NH2, GTP-200, GTP-300, H-142, Hemoparatide (PTH(1-37)), Hexapeptide copper II (PC-1358), Histrelin, hLF(1-11), HP-228, I-040302 (KUR-112), Icatibant (JE-049) (HOE-140), lcrocaptide (ITF-1697), IMX-942, lpamorelin (NNC-26-0161), IPP-201101, Iseganan (IB-367), ISF402, Iturelix (ORF-23541), JTP-2942, KAI-1455, KAI-1678, KM-9803, KP-101 (GHRP-1), L-346670, L-364343, Labradimil (RMP-7), Lagatide (BN-52080), Lanreotide (ITM-014), Larazotide (AT-1001) (SPD-550), Leconotide (AM-336), Leuprolide (SOT-375), Linaclotide (MD-1100) (MM-41775), Liraglutide (NN-2211), Lixisenatide (AVE-0010) (ZP-10), LSI-518P, Lucinactant, Lusupultide (BY-2001), LY-2189265, LY-2510924, LY-548806, LYN-001, Lypressin, MER-104, Met-enkephalin (INNO-105), Metkephamide (LY-127623), Mifamurtide (CGP-19835) (MLV-19835), Montirelin (CG-3703), MPL-TLB100, MS peptide, MT-li (PT-14), Murabutide (VA-101) (CY-220), Muramyl tripeptide, Nafarelin (RS-94991), NBI-6024, Nemifitide (INN-00835), Neogen, Nepadutant (MEN-11420), Nesiritide, Nifalatide (BW942C), NNZ-2566, NP-213, NFC-567, NPY (24-36) (PTL-041120), NT-13, Obinepitide (TM-30338), Octreotide (SMS-201-995), Oglufanide (IM-862), OGP 10-14L, Omiganan (CPI-226), OP-145, ORG-2766 Org-42982 (AG-4263), Ornithine vasopressin, Oxytocin, Ozarelix (D-63153) (SPI-153), p-1025, P-113 (PAC-113), Pasireotide (SOM-230), peg-TPOmp (RWJ-800088), Pentigetide(TA-521), Pep-F (5K), Peptide renin inhibitor, Peptide T (AIDS000530), Peptide YY 3-36, Pexiganan (MSI-78), PF-4603629, PI-0824, PI-2301, PL-3994, PLD-116, PMX-53, POL-6326, Posatirelin, PPI-1019, Pralmorelin, Pramlintide, Protirelin, PTH (7-34), PTHrP-(1-36), PTL-0901, PXL-01, R-1516, R-15-K, R-7089, RA peptide, Ramorelix (Hoe-013), RC-3095, Re-188-P-2045 (P2045), rGRF, Romiplostim (AMG-531), Romurtide (DJ-7041), ROSE-010 (GTP-010) (LY-307161), Rotigaptide (ZP-123) (GAP-486) (N-Acetyl-D-tyrosyl-D-prolyl-(4S)-4-hydroxy-D-prolylglycyl-D-alanylglycinamide), Rusalatide (TP-508), SAN-134, Saralasin (P-113), Secretin (human) (PGN-52) (R-52), Secretin (human) (RG-1068), Semaglutide (NN-9535), SGS-111, Sifuvirtide, SKF-101926, SKF-105494, SKF-110679 (U-75799E), Soblidotin (YHI-501) (TZT-1027), Somatostatin, Somatostatin (D-Trp, D-Cys analog), SP-304 (Guanilib), SPC-3, SPI-1620, SST analog, SUN-11031, SUN-E7001 (CS-872), SYN-1002, Tabilautide (RP-56142), TAK-448, TAK-683, Taltirelin (TA-0910), Tasidotin (ILX-651) (BSF-223651), Taspoglutide (BIM-51077), TCMP-80, Teduglutide(ALX-0600), Teriparatide (LY-333334), Terlakiren (CP-80794), Terlipressin, Tesamorelin (TH-9507), Teverelix (EP-24332), TH-0318, TH-9506, Thymalfasin, Thymodepressin, Thymonoctan (FCE-25388), Thymopentin (TP-5), Thymosin beta-4, Tifuvirtide (R-724) (T-1249), Tigapotide (PCK-3145), Tiplimotide (NBI-5788), TKS-1225 (Oxyntomodulin), TLN-232 (CAP-232)(TT-232), TM-30339, TP-9201, TRI-1144, Tridecactide (AP-214), Triletide (Z-420) (ZAMI-420), Triptorelin (WY-42462), TT-223 (El-INT), TT-235, TX14(A), Tyroserleutide (CMS-024), Tyroservatide (CMS-024-02), Ularitide (CDD-95-126) (ESP-305), Unacylated ghrelin (AZP-01) (TH-0332), Urocortin 11, Vapreotide (RC-160), Vasopressin, VIR-576, Xen-2174, XG-102, XOMA-629, Ziconotide (SNX-111), ZP-120, ZP-1846, and pharmaceutically acceptable salts thereof.

Synthesis of "Building Blocks"

Protected Hydrazide Building Blocks Preparation

Formation of activated hydrazine precursors in solution prior to their incorporation within a peptide sequence is a part of azapeptide synthesis. Substituted hydrazines are components in the synthesis, and the most common protecting groups for substituted hydrazines in solution and solid phase synthesis of azapeptide are tert-butoxycarbonyl, 9-fluorenylmethoxycarbonyl, 2-(3,5-dimethoxyphenyl)propan-2-yloxycarbonyl and as well as phthalimide. Two synthetic pathways can be used to prepare the protected hydrazides: (1) Reduction of protected hydrazones derived from the reaction of carbazate with either aldehyde or ketone; and (2) alkylation of protected hydrazide with an alkyl halide:

(1)

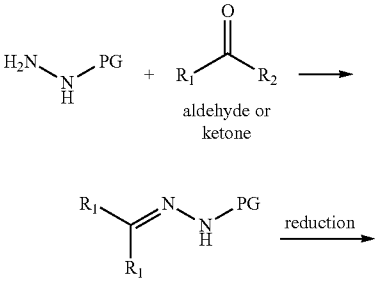

(2)

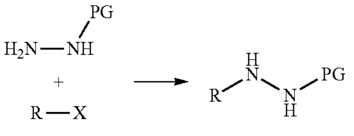

wherein R, $R_1$ and $R_2$ are as defined above, and PG is protecting group.

Preparation of Phth-Protected Carbamoyl Imidazoles

The compounds of Formula (IA), (TB), (II) and (III) may, e.g., be synthesized by reacting a Phth-protected alkyihydrazine derivative with 1,1'-Carbonyldiimidazole (CDI) or 1,1'-carbonyl-bis(3-ethyl imidazolium) triflate (CBET).

Synthesis of the following eight Phth-protected alkyihydrazines was reported with the following yields:

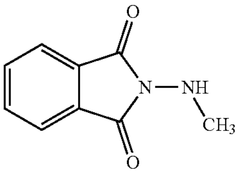

(98% yield)

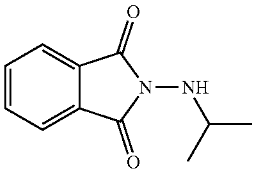

(75% yield)

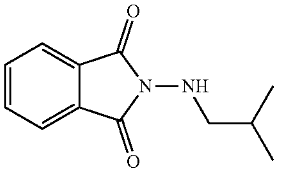

(77% yield)

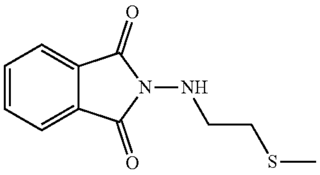

(89% yield)

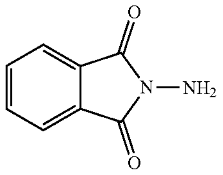

(75% yield)

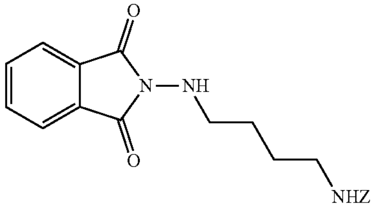

(67% yield)

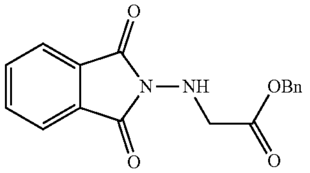

(85% yield)

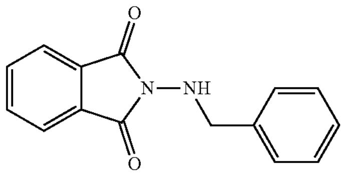

(81% yield)

The following Phth-protected alkylhydrazines can be synthesized by one of the ordinary skill without undue experimentation, in view of the information provided herein and knowledge available in the art:

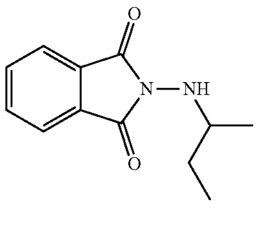

-continued

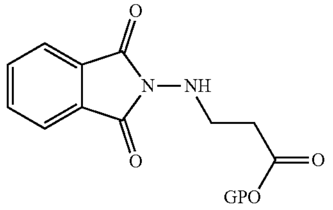

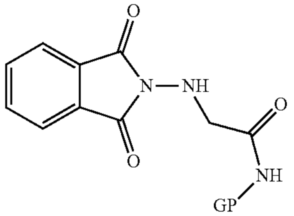

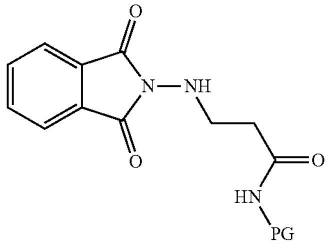

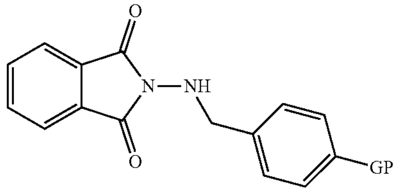

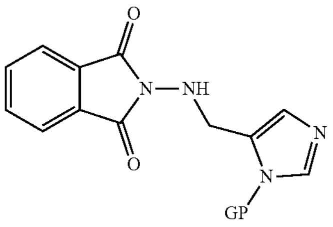

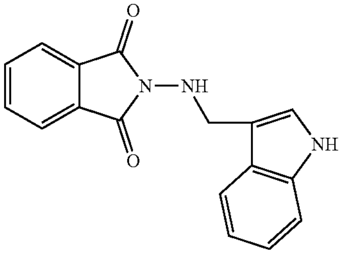

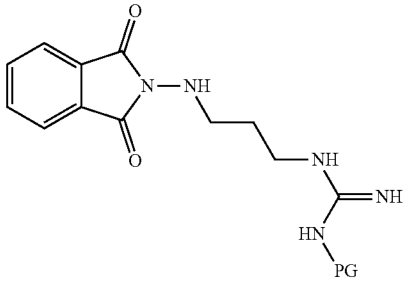

In certain embodiments, the compounds of Formula (IA), (IB), (II) and (III) may, e.g., be synthesized by reacting a Phth-protected alkylhydrazine derivative with 1,1'-Carbonyldiimidazole(CDI):

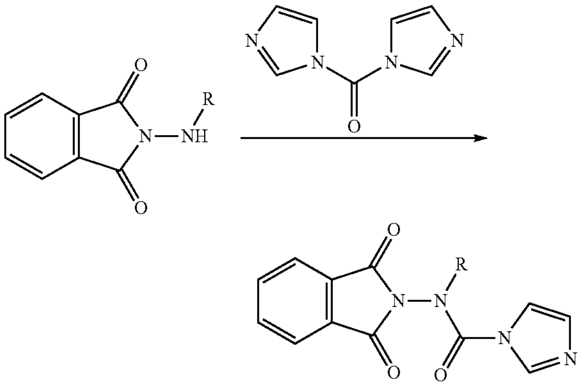

wherein R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine, and the side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

The advantages of this synthetic pathway include, e.g., that Phthalimide group bypasses the intramolecular cyclization side product, allows easy access to the alkylhydrazine monomers by reduction of phthaloyl-protected hydrazones derived from N,N-Phthaloylhydrazine with either an aldehyde or ketone, or, Mitsunobu reaction of alcohol with N-Boc-aminophthalimide, and can be used in both solution and solid phase syntheses. A 60% hydrazine in DMF for 1-3 hours gave the optimal yield in the phthaloyl deprotection in both solution and solid phase syntheses.

The compounds of Formula (IA), (IB), (II) and (III) may also be synthesized by reacting a Phth-protected alkylhydrazine derivative with 1,1'-carbonyl-bis(3-ethylimidazolium) triflate (CBEIT) to form carbamoylimidazolium triflate active building block. CBEIT is an efficient reagent for aminoacylations and peptide couplings:

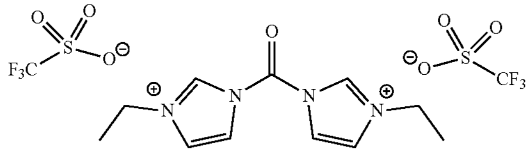

CBEIT

The following synthetic pathway may be used:

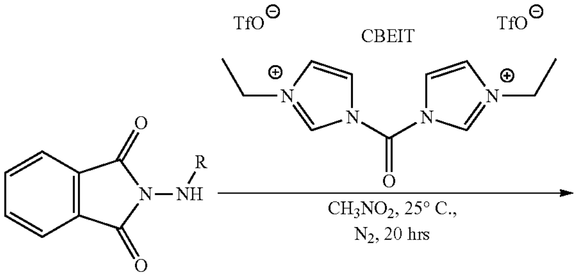

-continued

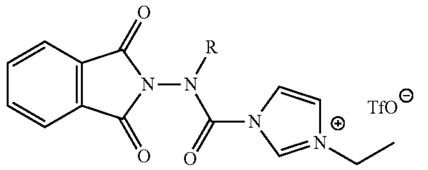

The Phth-protected alkylhydrazine derivative for these syntheses can be made, e.g., by acidic deprotection of a BOC group of phthalimide(Phth)-protected N-alkyl-aminophthalimides, the phthalimide(Phth)-protected N-alkyl-aminophthalimide made by Mitsunobu reaction of N-tert-butyloxycarbonylaminophthalimide with an appropriate alcohol:

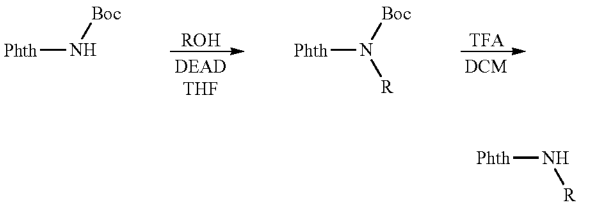

Phth =

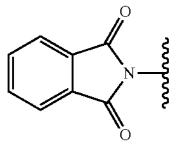

Preparation of Phth-protected Carbamoyl Benzotriazoles

The compounds of Formula (IA), I(B), (II), (III), and (IV) may, e.g., be synthesized by the following scheme:

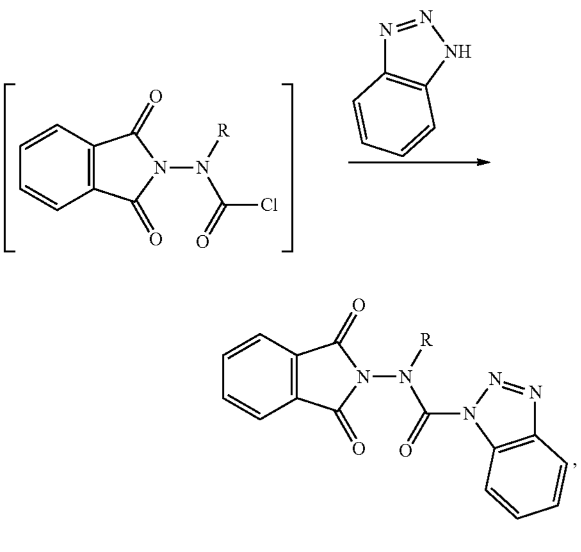

wherein R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine, and the side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurometh, etc.) or a protecting group (e.g., Phth, Boc, Fmoc, Ddz, etc.).

Synthesis of Azapeptides and Azatides

Compounds of Formula (IA), I(B), (II), (III), and (IV) can be coupled in a linear, stepwise, chain-lengthening fashion to each other, amino acids, aza-amino acids, peptides, azapeptides, and azatides by either solution or liquid phase synthetic methodologies to construct compounds of Formulas (V) and (VII).

Compounds of Formula (IA), I(B), (II), (III), and (IV) can also be used, e.g., as sub-monomers to elongate and/or cap peptides and azapeptides.

For example, in certain embodiments, compounds of Formula (IA), I(B), (II), (III), and (IV) may be activated by methylation of imidazole residue using Mel, and the activated compound may be coupled, e.g., a protected or unprotected aza-amino acid; a protected or unprotected a peptide; a protected or unprotected azapeptide; a protected or unprotected azatide; or a protected or unprotected compound of Formula (IA), Formula (IB) Formula (II), Formula (III), or Formula (IV); or a protected or unprotected hydrazine, by either solution or liquid phase synthetic methodologies, e.g., to form a compound of Formula (V) or Formula (VII). The amino acid, the aza-amino acid, the peptide, the azapeptide, compound of Formula (IA), I(B), (II), (III), and (IV) may each be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). The methylation of imidazole residue could, e.g., in acetonitrile at 25° C. under nitrogen for 20 hours.

The methods of the invention may be used to synthesize azapeptides and azatides from 2 to 200 mers in length, e.g., di-azatides, tri-azatides, tetra-azapeptides, penta-azapeptides, etc.

Azapeptide bonds are, e.g., formed by either activation of the hydrazine moiety or by activation of the N-terminus amine of peptides with carbonyl donating reagents. After activation, the aza-building blocks are coupled to either a hydrazine moiety or a peptide N-terminus amine to finish the azapeptide bond formation:

Hydrazide activation by
N-terminus peptide activation by
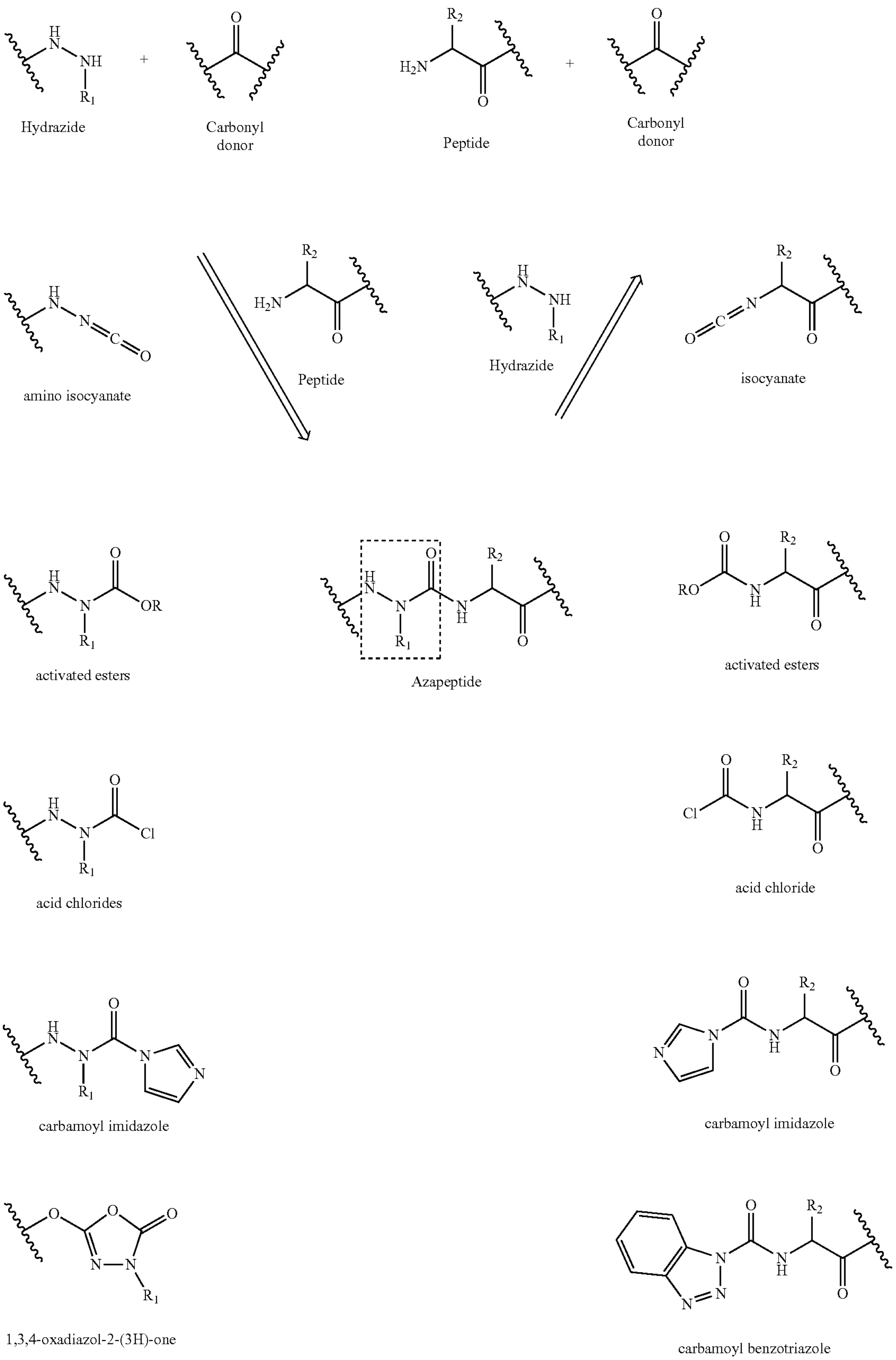
Hydrazide
Carbonyl donor
Peptide
Carbonyl donor
amino isocyanate
Peptide
Hydrazide
isocyanate
activated esters
Azapeptide
activated esters
acid chlorides
acid chloride
carbamoyl imidazole
carbamoyl imidazole
1,3,4-oxadiazol-2-(3H)-one
carbamoyl benzotriazole Following the bond formation, the peptide elongation is continued by conventional peptide synthesis (either solution or solid phase) until the final azapeptide target is reached.

In the methods of the present invention, azapeptides and azatides may be constructed from hydrazides and peptides with carbonyl donating reagents involving a combination of hydrazine chemistry and peptide synthesis:

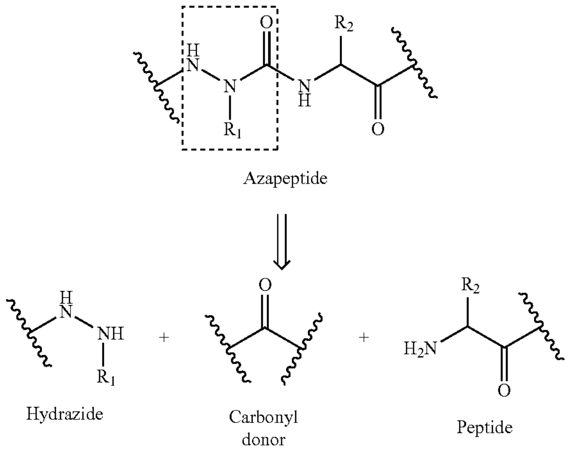

wherein $R_1$ and $R_2$ is each independently selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a C1-C6 alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, $R_1$ and $R_2$ is each independently selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, the hydrazide for this synthesis is a compound of Formula (IA), I(B), (II), (III), or (IV).

In certain embodiments, the carbonyl donor for this synthesis is a compound of Formula (IA), I(B), (II), (III), or (IV).

In certain embodiments, submonomer synthesis of azapeptides comprises constructing the azapeptides directly on a solid support using compounds of Formula (IA), I(B), (II), (III), and (IV). The process comprises acylation of the solid supported peptides with an activated benzylidene carbazate, regioselective alkylation of N-terminal semicarbazone, and deprotection of the semi-carbazone with $NH_2OH \cdot HCl$, then following the conventional Fmoc-based solid-phase peptide synthesis, elongate the azapeptide to the desired target.

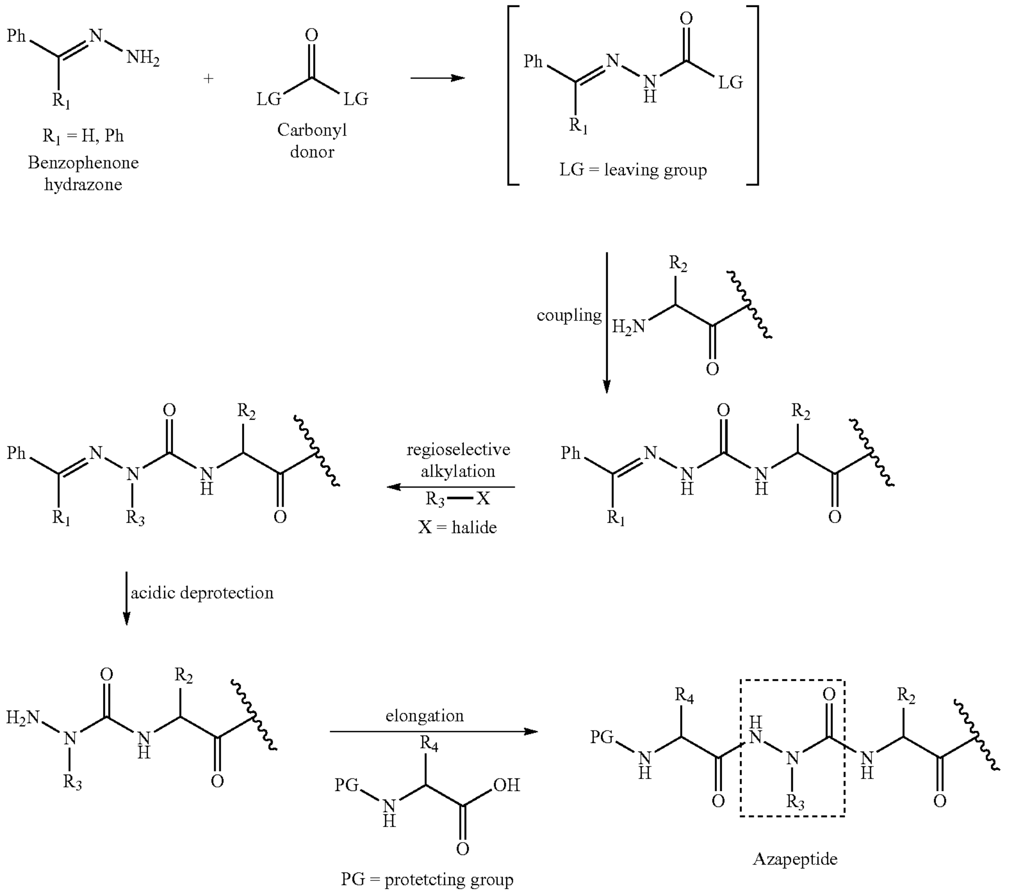

wherein $R_1$, $R_2$, $R_3$, and $R_4$ is each independently selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, $R_1$, $R_2$, $R_3$, and $R_4$ is each independently from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

The submonomer method allows for combinatorial library preparation of side chain and backbone diverse azapeptides for biological SAR studies.

In certain embodiments, the method of preparing an azapeptide or an azatide comprises hydrolysing a peptide, e.g., a compound of Formula (VI) or (VIII) into fragments and reacting one or more fragments with a compound of Formula (IA), (IB), (II), (III), or (VI).

In certain embodiments, the method of preparing an azapeptide or an azatide comprises cleaving a peptide, e.g., a compound of Formula (VI) or (VIII), into fragments and reacting one or more fragments with a compound of Formula (IA), (IB), (II), (III), or (VI).

In certain embodiments, the method of preparing an azapeptide or an azatide comprises cleaving an end of a peptide, e.g., a compound of Formula (VI) or (VIII), and reacting the cleaved peptide with a compound of Formula (IA), (IB), (II), (III), or (VI).

In certain embodiments, the method of preparing an azapeptide or an azatide comprises reacting a compound of Formula (IA), (IB), (II), (III), or (VI) with a truncated peptide.

In certain embodiments, the method of preparing an azapeptide or an azatide comprises conjugating a compound of Formula (IA), (IB), (II), (III), or (VI) with a truncated peptide, e.g., a compound of Formula (VI) or (VII).

In certain embodiments, a method of azapeptide or azatide synthesis comprises reacting (i) an imidazole derivative of an aza-amino acid comprising an aza-amino acid covalently bound (conjugated) to a protecting group at its N-terminus and to imidazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a hydrazide to form an azapeptide. In certain embodiments, the imidazole derivative is a compound of Formula (IA), (IB), (II) and (III).

In certain embodiments, a method of azapeptide or azatide synthesis comprises reacting (i) an imidazole derivative of an aza-amino acid comprising an aza-amino acid covalently bound (conjugated) to a protecting group at its N-terminus and to imidazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a peptide to form the azapeptide or azatide, wherein the azapeptide or azatide is a compound of formula (V) or (VII).

In certain embodiments, a method of azapeptide or azatide synthesis compries reacting (i) a benzotriazole derivative of an aza-amino acid comprising the aza-amino acid covalently bound (conjugated) to a protecting group at its N-terminus and to benzotriazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a hydrazide to form an azapeptide or azatide, wherein the azapeptide or azatide is a compound of formula (V) or (VII).

In certain embodiments, a method of peptide synthesis comprises reacting (i) a benzotriazole derivative of an aza-amino acid comprising the aza-amino acid covalently bound (conjugated) to a protecting group at its N-terminus and to benzotriazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a peptide to form an azapeptide or azapeptide, wherein the azapeptide or azatide is a compound of formula (V) or (VII). The protecting group may, e.g., comprise phthalimide, frorenylmethoxycarbonyl, or 2-(3,5-dimethoxyphenyl)propan-2-yloxycarbonyl.

In certain embodiments, the peptide is therapeutically effective for the treatment of acne, acromegaly, alopecia, anemia, asthma, cancer, age-related macular degeneration, bone cysts, dental caries, cognitive enhancement, cystic fibrosis, chemoprevention, Cushing's syndrome, anorexia nervosa, depression, obsessive-compulsive disorder, diabetic retinopathy, diabetic macular edema, diabetic nephropathy, dyspepsia, brain edema, epilepsy, renal failure, gingivitis, lupus erythematosus, chronic lyphocytic leukemia, obesity, estrogen deficiency, emesis, endometriosis, endometrial thinning, gastrointestinal disorders, gigantism, bone injuries, tooth restoration, heart failure, myocardial infarction, cerebrovascular ischemia, ischemia, unstable angina pectoris, hypertension, isolated systolic hypertension, cardiovascular disease, coronary disorder, atherosclerosis, peripheral artery disease, arrhythmia, pain, vasodilatory hypotension, intradialytic hypotension, stroke, sepsis, thromboembolism, restenosis, hypercalcemia, inflammation, type 1 diabetes, type 2 diabetes, wound healing, eryrthropietic protoporphyria, photodamage, actinic keratosis, myasthenia gravis, multiple sclerosis, transplant rejection, lipid metabolism disorder, malnutrition, HIV, hepatitis, herpes, glaucoma, osteoporosis, erectile dysfunction, rheumatoid arthritis, Alzheimer's disease, dermal scarring, kelid scarring, atopic dermatitis, impetigo, uveitis, uterine contractions, acute coronary syndrome, thrombosis, neutropenia, thrombocytopenia (e.g., heparin-induced thrombocytopenia), female sexual dysfunction, female infertility, postpartum uterine atrophy, postpartum hemorrhage bleeding, Paget's disease, gastric disorders, Gram negative bacterial infection, mycosesm, bacteremia, candidemia, diarrhea, candida ablicans infection, vulvovaginal candidiasis, pancreatic dysfunction, benign prostatic hyperplasia, uterine fibroids, growth disorder, metabolic syndrome, metabolic disorder, HIV-associated lipodystrophy, cachexia, Factor VIII deficiency, multiple sclerosis, graft versus host disease, epilepsy, Parkinson's disease, schizophrenia, functional bowel disease, inflammatory bowel disease, irritable bowel syndrome, ulcerative colitis, Crohn's disease, Celiac disease, short bowel syndrome, ileus, systemic inflammatory response syndrome, brain edema, head injury, precocious puberty, polycystic ovary syndrome, uterine fibroids, nocturia, diabetis insipidus, enuresis, polyuria, primary nocturnal enuresis, Von Willebrand's disease, Hemophilia, hemopoietic disorder, female contraception, male contraception, scleroderma, diabetic foot ulcer, septic shock, cognition disorder, dementia, HIV-associated dementia, mild cognitive impairment, systemic lupus erythematosus, somatotropin deficiency, muscle wasting, skin disorders, reperfusion injury, inhibition of premature LH surges, Leukopenia, drug induced fungal infection, onychomycosis, immune disorder, viral infection, immune deficiency, Huntington's chorea, motor neuron disease, neurodegenerative disorder, psoriasis, tuberculosis, respiratory tract disorders, postoperative infections, lung disorders, radiation sickness, transplant rejection, hereditary angioedema, rhinitis, allergy, asthma, osteoarthritis, liver cirrhosis, respiratory distress syndrome, stomatitis, pneumonia, nutritional disorders, short stature, respiratory distress syndrome, lung malformation, postoperative ileus, vasoactive intestinal peptide, stem cell mobilisation, stem cell transplantation, myelofibrosis, catheter infection, rosacea, otitis, conjunctivitis, neuropathy, control of bleeding, delivery induction, labor initiation, labor stimulation, pemphigus vulgaris, muscle weakness, immune thrombocytopenic purpura, myelodysplastic syndrome, spinal fusion, chronic wounds, bleeding esophageal varices, spinocerebellar degeneration, renal disease, hepatorenal syndrome, insomnia, influenza virus, aspergillus infection, lung infection, primary immunodeficiencies, angiogenesis disorder, recurrent autoimmune cytopenia, decubitus ulcer, varicose ulcer, epidermolysis bullosa, eye surgery, deafness, or labyrinthitis (inflammation of inner ear).

In certain embodiments, the synthesized azapeptide or azatide is therapeutically effective for the treatment of acne, acromegaly, alopecia, anemia, asthma, cancer, age-related macular degeneration, bone cysts, dental caries, cognitive enhancement, cystic fibrosis, chemoprevention, Cushing's syndrome, anorexia nervosa, depression, obsessive-compulsive disorder, diabetic retinopathy, diabetic macular edema, diabetic nephropathy, dyspepsia, brain edema, epilepsy, renal failure, gingivitis, lupus erythematosus, chronic lyphocytic leukemia, obesity, estrogen deficiency, emesis, endometriosis, endometrial thinning, gastrointestinal disorders, gigantism, bone injuries, tooth restoration, heart failure, myocardial infarction, cerebrovascular ischemia, ischemia, unstable angina pectoris, hypertension, isolated systolic hypertension, cardiovascular disease, coronary disorder, atherosclerosis, peripheral artery disease, arrhythmia, pain, vasodilatory hypotension, intradialytic hypotension, stroke, sepsis, thromboembolism, restenosis, hypercalcemia, inflammation, type 1 diabetes, type 2 diabetes, wound healing, eryrthropietic protoporphyria, photodamage, actinic keratosis, myasthenia gravis, multiple sclerosis, transplant rejection, lipid metabolism disorder, malnutrition, HIV, hepatitis, herpes, glaucoma, osteoporosis, erectile dysfunction, rheumatoid arthritis, Alzheimer's disease, dermal scarring, kelid scarring, atopic dermatitis, impetigo, uveitis, uterine contractions, acute coronary syndrome, thrombosis, neutropenia, thrombocytopenia (e.g., heparin-induced thrombocytopenia), female sexual dysfunction, female infertility, postpartum uterine atony, postpartum hemorrhage bleeding, Paget's disease, gastric disorders, Gram negative bacterial infection, mycosesm, bacteremia, candidemia, diarrhea, candida ablicants infection, vulvovaginal candidiasis, pancreatic dysfunction, benign prostatic hyperplasia, uterine fibroids, growth disorder, metabolic syndrome, metabolic disorder, HIV-associated lipodystrophy, cachexia, Factor VIII deficiency, multiple sclerosis, graft versus host disease, epilepsy, Parkinson's disease, schizophrenia, functional bowel disease, inflammatory bowel disease, irritable bowel syndrome, ulcerative colitis, Crohn's disease, Celiac disease, short bowel syndrome, ileus, systemic inflammatory response syndrome, brain edema, head injury, precocious puberty, polycystic ovary syndrome, uterine fibroids, nocturia, diabetis insipidus, enuresis, polyuria, primary nocturnal enuresis, Von Willebrand's disease, Hemophilia, hemopoietic disorder, female contraception, male contraception, scleroderma, diabetic foot ulcer, septic shock, cognition disorder, dementia, HIV-associated dementia, mild cognitive impairment, systemic lupus erythematosus, somatotropin deficiency, muscle wasting, skin disorders, reperfusion injury, inhibition of premature LH surges, Leukopenia, drug induced fungal infection, onychomycosis, immune disorder, viral infection, immune deficiency, Huntington's chorea, motor neuron disease, neurodegenerative disorder, psoriasis, tuberculosis, respiratory tract disorders, postoperative infections, lung disorders, radiation sickness, transplant rejection, hereditary angioedema, rhinitis, allergy, asthma, osteoarthritis, liver cirrhosis, respiratory distress syndrome, stomatitis, pneumonia, nutritional disorders, short stature, respiratory distress syndrome, lung malformation, postoperative ileus, vasoactive intestinal peptide, stem cell mobilisation, stem cell transplantation, myelofibrosis, catheter infection, rosacea, otitis, conjunctivitis, neuropathy, control of bleeding, delivery induction, labor initiation, labor stimulation, pemphigus vulgaris, muscle weakness, immune thrombocytopenic purpura, myelodysplastic syndrome, spinal fusion, chronic wounds, bleeding esophageal varices, spinocerebellar degeneration, renal disease, hepatorenal syndrome, insomnia, influenza virus, aspergillus infection, lung infection, primary immunodeficiencies, angiogenesis disorder, recurrent autoimmune cytopenia, decubitus ulcer, varicose ulcer, epidermolysis bullosa, eye surgery, deafness, or labyrinthitis (inflammation of inner ear).

Methods of Treatment

A method of treating acne, acromegaly, alopecia, anemia, asthma, cancer, age-related macular degeneration, bone cysts, dental caries, cognitive enhancement, cystic fibrosis, chemoprevention, Cushing's syndrome, anorexia nervosa, depression, obsessive-compulsive disorder, diabetic retinopathy, diabetic macular edema, diabetic nephropathy, dyspepsia, brain edema, epilepsy, renal failure, gingivitis, lupus erythematosus, chronic lyphocytic leukemia, obesity, estrogen deficiency, emesis, endometriosis, endometrial thinning, gastrointestinal disorders, gigantism, bone injuries, tooth restoration, heart failure, myocardial infarction, cerebrovascular ischemia, ischemia, unstable angina pectoris, hypertension, isolated systolic hypertension, cardiovascular disease, coronary disorder, atherosclerosis, peripheral artery disease, arrhythmia, pain, vasodilatory hypotension, intradialytic hypotension, stroke, sepsis, thromboembolism, restenosis, hypercalcemia, inflammation, type 1 diabetes, type 2 diabetes, wound healing, eryrthropietic protoporphyria, photodamage, actinic keratosis, myasthenia gravis, multiple sclerosis, transplant rejection, lipid metabolism disorder, malnutrition, HIV, hepatitis, herpes, glaucoma, osteoporosis, erectile dysfunction, rheumatoid arthritis, Alzheimer's disease, dermal scarring, kelid scarring, atopic dermatitis, impetigo, uveitis, uterine contractions, acute coronary syndrome, thrombosis, neutropenia, thrombocytopenia (e.g., heparin-induced thrombocytopenia), female sexual dysfunction, female infertility, postpartum uterine atony, postpartum hemorrhage bleeding, Paget's disease, gastric disorders, Gram negative bacterial infection, mycosesm, bacteremia, candidemia, diarrhea, candida ablicants infection, vulvovaginal candidiasis, pancreatic dysfunction, benign prostatic hyperplasia, uterine fibroids, growth disorder, metabolic syndrome, metabolic disorder, HIV-associated lipodystrophy, cachexia, Factor VIII deficiency, multiple sclerosis, graft versus host disease, epilepsy, Parkinson's disease, schizophrenia, functional bowel disease, inflammatory bowel disease, irritable bowel syndrome, ulcerative colitis, Crohn's disease, Celiac disease, short bowel syndrome, ileus, systemic inflammatory response syndrome, brain edema, head injury, precocious puberty, polycystic ovary syndrome, uterine fibroids, nocturia, diabetis insipidus, enuresis, polyuria, primary nocturnal enuresis, Von Willebrand's disease, Hemophilia, hemopoietic disorder, female contraception, male contraception, scleroderma, diabetic foot ulcer, septic shock, cognition disorder, dementia, HIV-associated dementia, mild cognitive impairment, systemic lupus erythematosus, somatotropin deficiency, muscle wasting, skin disorders, reperfusion injury, inhibition of premature LH surges, Leukopenia, drug induced fungal infection, onychomycosis, immune disorder, viral infection, immune deficiency, Huntington's chorea, motor neuron disease, neurodegenerative disorder, psoriasis, tuberculosis, respiratory tract disorders, postoperative infections, lung disorders, radiation sickness, transplant rejection, hereditary angioedema, rhinitis, allergy, asthma, osteoarthritis, liver cirrhosis, respiratory distress syndrome, stomatitis, pneumonia, nutritional disorders, short stature, respiratory distress syndrome, lung malformation, postoperative ileus, vasoactive intestinal peptide, stem cell mobilisation, stem cell transplantation, myelofibrosis, catheter infection, rosacea, otitis, conjunctivitis, neuropathy, control of bleeding, delivery induction, labor initiation, labor stimulation, pemphigus vulgaris, muscle weakness, immune thrombocytopenic purpura, myelodysplastic syndrome, spinal fusion, chronic wounds, bleeding esophageal varices, spinocerebellar degeneration, renal disease, hepatorenal syndrome, insomnia, influenza virus, aspergillus infection, lung infection, primary immunodeficiencies, angiogenesis disorder, recurrent autoimmune cytopenia, decubitus ulcer, varicose ulcer, epidermolysis bullosa, eye surgery, deafness, or labyrinthitis (inflammation of inner ear), the method comprising administering to a subject in need thereof a therapeutically effective amount of a compound of Formula (V) or (VII).

In certain methods, the compound of Formula (V) or (VII) is a peptidomimetic agent comprising a backbone comprising from 2 to 200 carbonyl groups and α-nitrogen covalently bound to at least one of said carbonyl groups.

In certain methods, the peptidomimetic agent, including compounds of Formula (V) and (VII), is therapeutically effective for the treatment of a disorder in the mammal, while a peptide structurally different from the compound of Formula (V) and (VII) only in that that the peptide comprises α-carbon instead of said α-nitrogen is not therapeutically effective.

In certain methods, the compounds of Formula (V) and (VII) have a therapeutic efficacy greater than a peptide structurally different from the compounds of Formula (V) and (VII) only in that the peptide comprises α-carbon instead of said α-nitrogen.

In certain methods, the compounds of Formula (V) and (VII) have longer duration of therapeutic activity than a peptide structurally different from the compounds of Formula (V) and (VII) only in that the peptide comprises α-carbon instead of said α-nitrogen.

In certain methods, the compounds of Formula (V) and (VII) are more resistant to protease degradation than a peptide structurally different from the compounds of Formula (V) and (VII) only in that the peptide comprises α-carbon instead of said α-nitrogen.

In certain methods, the compounds of Formula (V) and (VII) have a greater selectivity to a biological receptor than a peptide structurally different from the compounds of Formula (V) and (VII) only in that the peptide comprises α-carbon instead of said α-nitrogen.

In certain methods, the compounds of Formula (V) and (VII) have a greater bioavailability than a peptide structurally different from the compound of Formula (V) and Formula (VII) only in that that the peptide comprises α-carbon instead of said α-nitrogen.

In certain embodiments, thrombosis is coronary thrombosis.

In certain embodiments, diarrhea is *Clostridium difficile*-associated diarrhea.

In certain embodiments, diarrhea is chemotherapy induced diarrhea.

In certain embodiments, respiratory distress syndrome is neonatal respiratory distress syndrome.

In certain embodiments, respiratory distress syndrome is adult distress syndrome.

In certain embodiments, said arrhythmia is ventricular arrhythmia.

In certain embodiments, arrhythmia is atrial fibrillation.

In certain embodiments, rhinitis is allergic rhinitis.

In certain embodiments, conjunctivitis is allergic conjunctivitis.

In certain embodiments, osteoporosis is postmenoposal osteoporosis.

In certain embodiments, bone injury is a bone fracture.

In certain embodiments, bacteria is *Staphylococcus aureus.*

In certain embodiments, neuropathy is diabetic neuropathy.

In certain embodiments, anemia is aplastic anemia, hypoplastic anemia,

In certain embodiments, hepatitis is hepatitis A, hepatitis B or hepatitis C.

Cardiovascular Disorders

A method of treating a cardiovascular disorder comprising administering a therapeutically effective amount of a compound of Formula (V) or (VII) to a subject in need thereof.

In certain embodiments, compounds of Formula (V) are (VII) are aza-analogues of a peptide selected from a group consisting of AC-2592, AC-625, Anaritide, APL-180, Atriopeptin, BGC-728, Carperitide (SUN-4936), CD-NP, CG-77X56, D-4F (APP-018), Danegaptide (ZP-1609) (WAY-261134) (GAP-134), DMP-728 (DU-728), Efegatran (LY-294468), EMD-73495, Eptifibatide (C68-22), ET-642 (RLT-peptide), FE 202158, FX-06, Icatibant (JE-049) (HOE-140), icrocaptide (ITF-1697), KAI-1455, KM-9803, L-346670, L-364343, LSI-518P, Nesiritide, Peptide renin inhibitor, PL-3994, Rotigaptide (ZP-123) (GAP-486), Saralasin (P-113), SKF-105494, Terlakiren (CP-80794), Tridecactide (AP-214), Ularitide (CDD-95-126) (ESP-305), Urocortin 11, Ziconotide (SNX-111), and ZP-120.

CNS Disorders

A method of treating a CNS disorder comprising administering a therapeutically effective amount of a compound of Formula (V) or (VII) to a subject in need thereof.

In certain embodimeents, compounds of Formula (V) and (VII) are aza-analogues of a peptide selected from a group consisting of Azetirelin (YM-14673), Conantokin G, Corticorelin (NEU-3002), CTS-21166 (ASP-1702) (ATG-Z1) (OM-00-3) (OM-99-2), Davunetide (AL-108) (AL-208), Deltibant (CP-0127), Ebiratide (Hoe-427), FGLL, Glypromate, JTP-2942, Montirelin (CG-3703), Nemifitide (INN-00835), NNZ-2566, NT-13, ORG-2766, Peptide T (AIDS000530), Posatirelin, PPI-1019, Protirelin, Secretin (human) (RG-1068), SGS-111, Taltirelin (TA-0910), XG-102, and Ziconotide (SNX-111).

Immune System Disorder

A method of treating an immune system disorder comprising administering a therapeutically effective amount of a compound of Formula (V) or (VII).

In certain embodiments, the compounds of Formula (V) and (VII) are aza-analogues of a peptide selected from a group consisting of A-623 (AMG-623), AG-284, AI-502, Allotrap 2702 (B-2702), AZD-2315, Cnsnqic-Cyclic (802-2), Delmitide (RDP-58), Dirucotide (MBP-8298) Disitertide (NAFB-001) (P-144), dnaJPl (AT-001), Edratide (TV-4710), F-991, FAR-404, Glaspimod (SKF-107647), Glatiramer (COP-1), GMDP, IPP-201101, Icatibant (JE 049)(HOE-140), MS peptide, Org-42982 (AG-4263), Pentigetide(TA-521), PI-0824, PI-2301, PLD-116, PMX-53, PTL-0901, RA peptide, TCMP-80, Thymodepressin, Thymopentin (TP-5), Tiplimotide (NBI-5788), and ZP-1848.

Metabolic Disorders

A method of treating a metabolic disorder comprising administering a therapeutically effective amount of a compound of Formula (V) or (VII) to a subject in need thereof.

In certain embodiments, the compounds of Formula (V) and (VII) are aza-analogues of a peptide selected from a group consisting of A-71378, AC-162352 (PYY 3-36), AC-253, AG2/102, AKL-0707 (LAB GHRH), Albiglutide (GSK-716155), AOD-9604, BAY-73-7977, BIM-44002, BMS-686117, BRX-0585, CJC-1131 (DAC:GLP-1), CJC-1134 (PC-DAC) (Exendin-4), CJC-1295 (DAC.GRF), CP-95253, CVX-096 (PF-4856883), Davalintide (AC-2307), Exenatide (AC-2993) (LY-2148568), Exsulin (INGAP Peptide), Glucagon, ISF402, Liraglutide (NN-2211), Lixisenatide (AVE-0010) (ZP-10), LY-2189265, LY-548806, nafarelin (RS 94991), NBI-6024, Obinepitide (TM-30338), Peptide YY 3-36, PF-4603629, Pramlintide, R-7089, Semaglutide (NN-9535), SST analog, SUN-E7001 (CS-872), Taspoglutide (BIM-51077), Tesamorelin (TH-9507), TH-0318, TKS-1225 (Oxyntomodulin), TM-30339, TT-223 (El-INT), Unacylated ghrelin (AZP-01) (TH-0332), and ZT0131.

Fertility

A method of treating fertility comprising administering a therapeutically effective amount of a compound of Formula (V) or (VII) to a subject in need thereof.

In certain embodiments, the compound of Formula V and (VII) are aza-analogues of a peptide selected from a group consisting of A-75998, Buserelin, Cetrorelix (NS-75), Detirelix (RS-68439), Ganirelix (Org-37462) (RS-26306), Iturelix, Nafarelin (RS-94991), and triproletin (WY-42462).

Dental

A method of treating a dental condition comprising administering a therapeutically effective amount of a compound of Formula (V) or (VII) to a subject in need thereof.

In certain embodiments, the compound of Formula (V) and (VII) are aza-analogues of AC-100 or p-1025.

Pain

A method of treating pain comprising administering a therapeutically effective amount of a compound of Formula (V) or (VII).

In certain embodiments, the compounds of Formula (V) and (VII) are aza-analogues of a peptide selected from a group consisting of ACV-1, Conantokin G, CJC-1008 (DAC: Dynorphin A), Contulakin G (CGX-1007), CR-665, CR-845, Dynorphin A, E-2078, Felypressin, Frakefamide (LEF-576) (SPD-759) (BCH-3963), HP-228, Icatibant (JE-049) (HOE-140), KAI-1678, Leconotide (AM-336), Metkephamide (LY-127623), MPL-TLB100, NT-13, SYN-1002, TX14(A), Xen-2174, and Ziconotide (SNX-111).

Dermatology

A method of treating a dermatologic condition comprising administering a therapeutically effective amount of a compound of Formula (V) or (VII) to a subject in need thereof.

In certain embodiments, the compounds of Formula (V) and (VII) are aza-analogues of a peptide selected from a group consisting of afamelanotide (EP-1647) (CUV-1647) (Melanotan I), AZX-100, DPK-060, DSC-127, Hemoparatide (PTH(1-37)), Hexapeptide copper II (PC-1358), Pexiganan (MSI-78), PTH (7-34), PXL-01, SKF-110679 (U-75799E), and Thymosin beta-4.

Blood Disorders

A method of treating a blood disorder comprising administering a therapeutically effective amount of a compound of Formula (V) or (VII) to a subject in need thereof.

In certain embodiments, compounds of Formula (V) and (VII) are aza-analogues of a peptide selected from a group consisting of AF-37702, Bivalirudin (BG-8865), carfilomib, (PR-171), CTCE-0214, ETRX 101, H-142, OGP 10-14L, Ornithine vasopressin, peg-TPOmp (RWJ-800088), R-1516, Romiplostim (AMG-531), and TP-9201.

Infection

A method of treating an infection comprising administering a therapeutically effective amount of a compound of Formula (V) or (VII) to a subject in need thereof.

In certain embodiments, compounds of Formula (V) and (VII) are aza-analogues of a peptide selected from a group consisting of Albuvirtide, ALG-889, Alloferon, ALX-40-4C, CB-182804, CB-183315, CZEN-002, Enfuvirtide (T-20), Glucosamyl muramyl tripeptide, Golotimod (SCV-07), GPG-NH2, hLF(1-11), IMX-942, Iseganan (IB-367), Murabutide (VA-101) (CY-220), Neogen, NP-213, Oglufanide (IM-862), Omiganan (CPI-226), OP-145, p-1025, P-113 (PAC-113), Pep-F (5K), R-15-K, Sifuvirtide, SPC-3, Thymalfasin, Thymonoctan (FCE-25388), Tifuvirtide (R-724) (T-1249), TRI-1144, VIR-576, and XOMA-629.

Eye Disorders

A method of treating an eye disorder comprising administering a therapeutically effective amount of a compound of Formula (V) or (VII) to a subject in need thereof.

In certain embodiments, compounds of Formula (V) or (VII) are aza-analogues of a peptide selected from a group consisting of ALTY-0601, B27PD, BDM-E, BIM-23190, CBT-101, Compstatin (POT-4), Eledoisin (ELD-950), and LYN-001.

Gynecologic Disorder

A method of treating an OB-GYN disorder comprising administering a therapeutically effective amount of a compound of Formula (V) or (VII) to a subject in need thereof.

In certain embodiments, compounds of Formula (V) and (VII) are aza-analogues of a peptide selected from a group consisting of Atosiban (ORF-22164), Barusiban (FE-200400), Carbetocin, Cargutocin (Y-5350), Deslorelin, Oxytocin, and TT-235.

Urologic Disorders

A method of treating a urologic disorder comprising administering a therapeutically effective amount of a compound of Formula (V) or (VII) to a subject in need thereof.

In certain embodiments, compounds of Formula (V) and (VII) are aza-analogues of a peptide selected from a group consisting of Aviptadil (PSD-510), Bremelanotide (PT-141), C-peptide (SPM-933), Desmopressin, EA-230, Lypressin, MER-104, MT-ll (PT-14), SKF-101926, and Vasopressin.

Bone and Connective Tissue Disorders

A method of treating a bone or a connective tissue disorder comprising administering a therapeutically effective amount of a compound of Formula (V) or (VII) to a subject in need thereof.

In certain embodiments, compounds of Formula (V) and (VII) are an aza-analogues of a peptide selected from a group consisting of AC-100, BA-058, Calcitonin (Human), Calcitonin (Salmon), Elcatonin, I-040302 (KUR-112), PTHrP-(1-36), Rusalatide (TP-508), SAN-134, Teriparatide (LY-333334), and ZT031.

Respiratory Disorders

A method of treating a respiratory disorder comprising administering a therapeutically effective amount of a compound of Formula (V) or (VII) to a subject in need thereof.

In certain embodiments, compounds of Formula (V) and (VII) are an aza-analogues of a peptide selected from a group consisting of BIO-1211, CGRP (LAB-CGRP), Glucosamyl muramyl tripeptide, GMDP, Icrocaptide (ITF-1697), Lucinactant, Lusupultide (BY-2001), NPC-567, NPY (24-36) (PTL-041120), and Secretin (human) (PGN-52) (R-52).

Gastrointestinal Tract Disorders

A method of treating a disorder of a gastrointestinal tract comprising administering a therapeutically effective amount of a compound of Formula (V) or (VII).

In certain embodiments, compounds of Formula (V) and (VII) are aza-analogues of a peptide selected from a group consisting of Casokefamide, CCK (25-33), Lagatide (BN-52080), Larazotide (AT-1001) (SPD-550), Linaclotide (MD-1100) (MM-41775), Nepadutant (MEN-11420), Nifalatide (BW942C), ROSE-010 (GTP-010) (LY-307161), Somatostatin, Somatostatin (D-Trp, D-Cys analog), SP-304 (Guanilib), Teduglutide(ALX-0600), Terlipressin, Triletide (Z-420) (ZAMI-420), Vapreotide (RC-160), ZP-1846, and ZP-1846.

Disorders of Endocrine System

A method of treating a disorder of endocrine system comprising administering a therapeutically effective amount of a compound of Formula (V) or (VII) to a subject in need thereof.

In certain embodiments, compounds of Formula (V) and (VII) are aza-analogues of a peptide selected from a group consisting of CJC-1295 (DAC:GRF), DG-3173 (PTR-3173), Dopastatin (BIM-23A760), EP-51216 (EP-51389), Examorelin (EP-23905) (MF-6003), GTP-200 (GTP-300), lpamorelin (NNC-26-0161), Iturelix (ORF-23541), KP-101 (GHRP-1), Lanreotide (ITM-014), Octreotide (SMS-201-995), Pasireotide (SOM-230), Pralmorelin, rGRF, SUN-11031, TH-9506, ZT0131, and vapreotide (RC-160).

Cancer

A method of treating cancer comprising administering a compound of Formula (V) or (VII) to a subject in need thereof.

In certain embodiments, compounds of Formula (V) and (VII) are aza-analogues of a peptide selected from the group consisting of A-6, Abarelix (PPI-149), ABT-510, ADH-1, AEZS-108 (AN-152) (ZEN-008), Ambamustine (PTT-119), Antagonist G (PTL-68001), ATN-161, Avorelin (EP-23904), Buserelin, Carfilzomib (PR-171), CBP-501, Cemadotin (LU-103793), Chlorotoxin (TM-601), Cilengitide (EMD-121974) (EMD-85189), CTCE-9908, CVX-045, CVX-060, Degarelix (FE 200486), Didemnin B (NSC-325319), DRF-7295, Edotreotide (SMT-487), Elisidepsin (PM-02734), EP-100, Glutoxim (NOV-002), Goralatide (BIM-32001), Goserelin (ICI-118630),Histrelin, Labradimil (RMP-7), Leuprolide (SOT-375), LY-2510924, Met-enkephalin (INNO-105), Mifamurtide (CGP-19835) (MLV-19835), Muramyl tripeptide, Ozarelix (D-63153) (SPI-153), POL-6326, Ramorelix (Hoe-013), RC-3095, Re-188-P-2045 (P2045), Romurtide (DJ-7041), Soblidotin (YHI-501) (TZT-1027), SPI-1620, Tabilautide (RP-56142), TAK-448, TAK-683, Tasidotin (ILX-651) (BSF-223651), Teverelix (EP-24332), Tigapotide (PCK-3145), TLN-232 (CAP-232)(TT-232), Triptorelin (WY-42462), Tyroserleutide (CMS-024), Tyroservatide (CMS-024-02), ZP-1848, and ZT0131.

In certain embodiments, the cancer is breast cancer, colorectal cancer, carcinoid cancers, carcinoma, renal cell carcinoma, endometrial carcinoma, glioma, glioblastoma, hepatocellular carcinoma, lymphoma, non-small lung cancer, ovarian cancer, gastrointestinal cancer, pancreatic cancer, prostate cancer, sarcoma, solid tumors, metastatic melanoma, multiple myeloma, malignant melanoma, neuroblastoma, skin cancer, non-hodgkin lymphoma, small-cell lung cancer, non-small-lung cancer, mesothelioma, pancreatic cancer, hematological neoplasm, neuroendocrine tumors, pituitary cancer, uterine cancer, or osteosarcoma.

Inflammation

A method of attenuating HMGB1-driven inflammation without impairing the immune response to microbes with acute lung injury (ALI), comprising administering a compound of Formula (V) or (VII) to a subject in need thereof.

Drug Discovery and Development

In certain embodiments, the invention is directed to a method of increasing in vivo half-life of a therapeutic peptide, the method comprising replacing terminal peptide bonds in the therapeutic peptide with an azapeptide or azatide linkages, thereby providing a compound of Formula (V) or (VII).

embodiments, the invention is directed to a method of increasing in vivo half-life of a therapeutic peptide, the method comprising replacing peptide bonds adjacent to the terminal peptide bonds in the therapeutic peptide with an azapeptide or azatide linkages, thereby providing a compound of Formula (V) or (VII).

In certain embodiments, the invention is directed to a method of increasing in vivo half-life of a therapeutic peptide, the method comprising replacing peptide bonds between the first and second residues of the therapeutic peptide with an azapeptide or azatide linkages, thereby providing a compound of Formula (V) or (VII).

In certain embodiments, the invention is directed to a method of improving therapeutic efficacy of a 2 to 200 amino acid peptide, the method comprising replacing terminal peptide bonds in the therapeutic peptide with an azapeptide or azatide linkages, thereby providing a compound of Formula (V) or (VII).

In certain embodiments, the invention is directed to a method of rendering a peptide therapeutic, the method comprising replacing one or more amino acids of the peptide with a corresponding aza-amino acid, thereby providing a compound of Formula (V) or (VII).

In additional embodiments, the invention is directed to a drug development process comprising synthesizing an aza-analogue of a peptide differing from the peptide in that that an α-carbon of the peptide is replaced with an α-nitrogen by utilizing compounds of Formula (IA), I(B), (II), (III), and (IV). In some of these embodiments, the analogue is therapeutic, and the peptide is not. In certain embodiments, the aza-analogue has a longer duration of therapeutic activity than the peptide. In certain embodiments, the aza-analogue analogue has a longer half-life than the peptide. In certain embodiments, the aza-analogue has has an improved efficacy, as compared to the peptide. In certain embodiments, the aza-analogue is more stable to protease degradation than the peptide. In certain embodiments, the aza-analogue has less adverse effects than the peptide.

Methods of Improving Efficacy

A method of improving efficacy of a 2 to 50 amino acid peptide comprising providing an analogue of a peptide, the analogue differing from the peptide in that at least one of the amino acids of the peptide is replaced with a corresponding aza-amino acid, wherein the analogue is a compound of Formula (V) or (VII).

Methods of Modulating a Protease Activity

A method of modulating a protease activity comprising exposing the peptidase to an analogue of a 2 to 50 peptide, the analogue differing from the peptide in that at least one of the amino acids of the peptide is replaced with a corresponding aza-amino acid, wherein the analogue is a compound of Formula (V) or (VII).

Methods of Inhibiting a Peptidase

A method of inhibiting a peptidase in a subject comprising administering an analogue of a peptide to the subject, the analogue differing from the peptide in that at least one of the amino acids of the peptide is replaced with a corresponding aza-amino acid, wherein the analogue is a compound of Formula (V) or (VII).

In certain embodiments, the peptidase is an endopeptidase.

In certain embodiments, the peptidase is an exopeptidase.

In certain embodiments, the peptidase is an aspartic protease, a glutamic protease or an asparagine peptide lyase.

In certain embodiments, the peptidase is a retroviral protease.

Pharmaceutical Compositions

Pharmaceutical compositions in accordance with the invention comprise a compound of Formula (V) or Formula (VI) and one or more pharmaceutically acceptable excipient(s).

The pharmaceutically acceptable excipients are described in the the Handbook of Pharmaceutical Excipients, Pharmaceutical Press and American Pharmacists Association, sixth ed., (2009), incorporated by reference herein, for all purposes.

The pharmaceutical compositions are designed to be appropriate for the selected mode of administration, and pharmaceutically acceptable excipients such as, e.g., compatible dispersing agents, buffers, surfactants, preservatives, solubilizing agents, isotonicity agents, stabilizing agents and the like are used as appropriate.

The concentration of the compounds of Formula (V) and Formula (VII) in compositions to be administered is an effective amount and ranges from as low as about 0.1% by weight to as much as about 95% or about 99.9% by weight.

Typical therapeutically effective amounts or doses can be determined and optimized using standard clinical techniques and will be dependent on the mode of administration in view of the information provided herein and knowledge available in the art.

In certain embodiments, the therapeutically effective amount is a total daily dose of from about 0.0003 to about 50 mg of a compound of Formula (V) or (VI) per kg of body weight of the subject.

The pharmaceutical compositions can be formulated, e.g., for oral administration in solid or liquid form, for parenteral intravenous, subcutaneous, intramuscular, intraperitoneal, intra-arterial, or intradermal injection, for or for vaginal, nasal, topical, or rectal administration.

Pharmaceutical compositions of the present invention suitable for oral administration can be presented as discrete dosage forms, e.g., tablets, chewable tablets, caplets, capsules, liquids, and flavored syrups. Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Parenteral dosage forms can be administered to subjects by various routes including subcutaneous, intravenous (including bolus injection), intramuscular, and intraarterial. Because their administration typically bypasses patients, natural defenses against contaminants, parenteral dosage forms are specifically sterile or capable of being sterilized prior to administration to a patient. Examples of parenteral dosage forms include, e.g., solutions ready for injection, dry products ready to be dissolved or suspended in a pharmaceutically acceptable vehicle for injection, suspensions ready for injection, and emulsions. Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions.

Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants. These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof. If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by, e.g., forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed, e.g., with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration include, e.g., suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include, e.g., pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include, e.g., ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Ophthalmic formulation, ear drops, eye ointments, powders and solutions are also contemplated as being within the scope of this invention.

Powders and sprays can contain, in addition to the compounds of this invention, e.g., lactose, talc, silicic acid, aluminum hydroxide, calcium silicates and polyamide powder, or mixtures of these substances. Sprays can additionally contain customary propellants such as, e.g., chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Actual dosage levels of active ingredients in the pharmaceutical compositions of the invention can be varied so as to obtain an amount of the active compound(s) that is effective to achieve the desired therapeutic response for a particular subject, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

An effective amount of one of the compounds of the invention can be employed in pure form or, where such forms exist, in pharmaceutically acceptable salt form. Alternatively, the compound can be administered as a pharmaceutical composition containing the compound of interest in combination with one or more pharmaceutically acceptable excipient(s). It will be understood, however, that the total daily usage of the compounds and compositions of the invention will be decided by the attending physician within the scope of sound medical judgment. The specific effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; the risk/benefit ratio; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention as administered to a human or lower animal may range from about 0.0003 to about 50 mg/kg of body weight. For purposes of oral administration, more preferable doses can be in the range of from about 0.0003 to about 5 mg/kg body weight. If desired, the effective daily dose can be divided into multiple doses for purposes of administration; consequently, single dose compositions may contain such amounts or submultiples thereof to make up the daily dose. For oral administration, the compositions of the invention are preferably provided in the form of tablets containing about 1.0, about 5.0, about 10.0, about 15.0, about 25.0, about 50.0, about 100, about 250, or about 500 milligrams of the compound of Formula (V) or (VII).

Administration

Compounds of Formula (V) and (VII) can be used as therapy to treat a variety of disorders.

Effective doses of the compounds of Formula (V) and Formula (VII), for the treatment of the above described conditions vary depending upon many different factors, including means of administration, target site, physiological state of the patient, other medications administered, and whether treatment is diagnostic, prophylactic or therapeutic. One of the ordinary skill in the art can determine effective doses of compounds of Formula (V) and (VII) without undue experimentation.

Administration is performed using standard effective techniques, including, e.g., orally, intravenously, intraperitonealy, subcutaneously, via inhalation, transdermally, intramuscullary, intranasaly, buccaly, sublingualy, or via suppository administration.

Humans amenable to treatment include individuals at risk of disease but not showing symptoms, as well as patients presently showing symptoms.

Example 1

Preparation of Boc-Protected Alkylhydrazines

Janda's group proposed the preparation of 20 Boc-protected alkylhydrazines by alkylation of hydrazine with an alkyl halide followed by Boc-protection [56]. Six of the Boc-protected alkylhydrazine monomers were reported and used as the building blocks to construct diazatides by solution phase synthesis and Leu-Enkephalin azatides by PEG-supported liquid phase synthesis:

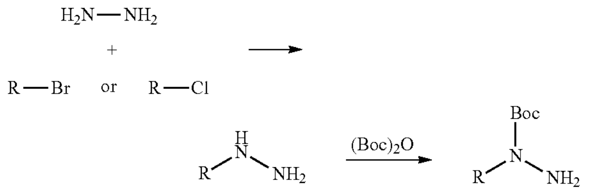

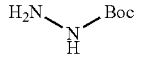

with Gly-R-group

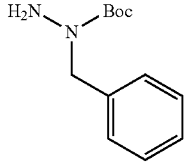

with Phe-R-group

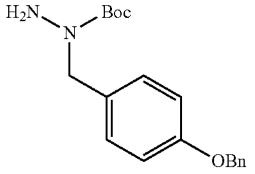

with Tyr-R-group

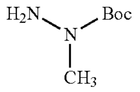

with Ala-R-group

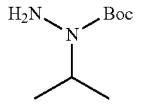

with Val-R-group

-continued

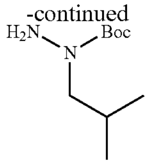

with Leu-R-group (Janda, K. D., and Han, H. (1997). Azatide peptidomimetics. (Scripps Research Institute, USA; Janda, Kim D.; Han, Hyunsoo.), p. 78).

Example 2

Synthesize of Boc-Protected Hydrazines

Lubell's group synthesized five Boc-protected hydrazines to mimic amino acid side-chains of Gly, Phe, Val, Ala and Pro:

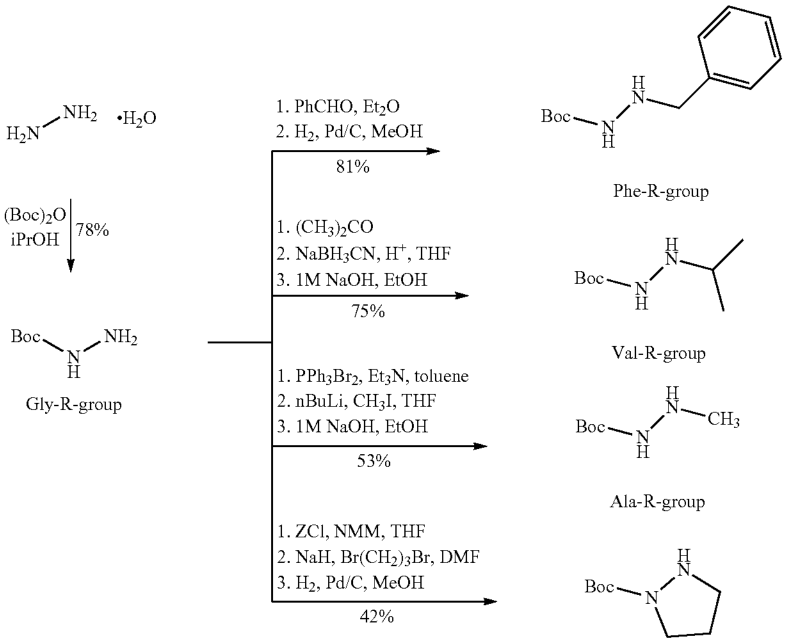

Pro-R-group (Melendez, R. E., and Lubell, W. D. (2004). Aza-Amino Acid Scan for Rapid Identification of Secondary Structure Based on the Application of N-Boc-Azal-Dipeptides in Peptide Synthesis. Journal of the American Chemical Society 126, 6759-6764.)

These building blocks were used to synthesize six N-Boc-aza-dipeptides and then were subsequently introduced into analogues of C-terminal peptide fragment of human calcitonin gene-related peptide (hCGRP).

Example 3

Preparation of Fmoc-Protected Alkylhydrazines

Lubell's group prepared eleven Fmoc-protected N'-alkylhydrazines by condensations of Fmoc-protected hydrazine with an appropriate aldehyde or ketone to an acyl hydrazone which was reduced by the catalytic hydrogenation and hydride addition:

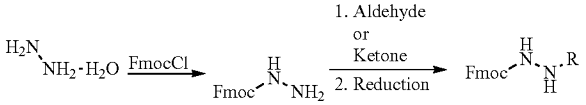

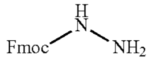

with Gly-R-group (99% yield)

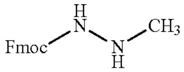

with Ala-R-group (77% yield)

-continued

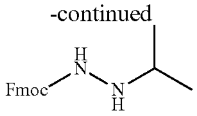

with Val-R-group (68% yield)

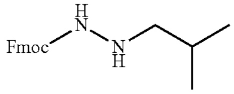

with Leu-R-group (72% yield)

-continued

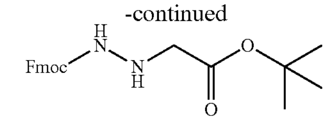

with Asp-R-group (OtBu)
(20% yield)

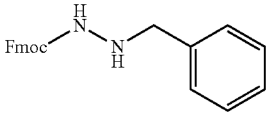

with Phe-R-group
(94% yield)

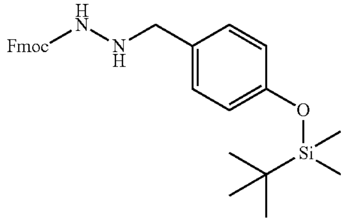

with Tyr-R-group
(OSi(Me)$_2$tBu)
(70% yield)

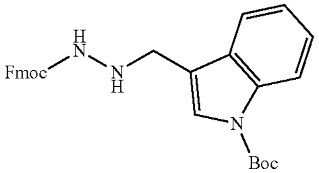

with Trp-R-group (Boc)
(75% yield)

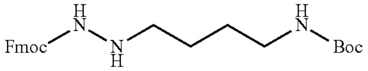

with Lys-R-group (Boc)
(74% yield)

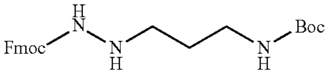

with Orn-R-group (Boc)
(74% yield)

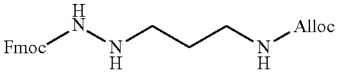

with Orn-R-group (Alloc)
(76% yield)

These monomers were used to construct three biologically active peptides by partial aza-amino acid scans: the tetrapeptide melanocortin receptor (MCR) agonist, the hexapeptide growth hormone secretagogue (GMIP-6) and the human calcitonin gene-related peptide (hCGRO) antagonist.

Example 4

Preparation of Ddz-Protected Alkylhydrazines

Gilon's group prepared thirteen Ddz-protected N'-alkylhydrazines by condensations of commercially available 2-(3,5-dimethoxyphenyl)propan-2-yl carbazate (Ddz hydrazine) with either aldehyde or ketone to anacyl hydrazone that was reduced by the catalytic hydrogenation to yield the desired N'-substituted Ddz hydrazines:

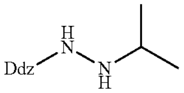

(78% yield)
with Val-R-group

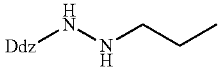

(86% yield)
with nor Val-R-group

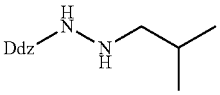

(61% yield)
with Leu-R-group

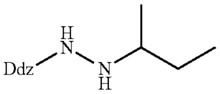

(86% yield)
with Ile-R-group

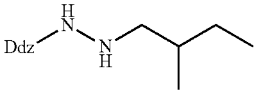

(83% yield)
with homolle-R-group

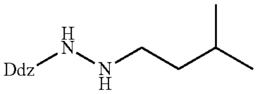

(87% yield)
with homoLeu-R-group

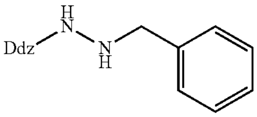

(95% yield)
with Phe-R-group

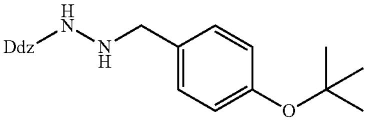

(78% yield)
with Tyr-R-group (OtBu)

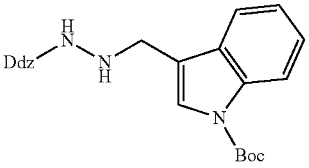

(68% yield)
with Trp-R-group (Boc)

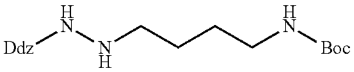

(76% yield)
with Lys-R-group (Boc)

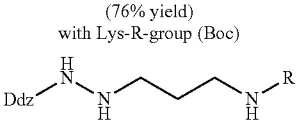

(R = Allec; 73% yield)
(R = Boc; 70% yield)
with Orn-R-group

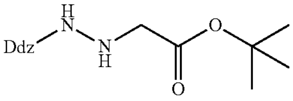

(62% yield)
with Asp-R-group (OtBu)

The side chain corresponding to aspartic acid was made by nucleophilic substitution of alkyl halide with Ddz hydrazide. Ddz deprotection was achieved by mild Lewis acid, Mg(ClO4)2, which is orthogonal with the Boc and Fmoc protecting groups and make the solid phase azapeptide synthesis with Ddz-protected alkylhydrazines compatible with both the Boc and the Fmoc strategies.

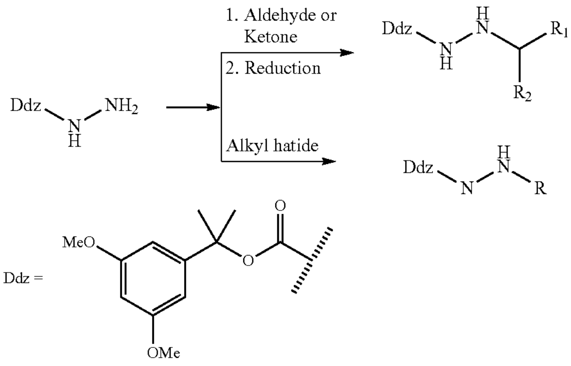

Freeman, N. S., Hurevich, M., and Gilon, C. (2009). Synthesis of N'-substituted Ddz-protected hydrazines and their application in solid phase synthesis of aza-peptides. Tetrahedron 65, 1737-1745).

Example 5

Preparation of Phth-Protected Alkylhydrazines

Vanderesse's group prepared seven phthalimide(Phth)-protected N-alkyl-aminophthalimides by Mitsunobu reaction of N-tert-butyloxycarbonylaminophthalimide with an appropriate alcohol, followed by the acidic deprotection of the Boc group [59]:

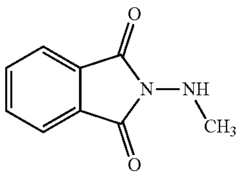

with Ala-R-group (98% yield)

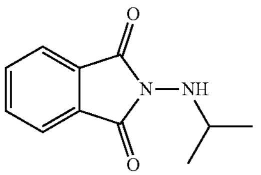

with Val-R-group (75% yield)

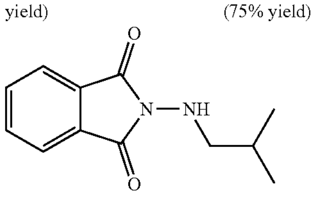

with Leu-R-group (77% yield)

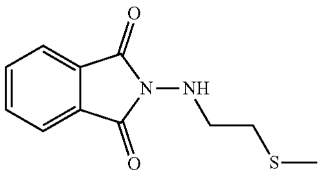

with Met-R-group (89% yield)

-continued

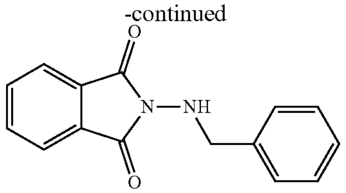

with Phe-R-group (81% yield)

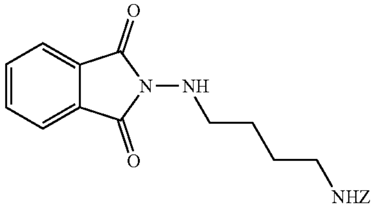

with Lys-R-group (Cbz) (67% yield)

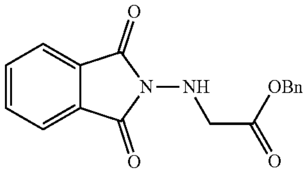

with Asp-R-group (OBn) (85% yield)

The activated Phth-protected alkylhydrazines monomers were reacted with H-Ala-OMe to give the corresponding aza-dipeptides, which can be introduced into biologically active peptides and oligomers to form stable p-turn structures:

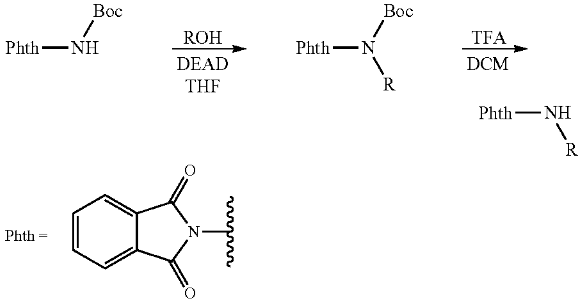

Example 6

Activation and Coupling of Aza-Amino Acids

Historically, azapeptide bonds are formed by either activation of the hydrazine moiety or by activation of the N-terminus amine of peptides with carbonyl donating reagents to generate the activated units such as amino isocyanate or isocyanate, activated esters, acid chlorides, carbamoyl imidazole, carbamoyl benzotriazole and 1,3,4-oxadiazol-2-(3H)-one, which serve as the activated aza-building blocks. The common carbonyl donors used to activate both the hydrazines and the N-terminus of the growing peptide including p-nitrophenylchloroformate, bis (2,4-dinitrophenyl) carbonate, bis(pentafluorophenyl) carbonate, N,N'-disuccinimidyl carbonate (DSC), carbonyldiimidazole (CDI), phosgene and triphosgene.

p-Nitrophenylchloroformate p-Nitrophenylchloroformate was used as the carbonyl donor source to activate hydrazine. It proved a safer alternative to phosgene and furnished a more stable activated ester intermediate:

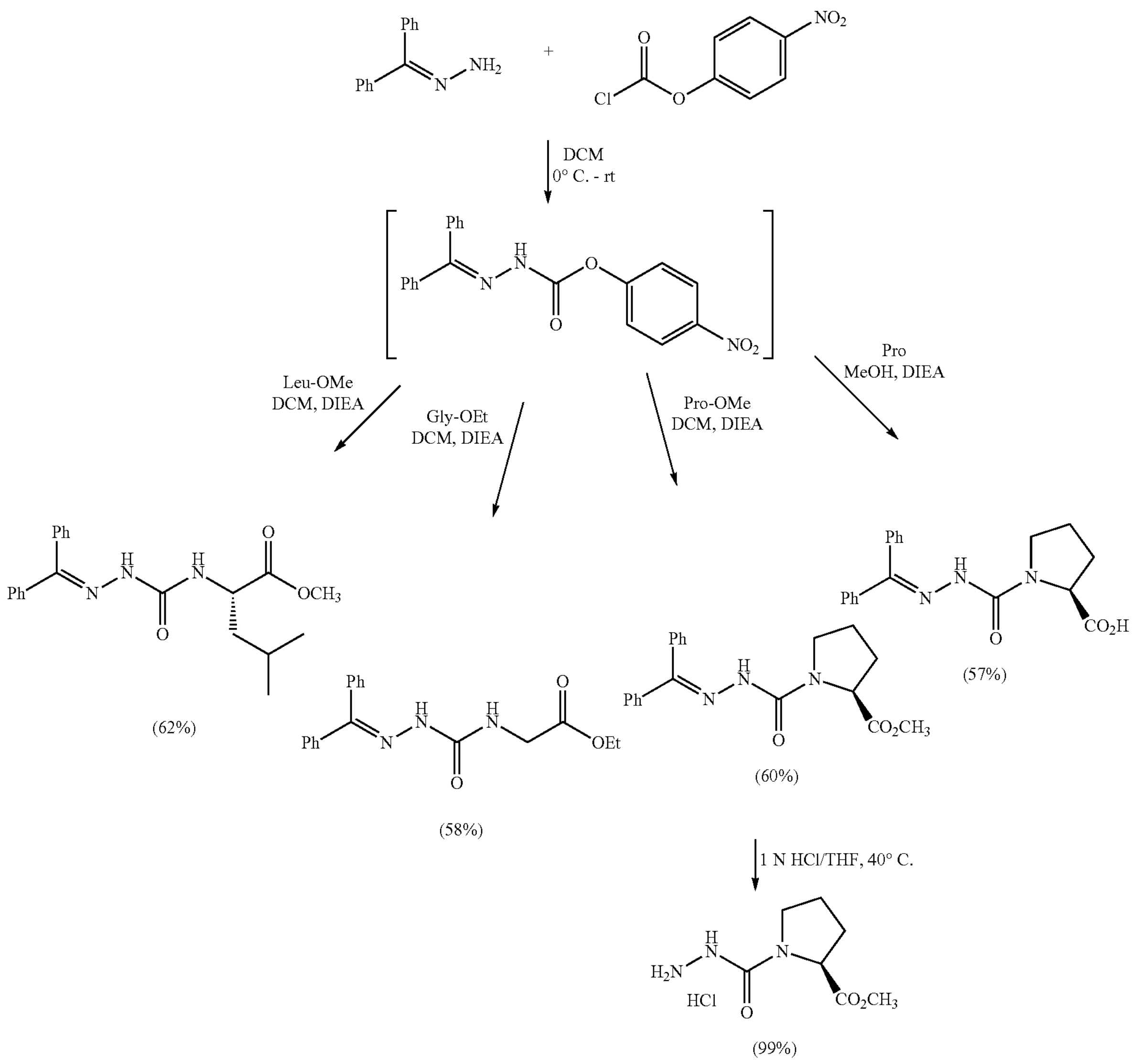

Bis(2,4-dinitrophenyl) carbonate

Bis(2,4-dinitrophenyl) carbonate was used to convert resin-bound N-terminal amino groups into isocyanate, which reacted with a protected amino acid hydrazide to complete the formation of the azapeptide. Hydantoin formation is the major problem, but can be minimized or eliminated by omission of the base from the activation procedure [45] and/or introducing a reversible amide bond protecting group [61].

Bis(pentafluorophenvl) Carbonate

Bis(pentafluorophenyl) carbonate was used as the carbonyl activating reagent in preparing azatides [6]. The highly reactivated and easily handled carbonyl donor of bis(pentafluorophenyl) carbonate activated a wide variety of Boc-protected a-aza-amino acids monomers and coupled to the azatides. By detailed study, the activated complex was found to be the amino isocyanate, not the proposed carbamate.

1. Starting from 1-R'-hydrazine Carboxylic Acid,1,1-dimethylethyl Ester

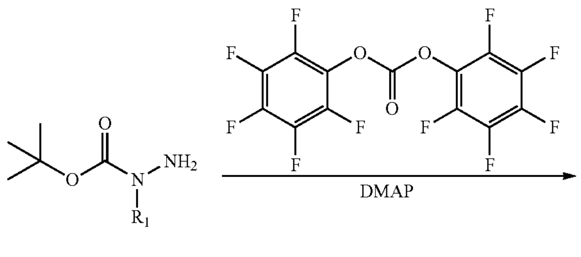

-continued

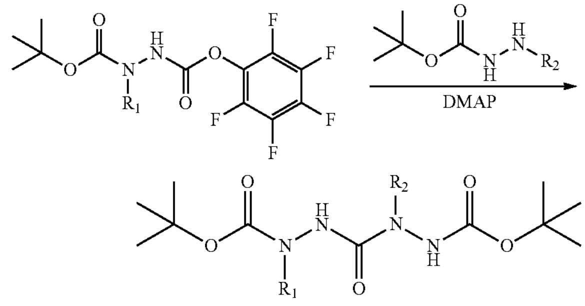

2. Starting from 2-R'-hydrazine Carboxylic Acid,1,1-dimethylethyl Ester

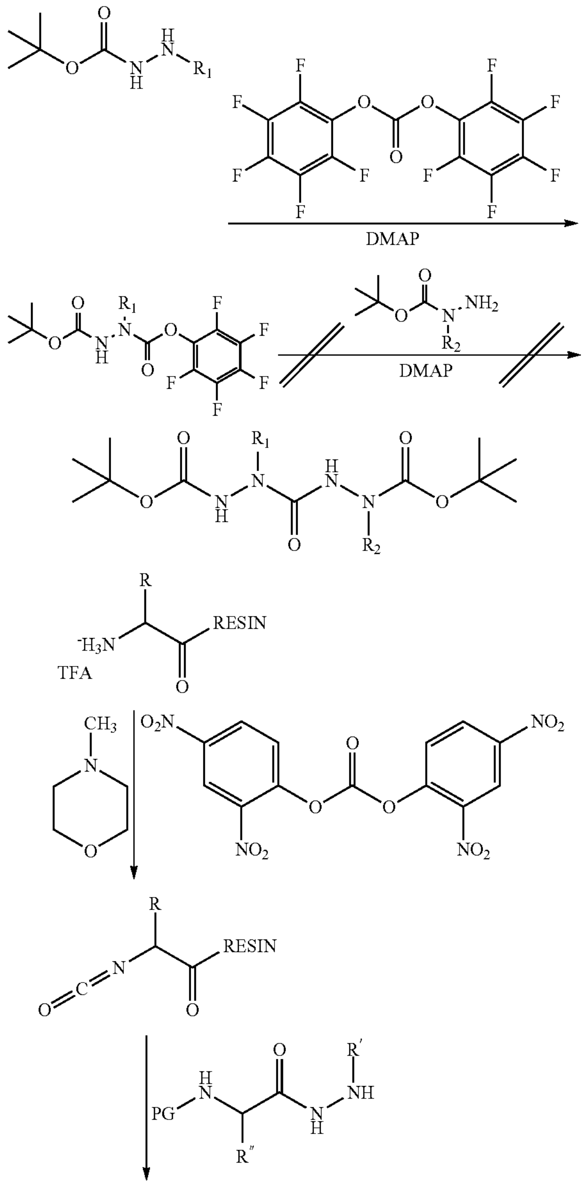

-continued

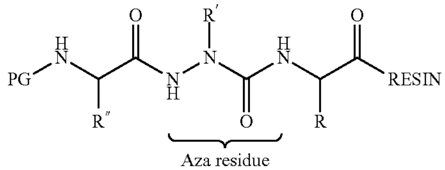

Liley, M., and Johnson, T. (2000). Solid phase synthesis of azapeptides utilising reversible amide bond protection to prevent hydantoin formation. Tetrahedron Letters 41, 3983-3985.

Other common carbonyl donors failed in coupling reactions due to the complicated side reactions, poor reaction yields, and/or prolonged reaction time.

N,N'-disuccinimidyl Carbonate

N,N'-disuccinimidyl carbonate[62, 63] was employed as the carbonyl source to activate benzophenone hydrazone for the synthesis of aza-glycinyl dipeptides with higher yields and simpler purification:

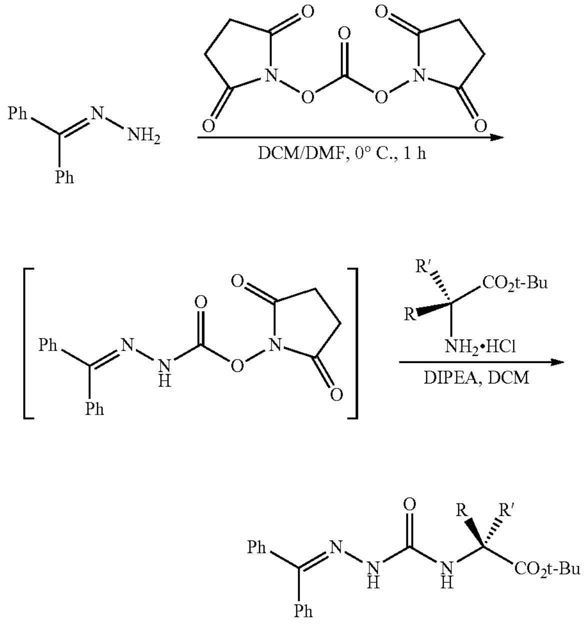

a: R = $CH_2Ph$, R' = H
b: R = R' = H
c: R = R' = CH3

Carbonyl Diimidazole

Carbonyl diimidazole (CDI) is a useful coupling reagent in amide bond formation, and it also reacted with amines to give stable carbamoylimidazoles in high yields[64]. Therefore, CDI can be used as a carbonyl donor to activate both amino acid esters and hydrazides in azapeptide formation [65-69]. Azadipeptide synthesis was reported via activation of the amino acid ester hydrochloride salts by CDI in the presence of DIPEA into the active carbamates, which was converted to the isocyanate intermediates. The reactive isocyantes reacted quickly with hydrazide to afford azadipeptides:

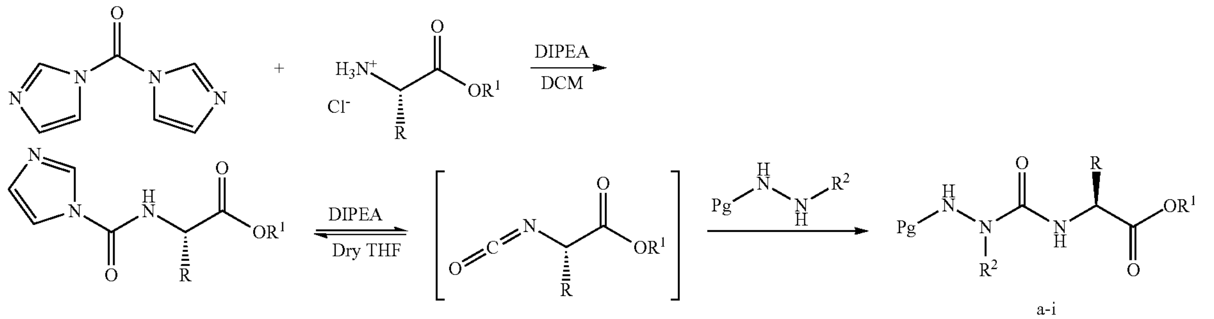

a-i a: Pg = Cbz, $R^2 = CH_3$, R = CH2Ph, $R^1 = CH_3$, Yield = 90%
b: Pg = Cbz, $R^2 = CH_3$, $R = CH(CH_3)_2$, $R^1$ $C(CH_3)_3$, Yield = 82%
c: Pg = Boc, $R^2 = CH(CH_3)_2$, $R = CH_2CH(CH_3)_2$, $R^1 = CH_3$, Yield = 89%
d: Pg = Boc, $R^2 = CH(CH_3)_2$, $R = CH_3CH_2SCH_3$, $R^1 = CH_3$, Yield = 90%
e: Pg = Boc, $R^2 = CH_2Ph$, $R = CH_2CH(CH_3)_2$, $R^1 = CH_3$, Yield = 95%
f: Pg = Boc, $R^2$ = H, $R = CH_2Ph$, $R^1 = CH_3$, Yield = 80%
g: Pg = Fmoc, $R^2 = CH_3$, $R = CH(CH_3)_2$, $R^1 = C(CH_3)_3$, Yield = 85%
h: Pg = Fmoc, $R^2 = CH(CH_3)_2$, $R = CH_2CH(CH_3)_2$, $R^1 = C(CH_3)_3$, Yield = 78%
i: Cbz = Cbz, $R^2 = CH_2CO_2CH_3$, $R = CH(CH_3)_2$, $R^1 = C(CH_3)_3$, Yield = 92%

(Abo-Dya, N. E., Biswas, S., Basak, A., Avan, I., Alamry, K. A., and Katritzky, A. R. (2013). Benzotriazole-Mediated Synthesis of Aza-peptides: En Route to an Aza-Leuenkephalin Analogue. The Journal of Organic Chemistry 78, 3541-3552.)

Solid phase synthesis of Agly peptides was reported by reacting Fmoc-NHNH2 with CDI to yield a 1-Fmoc-2-oxoimidazole hydrazine derivative, which reacted with protected peptidyl resin to form the azapeptide resin. The peptide was elongated using standard Fmoc/tert-butyl SPPS to the desired target. Final deprotection and cleavage in concentrated TFA furnished Agly peptides with 31 to 53% yield after RP-HPLC purification:

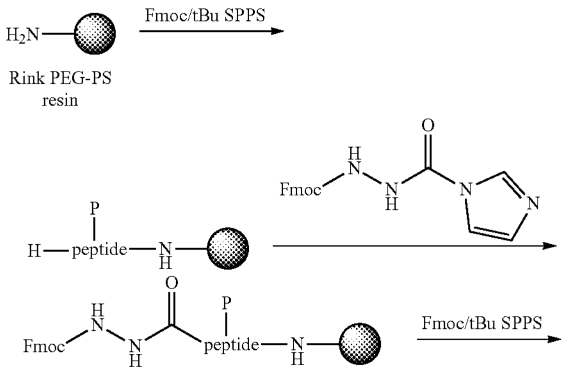

-continued

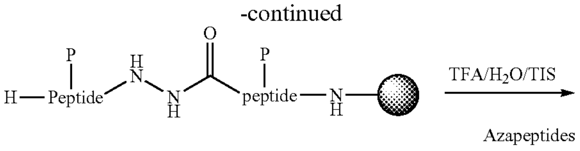

P = side-chain protecting groups (Mhidia, R., and Melnyk, O. (2010). Selective cleavage of an azaGly peptide bond by copper(II). Long-range effect of histidine residue. Journal of Peptide Science 16, 141-147)

Phosgene

Commerically available solutions of phosgene in toluene are a convenient source of carbonyl donors to activate the corresponding L-amino benzyl ester hydrochloride salts into amino ester isocyanates, which was involved in the aza-amino acid scan with N-Boc-aza-dipeptide strategy. Phosgene solution covered the Fmoc-hydrazine in presence of base to a highly activated azaglycine building block, the 1,3,4-oxadiazol-2(3H)-one. On the other hand, by using anhydrous dioxane as a solvent and in the absence of a tertiary base, phosgene solution converted the Fmoc-methylhydrazines into the corresponding carbazic acid chloride quantitatively at ambient temperature:

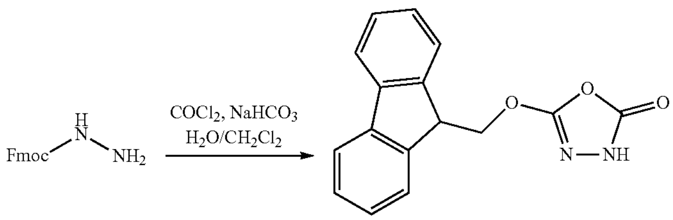

1,3,4-oxadiazol-2(3H)-one

-continued
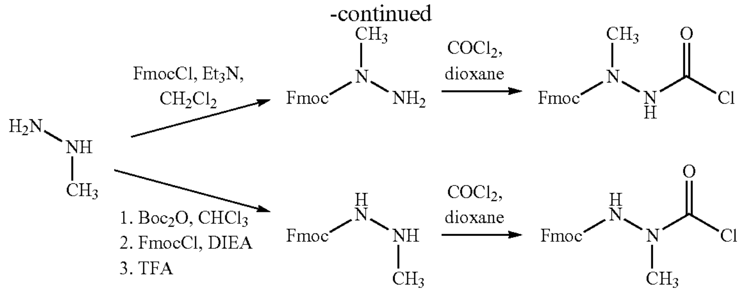
carbazic acid chloride
The activated Fmoc-aza-amino acid chloride building blocks have been used to construct Fmoc-Aza-dipeptides in solution phase synthesis:
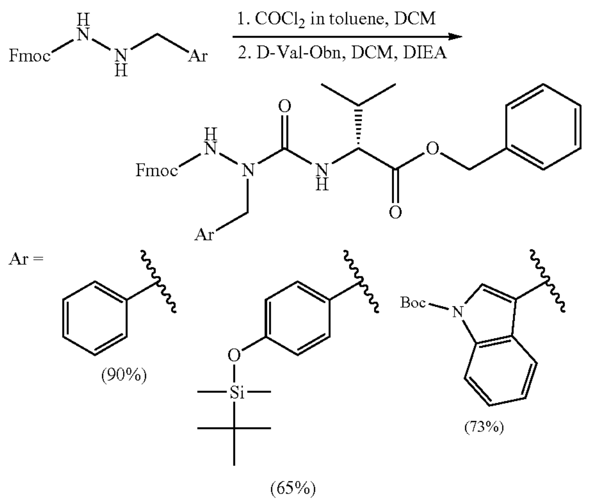
and the tetrapeptide melanocortin receptor agonist, Ac-His-D-Phe-Arg-Trp-NH2 on solid phase:
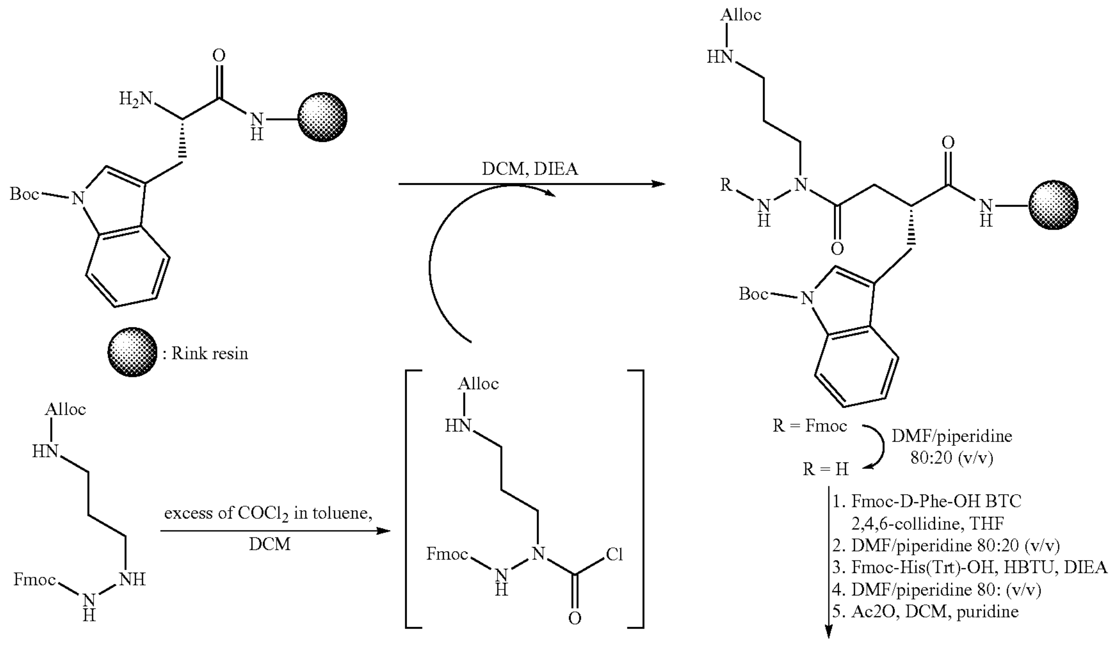

-continued

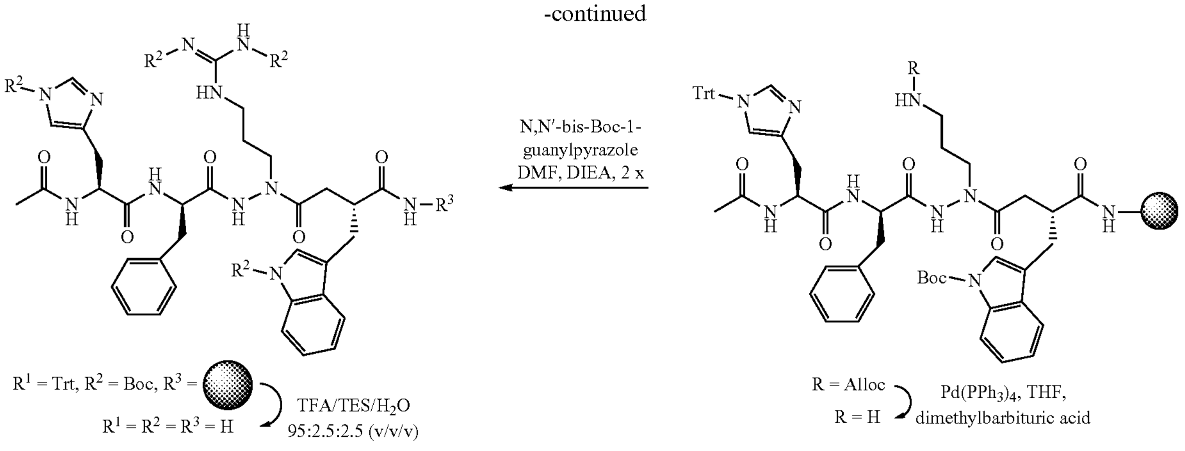

Triphosgene

Triphosgene or bis(trichloromethyl) carbonate is a mild, easy-to-handle and efficient carbonylating agent for azapeptide synthesis both in solution and on solid phase. It had been shown to be highly reactive, reducing the reaction temperature and coupling times with high yield and easy purification [70, 71]. The synthesis of various aza-analogues of dipeptides, tripeptides and decapeptides has been reported by using both liquid and solid-phase procedures. (Andre, F., Marraud, M., Tsouloufis, T., Tzartos, S. J., and Boussard, G. (1997). Triphosgene: an efficient carbonylating agent for liquid and solid-phase aza-peptide synthesis. Application to the synthesis of two aza-analogues of the AChR MIR decapeptide. Journal of Peptide Science 3, 429-441).

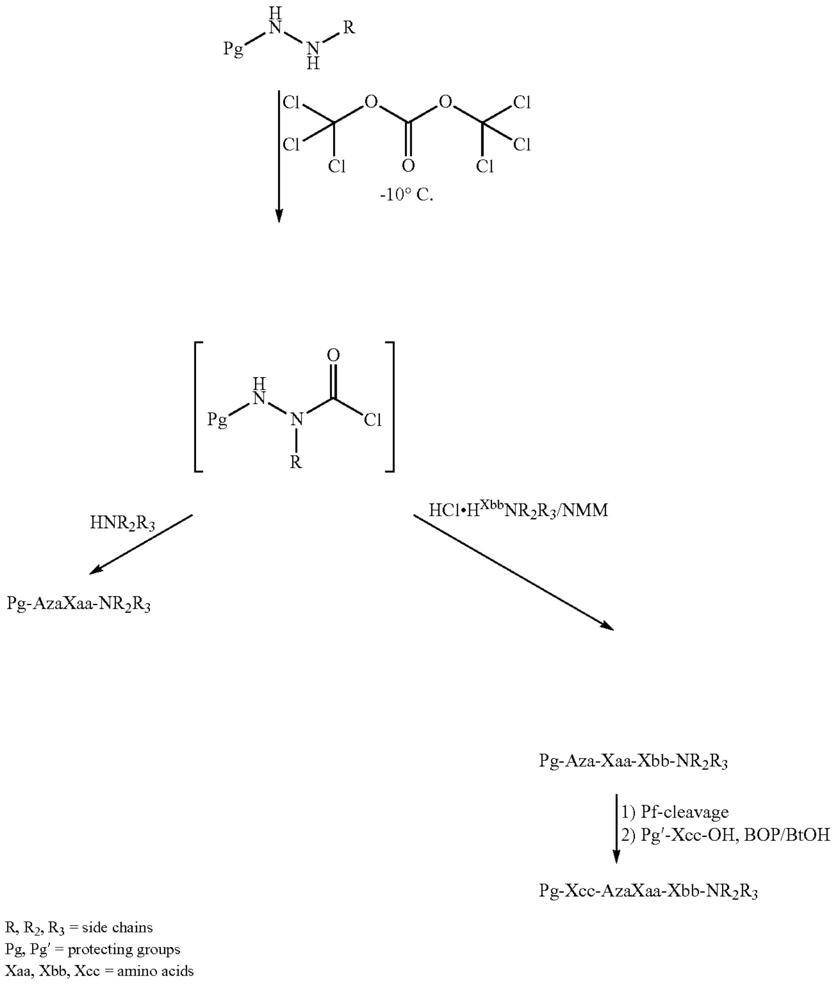

Mel

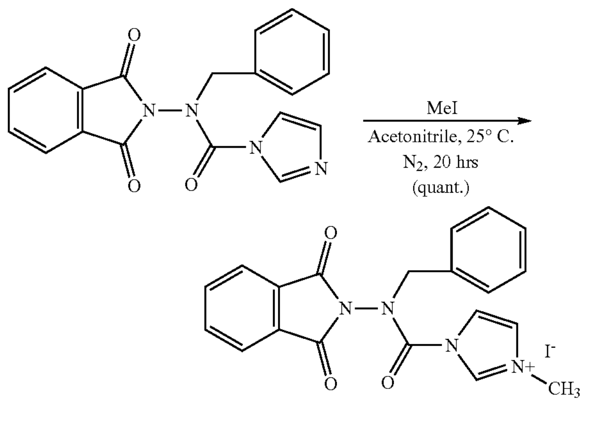 [SMILES: "MeI" ; O=C1c2ccccc2C(=O)N1N(Cc1ccccc1)C(=O)n1ccnc1 ; C[n+]1ccn(C(=O)N(Cc2ccccc2)N2C(=O)c3ccccc3C2=O)c1 ; [I-]]

To a solution of N-phenyl-N-carbamoylimidazole aminophthalimide (0.035 mmol) in acetonitrile (0.2 mL) was added Mel (0.175 mmol). The mixture was stirred at 25° C. under nitrogen for 20 hrs then concentrated to dryness and dried under vacuum pump to yield a pale yellow solid (quant.).

Example 7

Submonomer Synthesis of Azapeptides on Solid Phase

The use of activated aza building blocks to generate azapeptides both in solution and on solid phase has been successful for making small combinatorial libraries of bioactive compounds for SAR studies. For example, this methodology was used for generation of azapeptide analogs of the melanocortin receptor agonist (MCR), the growth hormone releasing peptide (GHRP-6) and the calcitonin gene-related peptide (CGRP) antagonist for exploring the effect of azapeptide structure on biological activity [21-25]. However, these are limited in generating side chain diversity, are difficult to use in preparation of aza amino acid building blocks, and are subject to contamination with significant side products such as hydantoin and oxadiazalone:

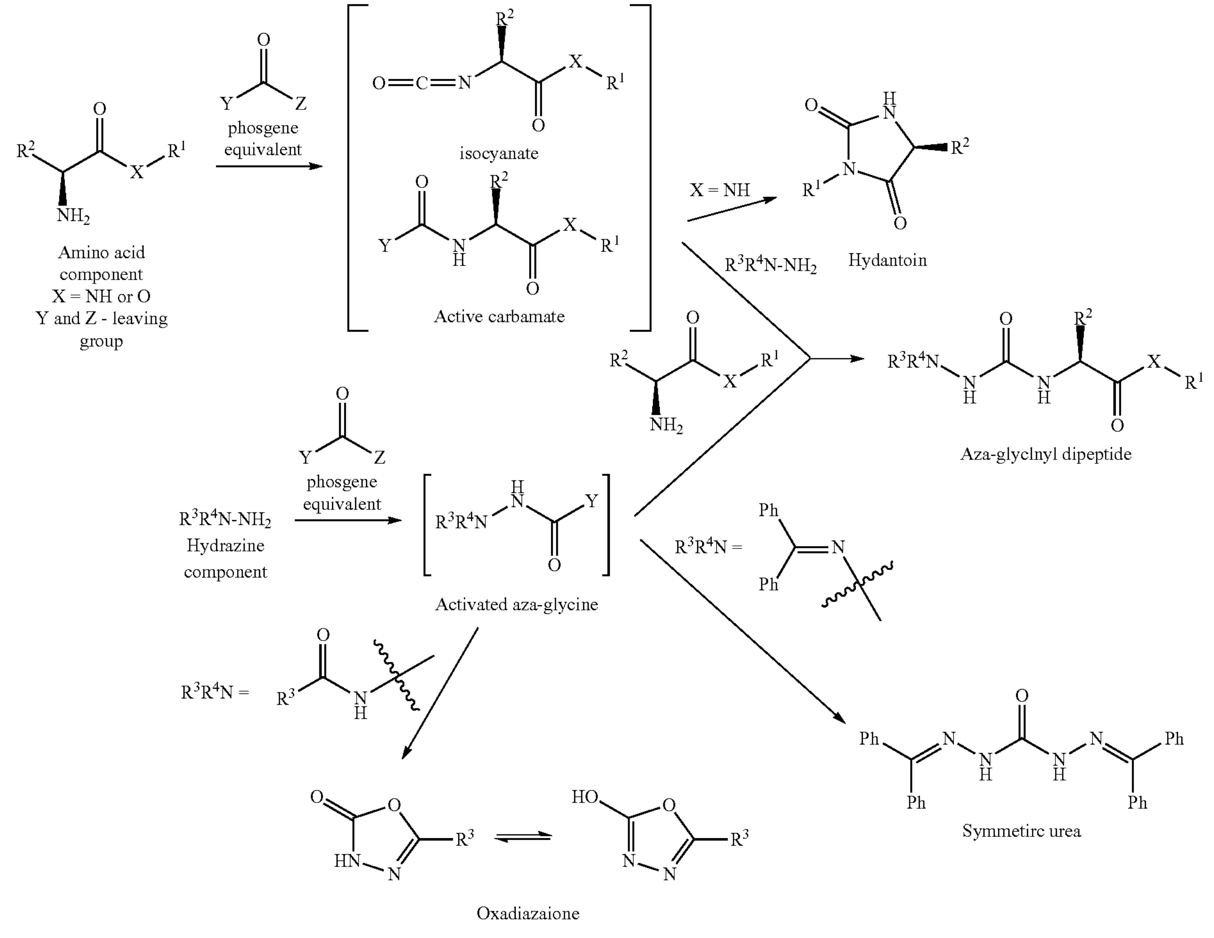

Therefore, a submonomer azapeptide synthesis strategy was introduced to construct the aza amino acid residue directly on the SPPS:
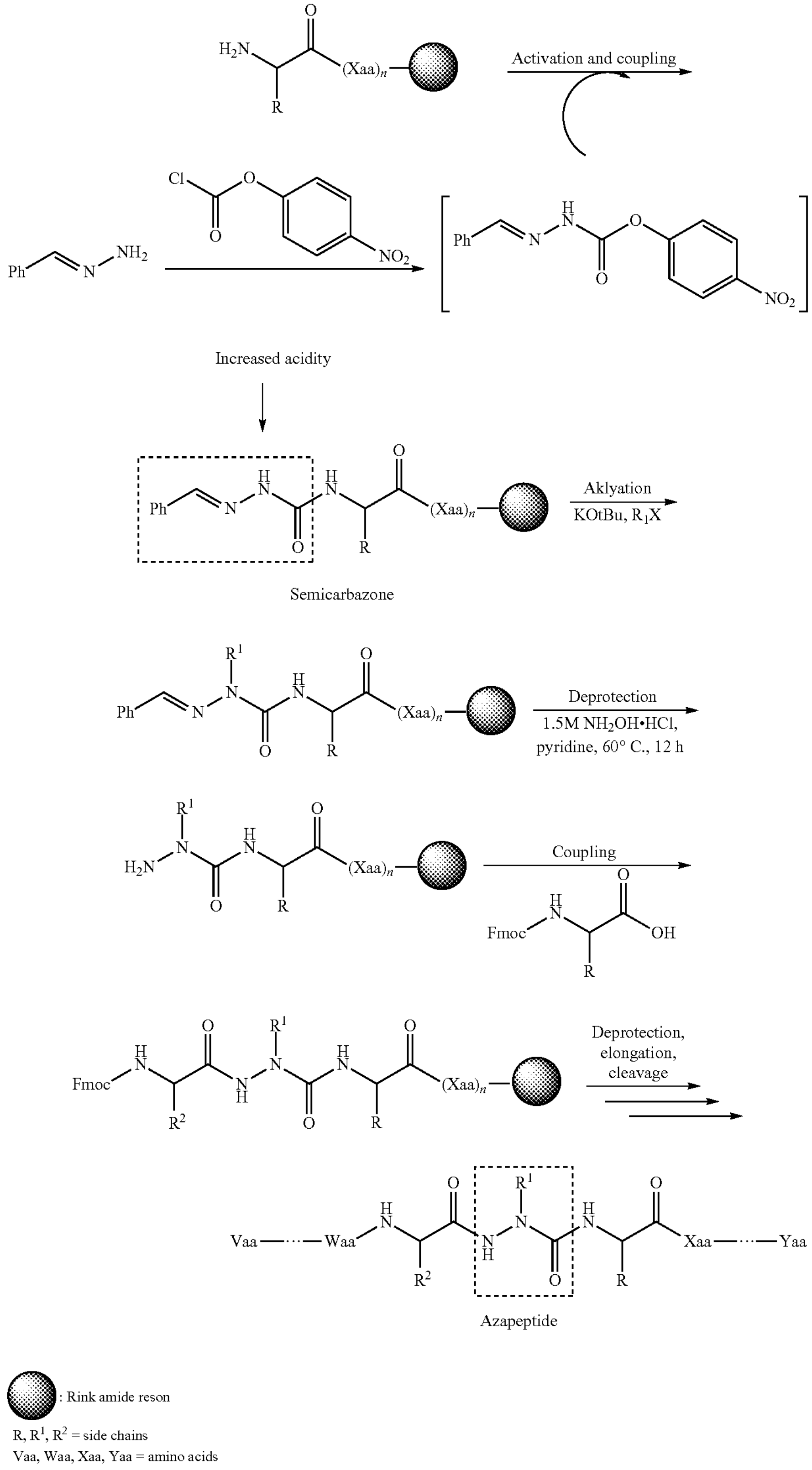

The new methodology simplifies azapeptide synthesis and opens the door for the combinatorial library preparation of side chain and backbone diverse azapeptides for SAR studies.

Example 8

Submonomer Synthesis of the Growth Hormone Releasing Peptide (GHRP-6) with Side Chain Diversity Growth hormone releasing peptide 6 (GHRP-6) [His-D-Trp2-Ala3-Trp4-D-Phe5-Lys6-NH2] is a hexapeptide that includes unnatural D-amino acids. GHRP-6 has bio-activity with CD36 receptor and GHS-R1a receptor. Submonomer synthesis produced ten aza-analogs of GHRP-6 at the D-Trp-Ala-Trp region with yield ranging from 14-42%:

| D-$Trp^2$ modifications | Ala$^3$ modifications | Trp$^4$ modifications |
|---|---|---|
| 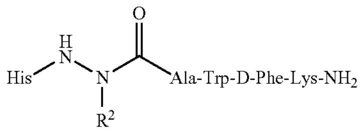 | 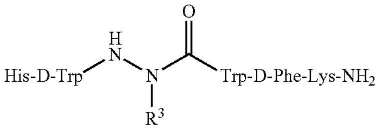 | 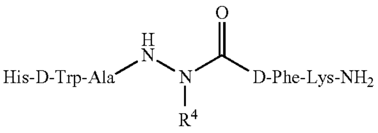 |
| $R^2$ = 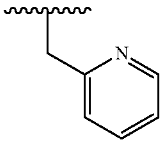 20% | $R^3$ = 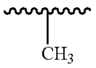 15% | $R^4$ = 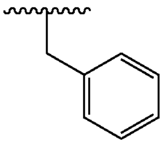 25% |
| $R^2$ = 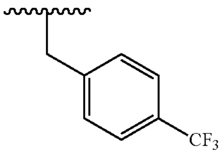 25% | $R^3$ = 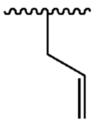 17% | $R^4$ = 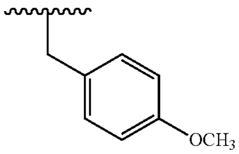 27% |
| $R^2$ = 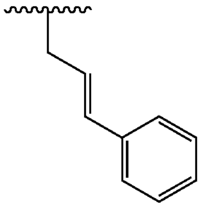 42% | $R^3$ = 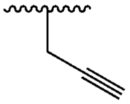 28% | $R^4$ = 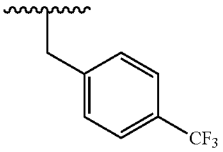 15% |
| | $R^3$ = 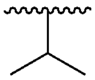 14% | |

Thirteen aza-arylglycine GHRP-6 analogs were also produced by copper-catalyzed chemoselective mono-N-arylation of resin-bound semicarbazone with yields ranging from 0.8-3.4% (FIG. 20):
| D-Trp$^2$ modifications | | Trp$^4$ modifications | |
|---|---|---|---|
| 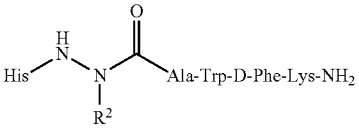 | | 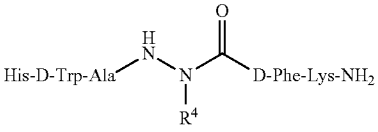 | |
| $R^2$ = 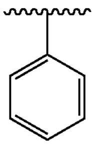 | 2.0% | $R^4$ = 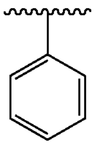 | 1.0% |
| $R^2$ = 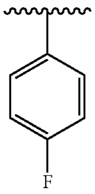 | 1.4% | $R^4$ = 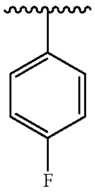 | 2.8% |
| $R^2$ = 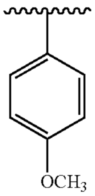 | 1.4% | $R^4$ = 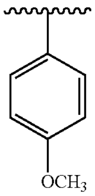 | 1.2% |
| $R^2$ = 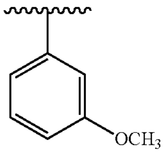 | 1.2% | $R^4$ = 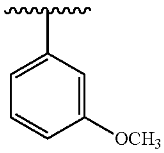 | 1.0% |
| $R^2$ = 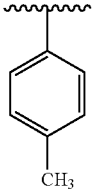 | 1.2% | $R^4$ = 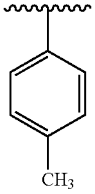 | 3.4% |
| $R^2$ = 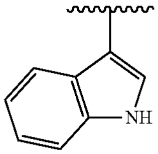 | 0.8% | $R^4$ = 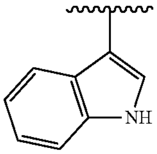 | 1.6% |
| | | $R^4$ = 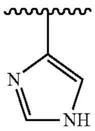 | 1.6% |

Proulx, C., and Lubell, W. D. (2010). Copper-Catalyzed N-Arylation of Semicarbazones for the Synthesis of Aza-Arylglycine-Containing Aza-Peptides. Organic Letters 12, 2916-2919.

The so-called 'libraries from libraries' methodology featured further diversification of the aza-residues and produced seven new GHRP-6 azapeptides containing aza-1,2,3-triazole-3-alanine residues by a copper-catalyzed 1,3-dipolar cycloadditiion reaction of aryl azides with aza-proparglycine residues. The isolated yield ranged from 5-11%:

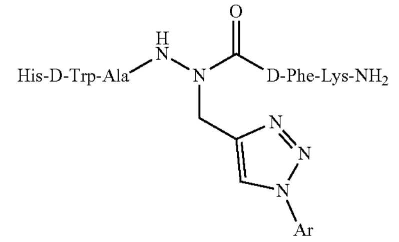

Trp[4] modifications

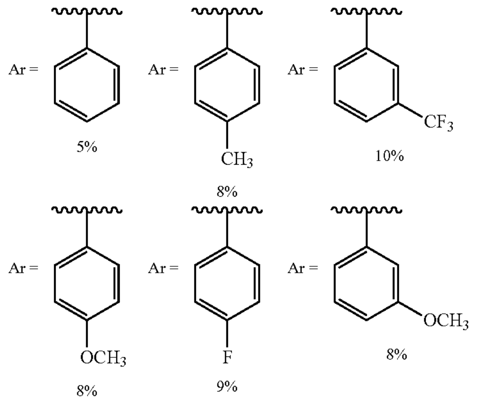

-continued

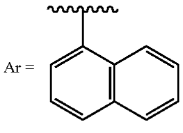

11%

The azapropargyl glycine residues from the submonoer synthesis procedure were also used for producing the constrained azalysine peptides. The reaction was accomplished by copper catalyzed coupling of Mannich reagents to azapropargyl glycine residues and eighteen aza-Lys GHRP-6 analogs were produced. Zhang, J., Proulx, C., Tomberg, A., and Lubell, W. D. (2014). Multicomponent Diversity-Oriented Synthesis of Aza-Lysine-Peptide Mimics. Organic Letters 16, 298-301.

Example 9

Submonomer Synthesis of Azapeptide Ligands of the Insulin Receptor Tyrosine Kinase (IRTK) with Side Chain Diversity The pentapeptide, Ac-Asp1-Ile2-Tyr3-Glu4-Thr5-NH2, derived from the activation loop of IRTK was found to inhibit IRTK phosphorylation. Kato, M., Abe, M., Kuroda, Y., Hirose, M., Nakano, M., and Handa, T. (2009). Synthetic pentapeptides inhibiting autophosphorylation of insulin receptor in a non-ATP-competitive mechanism. Journal of Peptide Science 15, 327-336. 75. Seven azapeptide analogs of the parent pentapeptide were made by submonomer solid phase synthesis to explore SAR studies on IRTK inhibitory activity in sufficient isolated yield (36-55%).

| Ile$^2$ modifications | | Tyr$^3$ modifications | | Glu$^4$ modifications | |
|---|---|---|---|---|---|
| 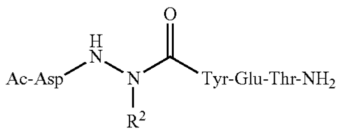 | | 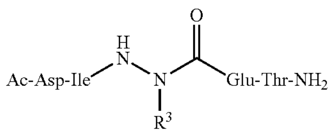 | | 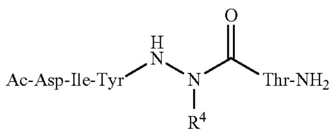 | |
| 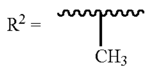 | 51% | 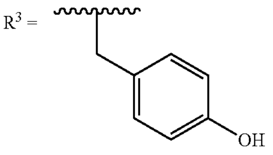 [SMILES: *Cc1ccc(O)cc1] | 50% | 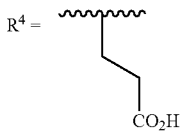 | 42% |
| 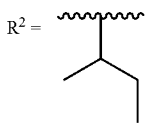 | 55% | 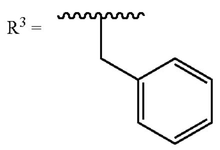 [SMILES: *Cc1ccccc1] | 43% | | |

-continued

| Ile$^2$ modifications | Tyr$^3$ modifications | Glu$^4$ modifications |
| --- | --- | --- |
| 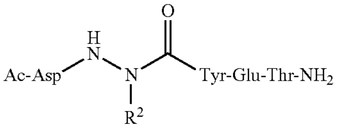 | 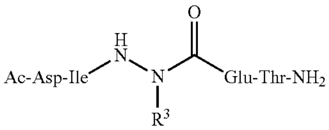 | 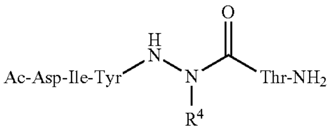 |
| $R^2$ = 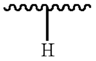 55% | $R^3$ = 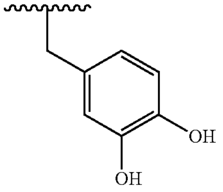 36% | |

Example 10

Synthesis of Phthalimide-Protected Carbamoyl Imidazole with Phe-R-Group

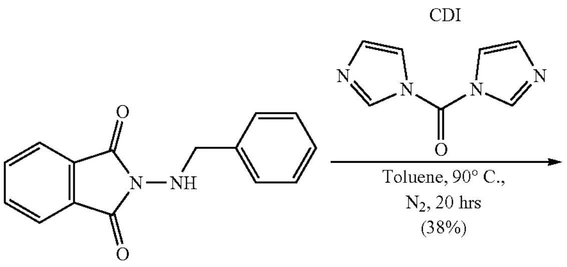

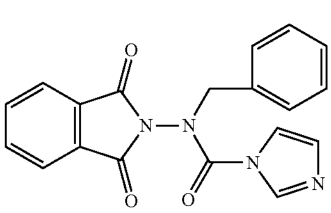

To a solution of N-phenyl-aminophthalimide (0.6 mmol) in toluene (2 mL) CDI (1.32 mmol) was added. The mixture was stirred at 90° C. under nitrogen for 20 hours then concentrated to dryness and dried under vacuum pump. The crude product was purified by flash silica gel column chromatography eluting with hexane/EtOAc (4:3) to afford the products as a white solids 80 mg (38% yield). $^1$H NMR (500 MHz, $CDCl_3$) δ 7.92 (s, 1H), 7.79-7.77 (m, 4H), 7.42-7.40 (m, 2H), 7.29-7.28 (m, 3H), 7.22 (dd, 1H), 6.95 (d, 1H), 5.03 (s, 2H) ppm. Mass Spectrum: (ESI) m/z 347.27 $(M+H)^+$.

Example 11

Synthesis of Phthalimide-Protected Carbamoyl Imidazole with Z-Lys-R-Group

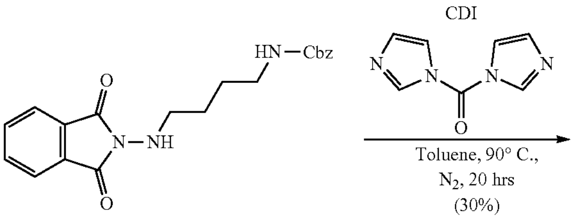

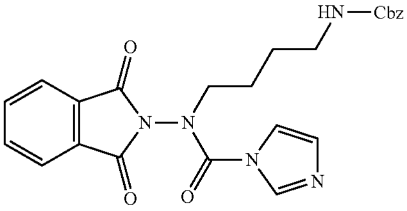

To a solution of N-(Z-Lys)-aminophthalimide (0.43 mmol) in toluene (1.5 mL) CDI (0.86 mmol) was added. The mixture was stirred at 90° C. under nitrogen for 20 hours then concentrated to dryness and dried under vacuum pump. The crude product was purified by flash silica gel column chromatography eluting with hexane/EtOAc (4:3) to afford the products as a white solids 60 mg (30% yield). $^1$H NMR (500 MHz, $CDCl_3$) δ 7.81-7.73 (m, 5H), 7.28-7.24 (m, 5H), 7.08 (s, 1H), 6.87 (s, 1H), 4.90 (s, 2H), 3.78 (t, 2H), 3.16-3.17 (m, 2H), 1.65-1.57 (m, 4H) ppm. Mass Spectrum: (ESI) m/z 347.27 $(M+H)^+$.

Example 12

Synthesis of CBEIT

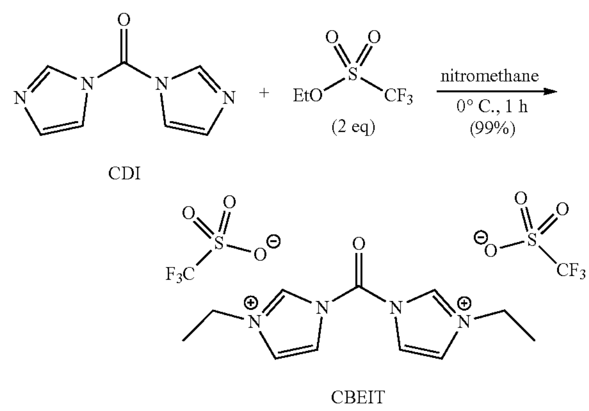

The synthesis of CBEIT was done directly by reaction of CDI with ethyl trifluoromethanesulfonate (triflate) in quantitative yield and no need for further purification before its use as the coupling reagent.

Example 13

Activation of phthalimide-protected carbamoyl imidazole with Phe-R-group by MeI

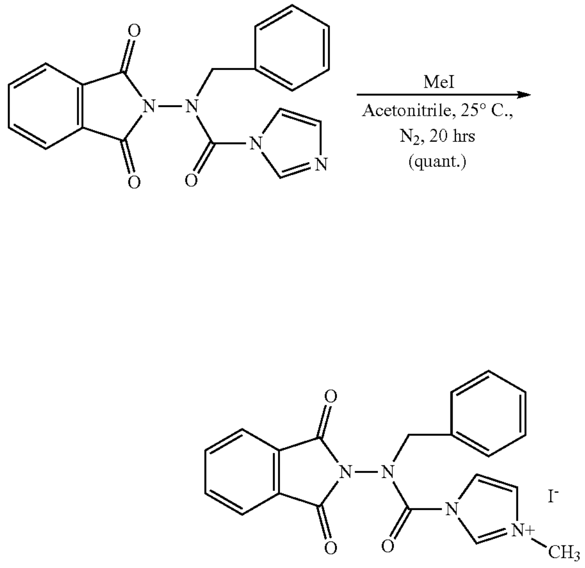

MeI (0.175 mmol) was added to a solution of N-phenyl-N-carbamoylimidazole aminophthalimide (0.035 mmol) in acetonitrile (0.2 mL). The mixture was stirred at 25° C. under nitrogen for 20 hours, and, then, concentrated to dryness and dried under vacuum pump to yield a pale yellow solid. The crude product was used directly for next step coupling without further purification. Mass Spectrum: (ESI) m/z 361.27 (M*).

Example 14

Coupling Reaction of Activated Phth-Protected Carbamoyl Imidazole Building Blocks with Protected Amino Acids

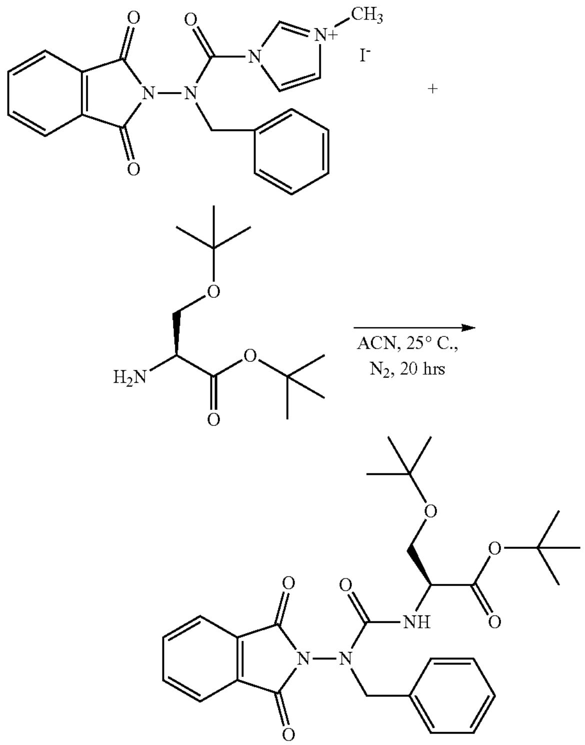

O-tert-Butyl-L-serine tert-butyl ester (0.04 mmol) was added to a solution of N-phenyl-N-carbamoylimidazolium iodide aminophthalimide (0.08 mmol) in acetonitrile (0.4 mL). The mixture was stirred at 25° C. under nitrogen for 20 hours and, then, concentrated to dryness and dried under vacuum pump. The crude product was purified by flash silica gel column chromatography eluting with hexane/EtOAc (4:3) to afford the products as a white solid. Mass Spectrum: (ESI) m/z 496.33 $(M+H)^+$, m/z 518.40 $(M+Na)^+$.

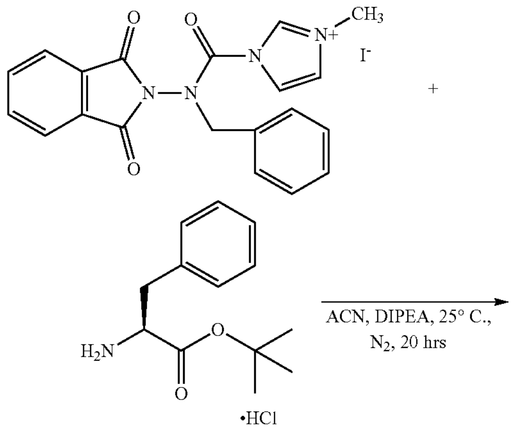

-continued

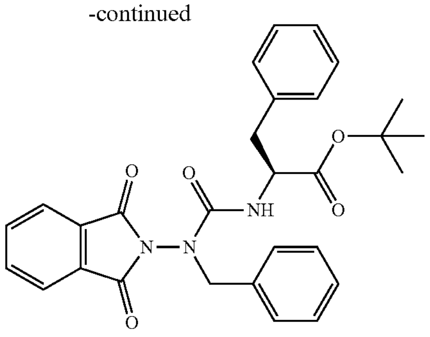

L-Phenylalanine tert-butyl ester hydrochloride (0.04 mmol) and DIPEA (0.06 mmol) were added to a solution of N-phenyl-N-carbamoylimidazolium iodide aminophthalimide (0.08 mmol) in acetonitrile (0.4 mL). The mixture was stirred at 25° C. under nitrogen for 20 hours, and, then, concentrated to dryness and dried under vacuum pump. The crude product was purified by flash silica gel column chromatography eluting with hexane/EtOAc (4:3) to afford the products as a white solid. Mass Spectrum: (ESI) m/z 522.40 $(M+H)^+$.

Example 15

Coupling Reaction of Activated Phth-Protected Carbamoyl Imidazole Building Blocks with Protected Hydrazines

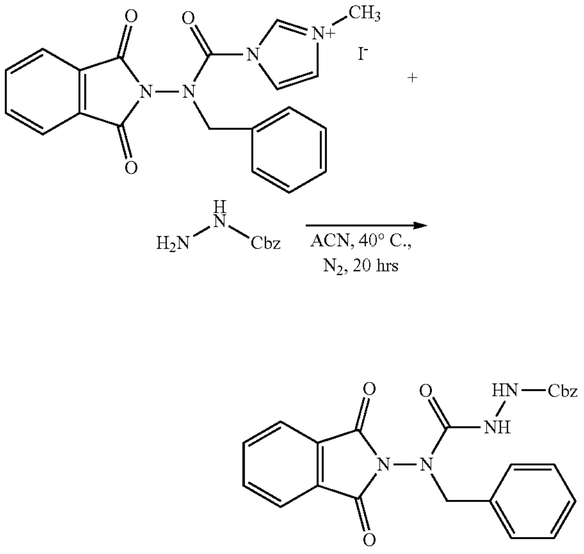

Cbz-hydrazine (0.03 mmol) was added to a solution of N-phenyl-N-carbamoylimidazolium iodide aminophthalimide (0.03 mmol) in acetonitrile (0.15 mL). The mixture was stirred at 40° C. under nitrogen for 20 hours then concentrated to dryness and dried under vacuum pump. The crude product was purified by flash silica gel column chromatography eluting with hexane/EtOAc (4:3) to afford the products as a white solid. Mass Spectrum: (ESI) m/z 445.53 $(M+H)^+$, m/z 467.47 $(M+Na)^+$.

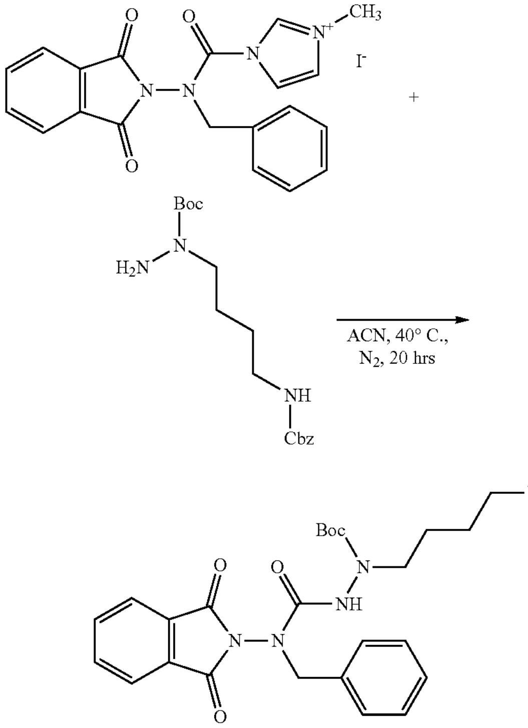

N-Boc-N-(Z-Lys)-hydrazine (0.03 mmol) was added to a solution of N-phenyl-N-carbamoylimidazolium iodide aminophthalimide (0.03 mmol) in acetonitrile (0.15 mL). The mixture was stirred at 40° C. under nitrogen for 20 hours then concentrated to dryness and dried under vacuum pump. The crude product was purified by flash silica gel column chromatography eluting with hexane/EtOAc (4:3) to afford the products as a white solid. Mass Spectrum: (ESI) m/z 516.53 $[(M-Boc)+H]^+$, m/z 638.33 $(M+Na)^+$.

Example 16

Fmoc-Phenylhydrazine was Converted into the Corresponding Carbazic Acid Chloride by Phosgene in Anhydrous Dichloromethane

Figure 13:
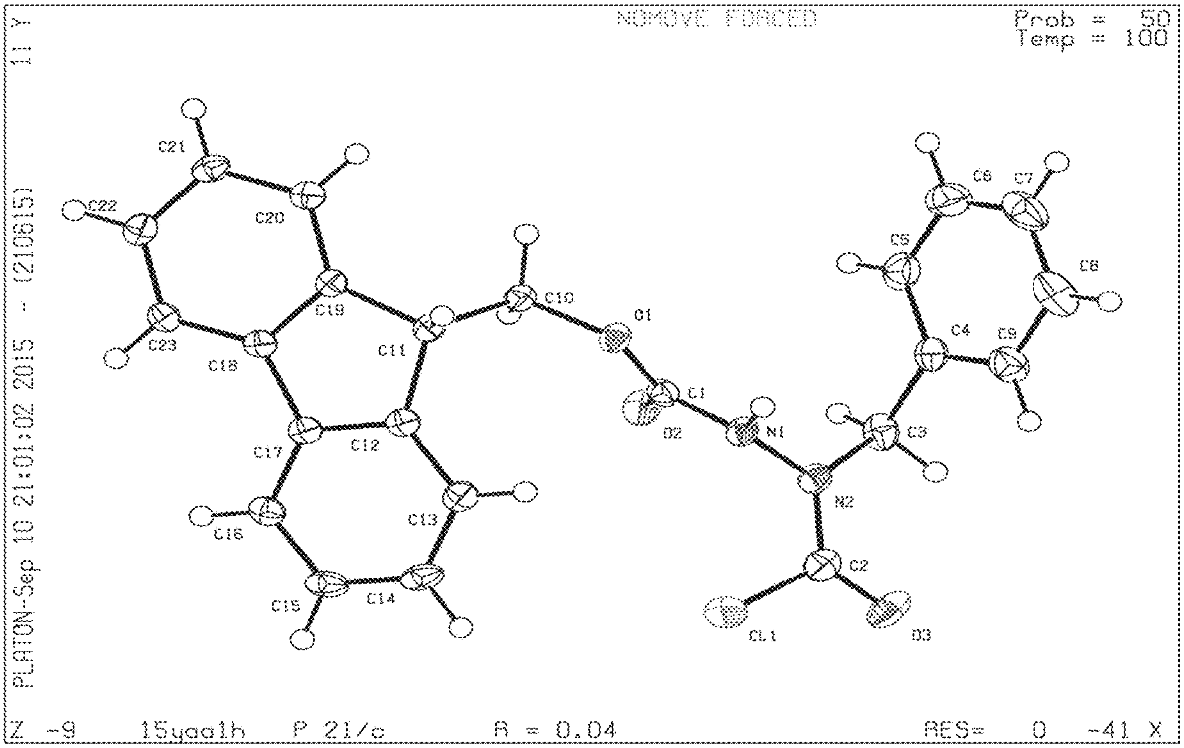
FIG. 13 is an image of X-ray crystallography of Fmoc-phenylhydrazine carbazic acid chloride.

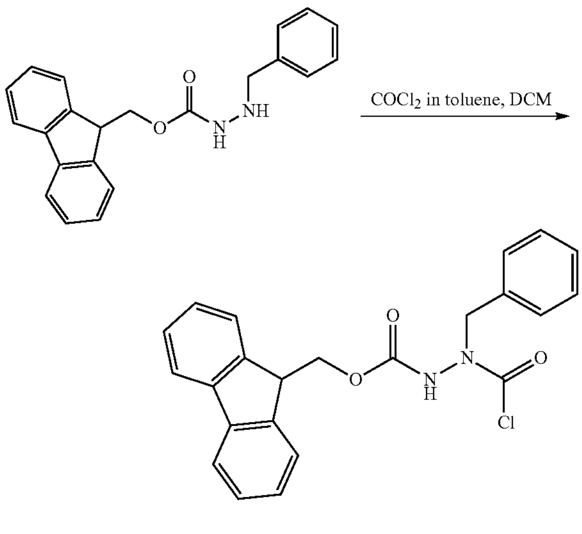

and was characterized by X-ray crystallography. X-ray crystallography of Fmoc-phenylhydrazine carbazic acid chloride is depicted in FIG. 13.

Example 17

Synthesis of Di-Azatides by Acid Chloride Coupling

The di-azatides 2 were prepared by coupling of hydrazine 2 with acid chloride in DCM/toluene at 25° C. or 50° C. to yield the N-Fmoc protected di-azatide 1 which was deprotected with piperidine to yield the final di-azatide 2:

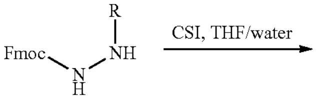

Hydrazine 1

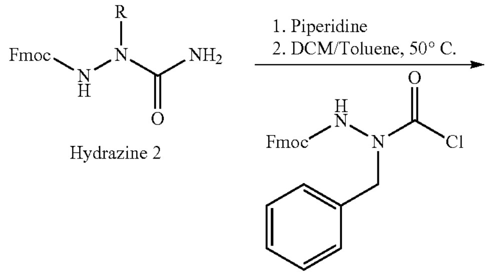

Hydrazine 2

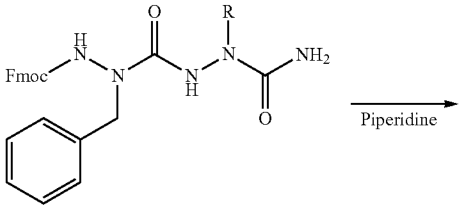

Di-aztide 1

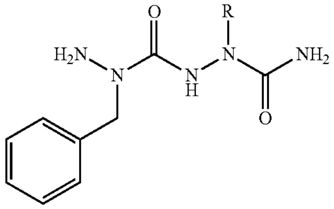

Di-azatide 2

Another route to the di-azatide 2 was through formation of the protected carbazide, and then coupling with an appropriate aldehyde to form an acyl hydrazone which was then reduced by catalytic hydrogenation and hydride addition to di-azatide 3. Chlorosulfonyl isocyanate (CSI) was then converted from the amine into the corresponding di-azatide 2:

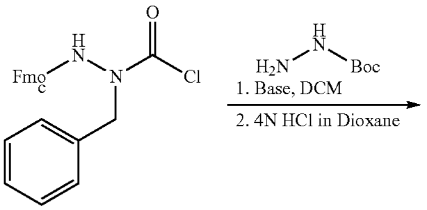

Acid Chloride

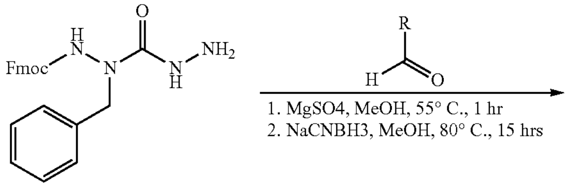

Carbazide 1

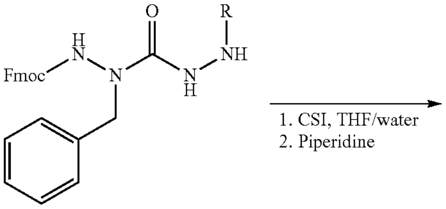

Di-azatide 3

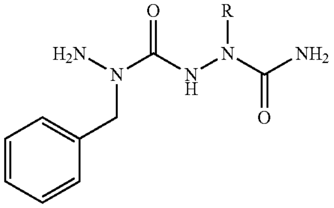

Di-azatide 2

General Procedure for Coupling of Hydrazine 2 with Acid Chloride (Method A):

The solution of acid chloride (0.367 mmol) and hydrazine 2 (0.367 mmol) in anhydrous DCM (3 mL) and anhydrous toluene (3 mL) was stirred at 50° C. under nitrogen for 15 hours. The mixture was concentrated to dryness and then the crude product was purified by flash silica gel column chromatography eluted with hexane/EtOAc mixtures to afford the di-azatide 1 as white solids or clear oils in 50-70% yield.

General Procedure for Coupling of Protected Carbazide 1 with Aldehydes (Method B):

To a solution of protected carbazide 1 (0.46 mmol) and aldehyde (0.69 mmol) in anhydrous methanol (20 mL), triethyl amine (60 uL until pH=7) was added, followed by anhydrous $MgSO_4$ (200 mg). The mixture was stirred at 55° C. under nitrogen for 1 hour and, then, $NaCNBH_3$ (2.3 mmol) was added, followed by acetic acid (2.3 mmol). The mixture was stirred at 80° C. under nitrogen for 15 hours, then concentrated to dryness and partitioned between water (100 mL) and EtOAc (100 mL). The aqueous layer was extracted with EtOAc (2×50 mL) and the combined organic phase was washed with brine (50 mL), dried over $Na_2SO_4$, filtered and concentrated to afford the crude product which was purified by flash silica gel column chromatography eluted with hexane/EtOAc mixtures to afford the di-zaatide 3 as white solids or clear oils in 40 to 60% yield.

General Procedure for Coupling of Hydrazine with Acid Chloride:

To a solution of acid chloride (0.367 mmol) and hydrazine (3.67 mmol) in anhydrous DCM (6 mL), N,N,N',N'-Tetramethyl-1,8-naphthalenediamine (0.734 mmol) was added. The solution was stirred at 25° C. under nitrogen for 15 hours and, then, concentrated to dryness and partitioned between 0.5N HCl (20 mL) and EtOAc (20 mL). The aqueous layer was extracted with EtOAc (2×25 mL) and, then, the combined organic phase was washed with brine (25 mL), dried over $Na_2SO_4$, filtered and concentrated to afford the crude product which was purified by flash silica gel column chromatography eluted with hexane/EtOAc mixtures to afford the products as white solids or clear oils in 70-80% yield.

General Procedure for Converting Amine into the Corresponding Amide:

To a solution of amine (2 mmol) in anhydrous THE (12 mL) at 0° C., chlorosulfonyl (CSI) (2 mmol) was added rapidly. The solution was stirred at 0° C. under nitrogen for 1 hour then water added (10 mL). The solution was warmed to room temperature then concentrated and partitioned between water (100 mL) and EtOAc (100 mL). The aqueous layer was extracted with EtOAc (2×50 mL) and the combined organic phase was washed with brine (50 mL), dried over $Na_2SO_4$, filtered and concentrated to afford the crude product which was purified by flash silica gel column chromatography eluted with hexane/EtOAc mixtures to afford the products as white solids in 80-90% yield.

General Procedure for Removing Fmoc Group with Piperidine:

The solution of N-Fmoc protected azatide (1.0 mmol) in piperidine (5 mL) was stirred at 35° C. under nitrogen for 15 mins. The mixture was concentrated to dryness and then the crude product was purified by flash silica gel column chromatography eluted with hexane/EtOAc mixtures to afford the products as white solids in 90-95% yield.

All species were analyzed by ESI mass spectroscopy and selected di-azatides were characterized by $^1H$ and $^{13}C$ NMR:

ESI Mass Spectrum:

| R = | 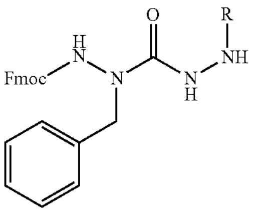 | 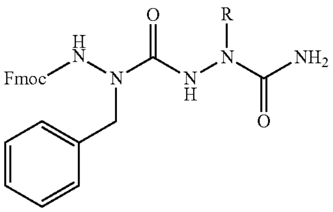 |
|---|---|---|
| H | Method B (60% yield)<br>m/z 403.07 $(M + H)^+$ | m/z 446.13 $(M + H)^+$<br>m/z 468.33 $(M + Na)^+$ |
| $CH_3$ | Method B (58% yield)<br>m/z 417.13 $(M + H)^+$<br>m/z 439.27 $(M + Na)^+$ | m/z 460.13 $(M + H)^+$<br>m/z 428.27 $(M + Na)^+$ |
| 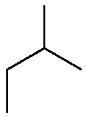 | | Method A (70% yield)<br>m/z 501.60 $(M + H)^+$<br>m/z 523.93 $(M + Na)^+$ |
| 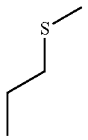 | | Method A (55% yield)<br>m/z 520.07 $(M + H)^+$<br>m/z 542.20 $(M + Na)^+$ |
| 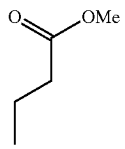 | | Method A (65% yield)<br>m/z 531.60 $(M + H)^+$<br>m/z 553.93 $(M + Na)^+$ |
| 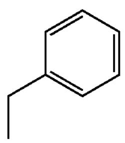 | Method B (50% yield)<br>m/z 493.07 $(M + H)^+$<br>m/z 515.07 $(M + Na)^+$ | m/z 535.93 $(M + H)^+$ |
| 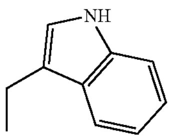 | Method B (45% yield)<br>m/z 532.13 $(M + H)^+$<br>m/z 554.33 $(M + Na)^+$ | m/z 575.07 $(M + H)^+$<br>m/z 597.20 $(M + Na)^+$ |

-continued
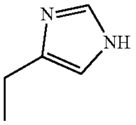
Method B (40% yield)
m/z 483.27 $(M + H)^+$
m/z 505.20 $(M + Na)^+$
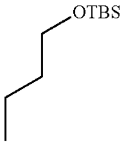
Method B (43% yield)
m/z 575.27 $(M + H)^+$
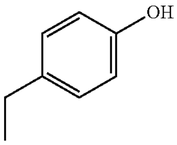
Method B (42% yield)
m/z 509.13 $(M + H)^+$
m/z 531.20 $(M + Na)^+$
Proline analogues
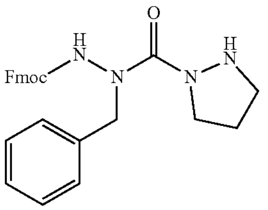
Method A (50% yield)
m/z 442.87 $(M + H)^+$
m/z 465.07 $(M + Na)^+$
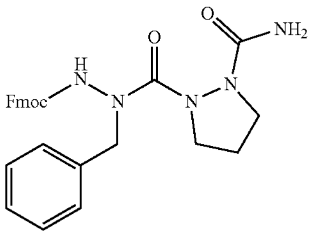
m/z 486.27 $(M + H)^+$
m/z 508.27 $(M + Na)^+$
Other analogues
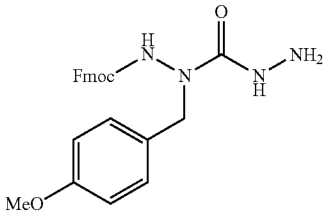
m/z 433.07 $(M + H)^+$
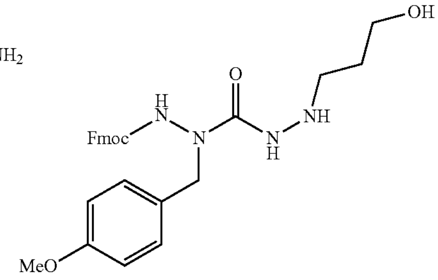
m/z 491.13 $(M + H)^+$
m/z 513.27 $(M + Na)^+$
Tri-azatide
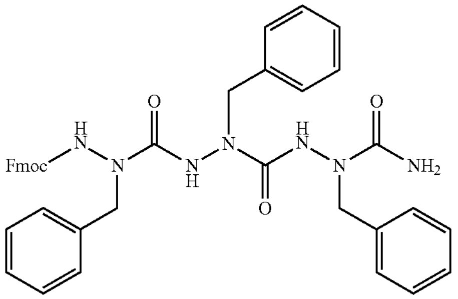
m/z 684.20 $(M + H)^+$
m/z 706.20 $(M + Na)^+$ -continued
| R = | 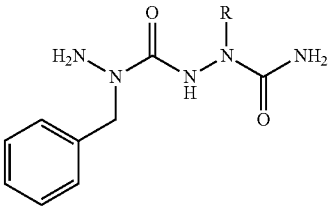 |
|---|---|
| H | m/z 224.07 (M + H)$^+$ |
| $CH_3$ | m/z 238.00 (M + H)$^+$ |
| 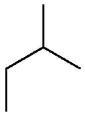 | m/z 280.07 (M + H)$^+$<br>m/z 303.20 (M + Na)$^+$ |
| 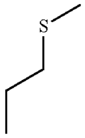 | m/z 298.00 (M + H)$^+$<br>m/z 320.13 (M + Na)$^+$ |
| 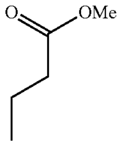 | m/z 310.13 (M + H)$^+$<br>m/z 332.20 (M + Na)$^+$ |
| 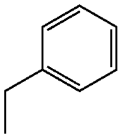 | m/z 314.00 (M + H)$^+$<br>m/z 336.00 (M + Na)$^+$ |
| Proline analogues | 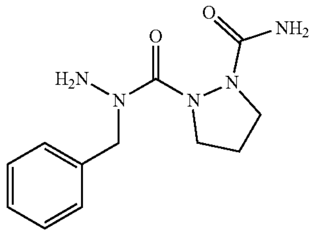<br>m/z 264.00 (M + H)$^+$<br>m/z 286.20 (M + Na)$^+$ |
| Other analogues | 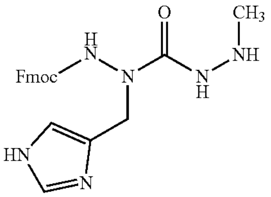<br>m/z 407.20 (M + H)$^+$<br>m/z 429.13 (M + Na)$^+$ |

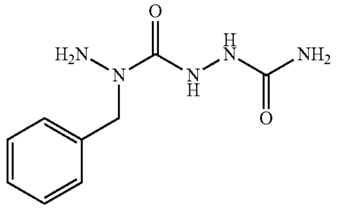 [SMILES: NC(=O)NNC(=O)N(N)Cc1ccccc1]

$^1$H NMR (500 MHz, $CD_3OD$) δ 7.31-7.23 (m, 7H), 4.99 (br. s, 2H), 4.83 (br. s, 2H), 4.07 (s, 2H) ppm. $^{13}$C NMR (125 MHz, $CD_3OD$) δ 159.83, 135.57, 130.30, 129.78, 129.39, 54.48 ppm. Mass Spectrum: (ESI) m/z 224.07 $(M+H)^+$.

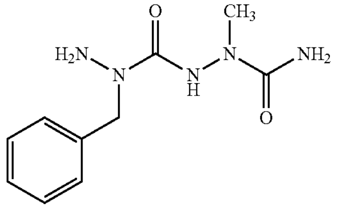 [SMILES: CN(NC(=O)N(N)Cc1ccccc1)C(N)=O]

$^1$H NMR (500 MHz, $CD_3OD$) δ 7.49-7.36 (m, 7H), 5.10 (br. s, 2H), 4.95 (br. s, 2H), 4.71 (s, 2H), 3.17 (s, 3H) ppm. $^{13}$CNMR (125 MHz, $CD_3OD$) δ 163.38, 135.48, 130.24, 129.75, 129.09, 57.49, 39.04 ppm. Mass Spectrum: (ESI) m/z 238.00 $(M+H)^+$.

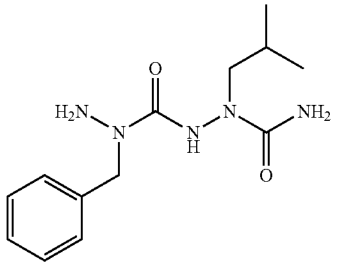 [SMILES: CC(C)CN(NC(=O)N(N)Cc1ccccc1)C(N)=O]

$^1$H NMR (500 MHz, $CD_3OD$) δ 7.40-7.33 (m, 5H), 5.10 (br. s, 2H), 4.69 (s, 2H), 4.00-3.00 (br, 2H), 1.90 (m, 1H), 0.94 (d, 6H) ppm. $^{13}$CNMR (125 MHz, $CD_3OD$) δ 162.90, 137.60, 129.98, 129.44, 129.01, 56.22, 54.51, 27.96, 20.64 ppm. Mass Spectrum: (ESI) m/z 280.07 $(M+H)^+$, m/z 303.20 $(M+Na)^+$.

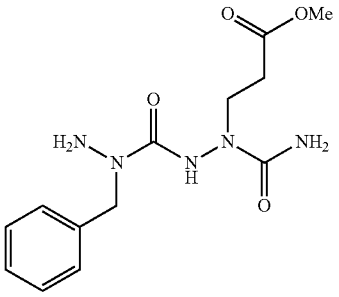 [SMILES: COC(=O)CCN(NC(=O)N(N)Cc1ccccc1)C(N)=O]

$^1$H NMR (500 MHz, $CD_3OD$) δ 7.27-7.19 (m, 5H), 4.56 (s, 2H), 3.80-3.60 (br., 2H), 3.53 (s, 3H), 2.53 (t, 2H) ppm. $^{13}$CNMR (125 MHz, $CD_3OD$) δ 174.42, 160.08, 137.61, 129.98, 129.44, 129.01, 54.58, 52.36, 45.75, 33.65 ppm. Mass Spectrum: (ESI) m/z 310.13 $(M+H)^+$, m/z 332.20 $(M+Na)^+$.

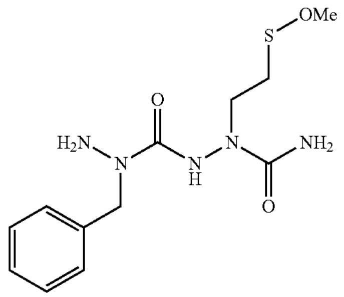 [SMILES: COSCCN(NC(=O)N(N)Cc1ccccc1)C(N)=O]

$^1$H NMR (500 MHz, $CD_3OD$) δ 7.38-7.19 (m, 5H), 4.68 (s, 2H), 2.71 (t, 2H) 1.98 (s, 3H) ppm. $^{13}$C NMR (125 MHz, $CD_3OD$) δ 162.22, 159.98, 137.61, 129.89, 129.42, 128.89, 54.50, 48.24, 32.53, 15.18 ppm. Mass Spectrum: (ESI) m/z 298.00 $(M+H)^+$, m/z 320.13 $(M+Na)^+$.

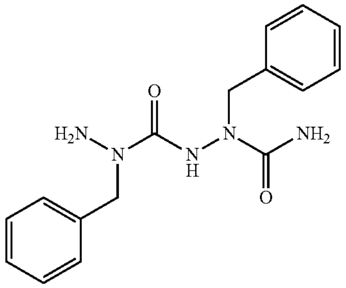 [SMILES: NC(=O)N(Cc1ccccc1)NC(=O)N(N)Cc1ccccc1]

$^1$H NMR (500 MHz, $CD_3OD$) δ 7.35-7.28 (m, 10H), 4.63 (br. s, 4H) ppm. $^{13}$CNMR (125 MHz, $CD_3OD$) δ 164.87, 159.88, 138.43, 138.14, 129.57, 129.52, 129.33, 139.23, 128.66, 128.56, 128.46, 128.38, 57.21 ppm. Mass Spectrum: (ESI) m/z 314.00 $(M+H)^+$, m/z 336.00 $(M+Na)^+$.

Example 18

The following Di-azatides were synthesized by following General Procedures described above:

Di-Azatide from N-to-C-Terminal Construction:

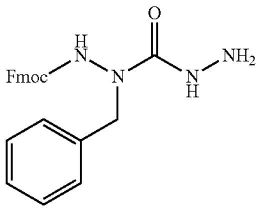

(60% yield)
m/z 403.07 $(M+H)^+$

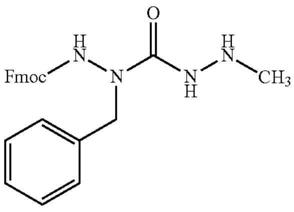

(58% yield)
m/z 417.13 $(M+H)^+$
m/z 439.27 $(M+Na)^+$

-continued
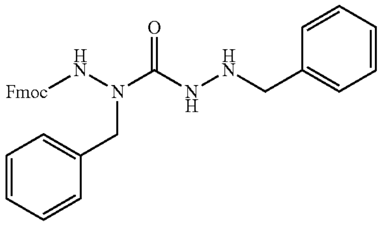
(50% yield)
m/z 493.07 (M+H)$^+$
m/z 515.07 (M +Na)$^+$
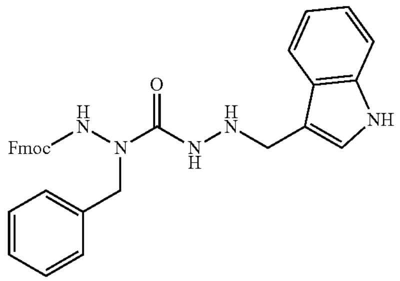
(45% yield)
m/z 532.13 (M+H)$^+$
m/z 554.33 (M +Na)$^+$
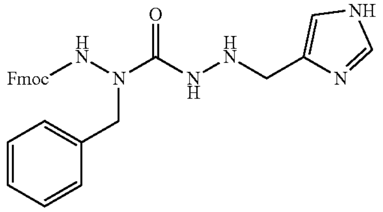
(40% yield)
m/z 483.27 (M+H)$^+$
m/z 505.20 (M +Na)$^+$
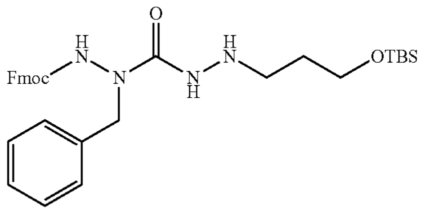
(43% yield)
m/z 575.27 (M+H)$^+$
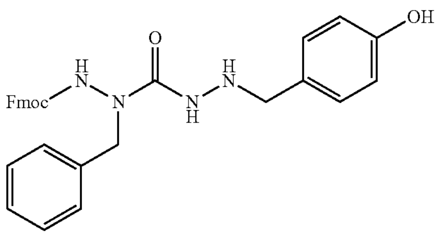
(42% yield)
m/z 509.13 (M+H)$^+$
m/z 531.20 (M +Na)$^+$
-continued
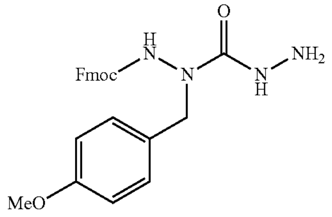
m/z 433.07 (M+H)$^+$
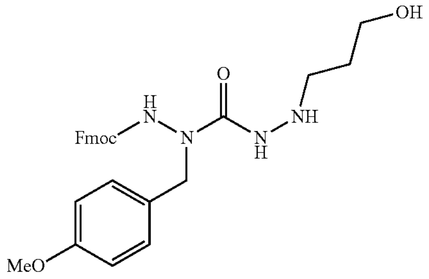
m/z 491.13 (M+H)$^+$
m/z 513.27 (M +Na)$^+$
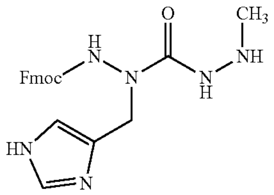
m/z 407.20 (M+H)$^+$
m/z 429.13 (M +Na)$^+$
Di-Azatide from C-to-N-Terminal Construction:
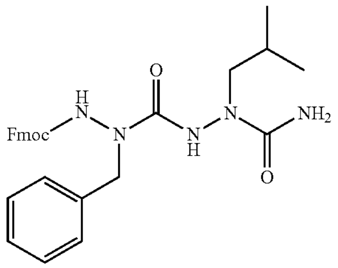
(70% yield)
m/z 501.60 (M + H)$^+$
m/z 553.93 (M + Na)$^+$
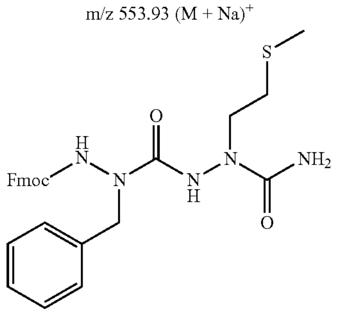
(55% yield)
m/z 520.07 (M + H)$^+$
m/z 542.20 (M + Na)$^+$ -continued

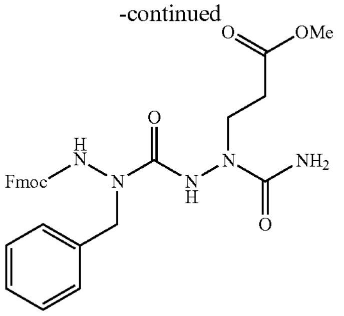

(65% yield)
m/z 531.60 (M + H)$^+$
m/z 553.93 (M + Na)$^+$

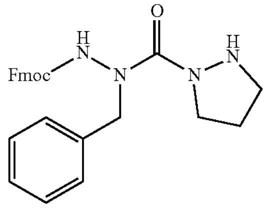

(50% yield)
m/z 442.87 (M + H)$^+$
m/z 465.07 (M + Na)$^+$

All species were analyzed by ESI mass spectroscopy and selected di-azatides were characterized by $^1$H and $^{13}$C NMR:

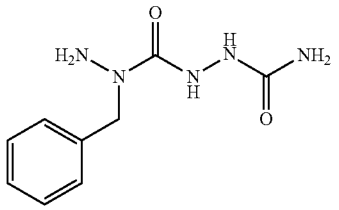 [SMILES: NC(=O)NNC(=O)N(N)Cc1ccccc1]

$^1$H NMR (500 MHz, $C_3OD$) δ 7.31-7.23 (m, 7H),4.99 (br. s, 2H), 4.83 (br. s, 2H), 4.07 (s, 2H) ppm. $^{13}$C NMR (125 MHz, $C_3OD$) δ 159.83, 135.57, 130.30, 129.78, 129.39, 54.48 ppm. Mass Spectrum: (ESI) m/z 224.07 (M+H)$^+$.

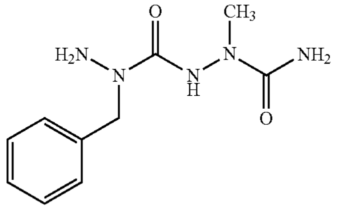 [SMILES: CN(NC(=O)N(N)Cc1ccccc1)C(N)=O]

$^1$H NMR (500 MHz, $CD_3OD$) δ 7.49-7.36 (m, 7H), 5.10 (br. s, 2H), 4.95 (br. s, 2H), 4.71 (s, 2H), 3.17 (s, 3H) ppm. $^{13}$CNMR (125 MHz, $CD_3OD$) δ 163.38, 135.48, 130.24, 129.75, 129.09, 57.49, 39.04 ppm. Mass Spectrum: (ESI) m/z 238.00 (M+H)$^+$.

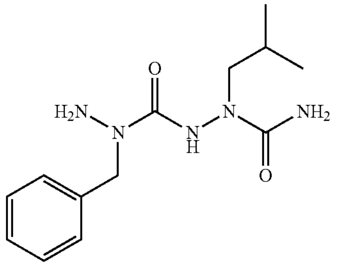 [SMILES: CC(C)CN(NC(=O)N(N)Cc1ccccc1)C(N)=O]

$^1$H NMR (500 MHz, $CD_3OD$) δ 7.40-7.33 (m, 5H), 5.10 (br. s, 2H), 4.69 (s, 2H), 4.00-3.00 (br, 2H), 1.90 (m, 1H), 0.94 (d, 6H) ppm. $^{13}$CNMR (125 MHz, $CD_3OD$) δ 162.90, 137.60, 129.98, 129.44, 129.01, 56.22, 54.51, 27.96, 20.64 ppm. Mass Spectrum: (ESI) m/z 280.07 (M+H)$^+$, m/z 303.20 (M+Na)$^+$.

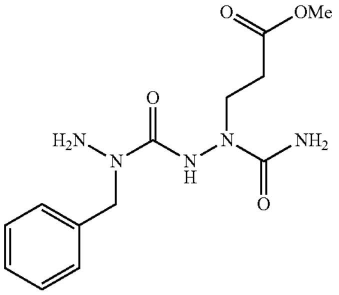 [SMILES: COC(=O)CCN(NC(=O)N(N)Cc1ccccc1)C(N)=O]

$^1$H NMR (500 MHz, $CD_3OD$) δ 7.27-7.19 (m, 5H), 4.56 (s, 2H), 3.80-3.60 (br., 2H), 3.53 (s, 3H), 2.53 (t, 2H) ppm. $^{13}$CNMR (125 MHz, $CD_3OD$) δ 174.42, 160.08, 137.61, 129.98, 129.44, 129.01, 54.58, 52.36, 45.75, 33.65 ppm. Mass Spectrum: (ESI) m/z 310.13 (M+H)$^+$, m/z 332.20 (M+Na)$^+$.

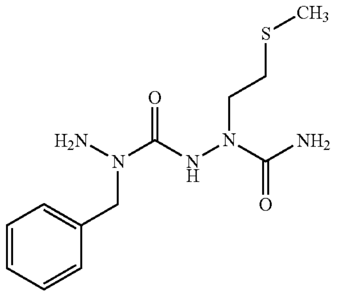 [SMILES: CSCCN(NC(=O)N(N)Cc1ccccc1)C(N)=O]

$^1$H NMR (500 MHz, $CD_3OD$) δ 7.38-7.19 (m, 5H), 4.68 (s, 2H), 2.71 (t, 2H) 1.98 (s, 3H) ppm. $^{13}$CNMR (125 MHz, $CD_3OD$) δ 162.22, 159.98, 137.61, 129.89, 129.42, 128.89, 54.50, 48.24, 32.53, 15.18 ppm. Mass Spectrum: (ESI) m/z 298.00 (M+H)$^+$, m/z 320.13 (M+Na)$^+$.

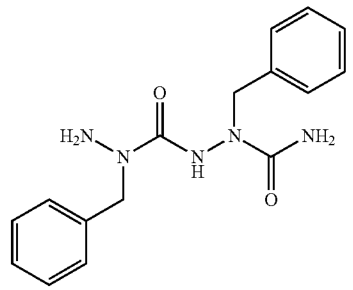 [SMILES: NC(=O)N(Cc1ccccc1)NC(=O)N(N)Cc1ccccc1]

$^1$H NMR (500 MHz, $CD_3OD$) δ 7.35-7.28 (m, 10H), 4.63 (br. s, 4H) ppm. $^{13}$C NMR (125 MHz, $CD_3OD$) δ 164.87, 159.88, 138.43, 138.14, 129.57, 129.52, 129.33, 139.23, 128.66, 128.56, 128.46, 128.38, 57.21 ppm. Mass Spectrum: (ESI) m/z 314.00 $(M+H)^+$, m/z 336.00 $(M+Na)^+$.

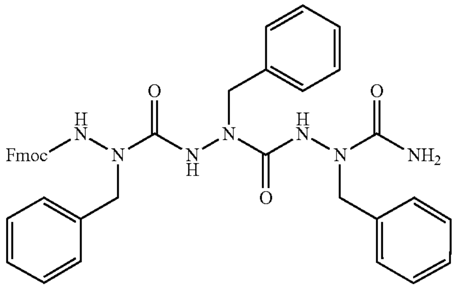

Mass Spectrum: (ESI) m/z 684.20 $(M+H)^+$, m/z 706.20 $(M+Na)^+$.

Example 19

The tri-azatide amide (8) was synthesized by coupling of Di-azatide amide (7) with acid chloride (2) in DCM/toluene at 50° C. to yield the N-Fmoc protected Tri-azatide amide (8), using the General Procedures described above.

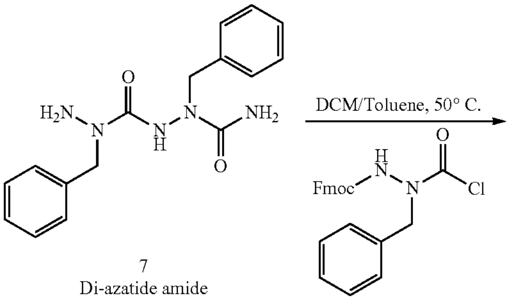

7
Di-azatide amide

2

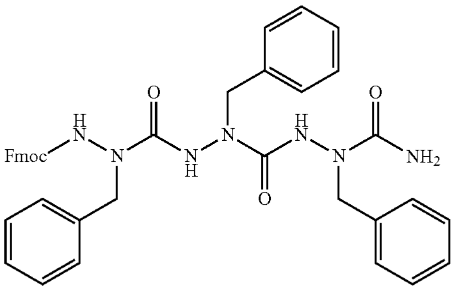

8
Fmoc-Tri-aztide amide

Example 20

Bradykinin amide and four aza-analogues of bradykinin were synthesized: (1)-aza-bradykinin, (8)-aza-bradykin, (1,9)-aza-bradykinin, and (1,8)-aza-bradykin. (1)-aza-bradykinin, (8)-aza-bradykin, (1,9)-aza-bradykinin, and (1,8)-aza-bradykin have the following structures:

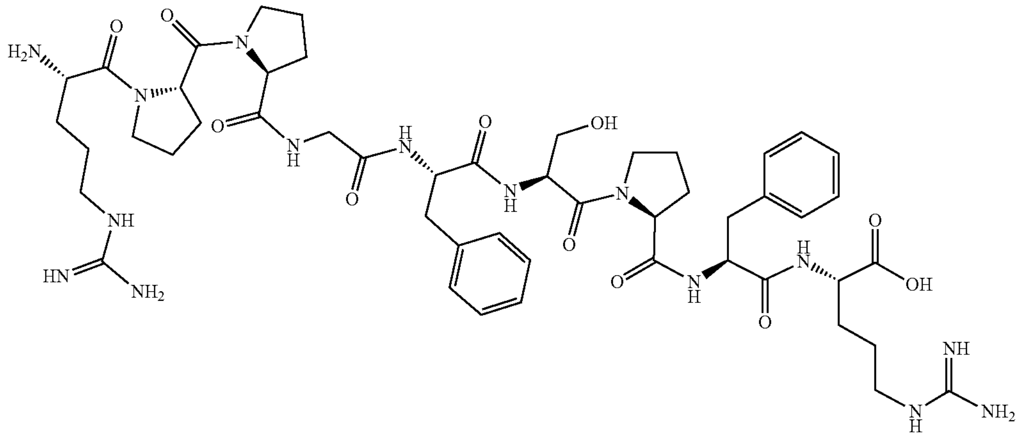

Bradykinin

-continued
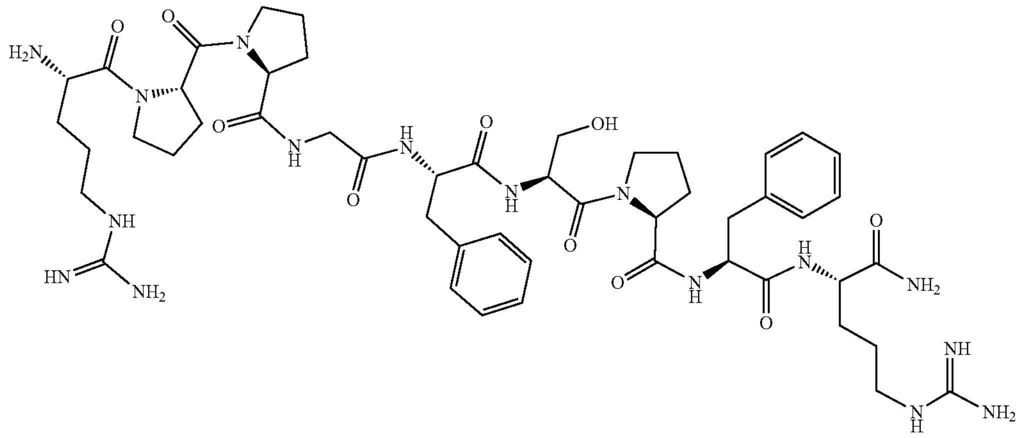
Bradykinin Amide
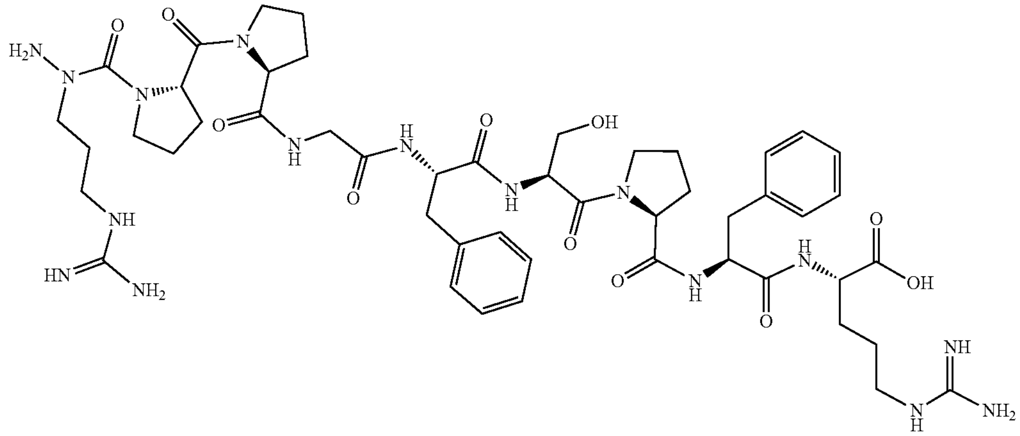
(1)-Aza-Bradykinin
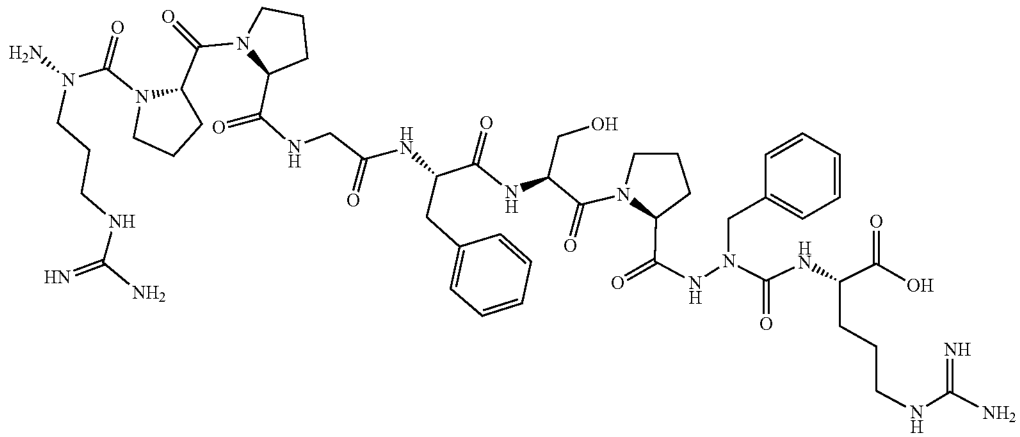
(8)-Aza-Bradykinin -continued
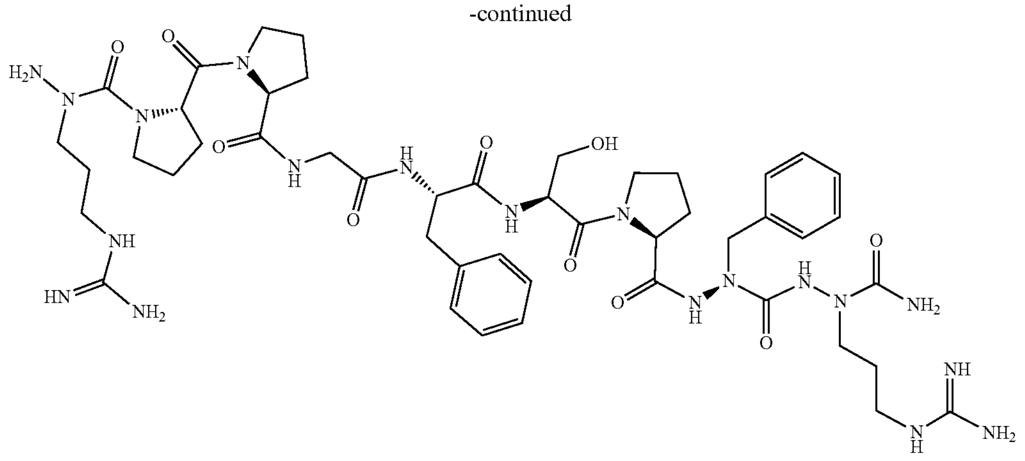
(1,9)-Aza-Bradykinin
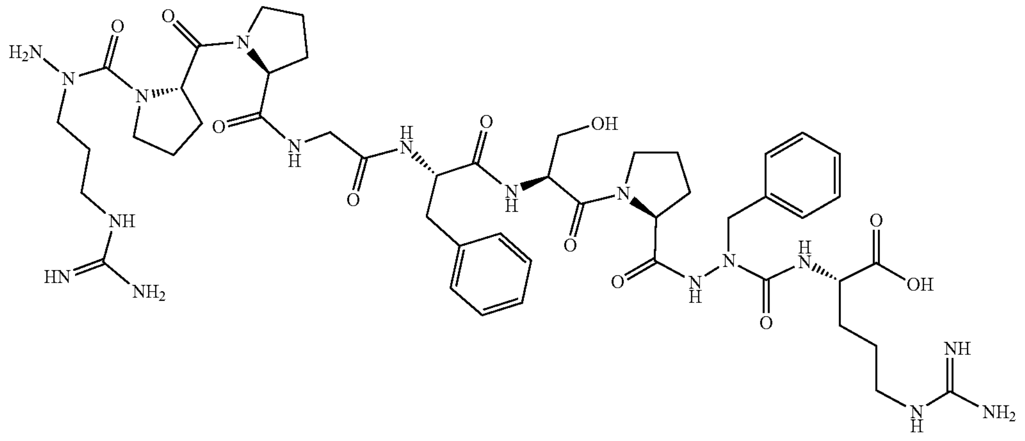
(1,8)-Aza-Bradykinin
(1,9)-aza-bradykinin differs from Aza-bradykinin in that the residues at the N and C terminals have been replaced with corresponding aza-amino acids.
Aza-Bradykinin (1) Synthesis:
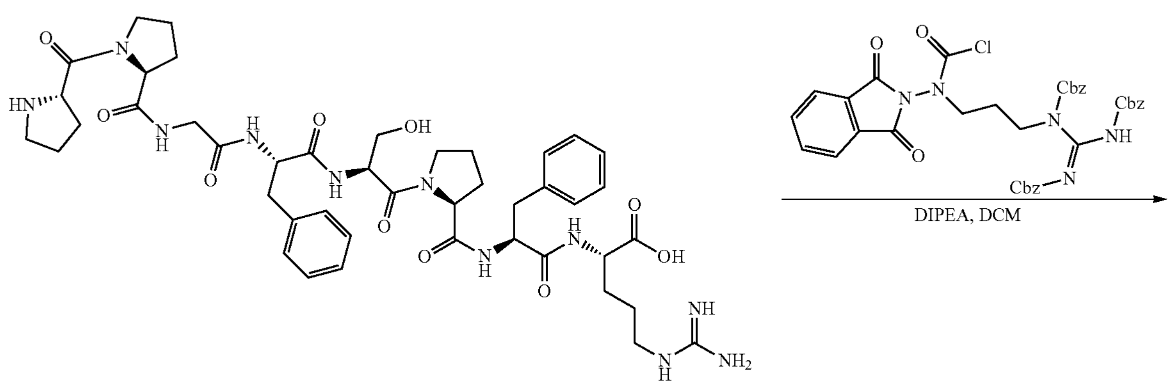
Bradykinin Fragment 2-9
Alfa
25 mg -continued
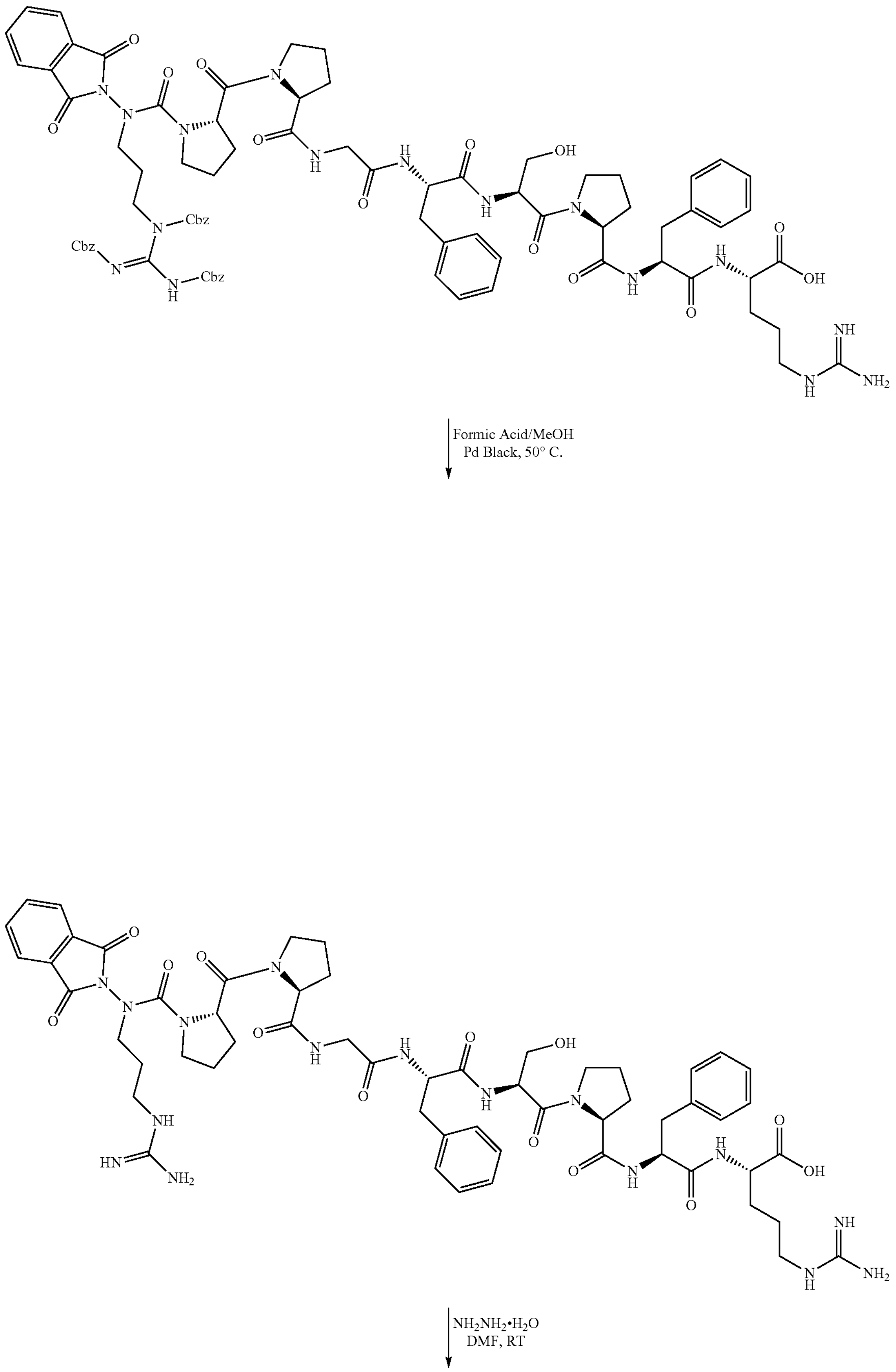

-continued
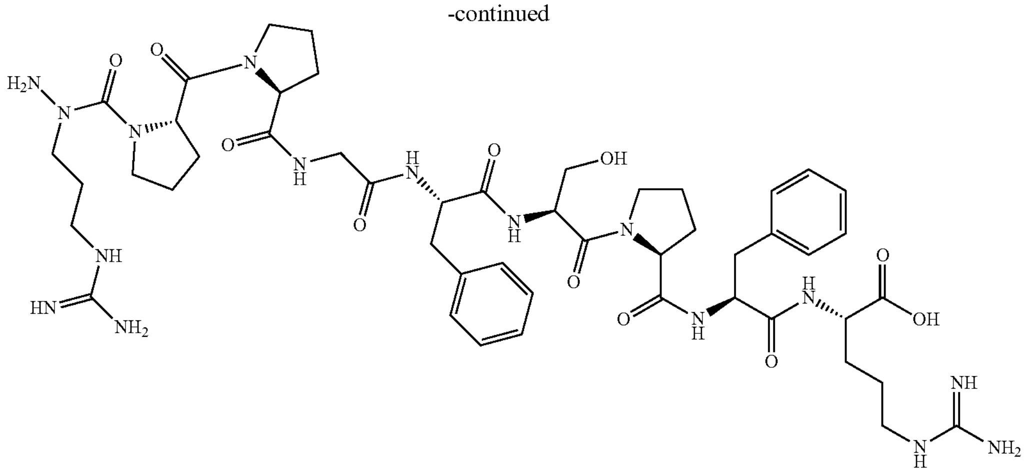
Target 2
(K1137Y)
Aza-Bradykinin (1,8) Synthesis:
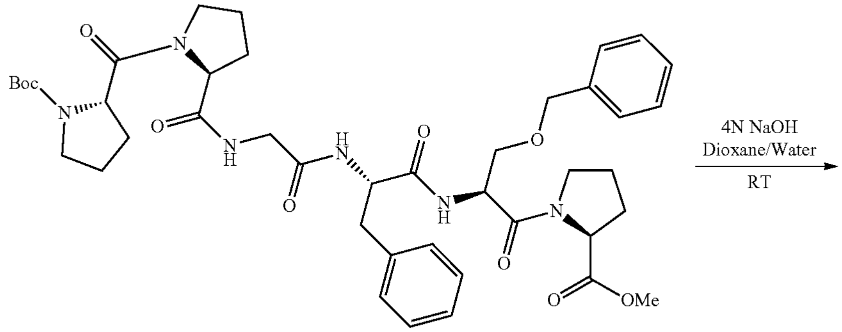
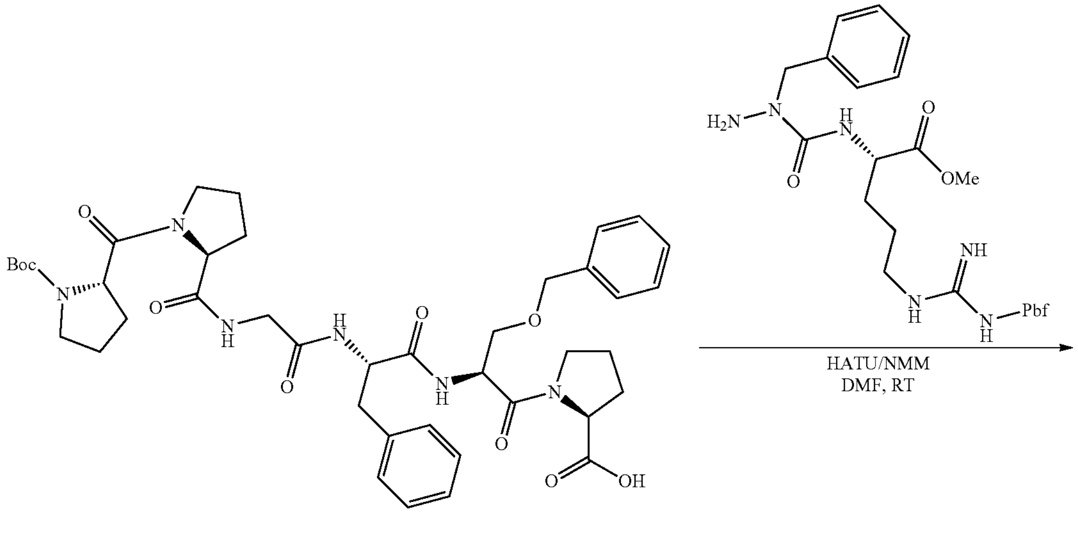

-continued
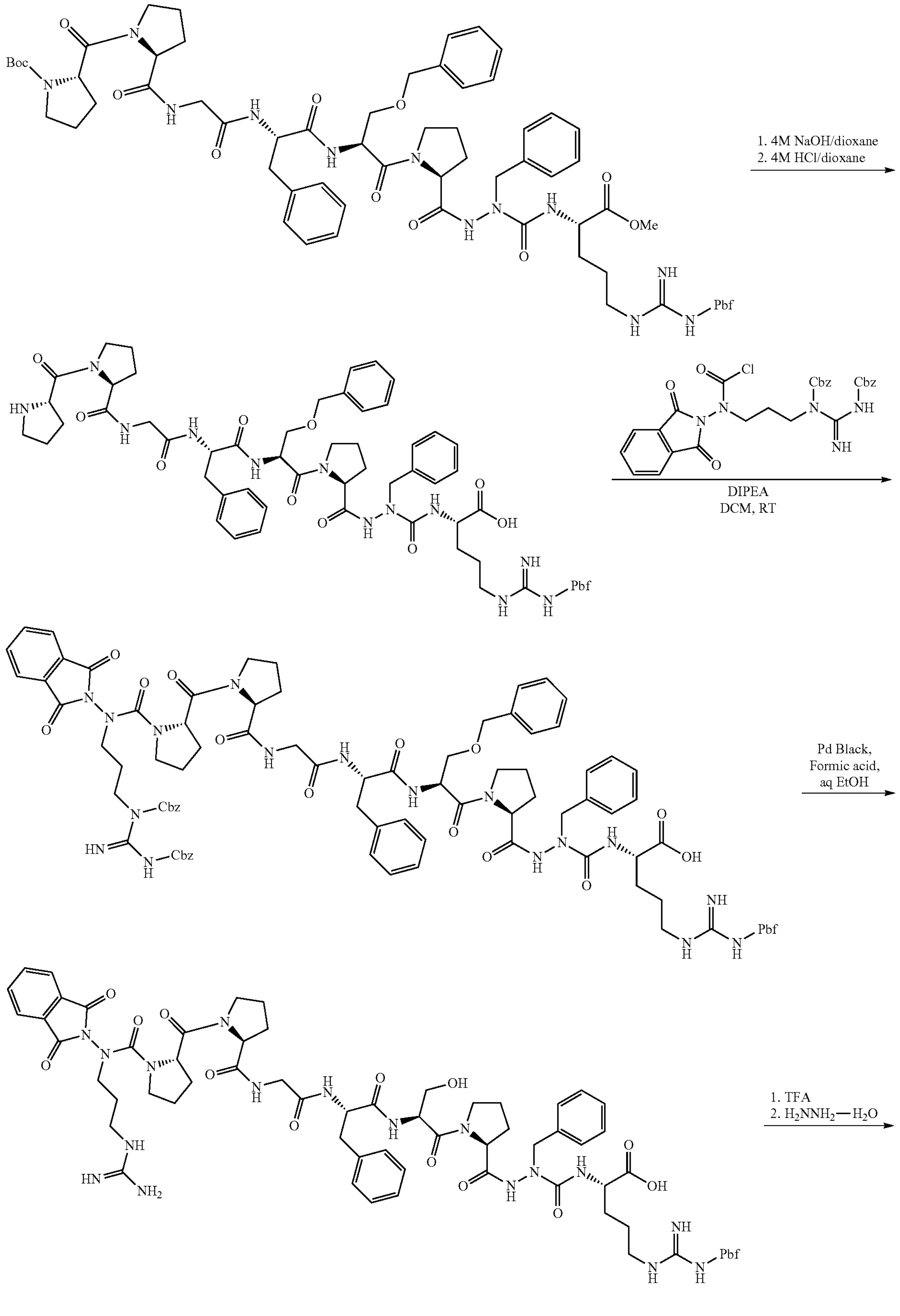

-continued
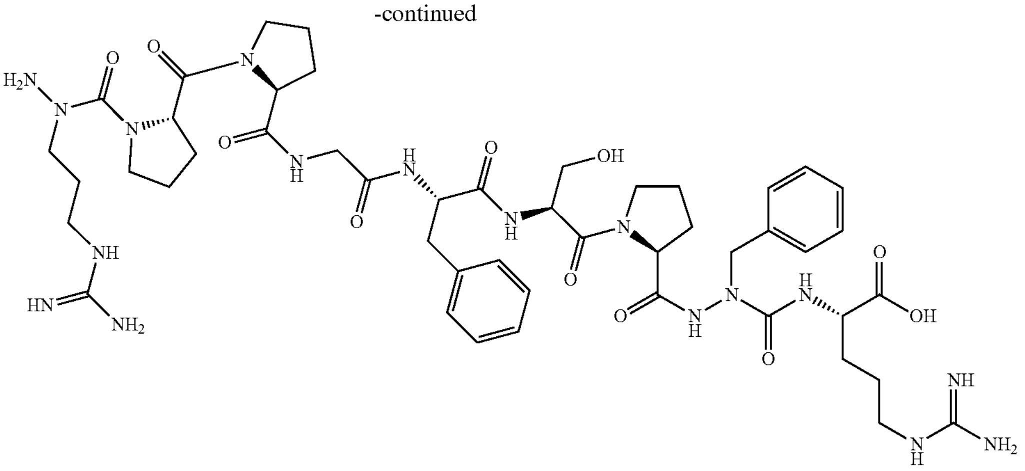
Target 3
(A567)
Aza-Bradykinin (8) Synthesis:
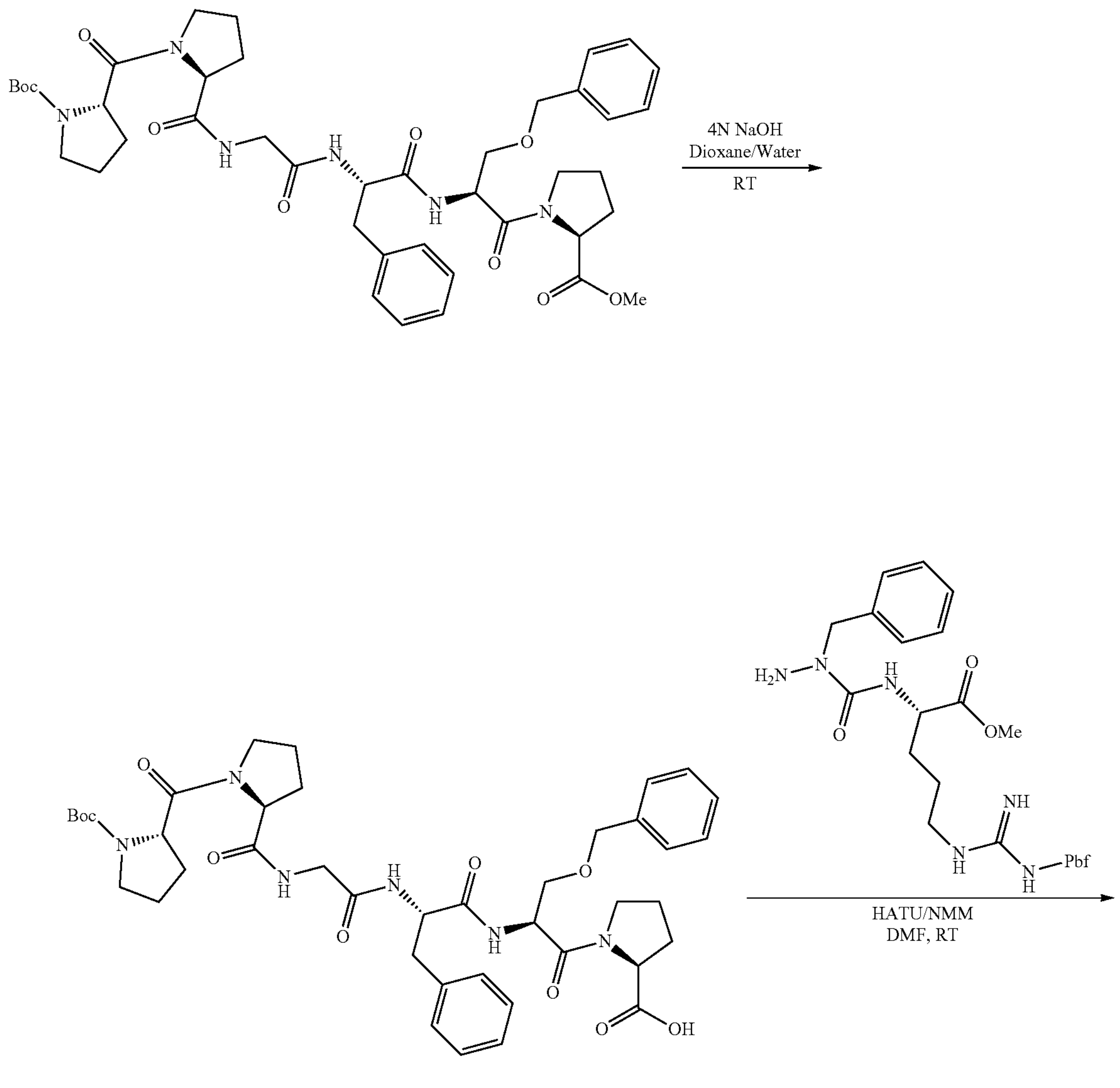

-continued
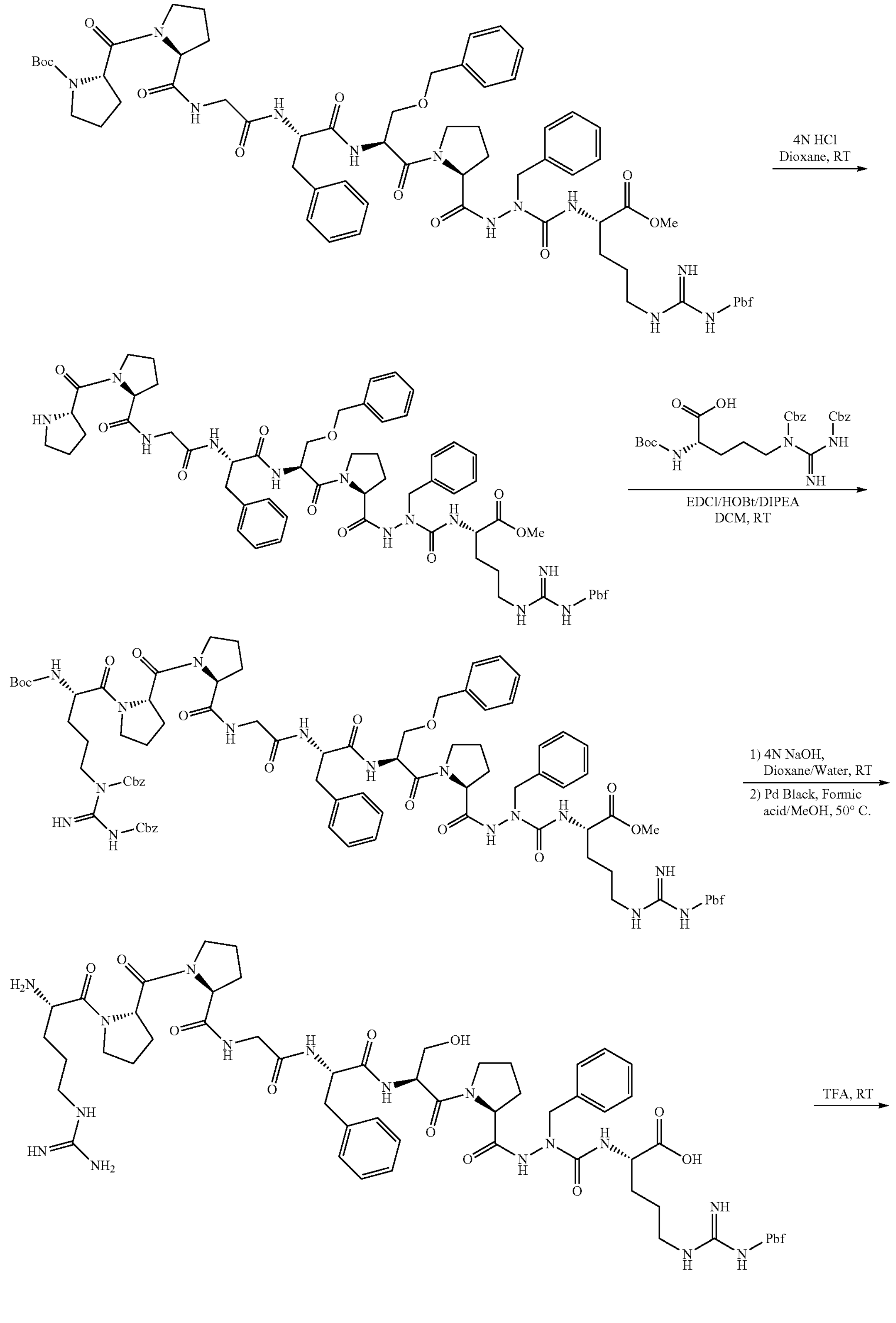

-continued
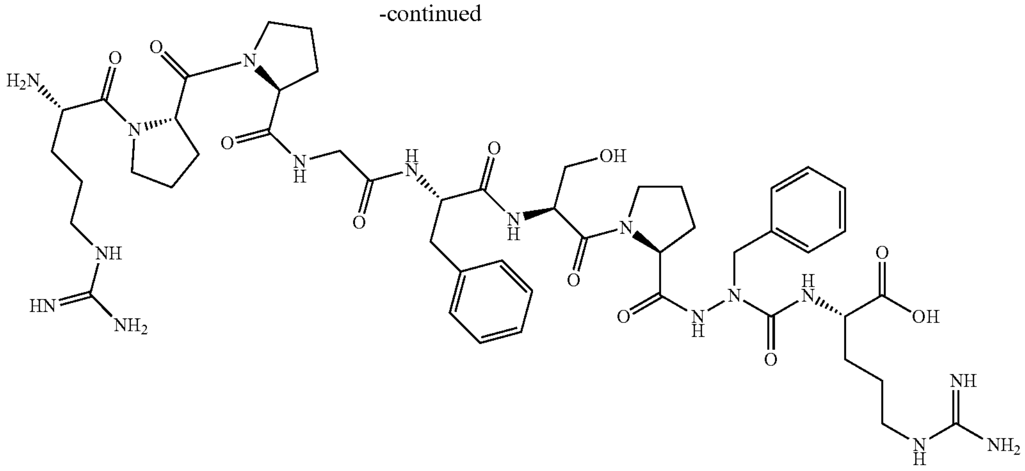
Target 4
(K1137Y)
Synthesis of (1,9)-Aza-Bradykinin:
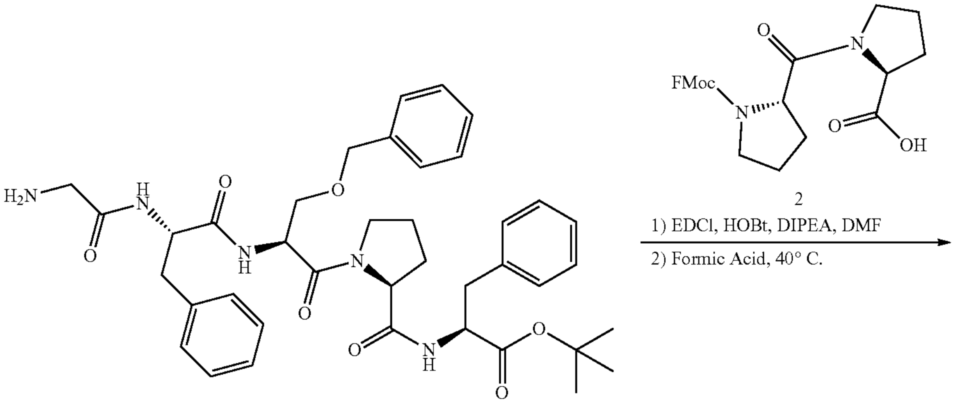
1
2
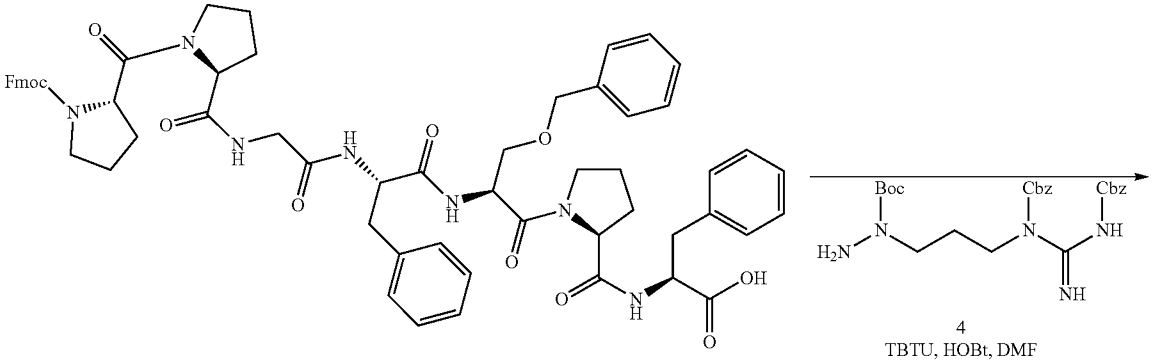
3
4

-continued
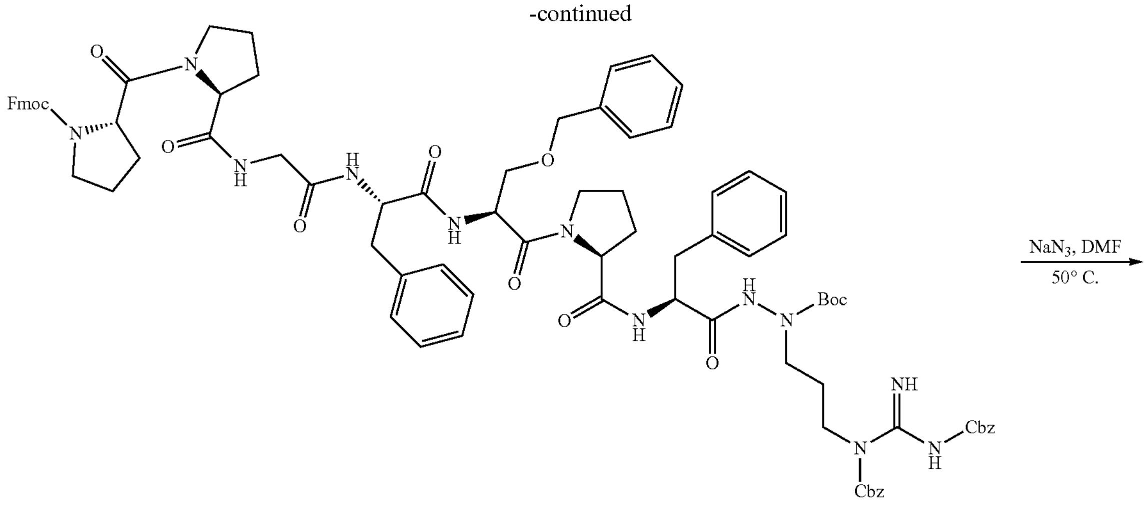
5
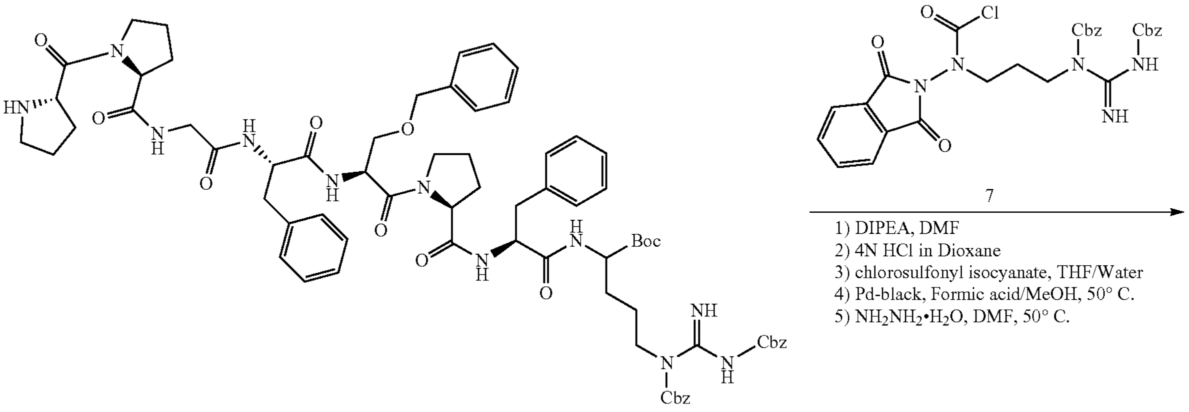
6
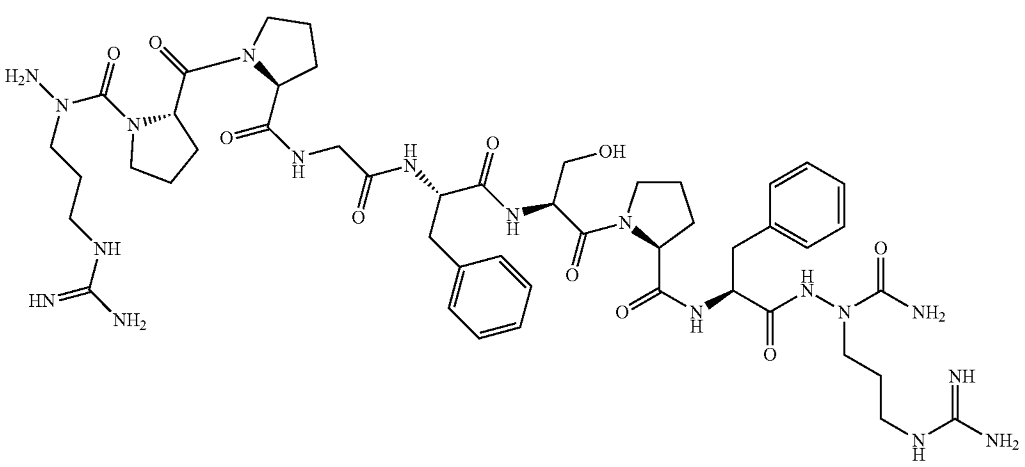
(1,9)-Aza-Bradykinin
K1123W (1,9)-Aza-Bradykinin was synthesized from commercially available penta-peptide (Gly-Phe-Ser(OBzl)-Pro-Phe-OtBu) (1) which was coupled with Fmoc-protected di-proline (2) in present of EDCI, HOBt and DIPEA in DCM to form the hepta-peptide (Fmoc-Pro-Pro-Gly-Phe-Ser (OBzl)-Pro-Phe-OtBu). After the OtBu group was hydrolysed in formic acid at 40° C., the acid (3) was further elongated to octa-azapeptide (5) with Boc-protected Arg $(Cbz)_2$ hydrazine (4) by applying TBTU and HOBt coupling reagents. After the Fmoc group was removed by $NaN_3$ in DMF, the free proline (6) was coupled with N-Phth-Arg $(Cbz)_2$ hydrazine carbazic acid chloride (7) in present of DIPEA in DCM to form the fully protected aza-bradykinin. N-Boc group was first removed by TFA in DCM, which was then converted into corresponding amide with CSI. Global deprotection of Cbz and OBzl groups was done by applying catalytic hydrogenation of palladium black and formic acid in methanol. Finally, the phthaloyl group was removed with a 60% hydrazine in ethanol at 50° C. to yield the (1,9)-aza-bradykinin (K1123W) which was purified and isolated by HPLC and characterized by ESI mass spectrum.

(3)

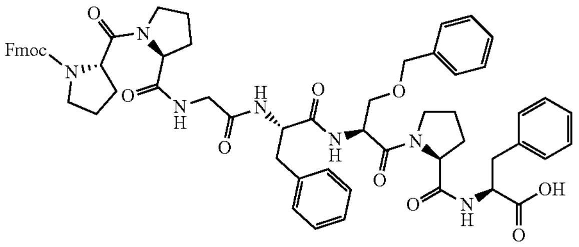

To make a crude hepta-peptide (3), EDCI (0.04 mmol), HOBt (0.02 mmol) and DIPEA (0.05 mmol) were added to a solution of penta-peptide (Gly-Phe-Ser(OBzl)-Pro-Phe-OtBu) (1) (0.02 mmol) and Fmoc-Pro-Pro-OH (2) (0.023 mmol) in anhydrous DCM (1 mL). The solution was stirred at 25° C. under nitrogen for 2 hours then concentrated to dryness and partitioned between water (5 mL) and EtOAc (5 mL). The aqueous layer was extracted with EtOAc (2x5 mL) and the combined organic phase were washed with brine (5 mL), dried over $Na_2SO_4$, filtered and concentrated to afford the crude product and used directly for next step. Mass Spectrum: (ESI) m/z 1116.60 $(M+H)^+$, m/z 1138.60 $(M+Na)^+$.

The crude hepta-peptide (0.02 mmol) was dissolved in formic acid (1 mL) and the solution was stirred at 35° C. under nitrogen for 3 hours then concentrated to dryness and precipitated from MeOH/ether and washed with hexanes to yield white solid. Mass Spectrum: (ESI) m/z 1060.53 $(M+H)^+$, m/z 1082.73 $(M+Na)^+$.

(5)

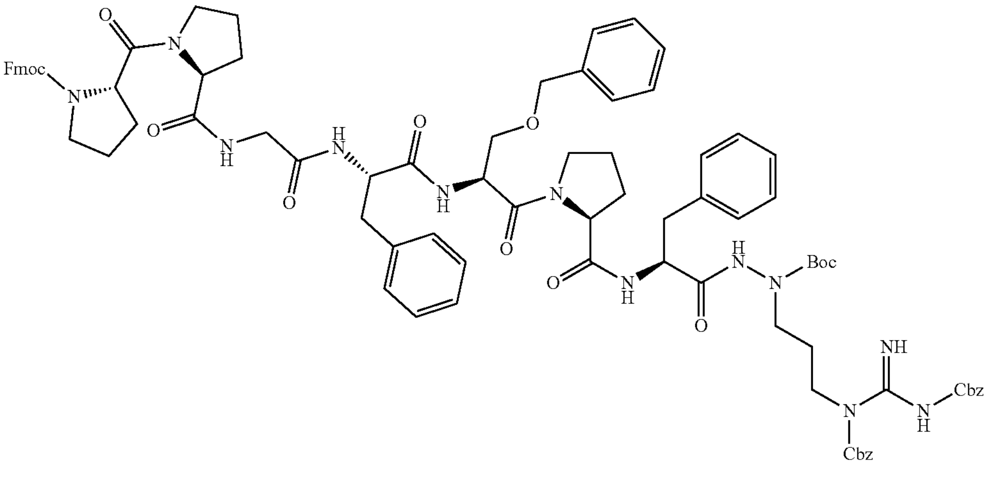

To a solution of hepta-peptide acid (3) (0.02 mmol) and Boc-protected $Arg(Cbz)_2$ hydrazine (4) (0.02 mmol) in anhydrous DMF (1 mL) was add TBTU (0.04 mmol), HOBt (0.02 mmol) and DIPEA (0.05 mmol). The solution was stirred at 40° C. under nitrogen for 2 hrs then concentrated to dryness and wash with water the crude octa-azapeptide was precipitated from MeOH/ether and washed with hexanes to yield white solid. Mass Spectrum: (ESI) m/z 1542.60 $(M+H)^+$, m/z 11564.47 $(M+Na)^+$.

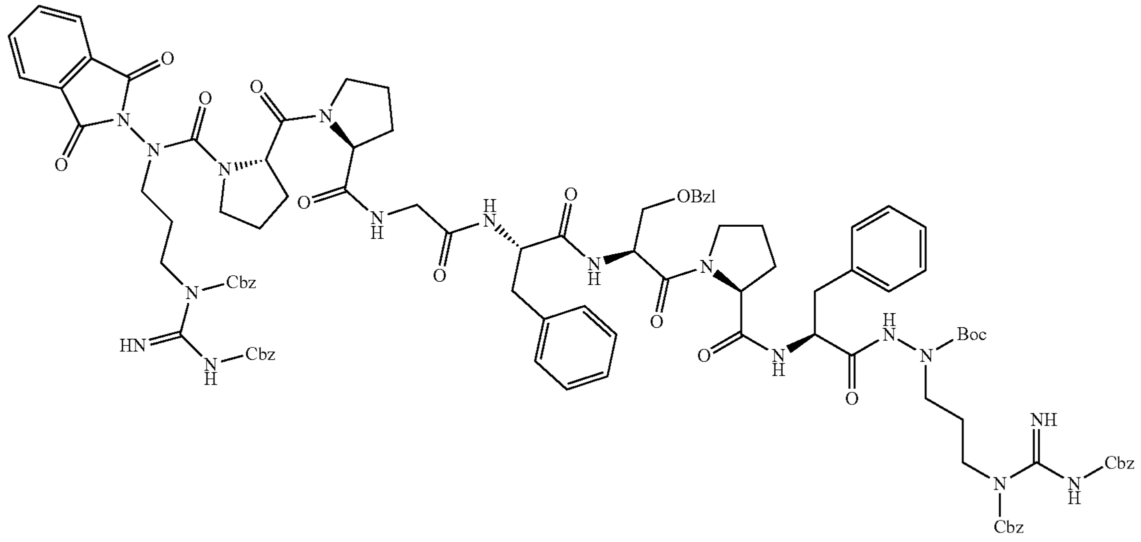

To a solution of octa-azapeptide (8.4 umol) in anhydrous DMF (0.3 mL) was added $NaN_3$ (42 umol). The mixture was stirred at 50° C. under nitrogen for 2 hours then concentrated to dryness and wash with water the crude octa-azapeptide amine (6) was precipitated from MeOH/ether and washed with hexanes to yield white solid. Mass Spectrum: (ESI) m/z 1319.67 $(M+H)^+$.

To a solution of octa-azapeptide amine (6) (8.4 umol) and N-Phth-Arg$(Cbz)_2$ hydrazine carbazic acid chloride (7) in anhydrous DCM (0.5 mL) was added DIPEA (2 uL). The mixture was stirred at 25° C. under nitrogen for 15 hrs then concentrated to dryness and wash with water the crude product was precipitated from MeOH/ether and washed with hexanes to yield white solid. Mass Spectrum: (ESI) m/z 1875.80 $(M+H)^+$, m/z 1897.40 $(M+Na)^+$.

The fully protected aza-bradykinin (6.4 umol) was dissolved in 4N HCl (500 uL). The solution was stirred at 25° C. under nitrogen for 1 hour then concentrated to dryness and used directly for next step. Mass Spectrum: (ESI) m/z 1776.33 $(M+H)^+$.

To a solution of the protected aza-bradykinin amine (6.4 umol) in anhydrous THE (0.3 mL) at 0° C. was added chlorosulfonyl (CSI) (9.6 umol) rapidly. The solution was stirred at 0° C. under nitrogen for 1 hour then water (0.3 mL) was added. The solution was warmed to room temperature then concentrated to dryness. The crude product was precipitated from MeOH/ether and washed with water to yield white solid. Mass Spectrum: (ESI) m/z 1818.40 $(M+H)^+$.

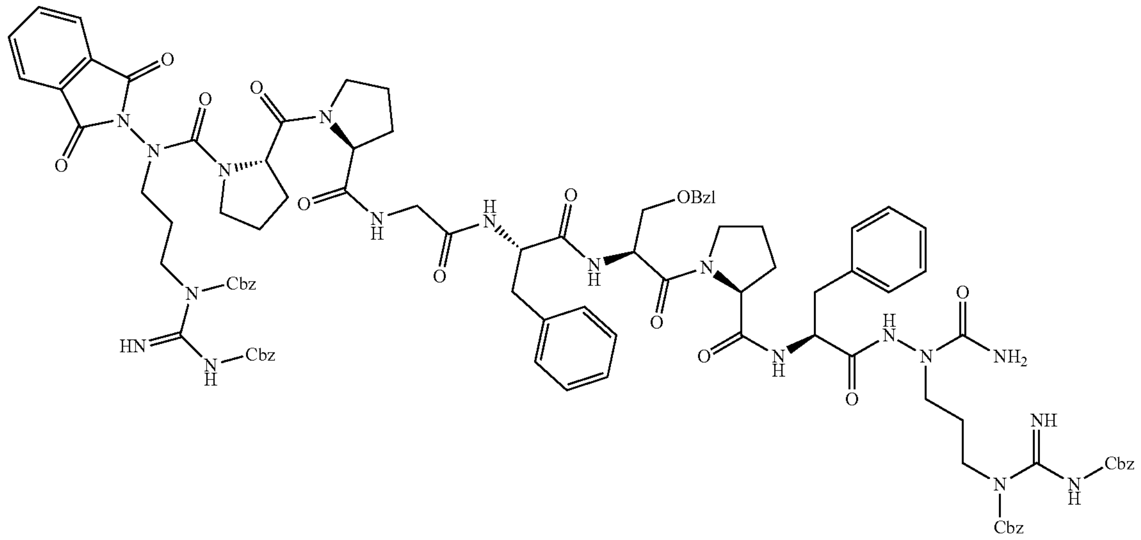

K1123W

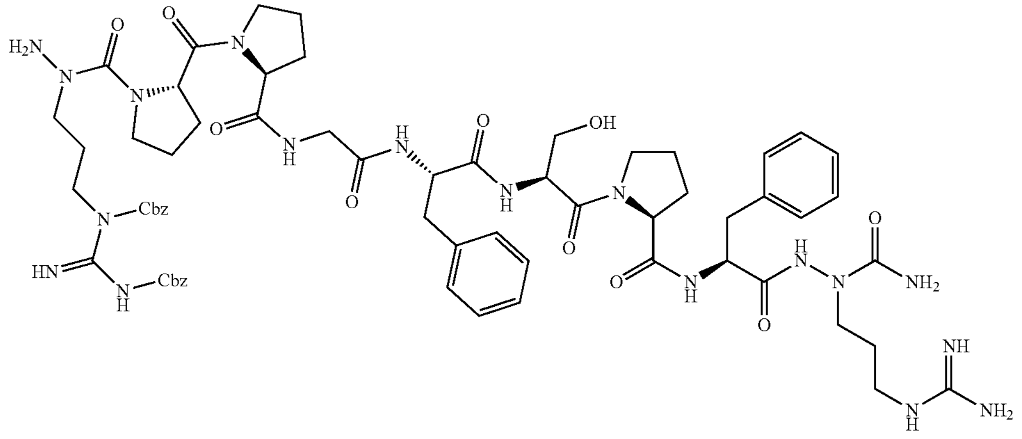

To a solution of the protected aza-bradykinin amide (2.75 umol) in anhydrous MeOH (0.4 mL) was added palladium black (5 mg) and formic acid (100 uL). The mixture was stirred at 60° C. under nitrogen for 5 hours then filtered through a pad of celite and concentrated to dryness for next step. Mass Spectrum: (ESI) m/z 1818.40 $(M+H)^+$.

To the crude product in ethanol (500 uL) was added 60% hydrazine (300 uL). The solution was stirred at 50° C. for 2 hours and concentrated to dryness. The Aza-Bradykinin was purified and isolated by HPLC to yield white solid. Mass Spectrum: (ESI) m/z 1062.67 $(M+H)^+$.

Stability of Bradykinin amide and (1-9)-Aza-Bradykinin in serum was measured. The results of stability testing are depicted in Tables 1 and 2 and FIG. 1 and FIG. 2.

TABLE 1

| Serum: 50 uL; Bradykinin amide: 10 ug | O.D. 220 nm (AUC) |
|---|---|
| Incubation time: 1 min, 30 min, 1 hr, | |
| 3 hr and 15 hr | |
| Bradykinin(10 ug) | 5305818 |
| 1 min | 4948859 |
| 30 min | 2600809 |
| 1 hour | 2135414 |
| 3 hours | 155100 |
| 15 hours | 58858 |

TABLE 2

| Serum: 50 uL; Aza-Bradykinin: 5ug | O.D. 220 nm (AUC) |
|---|---|
| Incubation time: 1 min, 30 min, 1 hr, | |
| 3 hr and 15 hr | |
| Aza-Bradykinin(5 ug) | 739361 |
| 1 min | 581369 |
| 30 min | 578373 |
| 1 hour | 484321 |
| 3 hours | 549322 |
| 15 hours | 521217 |

Figure 2:
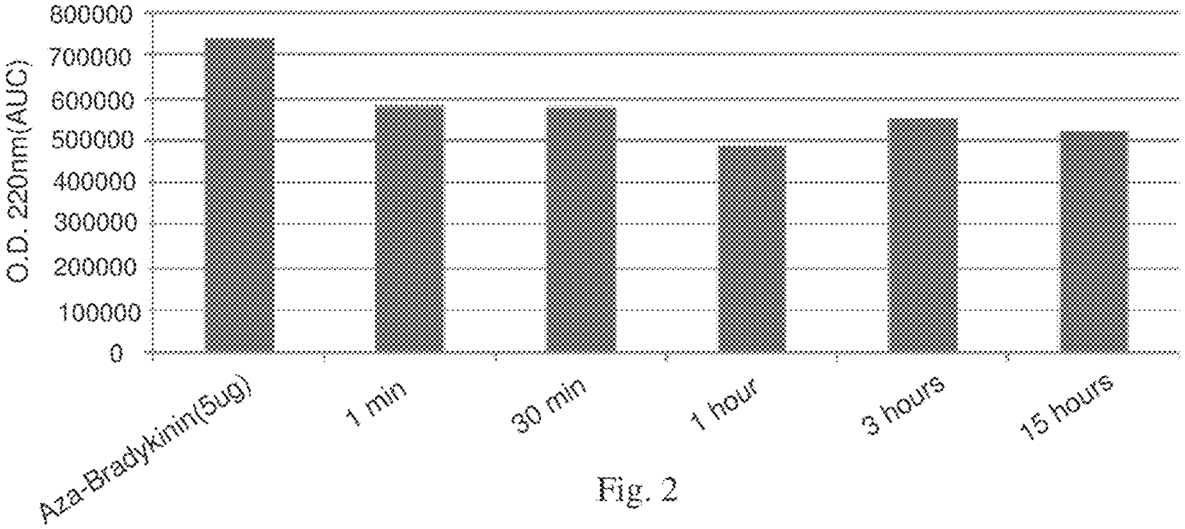
FIG. 2 is a graph depicting the higher stability of (1,9)-Aza-Bradykinin in serum.

As evident from Tables 1 and 2 and FIG. 1 and FIG. 2 (1-9)-Aza-Bradykinin is more stable in serum at 1 min, 30 min, 1, hour, 3 hours, and 15 hours.

Example 21

Aza-Endomorphin-2 (K763, tetra-azapeptide) of the following structure was synthesized:

K763

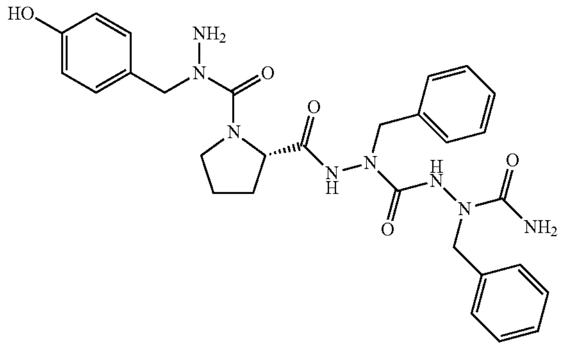

$C_{29}H_{34}N_8O_5$
Exact Mass: 574.27

Aza-Endomorphin-2 is an aza-analogue of Endomorphin-2:

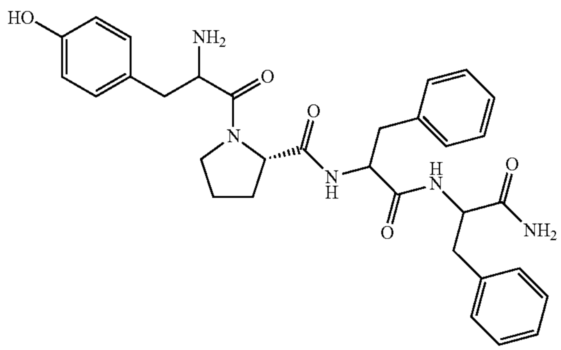

Endomorphin-2

Aza-Endomorphin-2 differs from Endomorphin-2 in that the
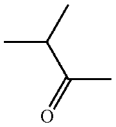
at the C-terminus and N-terminus of Endormin 2 are replaced with
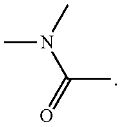
The following Scheme was used to synthesize Aza-Endomorphin-2:
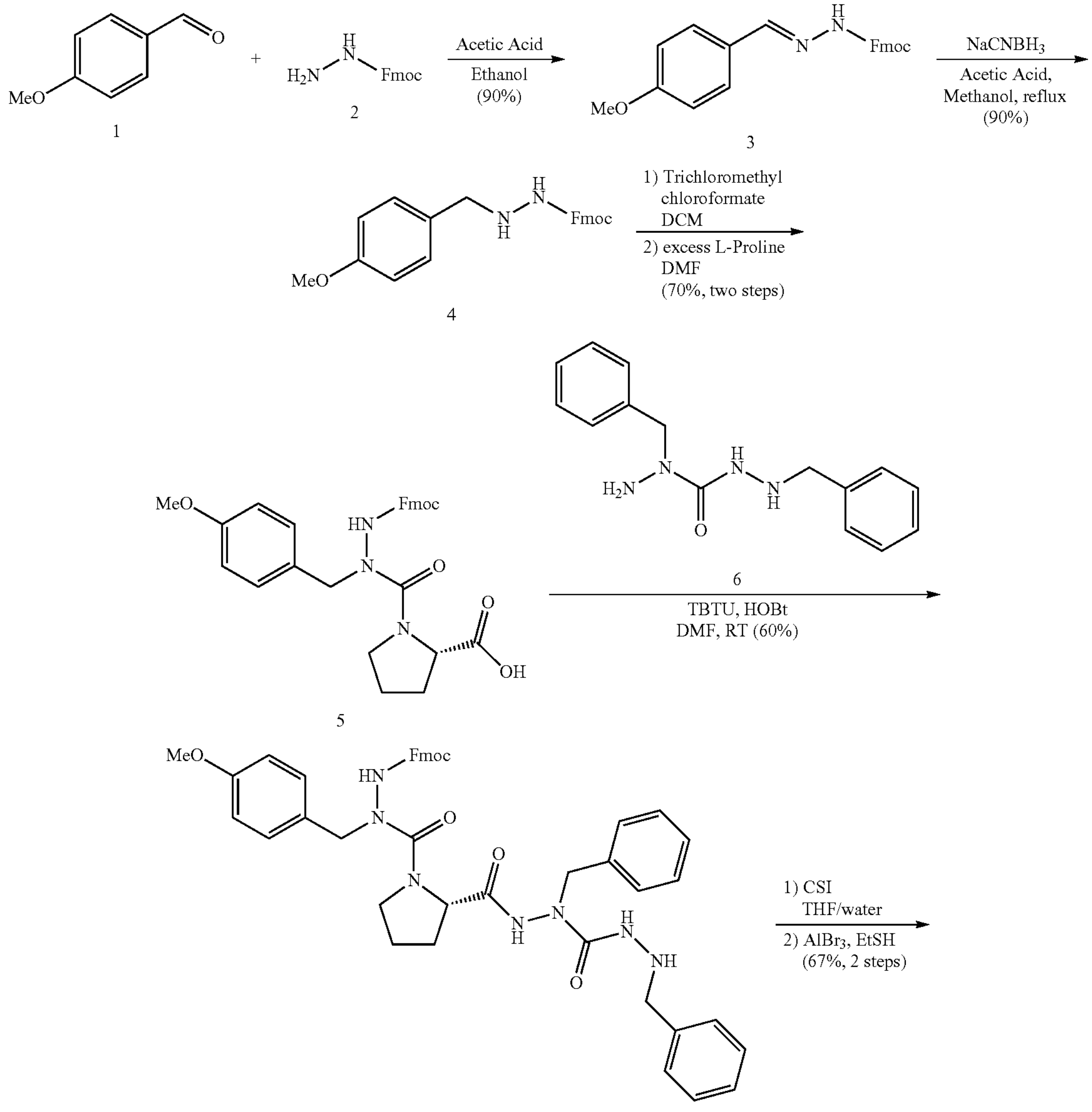
1
2
3
4
5
6
7

-continued

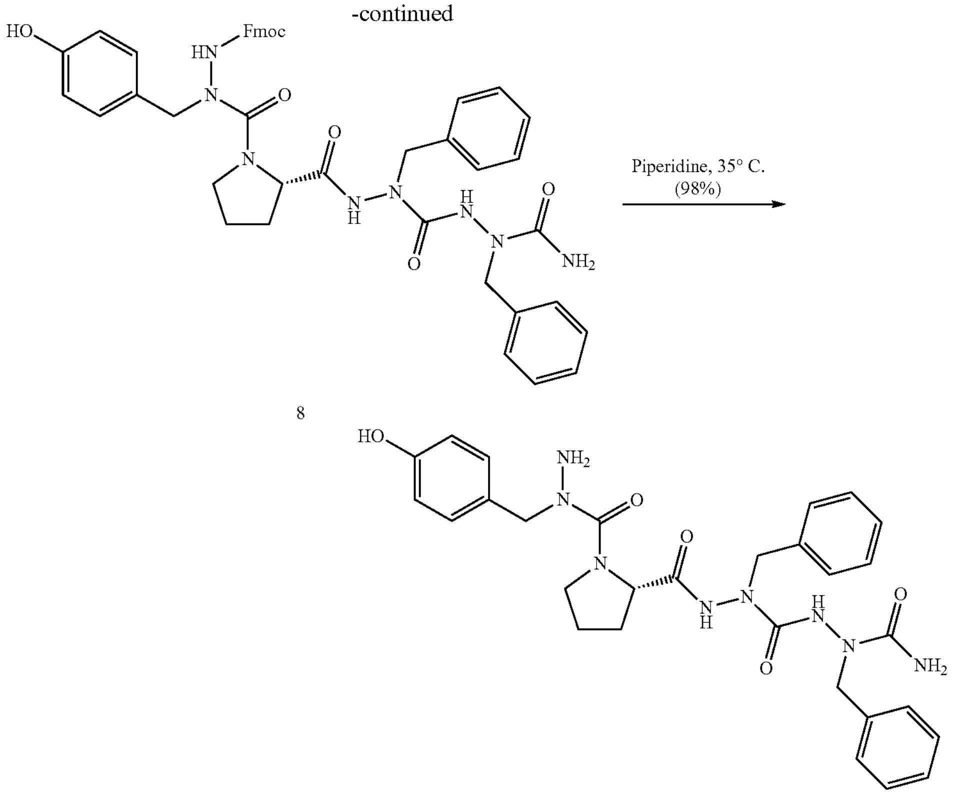

8

K763
8 Steps; total yield = 22%

Commercial available Fmoc-hydrazine (1) was coupled with an 4-Methoxybenzaldehyde (2) to form an acyl hydrazone (3) in 90% yield, which was reduced by the catalytic hydrogenation and hydride addition to Fmoc protected hydrazide (4) in 90%. The active intermediate acid chloride was generated from carbonyl donor trichloromethyl chloroformate (diphosgene) with the hydrazine (4), which was reacted with excess L-proline to form the azapeptide (5) in 70% (two steps). The key step was the coupling reaction between the azapeptide (5) and the diphenyl azatide (6) with coupling reagents of TBTU and HOBt in DMF to yield the protected tetra-azapeptide (7) in 60% yield. Chlorosulfonyl isocyanate (CSI) was then converted the amine into the corresponding amide and the $AlBr_3$ in EtSH was convert the methoxyl group into hydroxyl amide (8) in 67% (two steps). Finally, removed the Fmoc group with piperidine at 35° C. to get the Aza-Endomorphin-2 (K763) in 98% yield.

(5)

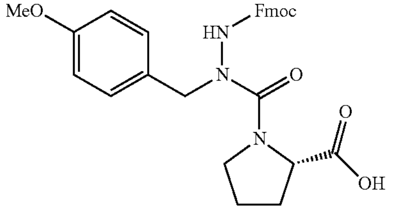

1-[N′-(9H-Fluoren-9-ylmethyoxycarbonyl)-N-(4-methoxy-benzyl)-hydrazinocarbonyl]-pyrrolidine-2-carboxylic acid To a solution of N-Fmoc-4-Methoxyphenylhydrazine (4) (1.06 mmol) and N,N,N',N'-Tetramethyl-1,8-naphthalenediamine (2.12 mmol) in anhydrous DCM (10 mL) at 0° C. was added dropwise the solution of trichloromethyl chloroformate in anhydrous DCM (10 mL). The solution was stirred and warmed to 25° C. under nitrogen for 30 mins then excess L-proline solution in DMF (5.3 mmol) was added. The solution was stirred at 25° C. under nitrogen for 15 hrs then concentrated to dryness and partitioned between 0.5N HCl (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 70% yield. Mass Spectrum: (ESI) m/z 515.93 $(M+H)^+$, m/z 538.00 $(M+Na)^+$.

(7)

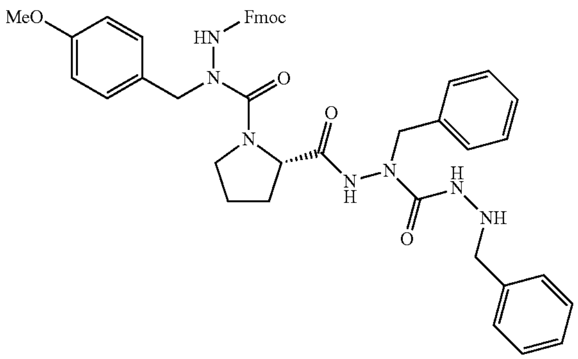

To a solution of the azapeptide (5) (2.18 mmol) in anhydrous DMF (11 mL) was added TBTU (2.57 mmol) and HOBt (2.18 mmol). The solution was stirred at room temperature for 10 mins and then added the phenyl diazatide (6) (2.58 mmol) solution in anhydrous DMF (10 mL) at 0° C. was added dropwise the solution of trichloromethyl chloroformate in anhydrous DCM (4 mL). The solution was stirred at 25° C. under nitrogen for 15 hours and, then, concentrated to dryness and partitioned between 0.5N HCl (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 60% yield. Mass Spectrum: (ESI) m/z 767.93 $(M+H)^+$, m/z 790.07 $(M+Na)^+$.

(K763)

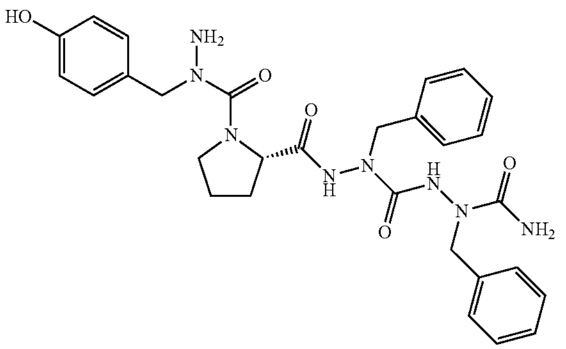

To a solution of the protected tetra-azapeptide (7) (0.52 mmol) in anhydrous THE (12 mL) at 0° C. was added chlorosulfonyl (CSI) (0.78 mmol) rapidly. The solution was stirred at 0° C. under nitrogen for 1 hour then added water (12 mL). The solution was warmed to room temperature then concentrated and partitioned between water (100 mL) and EtOAc (100 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with 5% MeOH in chloroform to afford the products as a white solids. (ESI) m/z 810.87 $(M+H)^+$. To a solution of azapeptide amide (0.35 mmol) in EtSH (20 mL) at 0° C. was added $AlBr_3$ solution (1M in DCM) (3.5 mmol). The solution was stirred and warmed to room temperature under nitrogen for 1.5 hours then concentrated to dryness. The crude product which was purified by flash silica gel column chromatography eluting with acetone: DCM (1:1 v/v) to afford the products as a white solids (67% yield, two steps). (ESI) m/z 796.80 $(M+H)^+$, m/z 819.00 $(M+Na)^+$. The solution of N-Fmoc protected azapeptide (8) (0.1 mmol) in piperidine (1 mL) was stirred at 35° C. under nitrogen for 15 mins. The mixture was concentrated to dryness and then the crude product was purified by flash silica gel column chromatography eluting with acetone: DCM (1:1 v/v) to afford the products as a white solids in 98% yield. (ESI) m/z 574.93 $(M+H)^+$, m/z 597.13 $(M+Na)^+$. The aza-Endomorphin (K763) has a similar $^1H$ and $^{13}C$ spectra as the Endomorphin-2 (EM2) in pyridine-$D_6$. Also aza-Endomorphin (K763) has 1:8 cis/trans conformers in DMSO-$D_6$ by $^1H$ NMR spectra of aromatic protons.

Synthesis of Aza-Endomorphin-2 at the proline site (K1167Y)

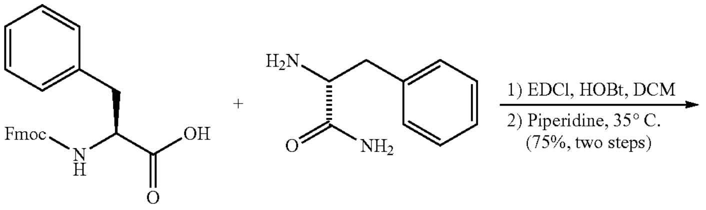

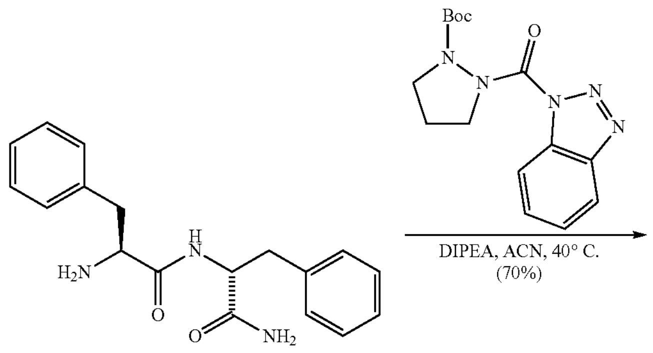

-continued
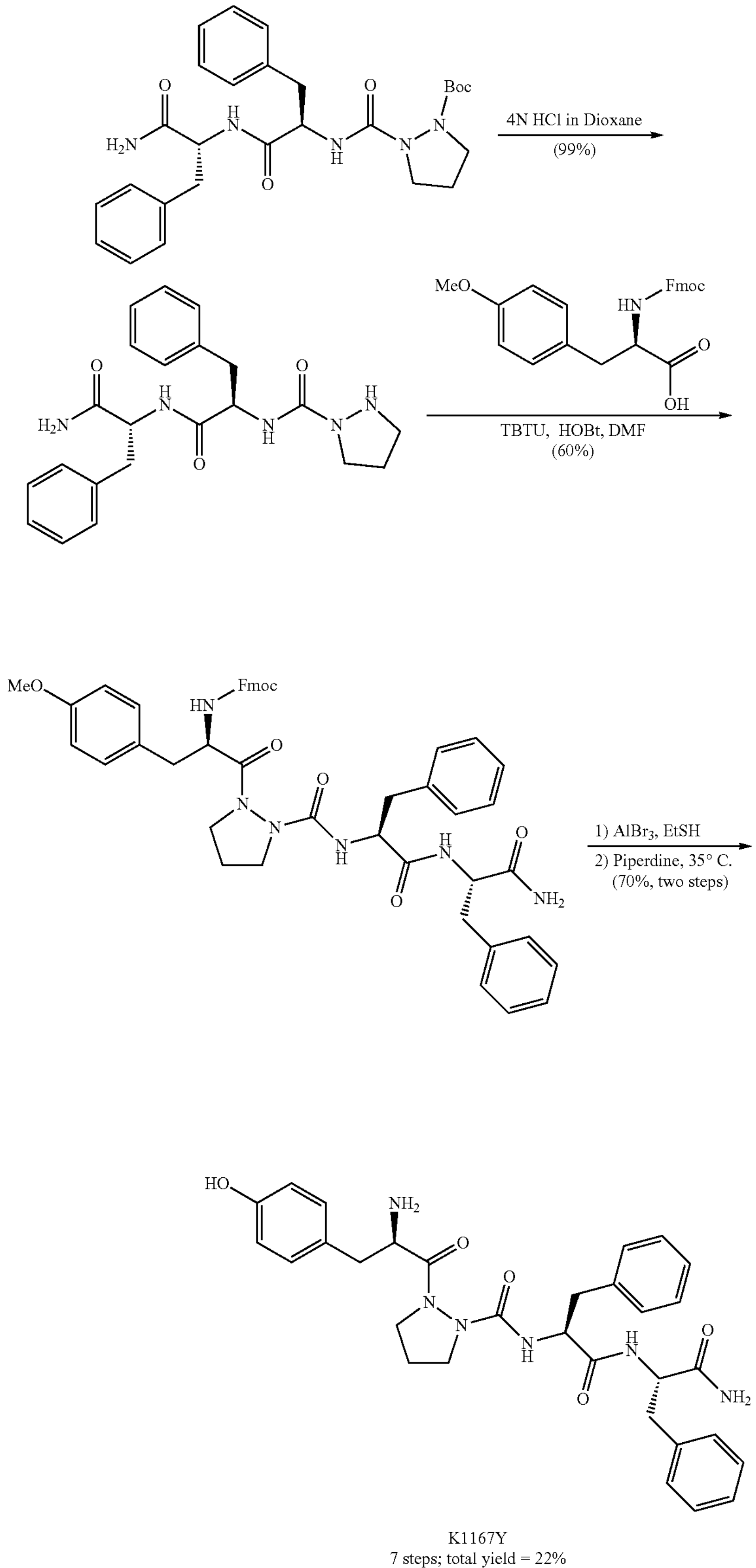
K1167Y
7 steps; total yield = 22%

Figure 3:
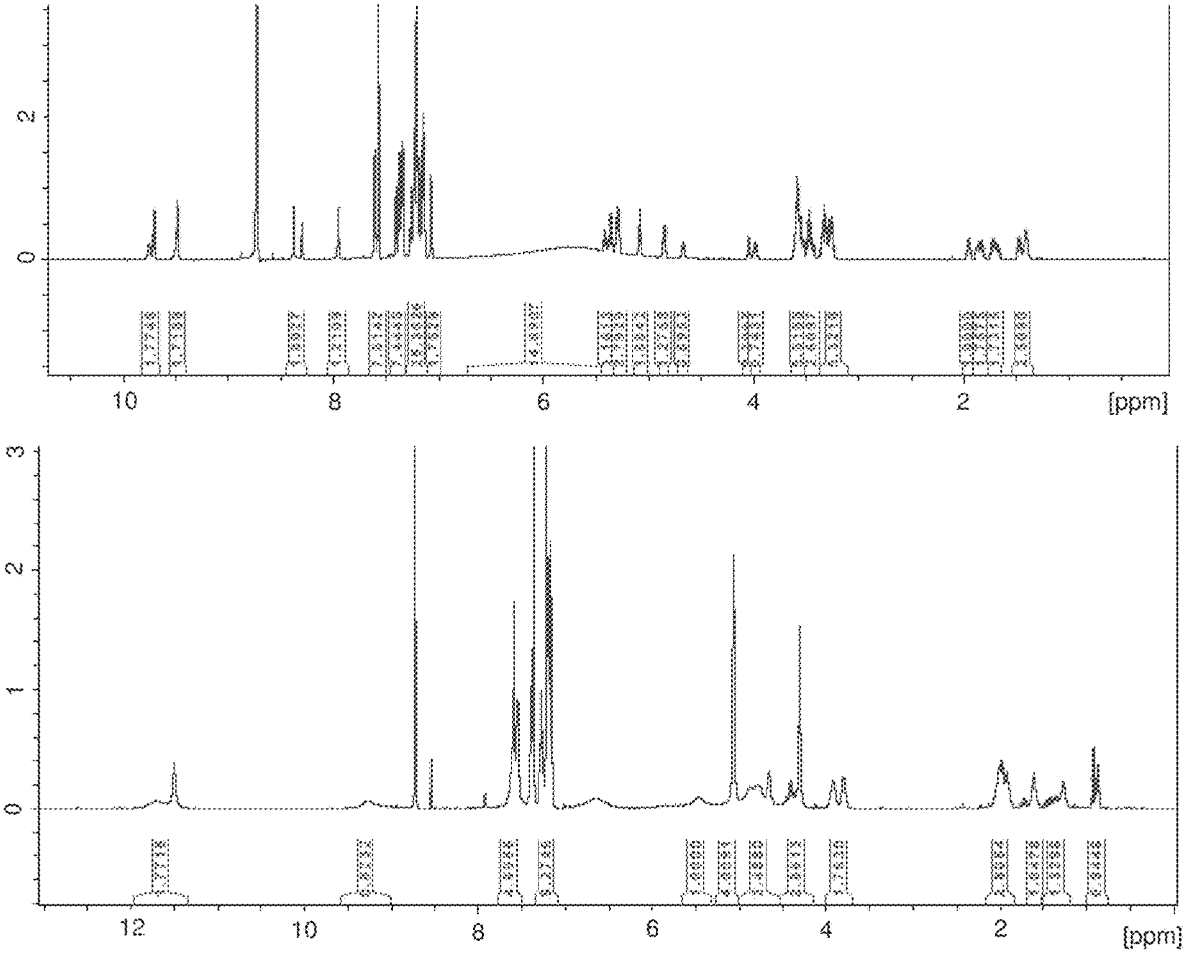
FIG. 3 depicts $^{1}H$ NMR spectra of Endomorphin-2 (EM2) and Aza-Endomorphin-2.

FIG. 3 depicts ¹H NMR spectra of Endomorphin-2 (EM2) and Aza-Endomorphin-2 (K763), respectively (Endomorphin-2 is depicted on top).

Figure 10:
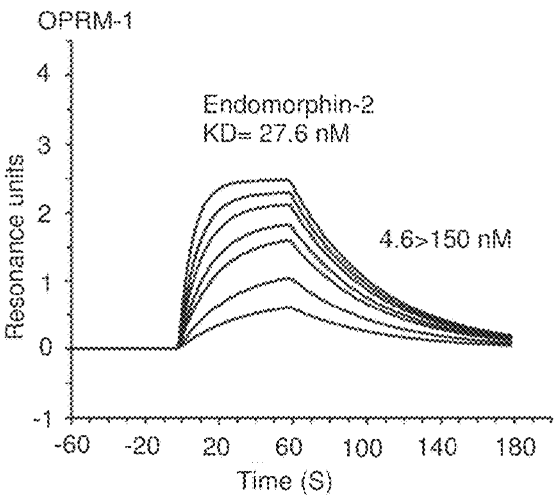
FIG. 10 are graphs depicting binding of K763 and Endomorphin-2 binding to OPRM-1. K763 binds OPRM-1 with a stronger affinity than Endomorphin-2.
Figure 10:
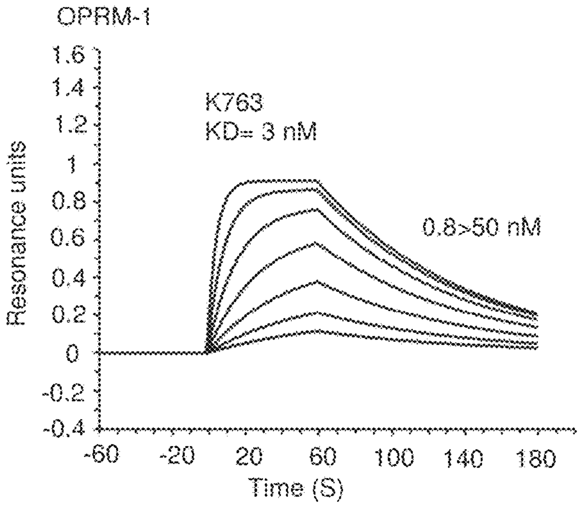
Figure 10:
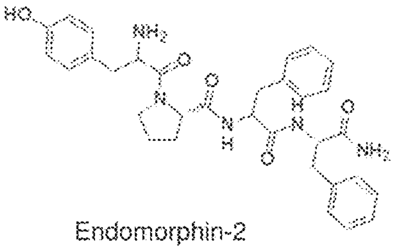
Figure 10:
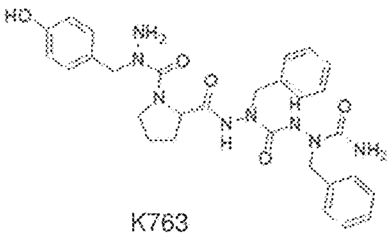

K763 was shown to bind OPRM-1 receptor. The binding is depicted in FIG. 10.

Figure 11:
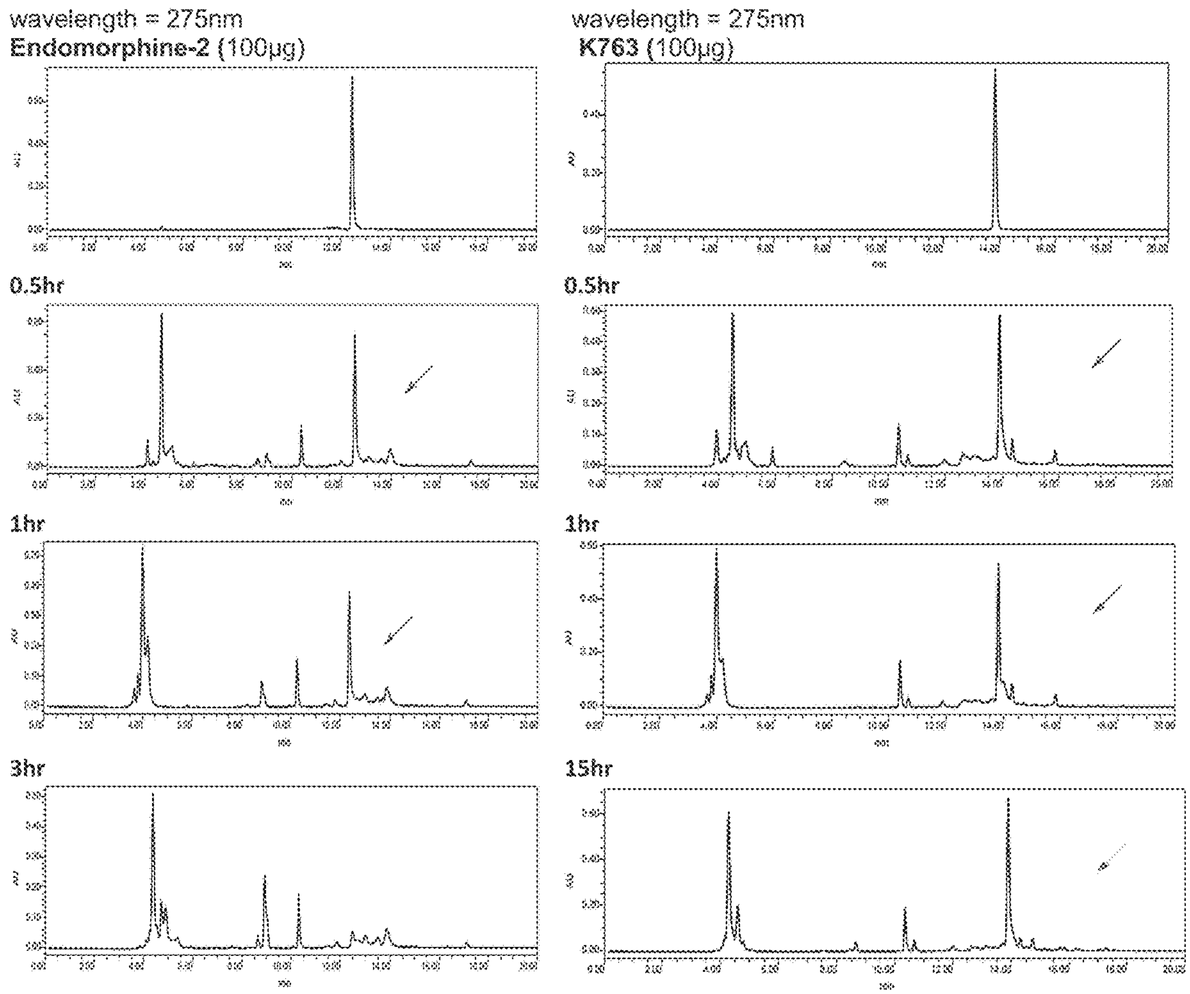
FIG. 11 is a graph depicting stability of EM2 and K763 in mice.

A graph of stability of EM2 and K763 in mice serum is depicted in FIG. 11.

Figure 12:
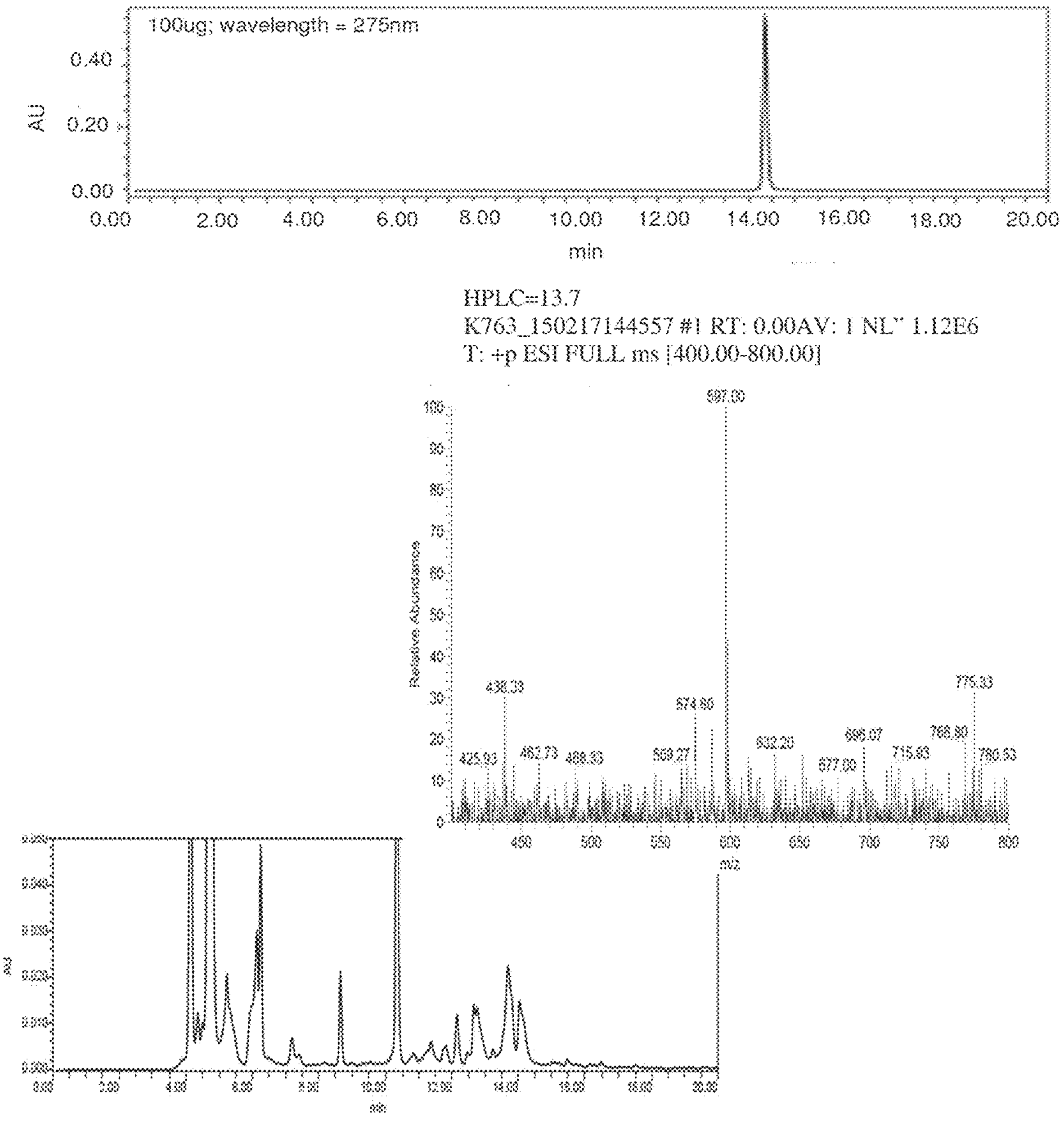
FIG. 12 is a graph depicting pharmacokinetics (PK) of K763 at 60 min in mice (IP) with acetonitrile extraction.

Pharmacokinetics of K763 at 60 min (IP) with acetonitrile extraction are depicted in FIG. 12.

Figure 14A:
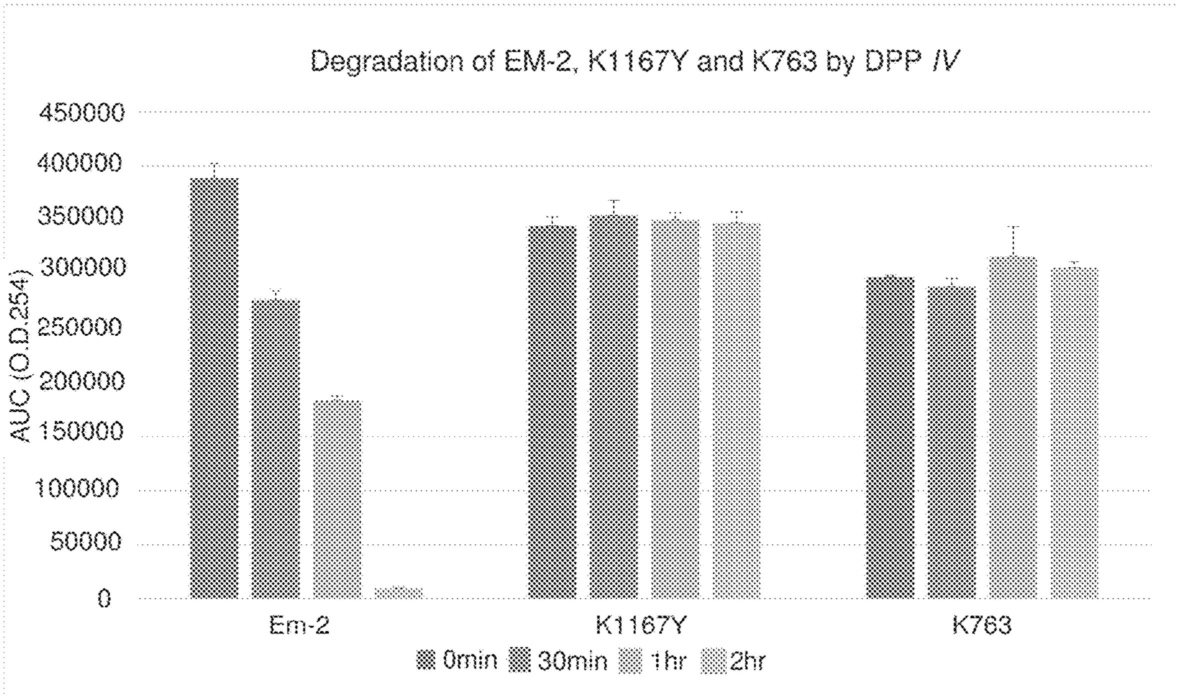
FIG. 14A depicts degradation of EM-2, K1167Y and K763 by DPPIV.

FIG. 14A depicts degradation of EM-2, K1167Y and K763 by DPPIV.

Figure 14B:
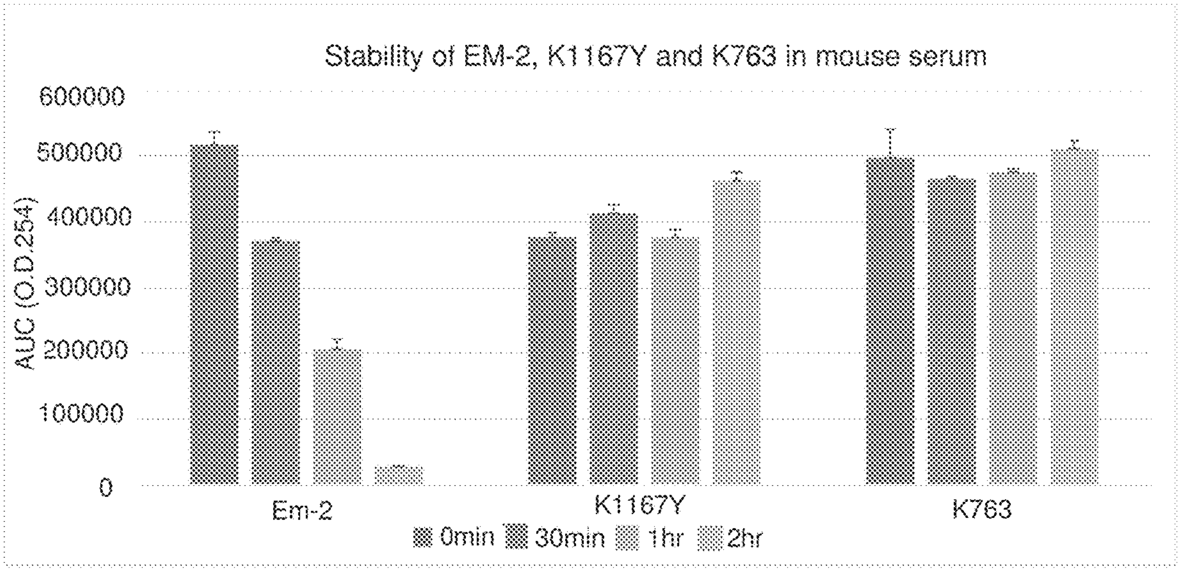
FIG. 14B depicts stability of EM-2, K1167Y and K763 in mouse serum.

FIG. 14B depicts stability of EM-2, K1167Y and K763 in mouse serum.

Example 22

K883, an azapeptide analogue of FSSE, was synthesized. FSSE and K883 have the following structures:

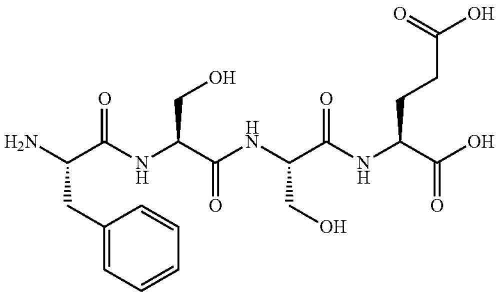

FSSE
$C_{20}H_{28}N_4O_9$
Exact Mass: 468.19

-continued

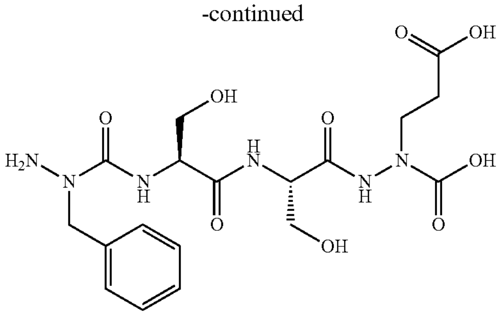

K883
$C_{18}H_{27}N_7O_8$
Exact Mass: 469.19

K883 differs from FSSE in that the

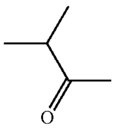

at the C-terminus and N-terminus of K883 is replaced with

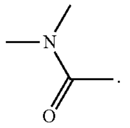

K883 was synthesized in 13 steps; the product of each step was purified, followed by LC-MS to confirm the purity. After purification, compounds were characterized by high resolution MS and NMR methods (¹H, and ¹³C).

The synthetic procedure was as follows:

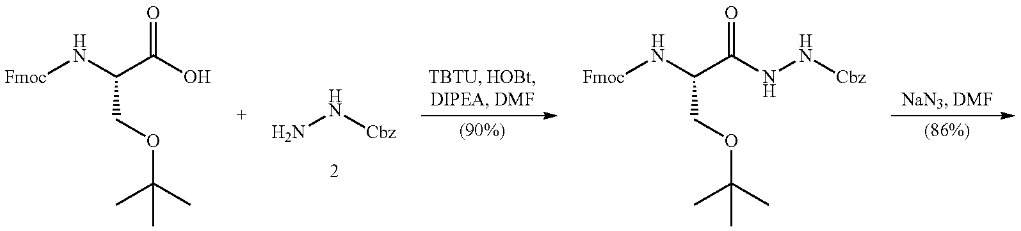

1 2 3

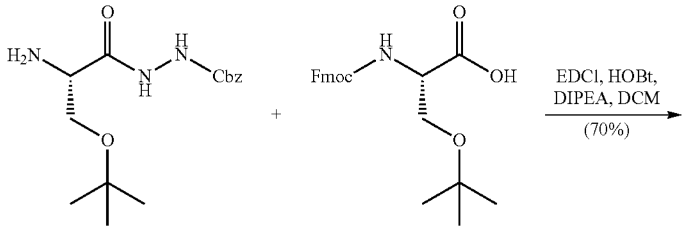

4 1

-continued
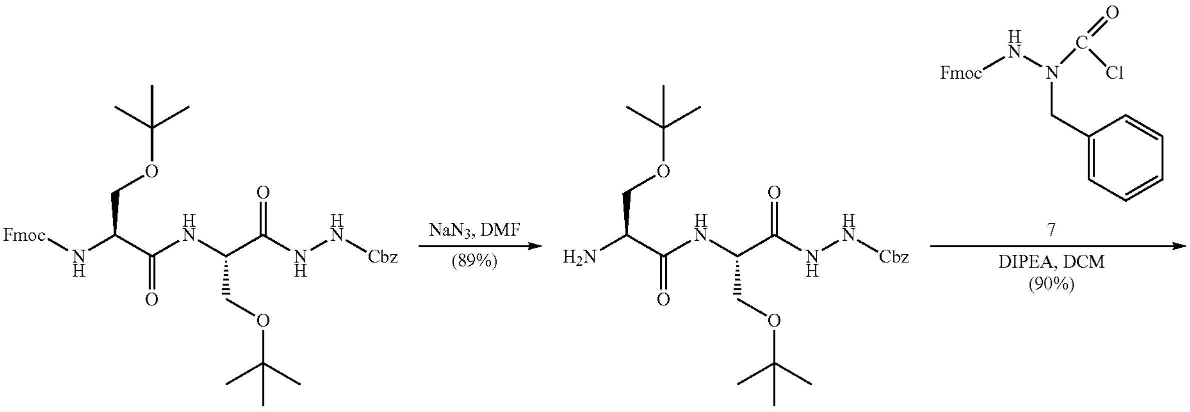
5 6
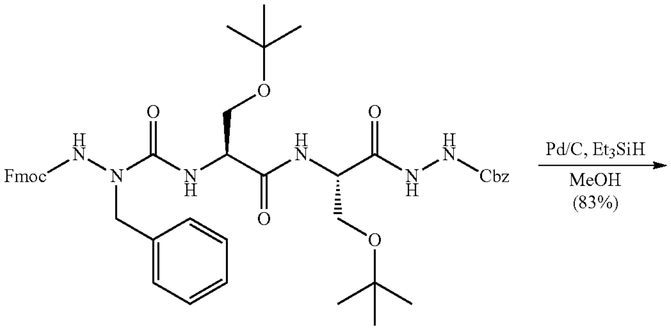
8
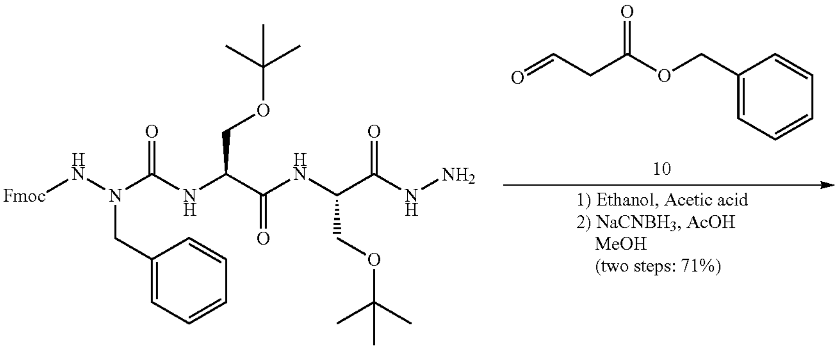
9
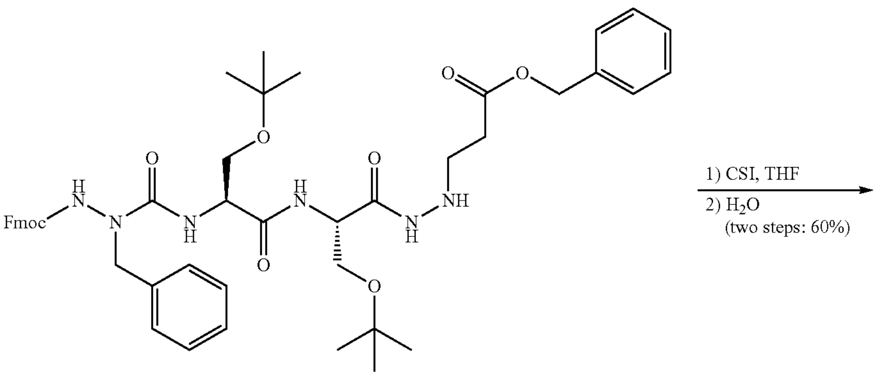
11

-continued
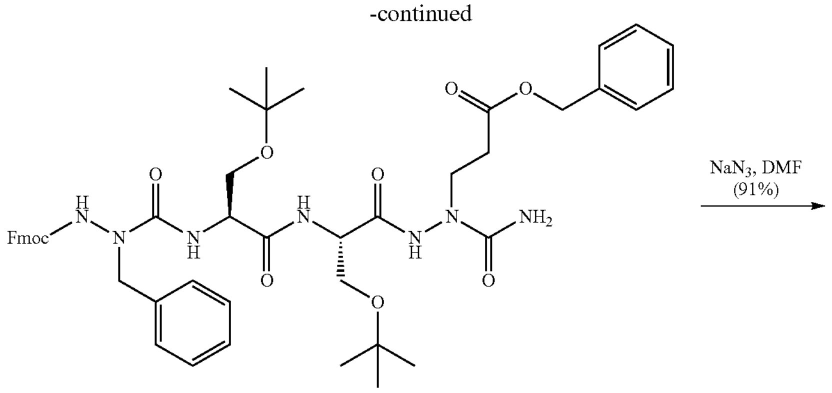
12
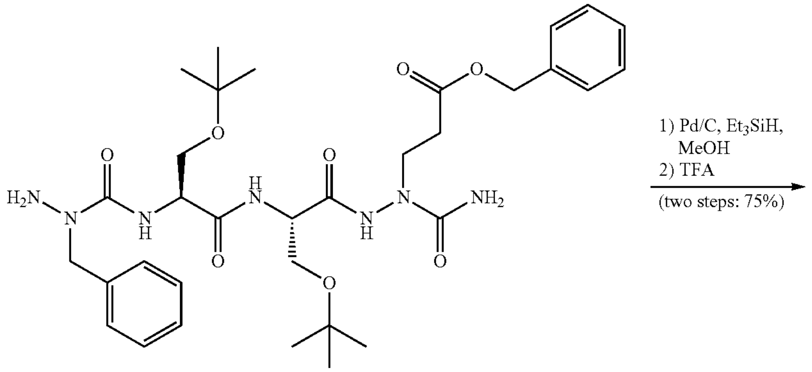
13
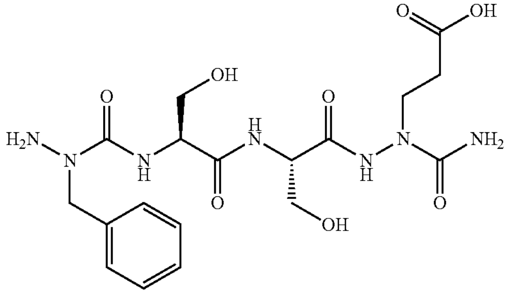
K883
13 steps; total yield = 10%

Commercially available Fmoc-O-tert-butyl-L-serine (1) and Cbz-hydrazine (2) were coupled in the presence of TBTU, HOBt and DIPEA in DMF to form the Cbz-protected semicarbazide (3) with 90% yield. The Fmoc group of the semicarbazide (3) was removed by sodium azide in DMF to yield the free amine (4) (86% yield), which was further elongated with another Fmoc-O-tert-butyl-L-serine (1) in the presence of EDCI, HOBt and DIPEA in DCM to di-Serine Cbz-protected semicarbazide (5) (70% yield). After removal of the Fmoc group with sodium azide in DMF (89% yield), the free amine (6) was coupled with N-Fmoc-phenyl hydrazine acid chloride (7) in present of DIPEA in DCM to form the azapeptide (8) in 90% yield. Then, the Cbz group was de-protected with Pd/C and $Et_3SiH$ in methanol to get the semicarbazide (9) in 83% yield. Condensations of Fmoc-protected semicarbazide (9) with 3-Benzylpropionate aldehyde (10) (Dess Martine oxidation of Benzyl 3-Hydroxypropinonate) to an acyl hydrazone which was reduced by the catalytic hydrogenation and hydride addition to the protected aza-tetrapeptide (11) (two steps, 71% yield). CSI then converted the amine (11) into the corresponding amide (12) (two steps, 60% yield). Fmoc group was removed with sodium azide in DMF to yield the tretra azapeptide (13) (91% yield). De-protection of O-tert-butyl-L-serine with TFA and O-benzyl with Pd/C and $Et_3SiH$ in methanol to get the Aza-FSSE (K883) (two steps, 75% yield). There are thirteen reaction steps to the final molecule with the total yield of 10%.

(3)

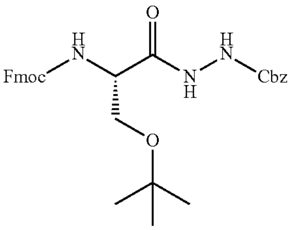

N'-[3-tert-butoxy-2-(9H-fluoren-9-ylmethoxycarbonylamino)-propionyl]-hydrazinecarboxylic acid benzyl ester To a solution of Cbz-hydrazine (2) (3.0 mmol) and Fmoc-O-tert-butyl-L-serine (1) (3.0 mmol) in anhydrous DMF (30 mL) TBTU (3.6 mmol), HOBt (3.0 mmol) and DIPEA (3.0 mmol) were added. The solution was stirred at 25° C. under nitrogen for 15 hours, and then concentrated to dryness and partitioned between 0.5N HCl (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 90% yield. $^1H$ NMR (500 MHz, $CDCl_3$) δ 8.56 (br, 1H), 7.78 (d, 2H), 7.61 (m, 2H), 7.44-7.28 (m, 9H), 6.87 (br, 1H), 5.78 (br, 1H), 5.19 (s, 2H), 4.43-4.37 (m, 3H), 4.24 (t, 1H), 3.81 (m, 1H), 3.47 (m, 1H), 1.27 (s, 9H) ppm. $^{13}C$ NMR (125 MHz, $CDCl_3$) δ 170.59, 156.32, 156.12, 144.03, 143.81, 141.46, 135.62, 128.73, 128.65, 128.58, 128.37, 127.90, 127.24, 125.26, 120.02, 74.85, 68.04, 67.35, 61.42, 53.71, 47.24, 27.53 ppm. Mass Spectrum: (ESI) m/z 532.40 $(M+H)^+$, m/z 554.40 $(M+Na)^+$.

(4)

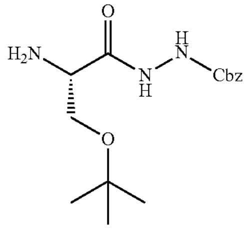

N'-(2-Amino-3-tert-butoxy-propionyl)-hydrazinecarboxylic acid benzyl ester

To a solution of Cbz-protected semicarbazide (3) (5.65 mmol) in anhydrous DMF (30 mL) $NaN_3$ (6.78 mmol) was added. The mixture was stirred at 50° C. under nitrogen for 3 hours then concentrated to dryness and partitioned between water (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc/MeOH mixtures to afford the products as a white solids in 86% yield. $^1H$ NMR (500 MHz, $CDCl_3$) δ 7.36-7.28 (m, 5H), 6.87 (br, 1H), 5.03 (s, 2H), 3.51-3.48 (m, 3H), 1.23 (s, 9H) ppm. $^{13}C$ NMR (125 MHz, $CDCl_3$) δ 172.83, 156.13, 135.80, 128.72, 128.51, 128.35, 73.86, 667.87, 67.35, 63.66, 54.87, 27.62 ppm. Mass Spectrum: (ESI) m/z 310.20 $(M+H)^+$, m/z 332.20 $(M+Na)^+$.

(5)

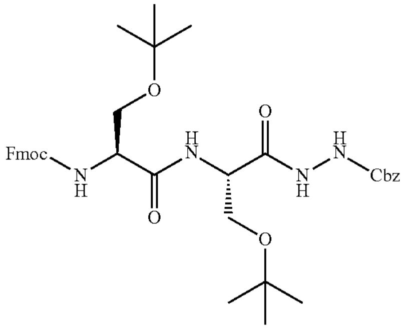

N'-{3-tert-Butoxy-2-[3-tert-butoxy-2-(9H-fluoren-9-ylmethoxycarbonylamino)-propionylamino]-propionyl}-hydrazinecarboxylic acid benzyl ester To a solution of Cbz-semicarbazide amine (4) (2.9 mmol) and Fmoc-O-tert-butyl-L-serine (1) (3.2 mmol) in anhydrous DCM (50 mL) EDCI (4.3 mmol), HOBt (0.58 mmol) and DIPEA (2.9 mmol) were added. The solution was stirred at 25° C. under nitrogen for 5 hours then concentrated to dryness and partitioned between water (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 70% yield. $^1H$ NMR (500 MHz, $CDCl_3$) δ 8.82 (br, 1H), 7.80 (d, 2H), 7.63 (d, 2H), 7.44-7.28 (m, 9H), 7.18 (br, 1H), 6.71 (br, 1H), 5.83 (br, 1H), 5.17 (s, 2H), 4.62 (br, 1H) 4.42 (d, 2H), 4.28-4.23 (m, 2H), 3.93 (m, 1H), 3.82 (m, 1H), 3.48

(m, 2H), 1.24 (s, 18H) ppm. $^{13}C$ NMR (125 MHz, $CDCl_3$) δ 170.17, 170.02, 156.21, 155.95, 144.00, 143.81, 141.47, 141.44, 135.74, 128.68, 128.50, 128.35, 127.91, 127.25, 125.28, 120.18, 75.30, 74.42, 67.90, 67.41, 62.08, 60.80, 60.58, 54.95, 53.03, 47.24, 27.52 ppm. Mass Spectrum: (ESI) m/z 675.13 $(M+H)^+$, m/z 692.07 $(M+Na)^+$.

(6)

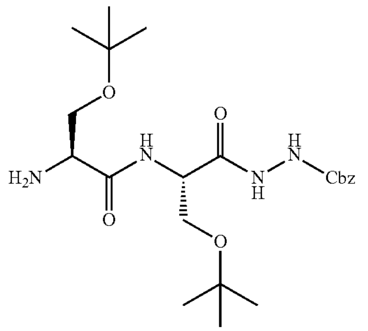

N'-[2-(2-Amino-3-tert-butoxy-propionylamino)-3-tert-butoxy-propionyl]-hydrazinecarboxylic acid benzyl ester To a solution of Cbz-protected di-serine semicarbazide (5) (2.49 mmol) in anhydrous DMF (10 mL) was added $NaN_3$ (3.02 mmol). The mixture was stirred at 50° C. under nitrogen for 3 hours then concentrated to dryness and partitioned between water (25 mL) and EtOAc (25 mL). The aqueous layer was extracted with EtOAc (2×25 mL) and the combined organic phase were washed with brine (25 mL), dried over $Na_2SO_4$, filtered and concentrated to afford the crude product which was purified by flash silica gel column chromatography eluting with hexane/EtOAc mixtures to afford the products as a white solids in 89% yield. Mass Spectrum: (ESI) m/z 453.20 $(M+H)^+$, m/z 475.33 $(M+Na)^+$.

(8)

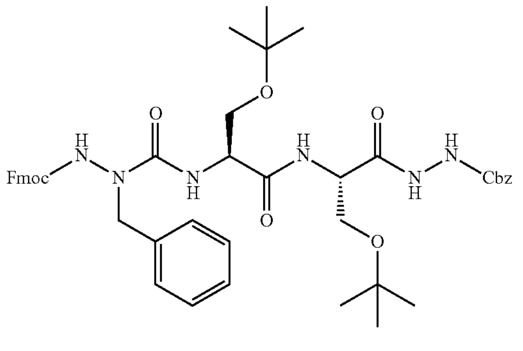

To a solution of Cbz-protected di-serine semicarbazide amine (6) (2.44 mmol) and N-Fmoc-phenyl hydrazine acid chloride (7) (2.44 mmol) in anhydrous DCM (24 mL) at 0° C. was added DIPEA (2.44 mmol). The solution was stirred and warmed to 25° C. under nitrogen for 5 hours then concentrated to dryness and partitioned between water (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 90% yield. $^1H$ NMR (500 MHz, $CDCl_3$) δ 8.93 (br, 1H), 7.80 (d, 2H), 7.54 (d, 2H), 7.44 (t, 2H), 7.35-7.31 (m, 12H), 7.18 (br, 2H), 6.63 (br, 1H), 6.48 (br, 1H) 6.32 (br, 1H), 5.16 (s, 2H), 4.62 (m, 1H) 4.53 (m, 2H), 4.36 (m, 1H), 4.20 (m, 1H), 3.91 (m, 1H), 3.80 (m, 1H), 3.49 (m, 2H), 1.20 (s, 18H) ppm. $^{13}C$ NMR (125 MHz, $CDCl_3$) δ 170.65, 169.92, 157.26, 155.90, 155.88, 155.21, 143.27, 143.18, 141.37, 135.62, 135.53, 129.00, 128.51, 128.29, 128.14, 128.06, 127.95, 127.20, 124.93, 120.12, 74.94, 74.12, 67.70, 61.97, 60.70, 54.76, 52.92, 50.77, 46.96, 27.38 ppm.

(9)

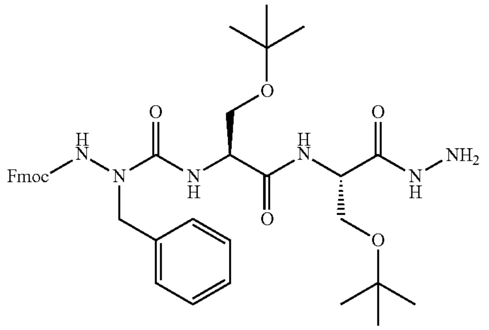

To a solution of Cbz-protected di-serine semicarbazide (8) (2.05 mmol) in anhydrous MeOH (10 mL) was added 10% Pd/C (340 mg) followed by $Et_3SiH$ (20.5 mmol). The mixture was stirred at 25° C. under nitrogen for 20 mins then filtered through a pad of celite and concentrated to dryness and partitioned between water (50 mL) and EtOAc (50 mL). The aqueous layer was extracted with EtOAc (2×50 mL) and the combined organic phase were washed with brine (50 mL), dried over $Na_2SO_4$, filtered and concentrated to afford the crude product which was purified by flash silica gel column chromatography eluting with hexane/EtOAc mixtures to afford the products as a white solids in 83% yield. $^1H$ NMR (500 MHz, $CDCl_3$) δ 8.26 (br, 1H), 7.79 (d, 2H), 7.54 (d, 2H), 7.44 (t, 2H), 7.35-7.28 (m, 5H), 7.18 (m, 2H), 6.99 (br, 1H), 6.39 (br, 1H), 6.48 (br, 1H) 6.30 (d, 1H), 4.50 (m, 3H), 4.37 (m, 1H), 4.20 (m, 1H), 3.91 (m, 1H), 3.82 (m, 1H), 3.49-3.39 (m, 2H), 1.26 (s, 9H), 1.18 (s, 9H) ppm. $^{13}C$ NMR (125 MHz, $CDCl_3$) δ 170.73, 170.64, 157.26, 155.34, 143.44, 143.38, 141.59, 135.75, 129.14, 129.08, 128.27, 128.15, 127.39, 125.09, 120.31, 75.18, 73.99, 67.95, 62.34, 61.11, 54.80, 53.18, 50.77, 47.21, 27.61, 27.58 ppm.

(11)

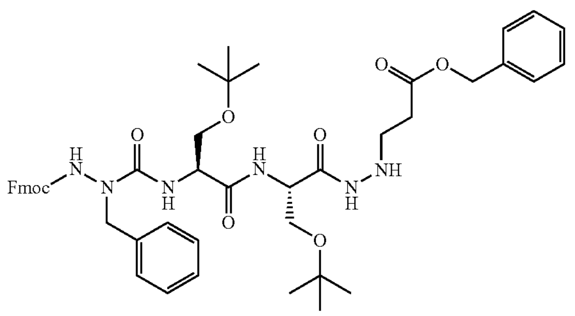

To a solution of protected di-serine semicarbazide (9) (0.87 mmol) and 3-Benzylpropionate aldehyde (10) (2.62 mmol) in anhydrous ethanol (6 mL) was added acetic acid (24 uL). The solution was stirred at 25° C. under nitrogen for 2 hrs then concentrated to dryness. The crude product re-dissolved in anhydrous MeOH (20 mL) and added $NaCNBH_3$ (4.35 mmol) followed by acetic acid (4.35 mmol). The mixture was stirred at 55° C. under nitrogen for 15 hours then concentrated to dryness and partitioned between water (50 mL) and EtOAc (50 mL). The aqueous layer was extracted with EtOAc (2×25 mL) and the combined organic phase were washed with brine (25 mL), dried over $Na_2SO_4$, filtered and concentrated to afford the crude product which was purified by flash silica gel column chromatography eluting with hexane/EtOAc mixtures to afford the products as a white solids in 71% yield (two steps). $^1$H NMR (500 MHz, $CDCl_3$) δ 8.43 (br, 1H), 7.80 (d, 2H), 7.54 (d, 2H), 7.44 (t, 2H), 7.36-7.31 (m, 10H), 7.17 (br, 2H), 7.01 (br, 1H), 6.30 (br, 2H), 5.12 (s, 2H), 4.52 (m, 3H), 4.33 (m, 1H), 4.21 (t, 1H), 3.91 (m, 1H), 3.81 (m, 1H), 3.42 (m, 2H), 3.14 (t, 2H), 2.56 (t, 2H), 1.22 (s, 9H), 1.17 (s, 9H) ppm. $^{13}$C NMR (125 MHz, $CDCl_3$) δ 172.08, 170.59, 169.75, 157.38, 143.40, 143.35, 141.56, 136.00, 135.64, 129.13, 129.09, 128.69, 128.41, 128.37, 128.27, 128.13, 127.37, 125.08, 125.07, 120.30, 75.10, 73.96, 67.91, 66.54, 62.20, 61.11, 60.60, 54.94, 53.23, 50.78, 47.34, 47.15, 32.82, 27.58 ppm. Mass Spectrum: (ESI) m/z 851.33 $(M+H)^+$, m/z 873.40 $(M+Na)^+$.

(12)

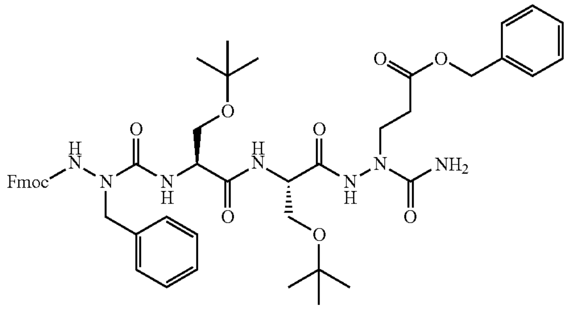

To a solution of the protected aza-tetrapeptide amine (11) (0.70 mmol) in anhydrous THF (5 mL) at 0° C. was added chlorosulfonyl (CSI) (0.84 mmol) rapidly. The solution was stirred at 0° C. under nitrogen for 1 hour then added water (5 mL). The solution was warmed to room temperature and, then, concentrated and partitioned between water (25 mL) and EtOAc (25 mL). The aqueous layer was extracted with EtOAc (2×15 mL) and the combined organic phase were washed with brine (25 mL), dried over $Na_2SO_4$, filtered and concentrated to afford the crude product which was purified by flash silica gel column chromatography eluting with hexane/EtOAc mixtures afford the products as a white solids in 60% yield (two steps). $^1$H NMR (500 MHz, $CDCl_3$) δ 9.05 (br, 1H), 7.70 (d, 2H), 7.43 (d, 2H), 7.34 (t, 2H), 7.24-7.21 (m, 10H), 7.06 (m, 4H), 6.68 (br, 1H), 6.30 (br, 1H), 5.14 (br, 2H), 4.47 (m, 1H), 4.34 9m, 2H), 4.13 (m, 1H), 4.09 (m, 2H), 3.82 (m, 2H), 3.76 (m, 2H), 3.63 (m, 2H), 3.51 (m, 1H), 3.45 (m, 2H), 3.23 (t, 2H), 1.08 (s, 18H) ppm. $^{13}$C NMR (125 MHz, $CDCl_3$) δ 172.10, 170.56, 169.75, 157.36, 157.34, 143.40, 143.35, 141.57, 136.03, 136.65, 129.14, 129.09, 128.70, 128.41, 128.37, 128.28, 128.14, 127.38, 125.08, 120.31, 75.12, 73.96, 69.94, 66.52, 62.23, 61.13, 54.86, 53.24, 50.78, 47.36, 47.10, 32.92, 27.47 ppm. Mass Spectrum: (ESI) m/z 894.40 $(M+H)^+$, m/z 916.47 $(M+Na)^+$.

(13)

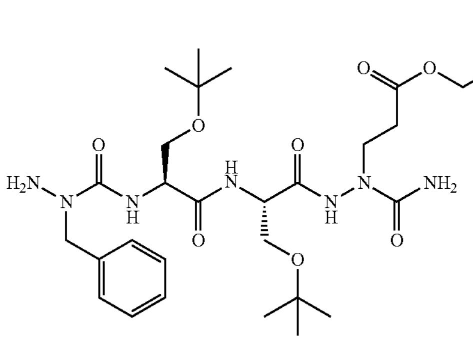

To a solution of protected aza-tetrapeptide amide (12) (0.48 mmol) in anhydrous DMF (5 mL) was added $NaN_3$ (0.72 mmol). The mixture was stirred at 50° C. under nitrogen for 2 hours then concentrated to dryness for and partitioned between water (5 mL) and EtOAc (5 mL). The aqueous layer was extracted with EtOAc (2×5 mL) and the combined organic phase were washed with brine (5 mL), dried over $Na_2SO_4$, filtered and concentrated to afford the crude product which was purified by flash silica gel column chromatography eluting with hexane/EtOAc/MeOH mixtures to afford the products as a white solids in 91% yield. Mass Spectrum: (ESI) m/z 672.47 $(M+H)^+$, m/z 694.33 $(M+Na)^+$.

(K883)

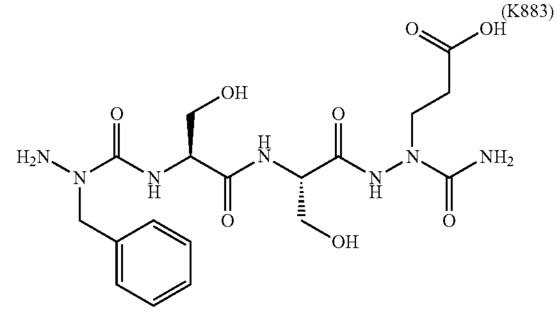 [SMILES: NC(=O)N(CCC(=O)O)NC(=O)[C@H](CO)NC(=O)[C@H](CO)NC(=O)N(N)Cc1ccccc1]

To a solution of aza-tetrapeptide amide (13) (0.43 mmol) in anhydrous MeOH (5 mL) was added 10% Pd/C (58 mg), followed by $Et_3SiH$ (4.3 mmol). The mixture was stirred at 25° C. under nitrogen for 20 mins then filtered through a pad of celite and concentrated to dryness. The acid was used directly for next step. Mass Spectrum: (ESI) m/z 582.20 $(M+H)^+$, m/z 604.27 $(M+Na)^+$.

The crude acid (0.43 mmol) was dissolved in 10 mL TFA at 0° C. then was stirred and warmed to 25° C. under nitrogen for 1 hour. After concentrated to dryness, the crude product was purified by flash silica gel column chromatography eluting with CHCl3/MeOH (4:1 v/v) mixture to afford the Aza-FSSE (K883) as a white solids in 75% yield (two steps). $^1$H NMR (600 MHz, $CDCl_3$) δ 7.3-7.30 (m, 5H), 4.69 (s, 2H), 4.40 (t, 1H), 4.36 (t, 1H), 3.98 (dd, 1H), 3.95 (dd, 1H), 3.85 (dd, 1H), 3.82 (dd, 1H), 3.80 (br, 2H), 2.48 (t, 2H) ppm. $^{13}$C NMR (125 MHz, $CDCl_3$) δ 178.10, 173.33, 170.83, 160.27, 159.81, 136.77, 128.67, 128.07, 127.52, 62.31, 61.21, 56.63, 55.42, 52.80, 44.88, 34.91 ppm. Mass Spectrum: (ESI) m/z 470.00 $(M+H)^+$, m/z 492.07 $(M+Na)^+$.

The in vitro and in vivo half-lives of K883 and FSSE were measured. The in vitro half-life of K883 was greater than 15 hours, while the in vitro half-life of the native peptide (FSSE) was 60 min. The in vivo half-life of K883 was greater than 69 min, while the in vivo half-life of the native peptide (FSSE) was less than 1 min. The results are provided in Tables 3 and 4 below:

TABLE 3

Individual and Average Plasma Concentrations (ng/ml) for FSSE after Intravenous Administration at 1 mg/KG in Male Sprague-Dawley rats
Intravenous (1 mg/kg)

| | Rat # | | | | |
|---|---|---|---|---|---|
| Time (hr) | 970 | 971 | 972 | Mean | SD |
| 0 (pre-dose) | BLOQ | BLOQ | BLOQ | ND | ND |
| 0.017 | BLOQ | BLOQ | BLOQ | ND | ND |
| 0.033 | BLOQ | BLOQ | BLOQ | ND | ND |
| 0.083 | BLOQ | BLOQ | BLOQ | ND | ND |
| 0.167 | BLOQ | BLOQ | BLOQ | ND | ND |
| 0.25 | BLOQ | BLOQ | BLOQ | ND | ND |
| 0.33 | BLOQ | BLOQ | BLOQ | ND | ND |
| 0.50 | BLOQ | BLOQ | BLOQ | ND | ND |
| Animal Weight (kg) | 0.284 | 0.271 | 0.281 | 0.279 | 0.007 |
| Volume Dosed (mL) | 0.28 | 0.27 | 0.28 | 0.28 | 0.01 |
| $C_0$ (ng/mL)[1] | ND | ND | ND | ND | ND |
| $t_{max}$ (hr)[1] | ND | ND | ND | ND | ND |
| $t_{1/2}$ (hr) | ND | ND | ND | ND | ND |
| $MRT_{last}$ (hr) | ND | ND | ND | ND | ND |
| CL (L/hr/kg) | ND | ND | ND | ND | ND |
| $V_{ss}$ (L/kg) | ND | ND | ND | ND | ND |
| $AUC_{last}$ (hr · ng/mL) | ND | ND | ND | ND | ND |
| $AUC_{\infty}$ (hr · ng/mL) | ND | ND | ND | ND | ND |

TABLE 4

Individual and Average Plasma Concentrations (ng/ml) for K883 after Intravenous Administration at 1 mg/KG in Male Sprague-Dawley Rats
Intravenous (1 mg/kg)

| | Rat # | | | | |
|---|---|---|---|---|---|
| Time (hr) | 973 | 974 | 975 | Mean | SD |
| 0 (pre-dose) | BLOQ | BLOQ | BLOQ | ND | ND |
| 0.25 | 4360 | 4240 | 3830 | 4143 | 278 |
| 0.50 | 3020 | 2500 | 3220 | 2913 | 372 |
| 1.0 | 814 | 1160 | 1300 | 1091 | 250 |
| 1.5 | 281 | 258 | 280 | 273 | 13.0 |
| 2.0 | 133 | 130 | 142 | 135 | 6.24 |
| 4.0 | 17.0 | 15.1 | 17.7 | 16.6 | 1.35 |
| 6.0 | 6.49 | 4.04 | 4.77 | 5.10 | 1.26 |
| 8.0 | 2.01 | 0.871 | 1.68 | 1.52 | 0.586 |
| Animal Weight (kg) | 0.288 | 0.282 | 0.281 | 0.284 | 0.004 |
| Volume Dosed (mL) | 0.29 | 0.28 | 0.28 | 0.28 | 0.01 |
| $C_0$ (ng/mL)[1] | 6295 | 7191 | 4556 | 6014 | 1340 |
| $t_{max}$ (hr)[1] | 0 | 0 | 0 | 0 | 0 |
| $t_{1/2}$ (hr) | 1.30 | 0.972 | 1.18 | 1.15 | 0.165 |
| $MRT_{last}$ (hr) | 0.535 | 0.528 | 0.606 | 0.556 | 0.0430 |
| CL (L/hr/kg) | 0.265 | 0.263 | 0.267 | 0.265 | 0.00200 |
| $V_{ss}$ (L/kg) | 0.144 | 0.139 | 0.163 | 0.149 | 0.0127 |
| $AUC_{last}$ (hr · ng/mL) | 3772 | 3807 | 3749 | 3776 | 29.4 |
| $AUC_{\infty}$ (hr · ng/mL) | 3776 | 3808 | 3751 | 3778 | 28.5 |

Both K883 and FSSE were tested in animal studies and shown to be protective.

Figure 4:
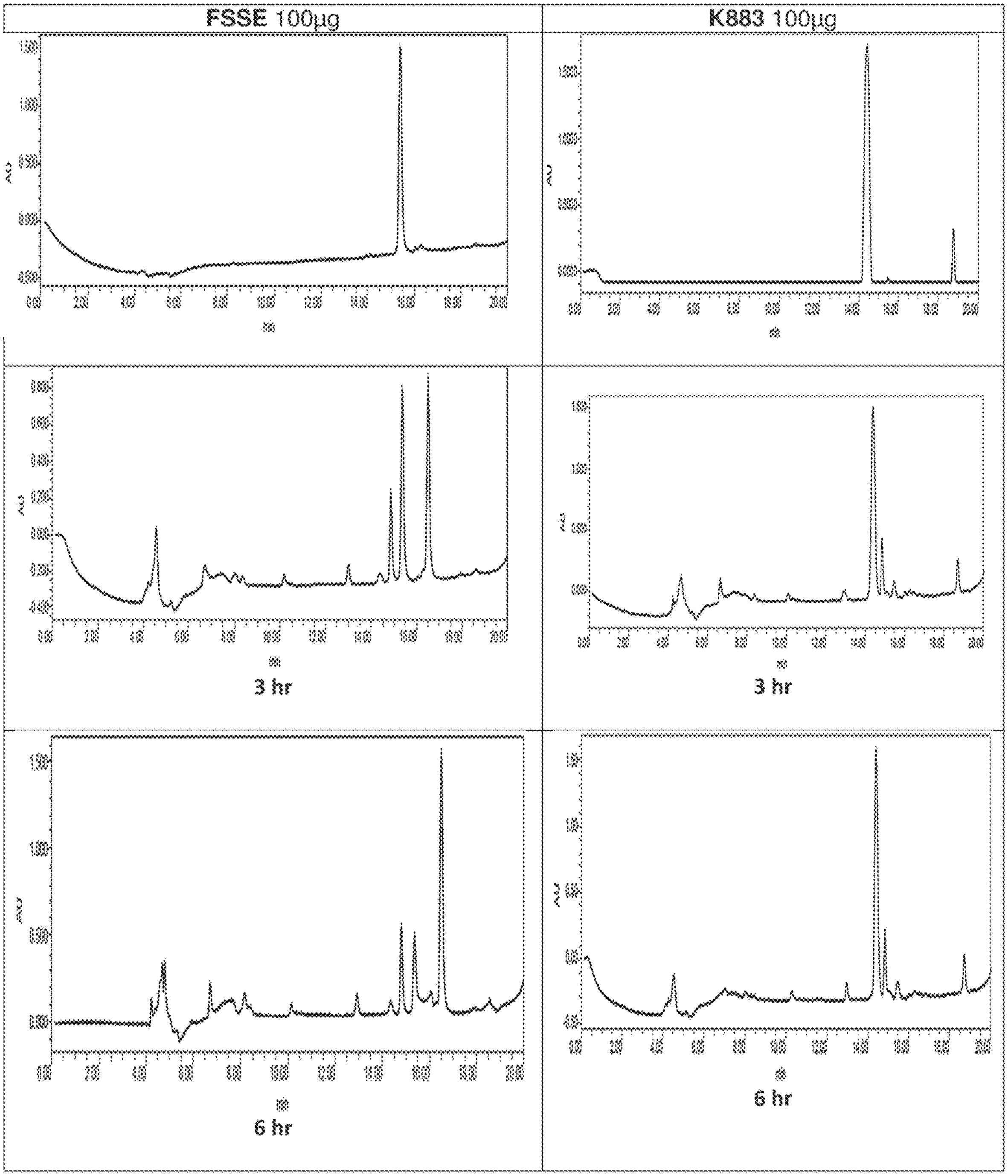
FIG. 4 contains graphs depicting relative stability of FSSE and K883 in mouse serum as indicated by the area under curve amounts of compounds monitored by HPLC at wavelength 210 nm (Y axis).
Figure 5:
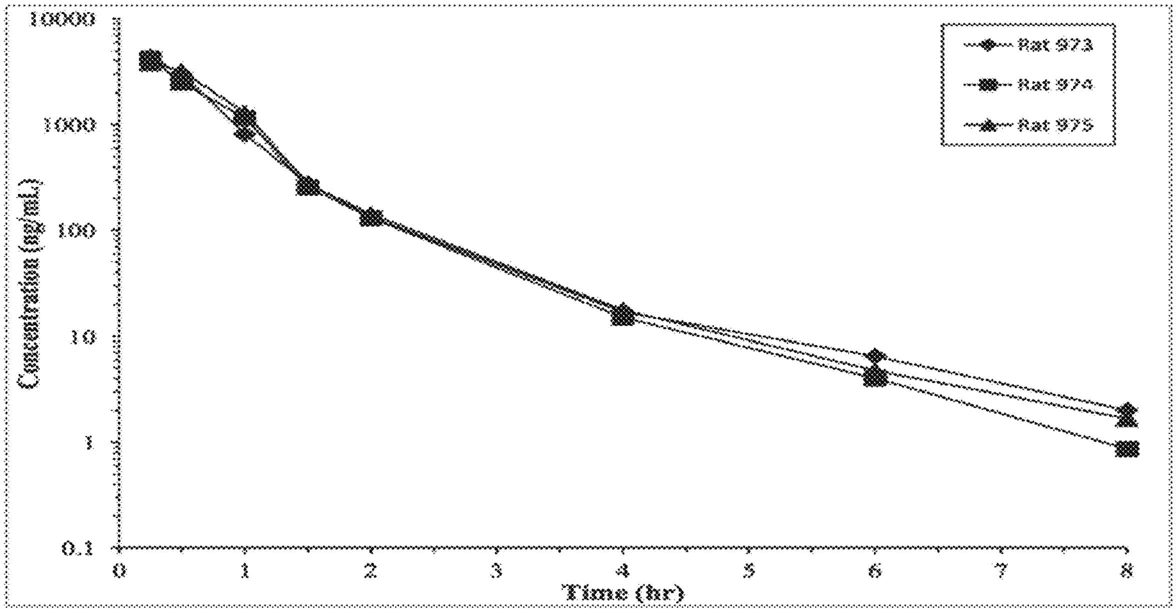
FIG. 5 is a graph of individual plasma concentrations of K883 after intravenous administration at 1 mg/kg in male Sprague-Dawley Rats.

The results of stability and pK study of FSSE and K833 in mice are depicted in FIGS. 4 and 5.

Figure 6:
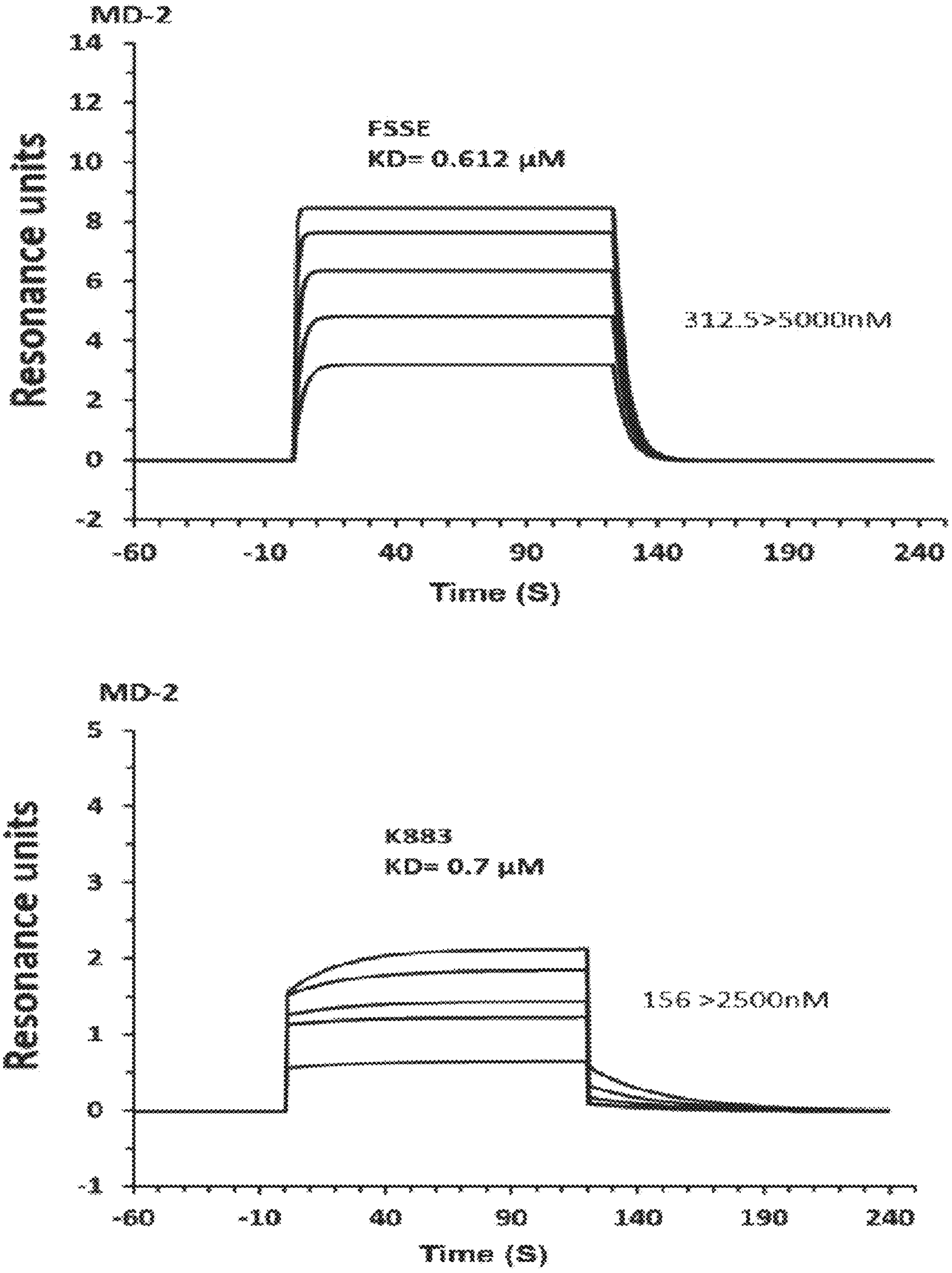
FIG. 6 is a graph depicting binding of FSSE and K883 to MD2.

The results of Ac-FSSE and K883 binding to MD-2 study are depicted in FIG. 6.

The results of Ac-FSSE and K883 inhibiting MD-2 binding to HMGB1 are depicted in FIG. 6.

Figure 7:
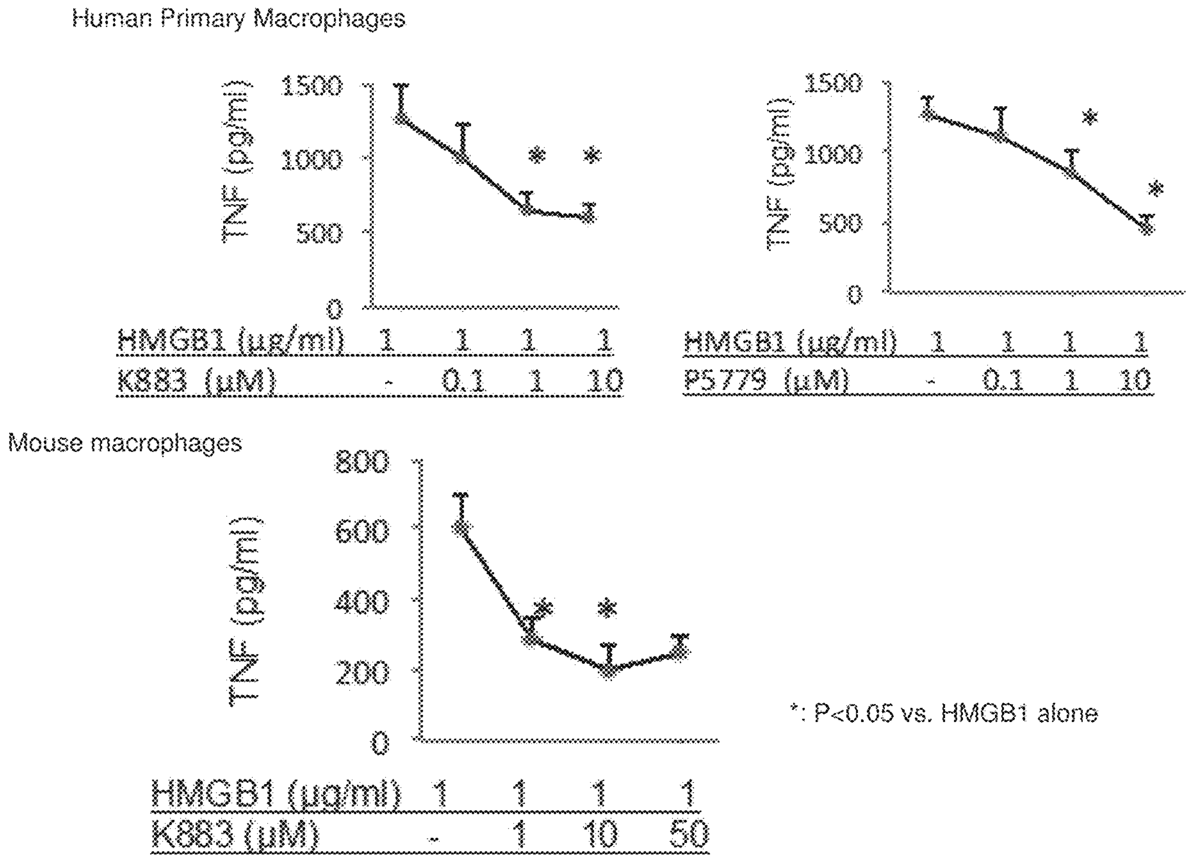
FIG. 7 contains graphs depicting K883 inhibition of HMGB1-induced TNF secretion.
Figure 8:
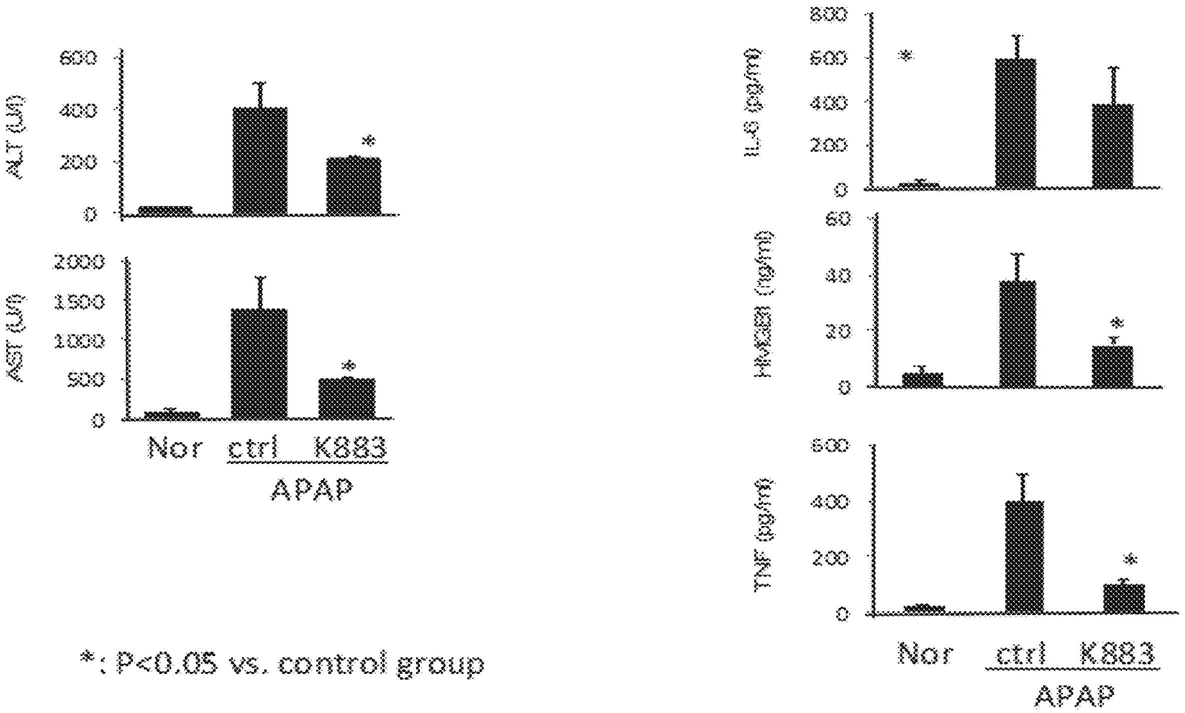
FIG. 8 contains graphs depicting K883 reduction of APAP-induced pro-inflammatory cytokines and serum liver enzymes.
Figure 8:
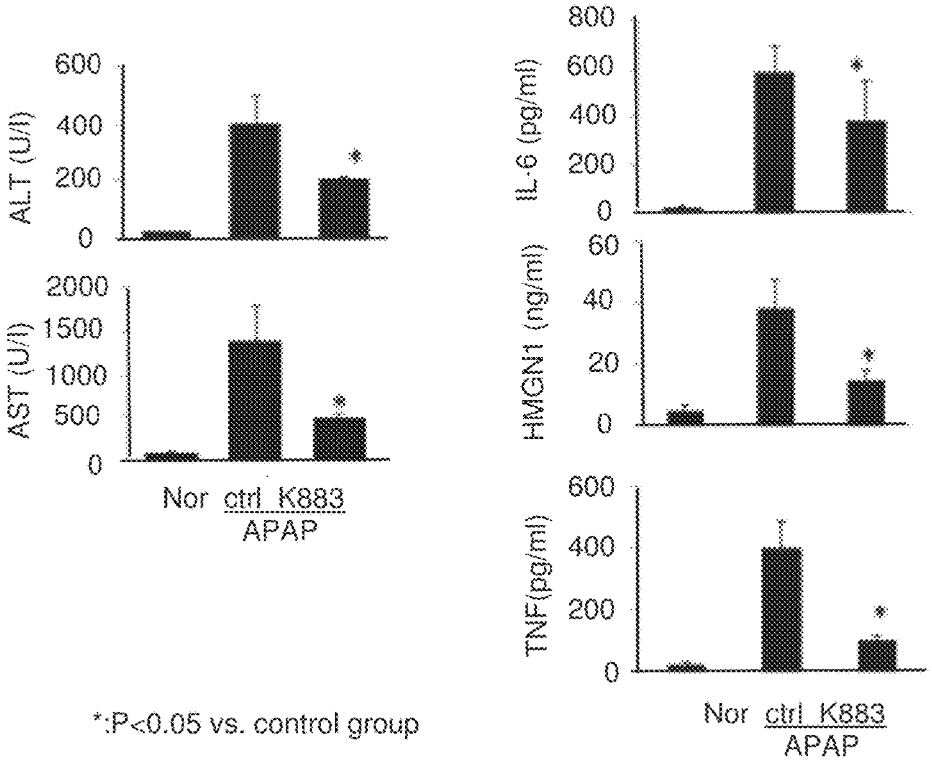
Figure 9:
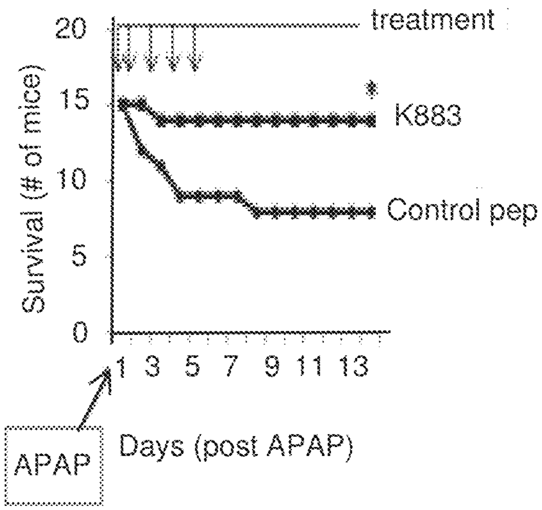
FIG. 9 is a graph showing that K883 reduced APAP-induced lethality in mice.

FIG. 7 depicts graphs showings that K883 inhibits HMGB1-induced TNF secretion.

Example 23

Synthesis of Phth-Phe-Aa-Di-Azapeptide

Phth-Phe-Aa-di-azapeptide was synthesized using the following reaction and conditions:

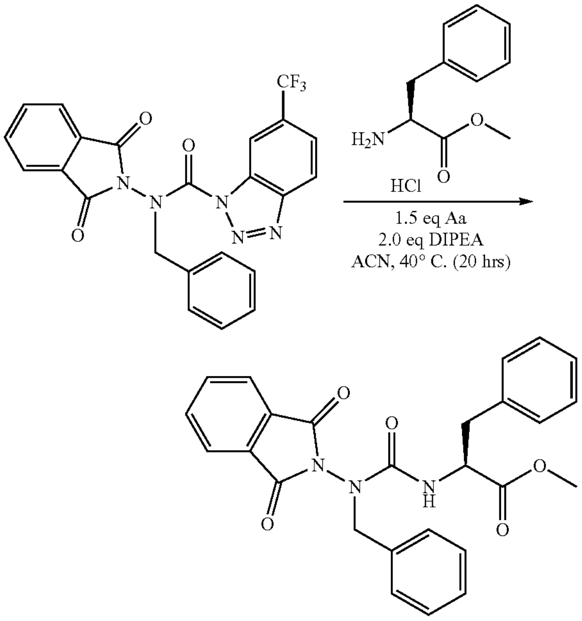

The yield was 70%.

Example 24

Synthesis of Phth-Phe-Aa-di-azapeptide

Phth-Phe-Aa-di-azapeptide was synthesized using the following reaction and conditions:

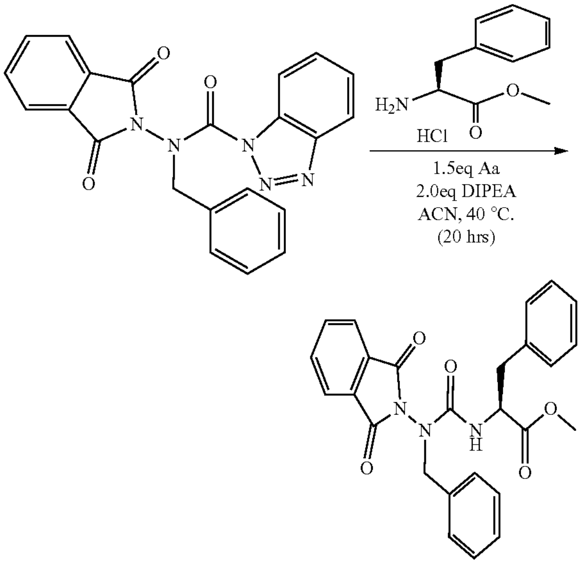

The yield was 80%.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense. All documents cited herein, as well as text appearing in the figures, are hereby incorporated by reference in their entirety for all purposes to the same extent as if each were so individually denoted.

BIBLIOGRAPHY

1. Gante, J. (1989). Azapeptides. Synthesis 21, 405-413.
2. Anamarija, Z. (2005). Azapeptides as Pharmacological Agents. Current Medicinal Chemistry 12, 589-597.
3. Proulx, C., Sabatino, D., Hopewell, R., Spiegel, J., Garcia Ramos, Y., and Lubell, W. D. (2011). Azapeptides and their therapeutic potential. Future Medicinal Chemistry 3, 1139-1164.
4. Jamieson, A. G., Boutard, N., Sabatino, D., and Lubell, W. D. (2013). Peptide scanning for studying structure-activity relationships in drug discovery. Chem Biol Drug Des 81, 148-165.
5. Avan, I., Hall, C. D., and Katritzky, A. R. (2014). Peptidomimetics via modifications of amino acids and peptide bonds. Chemical Society Reviews 43, 3575-3594.
6. Han, H., and Janda, K. D. (1996). Azatides: Solution and Liquid Phase Syntheses of a New Peptidomimetic. Journal of the American Chemical Society 118, 2539-2544.
7. Hsieh, A. H. C., Kichenadasse, G., Vatandoust, S., Roy, A., Sukumaran, S., Karapetis, C. S., Martin, H., Chong, L. C., and Koczwara, B. (2016). Goserelin toxicities and preferences for ovarian suppression method in pre-menopausal women with breast cancer. Intern. Med. J. 46, 1153-1159.
8. Boccardo, F., Barichello, M., Battaglia, M., Carmignani, G., Comeri, G., Ferraris, V., Lilliu, S., Montefiore, F., Portoghese, F., Cortellini, P., et al. (2002). Bicalutamide monotherapy versus flutamide plus goserelin in prostate cancer: Updated results of a multicentric trial. Eur. Urol. 42, 481-490.
9. Taylor, C. W., Green, S., Dalton, W. S., Martino, S., Rector, D., Ingle, J. N., Robert, N. J., Budd, G. T., Paradelo, J. C., Natale, R. B., et al. (1998). Multicenter randomized clinical trial of goserelin versus surgical ovariectomy in premenopausal patients with receptor-positive metastatic breast cancer: an intergroup study. J Clin Oncol 16, 994-999.
10. Tyrrell, C. J., Altwein, J. E., Klippel, F., Varenhorst, E., Lunglmayr, G., Boccardo, F., Holdaway, I. M., Haefliger, J. M., and Jordaan, J. P. (1991). A multicenter randomized trial comparing the luteinizing hormone-releasing hormone analogue goserelin acetate alone and with flutamide in the treatment of advanced prostate cancer. The International Prostate Cancer Study Group. J Urol 146, 1321-1326.
11. Niedrich, H. (1972). Hydrazine compounds as hetero-components in peptides. XVI. Synthesis of 9-hydrazino-acetic acid-, 9-azaglycine-, and 5-a-azaasparagineoxytocin. J. Prakt. Chem. 314, 769-779.
12. Hess, H.-J., Moreland, W. T., and Laubach, G. D. (1963). N-[2-Isopropyl-3-(L-aspartyl-L-arginyl)-carbazoyl]-L-tyrosyl-L-valyl-L-histidyl-L-prolyl-L-phenylalanine,1 an Isostere of Bovine Angiotensin I I. Journal of the American Chemical Society 85, 4040-4041.
13. Niedrich, H., and Oehme, C. (1972). Hydrazine compounds as hetero-components in peptides. XV. Synthesis of eledoisin octapeptides with the carbazyl residues azaglycine and a-azaasparagine instead of glycine and asparagine. J. Prakt. Chem. 314, 759-768.
14. Niedrich, H., Oehme, C., and Bergmann, J. (1974). Hydrazine compounds as hetero-components in peptides. XIX. Eledoisin peptides containing the N2-methylcarbazoyl radical (azaalanine). J. Prakt. Chem. 316, 741-749.
15. Oehme, P., Bergmann, J., Falck, M., Reich, J. G., Vogt, W. E., Niedrich, H., Pirrwitz, J., Berseck, C., and Jung, F. (1972). Pharmacology of hydrazino carbonic acids, hydrazino peptides and other hydrazine derivatives. Structure-action studies in heterologeous eledoisin octapeptide sequences. Acta Biol Med Ger 28, 109-120.
16. Dutta, A. S., Furr, B. J., Giles, M. B., and Morley, J. S. (1976). Synthesis and biological activity of alpha-azapeptides: alpha-aza-analogues of luteinizing hormone releasing hormone. Clin Endocrinol (Oxf) 5 Suppl, 291S-298S.
17. Dutta, A. S., Gormley, J. J., Hayward, C. F., Morley, J. S., Shaw, J. S., Stacey, G. J., and Turnbull, M. T. (1977). Enkephalin analogues eliciting analgesia after intravenous injection. Life Sci 21, 559-562.
18. Gacel, G., Zajac, J. M., Delay-Goyet, P., Dauge, V., and Roques, B. P. (1988). Investigation of the structural parameters involved in the .mu. and .delta. opioid receptor discrimination of linear enkephalin-related peptides. Journal of Medicinal Chemistry 31, 374-383.
19. Han, H., Yoon, J., and Janda, K. D. (1998). Investigations of azapeptides as mimetics of Leu-enkephalin. Bioorganic & Medicinal Chemistry Letters 8, 117-120.
20. Sulyok, G. A. G., Gibson, C., Goodman, S. L., Holzemann, G., Wiesner, M., and Kessler, H. (2001). Solid-Phase Synthesis of a Nonpeptide RGD Mimetic Library: New Selective avP3 Integrin Antagonists. Journal of Medicinal Chemistry 44, 1938-1950.
21. Sabatino, D., Proulx, C., Klocek, S., Bourguet, C. B., Boeglin, D., Ong, H., and Lubell, W. D. (2009). Exploring Side-Chain Diversity by Submonomer Solid-Phase Aza-Peptide Synthesis. Organic Letters 11, 3650-3653.
22. Sabatino, D., Proulx, C., Pohankova, P., Ong, H., and Lubell, W. D. (2011). Structure-Activity Relationships of GHRP-6 Azapeptide Ligands of the CD36 Scavenger Receptor by Solid-Phase Submonomer Azapeptide Synthesis. Journal of the American Chemical Society 133, 12493-12506.
23. Proulx, C., Picard, E., Boeglin, D., Pohankova, P., Chemtob, S., Ong, H., and Lubell, W. D. (2012). Azapeptide Analogues of the Growth Hormone Releasing Peptide 6 as Cluster of Differentiation 36 Receptor Ligands with Reduced Affinity for the Growth Hormone Secretagogue Receptor 1a. Journal of Medicinal Chemistry 55, 6502-6511.
24. Boeglin, D., Xiang, Z., Sorenson, N. B., Wood, M. S., Haskell-Luevano, C., and Lubell, W. D. (2006). Aza-scanning of the Potent Melanocortin Receptor Agonist Ac-His-d-Phe-Arg-Trp-$NH_2$. Chemical Biology & Drug Design 67, 275-283.
25. Boeglin, D., Hamdan, F. F., Melendez, R. E., Cluzeau, J., Laperriere, A., Heroux, M., Bouvier, M., and Lubell, W. D. (2007). Calcitonin Gene-Related Peptide Analogues with Aza and Indolizidinone Amino Acid Residues Reveal Conformational Requirements for Antagonist Activity at the Human Calcitonin Gene-Related Peptide 1 Receptor. Journal of Medicinal Chemistry 50, 1401-1408.
26. Kurian, L. A., Silva, T. A., and Sabatino, D. (2014). Submonomer synthesis of azapeptide ligands of the Insulin Receptor Tyrosine Kinase domain. Bioorganic & Medicinal Chemistry Letters 24, 4176-4180.

27. Magrath, J., and Abeles, R. H. (1992). Cysteine protease inhibition by azapeptide esters. Journal of Medicinal Chemistry 35, 4279-4283.

28. Asgian, J. L., James, K. E., Li, Z. Z., Carter, W., Barrett, A. J., Mikolajczyk, J., Salvesen, G. S., and Powers, J. C. (2002). Aza-Peptide Epoxides: A New Class of Inhibitors Selective for Clan C D Cysteine Proteases. Journal of Medicinal Chemistry 45, 4958-4960.

29. James, K. E., Asgian, J. L., Li, Z. Z., Ekici, O. D., Rubin, J. R., Mikolajczyk, J., Salvesen, G. S., and Powers, J. C. (2004). Design, Synthesis, and Evaluation of Aza-Peptide Epoxides as Selective and Potent Inhibitors of Caspases-1, -3, -6, and -8. Journal of Medicinal Chemistry 47, 1553-1574.

30. Ekici, O. D., Gotz, M. G., James, K. E., Li, Z. Z., Rukamp, B. J., Asgian, J. L., Caffrey, C. R., Hansell, E., Dvorik, J., McKerrow, J. H., et al. (2004). Aza-Peptide Michael Acceptors: A New Class of Inhibitors Specific for Caspases and Other Clan C D Cysteine Proteases. Journal of Medicinal Chemistry 47, 1889-1892.

31. Ekici, O. D., Li, Z. Z., Campbell, A. J., James, K. E., Asgian, J. L., Mikolajczyk, J., Salvesen, G. S., Ganesan, R., Jelakovic, S., Grutter, M. G., et al. (2006). Design, Synthesis, and Evaluation of Aza-Peptide Michael Acceptors as Selective and Potent Inhibitors of Caspases-2, -3, -6, -7, -8, -9, and -10. Journal of Medicinal Chemistry 49, 5728-5749.

32. Ganesan, R., Jelakovic, S., Campbell, A. J., Li, Z. Z., Asgian, J. L., Powers, J. C., and Grutter, M. G. (2006). Exploring the S4 and S Prime Subsite Specificities in Caspase-3 with Aza-Peptide Epoxide Inhibitors. Biochemistry 45, 9059-9067.

33. Sexton, K. B., Kato, D., Berger, A. B., Fonovic, M., Verhelst, S. H. L., and Bogyo, M. (2006). Specificity of aza-peptide electrophile activity-based probes of caspases. Cell Death Differ 14, 727-732.

34. Götz, M. G., James, K. E., Hansell, E., Dvořák, J., Seshaadri, A., Sojka, D., Kopáček, P., McKerrow, J. H., Caffrey, C. R., and Powers, J. C. (2008). Aza-peptidyl Michael Acceptors. A New Class of Potent and Selective Inhibitors of Asparaginyl Endopeptidases (Legumains) from Evolutionarily Diverse Pathogens. Journal of Medicinal Chemistry 51, 2816-2832.

35. Ovat, A., Muindi, F., Fagan, C., Brouner, M., Hansell, E., Dvořák, J., Sojka, D., Kopacek, P., McKerrow, J. H., Caffrey, C. R., et al. (2009). Aza-Peptidyl Michael Acceptor and Epoxide Inhibitors—Potent and Selective Inhibitors of *Schistosoma mansoni* and *Ixodes ricinus* Legumains (Asparaginyl Endopeptidases). Journal of Medicinal Chemistry 52, 7192-7210.

36. Semple, J. E., Rowley, D. C., Brunck, T. K., and Ripka, W. C. (1997). Synthesis and biological activity of P2-P4 azapeptidomimetic P1-argininal and P1-ketoargininamide derivatives: a novel class of serine protease inhibitors. Bioorganic & Medicinal Chemistry Letters 7, 315-320.

37. Randolph, J. T., Zhang, X., Huang, P. P., Klein, L. L., Kurtz, K. A., Konstantinidis, A. K., He, W., Kati, W. M., and Kempf, D. J. (2008). Synthesis, antiviral activity, and conformational studies of a P3 aza-peptide analog of a potent macrocyclic tripeptide HCV protease inhibitor. Bioorganic & Medicinal Chemistry Letters 18, 2745-2750.

38. Piliero, P. J. (2002). Atazanavir: a novel HIV-1 protease inhibitor. Expert Opinion on Investigational Drugs 11, 1295-1301.

39. Pérez-Elias, M. J. (2007). Atazanavir: simplicity and convenience in different scenarios. Expert Opinion on Pharmacotherapy 8, 689-700.

40. Zamora, L., and Gatell, J. M. (2008). Atazanavir en el tratamiento de simplificación. Enfermedades Infecciosas y Microbiologia Clinica 26, 14-21.

41. Inagaki, I., Adachi, M., Ito, H., Yasuda, M., Tsurumi, H., Deguchi, T., and Seishima, M. (2015). Atazanavir-Induced Urine Crystals Demonstrated by Infrared Spectroscopic Analysis. Urologia Internationalis 94, 121-124.

42. Stolle, R. (1910). Hydrazi-dicarbon-hydrazid. Berichte der deutschen chemischen Gesellschaft 43, 2468-2470.

43. Ronco, K., Prijs, B., and Erlenmeyer, H. (1956). Aminosure-Analoge aus der Hydrazinreihe II. Helvetica Chimica Acta 39, 1253-1257.

44. Gante, J., and Lautsch, W. (1964). Enzyme models. XLVI. Peptide-like systems. 1. a-(4-Semicarbazino)fatty acid groups as building units of novel oligo compounds. Chem. Ber. 97, 983-988.

45. Quibell, M., Turnell, W. G., and Johnson, T. (1993). Synthesis of azapeptides by the Fmoc/tert-butyl/polyamide technique. Journal of the Chemical Society, Perkin Transactions 1, 2843-2849.

46. Gibson, C., Goodman, S. L., Hahn, D., Hölzemann, G., and Kessler, H. (1999). Novel Solid-Phase Synthesis of Azapeptides and Azapeptoides via Fmoc-Strategy and Its Application in the Synthesis of RGD-Mimetics. The Journal of Organic Chemistry 64, 7388-7394.

47. Melendez, R. E., and Lubell, W. D. (2004). Aza-Amino Acid Scan for Rapid Identification of Secondary Structure Based on the Application of N-Boc-Azal-Dipeptides in Peptide Synthesis. Journal of the American Chemical Society 126, 6759-6764.

48. Kato, D., Verhelst, S. H. L., Sexton, K. B., and Bogyo, M. (2005). A General Solid Phase Method for the Preparation of Diverse Azapeptide Probes Directed Against Cysteine Proteases. Organic Letters 7, 5649-5652.

49. O'Donnell, M. J., Zhou, C., and Scott, W. L. (1996). Solid-Phase Unnatural Peptide Synthesis (UPS). Journal of the American Chemical Society 118, 6070-6071.

50. Ooi, T., Kameda, M., and Maruoka, K. (1999). Molecular Design of a $C_2$-Symmetric Chiral Phase-Transfer Catalyst for Practical Asymmetric Synthesis of a-Amino Acids. Journal of the American Chemical Society 121, 6519-6520.

51. Ooi, T., Tayama, E., and Maruoka, K. (2003). Highly Stereoselective N-Terminal Functionalization of Small Peptides by Chiral Phase-Transfer Catalysis. Angewandte Chemie International Edition 42, 579-582.

52. Zhao, L., and Li, C.-J. (2008). Functionalizing Glycine Derivatives by Direct C D C Bond Formation. Angewandte Chemie International Edition 47, 7075-7078.

53. Zhao, L., Basle, O., and Li, C.-J. (2009). Site-specific C-functionalization of free-(N H) peptides and glycine derivatives via direct C-H bond functionalization. Proceedings of the National Academy of Sciences of the United States of America 106, 4106-4111.

54. Dutta, A. S., and Morley, J. S. (1975). Polypeptides. Part XIII. Preparation of [small alpha]-aza-amino-acid (carbazic acid) derivatives and intermediates for the preparation of [small alpha]-aza-peptides. Journal of the Chemical Society, Perkin Transactions 1, 1712-1720.

55. Biel, J. H., Drukker, A. E., Mitchell, T. F., Sprengeler, E. P., Nuhfer, P. A., Conway, A. C., and Horita, A. (1959). Central Stimulants. Chemistry and Structure-Activity Relationship of Aralkyl Hydrazines. Journal of the American Chemical Society 81, 2805-2813.

56. Janda, K. D., and Han, H. (1997). Azatide peptidomimetics. (Scripps Research Institute, USA; Janda, Kim D.; Han, Hyunsoo.), p. 78 pp.

57. Boeglin, D., and Lubell, W. D. (2005). Aza-Amino Acid Scanning of Secondary Structure Suited for Solid-Phase Peptide Synthesis with Fmoc Chemistry and Aza-Amino Acids with Heteroatomic Side Chains. Journal of Combinatorial Chemistry 7, 864-878.

58. Freeman, N. S., Hurevich, M., and Gilon, C. (2009). Synthesis of N'-substituted Ddz-protected hydrazines and their application in solid phase synthesis of aza-peptides. Tetrahedron 65, 1737-1745.

59. Abbas, C., Pickaert, G., Didierjean, C., Gregoire, B. J., and Vanderesse, R. (2009). Original and efficient synthesis of 2:1-[a/aza]-oligomer precursors. Tetrahedron Letters 50, 4158-4160.

60. Bourguet, C. B., Sabatino, D., and Lubell, W. D. (2008). Benzophenone semicarbazone protection strategy for synthesis of aza-glycine containing aza-peptides. Peptide Science 90, 824-831.

61. Liley, M., and Johnson, T. (2000). Solid phase synthesis of azapeptides utilising reversible amide bond protection to prevent hydantoin formation. Tetrahedron Letters 41, 3983-3985.

62. Garcia-Ramos, Y., and Lubell, W. D. (2013). Synthesis and alkylation of aza-glycinyl dipeptide building blocks. Journal of Peptide Science 19, 725-729.

63. Doan, N.-D., Zhang, J., Traore, M., Kamdem, W., and Lubell, W. D. (2015). Solid-phase synthesis of C-terminal azapeptides. Journal of Peptide Science 21, 387-391.

64. Staab, H. A. (1962). New Methods of Preparative Organic Chmistry I V. Syntheses Using Heterocyclic Amides (Azolides). Angewandte Chemie International Edition in English 1, 351-367.

65. Wieczerzak, E., Drabik, P., Lankiewicz, L., Oldziej, S., Grzonka, Z., Abrahamson, M., Grubb, A., and Bromme, D. (2002). Azapeptides Structurally Based upon Inhibitory Sites of Cystatins as Potent and Selective Inhibitors of Cysteine Proteases. Journal of Medicinal Chemistry 45, 4202-4211.

66. Verhelst, S. H. L., Witte, M. D., Arastu-Kapur, S., Fonovic, M., and Bogyo, M. (2006). Novel Aza Peptide Inhibitors and Active-Site Probes of Papain-Family Cysteine Proteases. ChemBioChem 7, 943-950.

67. Ollivier, N., Besret, S., Blanpain, A., and Melnyk, O. (2009). Silver-Catalyzed azaGly Ligation. Application to the Synthesis of Azapeptides and of Lipid-Peptide Conjugates. Bioconjugate Chemistry 20, 1397-1403.

68. Mhidia, R., and Melnyk, O. (2010). Selective cleavage of an azaGly peptide bond by copper(I I). Long-range effect of histidine residue. Journal of Peptide Science 16, 141-147.

69. Abo-Dya, N. E., Biswas, S., Basak, A., Avan, I., Alamry, K. A., and Katritzky, A. R. (2013). Benzotriazole-Mediated Synthesis of Aza-peptides: En Route to an Aza-Leuenkephalin Analogue. The Journal of Organic Chemistry 78, 3541-3552.

70. Andre, F., Marraud, M., Tsouloufis, T., Tzartos, S. J., and Boussard, G. (1997). Triphosgene: an efficient carbonylating agent for liquid and solid-phase aza-peptide synthesis. Application to the synthesis of two aza-analogues of the AChR MIR decapeptide. Journal of Peptide Science 3, 429-441.

71. Frochot, C., Vanderesse, R., Driou, A., Linden, G., Marraud, M., and Cung, M. T. (1997). A solid-phase synthesis of three aza-, iminoaza- and reduced aza-peptides from the same precursor. Letters in Peptide Science 4, 219-225.

72. Zhang, J., Proulx, C., Tomberg, A., and Lubell, W. D. (2014). Multicomponent Diversity-Oriented Synthesis of Aza-Lysine-Peptide Mimics. Organic Letters 16, 298-301.

73. Proulx, C., and Lubell, W. D. (2010). Copper-Catalyzed N-Arylation of Semicarbazones for the Synthesis of Aza-Arylglycine-Containing Aza-Peptides. Organic Letters 12, 2916-2919.

74. Proulx, C., and Lubell, W. D. (2010). Aza-1,2,3-triazole-3-alanine Synthesis via Copper-Catalyzed 1,3-Dipolar Cycloaddition on Aza-progargylglycine. The Journal of Organic Chemistry 75, 5385-5387.

75. Kato, M., Abe, M., Kuroda, Y., Hirose, M., Nakano, M., and Handa, T. (2009). Synthetic pentapeptides inhibiting autophosphorylation of insulin receptor in a non-ATP-competitive mechanism. Journal of Peptide Science 15, 327-336.

What is claimed is:

1. A compound of Formula (IA):

(IA)

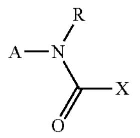

wherein

X is imidazolyl,

A is $NR_1R_2$, wherein $R_1$ is H and $R_2$ is tert-butoxycarbonyl, 9-fluorenylmethoxycarbonyl or 2-(3,5-dimethoxyphenyl) propan-2-yloxycarbonyl; and R is selected from the group consisting of side chain radicals of aspartic acid, phenylalanine, alanine, histidine, glutamic acid, tryptophan, valine, leucine, lysine, methionine, tyrosine, isoleucine, arginine, asparagine, serine, cysteine, threonine, and glutamine, wherein said side chain radicals are unsubstituted or are substituted with one or more substituents selected from the group consisting of a halogen, a $C_1$-$C_6$ alkyl, hydroxyl, —COOH, —COH, methoxyl, ethoxyl, propoxyl, a $C_1$-$C_6$ haloalkyl, and a protecting group.

2. The compound of claim 1, wherein the side chain radical is unsubstituted.

3. A compound of Formula (IA):

(IA)

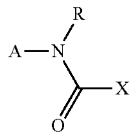

wherein

X is imidazolyl or benzotriazolyl,

A is phthalimidyl, and

R is selected from the group consisting of side chain radicals of phenylalanine, histidine, glutamic acid, tryptophan, valine, leucine, lysine, methionine, tyrosine, isoleucine, arginine, glycine, serine, cysteine, threonine, and glutamine, wherein said side chain radicals are unsubstituted or are substituted with one or more substituents selected from the group consisting of a halogen, a $C_1$-$C_6$ alkyl, hydroxyl, —COOH, —COH, methoxyl, ethoxyl, propoxyl, a $C_1$-$C_6$ haloalkyl, and a protecting group.
4. The compound of claim 3, wherein X is imidazolyl.
5. The compound of claim 4, which is selected from the group consisting of
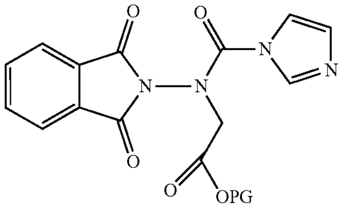
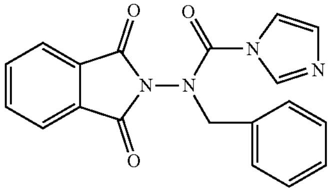
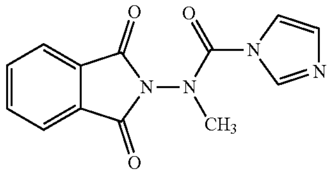
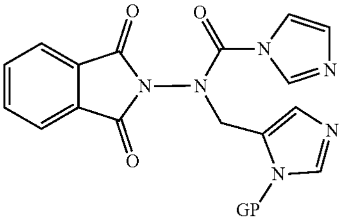
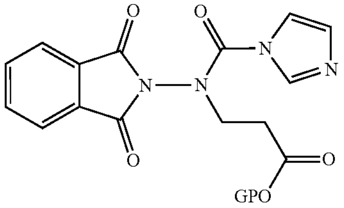
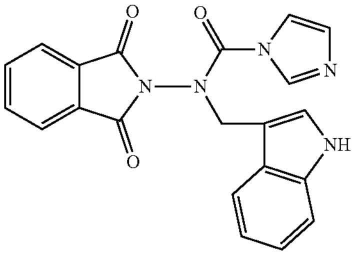
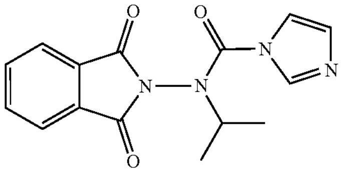
-continued
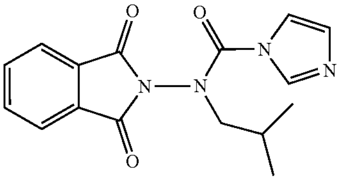
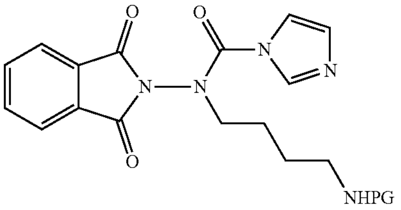
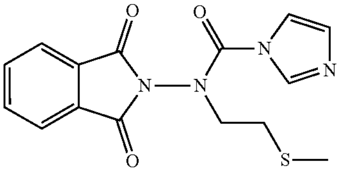
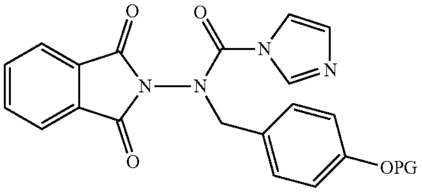
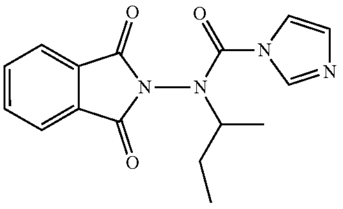
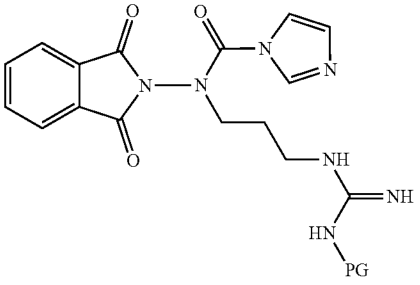
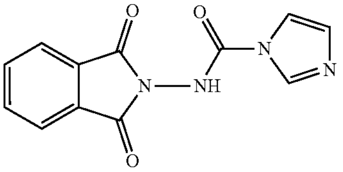
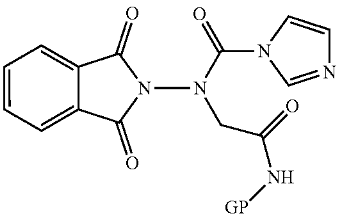

-continued
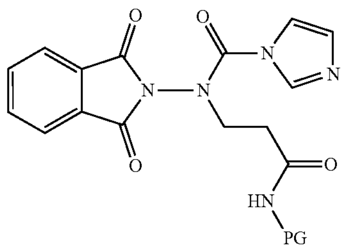
wherein PG is selected from the group consisting of H, phthalimidyl, tert-butoxycarbonyl, 9-fluorenylmethoxycarbonyl, and 2-(3,5-dimethoxyphenyl) propan-2-yloxycarbonyl.
6. The compound of claim 3, wherein X is benzotriazolyl.
7. The compound of claim 6, wherein the compound is selected from the group consisting of
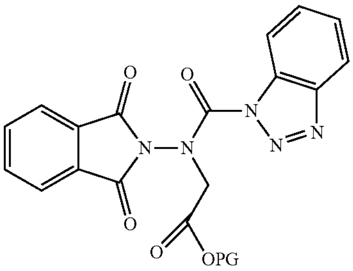
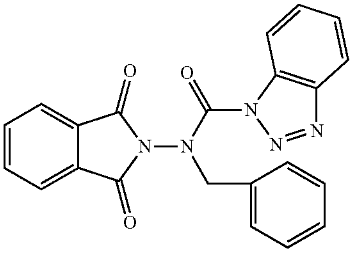
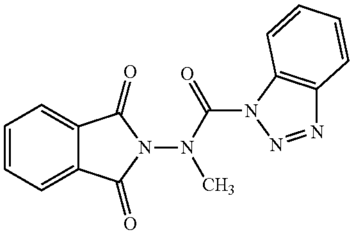
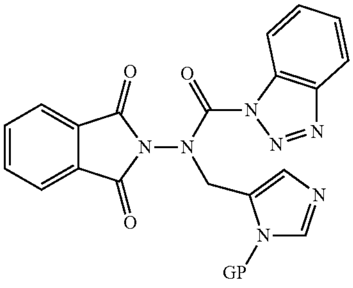
-continued
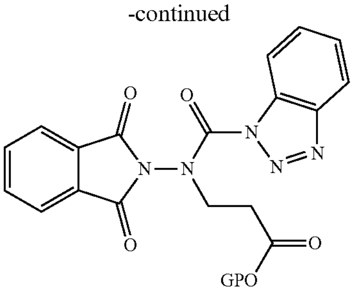
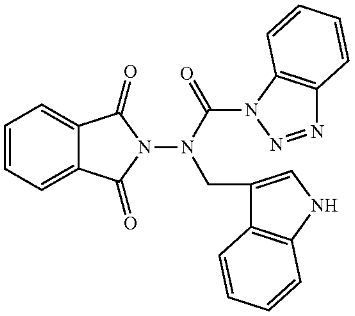
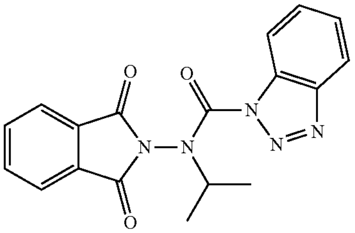
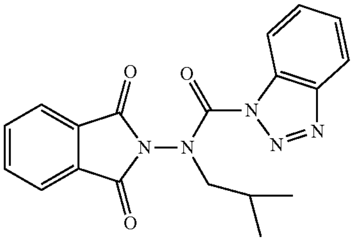
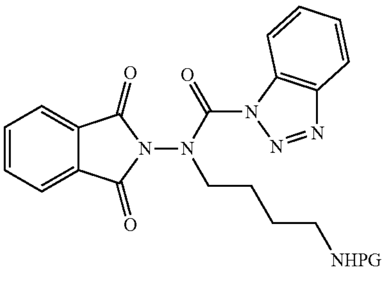
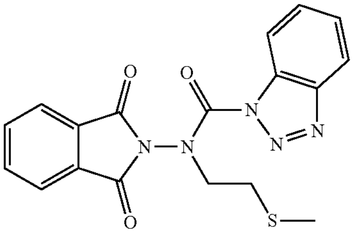

-continued

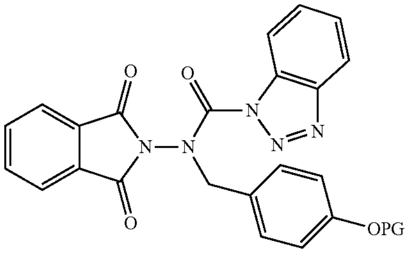

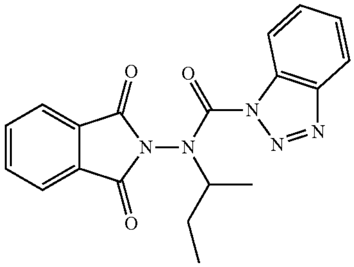

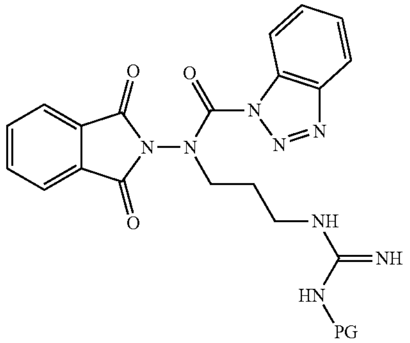

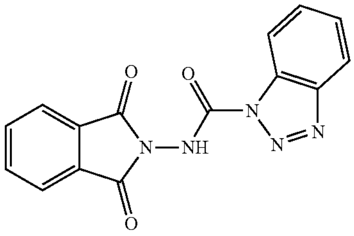

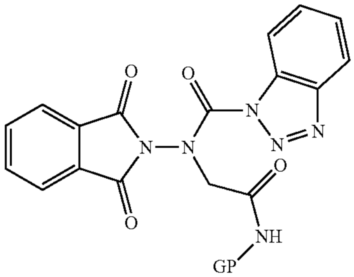

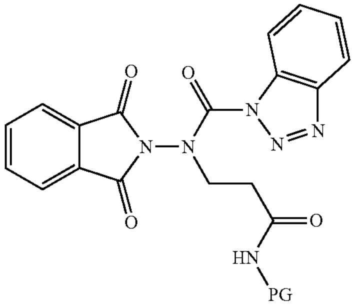

wherein PG is selected from the group consisting of H, phthalimidyl, tert-butoxycarbonyl, 9-fluorenylmethoxycarbonyl, and 2-(3,5-dimethoxyphenyl) propan-2-yloxycarbonyl.

8. A compound of Formula (IA):

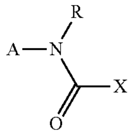

(IA)

wherein

X is imidazolyl or benzotriazolyl,

A is $NR_1R_2$,

R and $R_1$ are connected and together form a side chain radical of proline, and $R_2$ is tert-butoxycarbonyl, 9-fluorenylmethoxycarbonyl, or 2-(3,5-dimethoxyphenyl) propan-2-yloxycarbonyl.

9. A compound of Formula (IA):

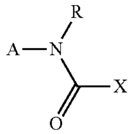

(IA)

wherein

X is benzotriazolyl,

A is phthalimidyl or $NR_1R_2$, wherein $R_1$ is H and $R_2$ is tert-butoxycarbonyl, 9-fluorenylmethoxycarbonyl, or 2-(3,5-dimethoxyphenyl) propan-2-yloxycarbonyl; and R is selected from the group consisting of side chain radicals of aspartic acid, phenylalanine, alanine, histidine, glutamic acid, tryptophan, valine, leucine, lysine, methionine, tyrosine, isoleucine, arginine, glycine, asparagine, serine, cysteine, threonine, and glutamine, wherein said side chain radicals are unsubstituted or are substituted with one or more substituents selected from the group consisting of a halogen, a $C_1$-$C_6$ alkyl, hydroxyl, —COOH, —COH, methoxyl, ethoxyl, propoxyl, a $C_1$-$C_6$ haloalkyl, and a protecting group.

10. The compound of claim 9, wherein A is $NR_1R_2$, wherein $R_1$ is H and $R_2$ is tert-butoxycarbonyl, 9-fluorenylmethoxycarbonyl, or 2-(3,5-dimethoxyphenyl) propan-2-yloxycarbonyl.

11. The compound of claim 10, wherein the side chain radical is unsubstituted.

12. A compound of Formula (IA):

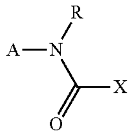

(IA)

wherein

X is imidazolyl or benzotriazolyl,

A is phthalimidyl or $NR_1R_2$, wherein $R_1$ is H and $R_2$ is 9-fluorenylmethoxycarbonyl or 2-(3,5-dimethoxyphenyl) propan-2-yloxycarbonyl; and R is selected from the group consisting of side chain radicals of aspartic acid, phenylalanine, alanine, histidine, glutamic acid, tryptophan, valine, leucine, lysine, methionine, tyrosine, isoleucine, arginine, glycine, asparagine, serine, cysteine, threonine, and glutamine, wherein said side chain radicals are unsubstituted or are substituted with one or more substituents selected from the group consisting of a halogen, a $C_1$-$C_6$ alkyl, hydroxyl, —COOH, —COH, methoxyl, ethoxyl, propoxyl, a $C_1$-$C_6$ haloalkyl, and a protecting group.

13. A compound of Formula (IA):

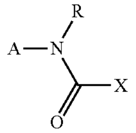

(IA)

wherein

X is imidazolyl or benzotriazolyl,

A is phthalimidyl or $NR_1R_2$, wherein $R_1$ is H and $R_2$ is 9-fluorenylmethoxycarbonyl or 2-(3,5-dimethoxyphenyl) propan-2-yloxycarbonyl, and R is a side chain radical of an amino acid, wherein one or more hydrogens on the side chain radical of the amino acid is substituted with a substituent selected from the group consisting of a halogen, a $C_1$-$C_6$ alkyl, hydroxyl, —COOH, —COH, methoxyl, ethoxyl, propoxyl, a $C_1$-$C_6$ haloalkyl, and a protecting group, and the amino acid is selected from a group consisting of aspartic acid, phenylalanine, alanine, histidine, glutamic acid, tryptophan, valine, leucine, lysine, methionine, tyrosine, isoleucine, arginine, glycine, asparagine, serine, cysteine, threonine, and glutamine.

14. The compound of claim 13, wherein A is phthalimidyl.

15. The compound of claim 13, wherein X is benzotriazolyl.

* * * * *